US012767667B2

(12) United States Patent
Kono et al.

(10) Patent No.: US 12,767,667 B2
(45) Date of Patent: Oct. 20, 2026

(54) MACROCYCLIC HETEROCYCLE COMPOUNDS AND USE THEREOF

(71) Applicant: TAKEDA PHARMACEUTICAL COMPANY LIMITED, Osaka (JP)

(72) Inventors: Mitsunori Kono, Kanagawa (JP); Yusuke Sasaki, Kanagawa (JP); Yuya Oguro, Kanagawa (JP); Zenichi Ikeda, Kanagawa (JP); Osamu Kubo, Kanagawa (JP); Masaki Seto, Kanagawa (JP); Toru Yamashita, Kanagawa (JP); Makoto Kamata, Kanagawa (JP); Kenjiro Sato, Kanagawa (JP); Matthew Thomas Reynolds, Kanagawa (JP); Kazuaki Takami, Kanagawa (JP); Asato Kina, Kanagawa (JP); Takafumi Yukawa, Kanagawa (JP); Minoru Nakamura, Kanagawa (JP); Taku Kamei, Kanagawa (JP); Hiroyuki Kakei, Kanagawa (JP); Fumie Yamaguchi, Kanagawa (JP); Tomohiro Ohashi, Kanagawa (JP); Keiko Kakegawa, Kanagawa (JP); Takuto Kojima, Kanagawa (JP); Florian Pünner, Kanagawa (JP); Masataka Murakami, Kanagawa (JP); Takahiko Taniguchi, Kanagawa (JP); Tatsuki Koike, Kanagawa (JP); Yuichi Kajita, Kanagawa (JP); Yuhei Miyanohana, Kanagawa (JP); Kohei Takeuchi, Kanagawa (JP); Yoshiteru Ito, Kanagawa (JP); Norihito Tokunaga, Kanagawa (JP); Yasushi Hattori, Kanagawa (JP); Eiji Kimura, Kanagawa (JP); Martin Alexander Pawliczek, Kanagawa (JP); Marilena Pira, Kanagawa (JP); Shuhei Ikeda, Kanagawa (JP); Noriyuki Tezuka, Kanagawa (JP); Yoshikazu Watanabe, Kanagawa (JP); Kevin Curran, San Diego, CA (US); Nicolle Doering, San Diego, CA (US); Maria Hopkins, San Diego, CA (US); Ben Johnson, San Diego, CA (US); Andre Kiryanov, San Diego, CA (US); Jon Lam, San Diego, CA (US); Sean Murphy, San Diego, CA (US); Natasha O'Rourke, San Diego, CA (US); Holly Reichard, San Diego, CA (US); Paul Tanis, San Diego, CA (US); Yunlong Zhang, San Diego, CA (US)

(73) Assignee: Takeda Pharmaceutical Company Limited, Osaka (JP)

(*) Notice: Subject to any disclaimer, the term of this patent is extended or adjusted under 35 U.S.C. 154(b) by 320 days.

(21) Appl. No.: 18/606,857

(22) Filed: Mar. 15, 2024

(65) Prior Publication Data

US 2024/0309016 A1 Sep. 19, 2024

Related U.S. Application Data

(60) Provisional application No. 63/490,748, filed on Mar. 16, 2023.

(51) Int. Cl.
*C07D 498/14* (2006.01)
*A61K 31/407* (2006.01)
(Continued)

(52) U.S. Cl.
CPC .......... *C07D 498/14* (2013.01); *A61K 31/407* (2013.01); *A61K 31/437* (2013.01); *A61P 25/26* (2018.01); *C07D 498/04* (2013.01)

(58) Field of Classification Search
None
See application file for complete search history.

(56) References Cited

U.S. PATENT DOCUMENTS

| | | | |
|---|---|---|---|
| 9,527,807 | B2 | 12/2016 | Fukumoto et al. |
| 10,287,305 | B2 | 5/2019 | Fujimoto et al. |

(Continued)

FOREIGN PATENT DOCUMENTS

| | | | |
|---|---|---|---|
| WO | WO-2012137982 | A9 | 2/2013 |
| WO | WO-2015048091 | A1 | 4/2015 |

(Continued)

OTHER PUBLICATIONS

Busquets, X., et al., "Decreased Plasma Levels of Orexin-A in Sleep Apnea," Respiration 71(6):575-579, Karger, Switzerland (Nov. 2004).

(Continued)

*Primary Examiner* — Samantha L Shterengarts
(74) *Attorney, Agent, or Firm* — Sterne, Kessler, Goldstein & Fox P.L.L.C.

(57) ABSTRACT

The present invention provides a heterocyclic compound having an orexin type 2 receptor agonist activity.
A compound represented by the formula (I):

(I)

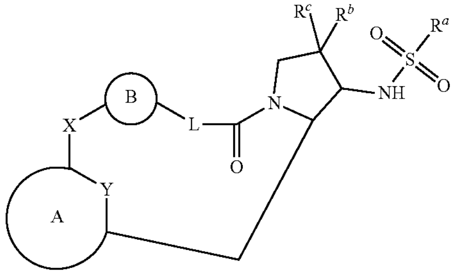

(Continued)

wherein each symbol is as described in the specification, or a salt thereof has an orexin type 2 receptor agonist activity, and is useful as an agent for the prophylaxis or treatment of narcolepsy.

26 Claims, No Drawings

(51) Int. Cl.

| | |
|---|---|
| ***A61K 31/437*** | (2006.01) |
| ***A61P 25/26*** | (2006.01) |
| ***C07D 498/04*** | (2006.01) |

(56) References Cited

U.S. PATENT DOCUMENTS

| | | | |
|---|---|---|---|
| 10,428,023 | B2 | 10/2019 | Kajita et al. |
| 10,508,083 | B2 | 12/2019 | Fujimoto et al. |
| 10,584,097 | B2 | 3/2020 | Kajita et al. |
| 10,898,737 | B2 | 1/2021 | Fujimoto et al. |
| 11,028,048 | B2 | 6/2021 | Hattori et al. |
| 11,034,700 | B2 | 6/2021 | Mikami et al. |
| 11,059,780 | B2 | 7/2021 | Daini et al. |
| 11,292,766 | B2 | 4/2022 | Fujimoto et al. |
| 11,319,286 | B2 | 5/2022 | Fujimoto et al. |
| 11,440,883 | B2 | 9/2022 | Kajita et al. |
| 11,655,241 | B2 | 5/2023 | Oda et al. |
| 11,987,586 | B1 | 5/2024 | Hattori et al. |
| 2021/0269420 | A1 | 9/2021 | Fujimoto et al. |
| 2022/0017514 | A1 | 1/2022 | Kajita et al. |
| 2022/0194958 | A1 | 6/2022 | Pennington et al. |
| 2023/0037557 | A1 | 2/2023 | Ito et al. |
| 2023/0042358 | A1 | 2/2023 | Miyanohana et al. |
| 2023/0063805 | A1 | 3/2023 | Kajita et al. |
| 2026/0146047 | A1 | 5/2026 | Kono et al. |

FOREIGN PATENT DOCUMENTS

| | | | |
|---|---|---|---|
| WO | WO-2015073707 | A1 | 5/2015 |
| WO | WO-2015147240 | A1 | 10/2015 |
| WO | WO-2017135306 | A1 | 8/2017 |
| WO | WO-2018164191 | A1 | 9/2018 |
| WO | WO-2018164192 | A1 | 9/2018 |
| WO | WO-2019027003 | A1 | 2/2019 |
| WO | WO-2019027058 | A1 | 2/2019 |
| WO | WO-2020004536 | A1 | 1/2020 |
| WO | WO-2020004537 | A1 | 1/2020 |
| WO | WO-2020122092 | A1 | 6/2020 |
| WO | WO-2020122093 | A1 | 6/2020 |
| WO | WO-2020158958 | A1 | 8/2020 |
| WO | WO-2020167701 | A1 | 8/2020 |
| WO | WO-2020167706 | A1 | 8/2020 |
| WO | WO-2021106975 | A1 | 6/2021 |
| WO | WO-2021108628 | A1 | 6/2021 |
| WO | WO-2022051583 | A1 | 3/2022 |
| WO | WO-2022109117 | A1 | 5/2022 |
| WO | WO-2022140316 | A1 | 6/2022 |
| WO | WO-2022232025 | A1 | 11/2022 |
| WO | WO-2022251302 | A1 | 12/2022 |
| WO | WO-2022251304 | A1 | 12/2022 |
| WO | WO-2023167925 | A1 | 9/2023 |
| WO | WO-2024189597 | A1 | 9/2024 |

OTHER PUBLICATIONS

Chemelli, R.M., et al., "Narcolepsy in Orexin Knockout Mice: Molecular Genetics of Sleep Regulation," Cell 98(4):437-451, Cell Press, United States (Aug. 1999).
Funato, H., et al., "Enhanced Orexin Receptor-2 Signaling Prevents Diet-induced Obesity and Improves Leptin Sensitivity," Cell Metabolism 9(1):64-76, Cell Press, United States (Jan. 2009).
Jaeger, L.B., et al., "Effects of Orexin-A on Memory Processing," Peptides 23(9):1683-1688, Elsevier Science Inc., United States (Sep. 2002).
Kushikata, T., et al., "Orexinergic Neurons and Barbiturate Anesthesia," Neuroscience 121(4):855-863, Elsevier Science, United States (Nov. 2003).
Lin, L., et al., "The Sleep Disorder Canine Narcolepsy is Caused by a Mutation in the Hypocretin (Orexin) Receptor 2 Gene," Cell 98(3):365-376, Cell Press, United States (Aug. 1999).
Mieda, M. and Sakurai, T., "Orexin (Hypocretin) Receptor Agonists and Antagonists for Treatment of Sleep Disorders. Rationale for Development and Current Status," CNS Drugs 27(2):83-90, Adis, Springer International, New Zealand (Feb. 2013).
Mieda, M., et al., "Orexin Peptides Prevent Cataplexy and Improve Wakefulness in an Orexin Neuron-ablated Model of Narcolepsy in Mice," Proceedings of the National Academy of Sciences of the United States of America 101(13):4649-4654, National Academy of Sciences, United States (Mar. 2004).
Perez, M.V., et al., "Systems Genomics Identifies a Key Role for Hypocretin/Orexin Receptor-2 in Human Heart Failure," Journal of the American College of Cardiology 66(22):2522-2533, Elsevier Biomedical, United States (Dec. 2015).
Sakurai, T., et al., "Orexins and Orexin Receptors: a Family of Hypothalamic Neuropeptides and G Protein-coupled Receptors That Regulate Feeding Behavior," Cell 92(4):573-585, Cell Press, United States (Feb. 1998).
Thannickal, T.C., et al., "Hypocretin (Orexin) Cell Loss in Parkinson's Disease," Brain 130(Pt 6):1586-1595, Oxford University Press, United Kingdom (Jun. 2007).
Willie, J.T., et al., "Distinct Narcolepsy Syndromes in Orexin Receptor-2 and Orexin Null Mice: Molecular Genetic Dissection of Non-REM and REM Sleep Regulatory Processes," Neuron 38(5):715-730, Cell Press, United States (Jun. 2003).
Firouzabadi, N., et al., "Orexin/Hypocretin Type 2 Receptor (HCRTR2) Gene as a Candidate Gene in Sertraline-Associated Insomnia in Depressed Patients," Neuropsychiatric Disease and Treatment 16:1121-1128, Dove Medical Press, New Zealand (May 2020).
Hong, C., et al., "Structures of active-state orexin receptor 2 rationalize peptide and small-molecule agonist recognition and receptor activation," Nature Communications 12(1):815, pp. 1-11, Nature Publishing Group, United Kingdom (Feb. 2021).
Mitsukawa, K., and Kimura, H., "Orexin 2 receptor (OX2R) protein distribution measured by autoradiography using radiolabeled OX2R-selective antagonist EMPA in rodent brain and peripheral tissues," Scientific Reports 12(1):8473, pp. 1-13, Nature Publishing Group, United Kingdom (May 2022).
Wang, C., et al., "The Orexin/Receptor System: Molecular Mechanism and Therapeutic Potential for Neurological Diseases," Frontiers in Molecular Neuroscience 11:220, pp. 1-16, Frontiers Research Foundation, Switzerland (Jun. 2018).
International Search Report and Written Opinion for International Application No. PCT/IB2024/052545, European Patent Office, Netherlands, mailed Jun. 12, 2024, 10 pages.
Office Action mailed Mar. 27, 2026, in U.S. Appl. No. 19/453,335, Kono, M., et al., filed Jan. 20, 2026, 12 pages.

MACROCYCLIC HETEROCYCLE COMPOUNDS AND USE THEREOF

TECHNICAL FIELD

The present invention relates to a heterocyclic compound, particularly, a heterocyclic compound having an orexin type 2 receptor agonist activity.

BACKGROUND OF THE INVENTION

Orexin is a neuropeptide specifically produced in particular neurons located sparsely in the lateral hypothalamus and its surrounding area, and consists of two subtypes, orexin A and orexin B. Both orexin A and orexin B are endogenous ligands of the orexin receptors, which are G protein-coupled receptors mainly present in the brain, and two types of subtypes, type 1 and type 2, are known for the orexin receptors (non-patent document 1).

Since orexin-producing neurons (orexin neurons) are localized in the vicinity of the feeding center, and intraventricular administration of orexin peptide results in an increase in food intake, orexin initially attracted attention as a neuropeptide having a feeding behavioral regulation. Thereafter, however, it was reported that the cause of dog narcolepsy is genetic variation of orexin type 2 receptor (non-patent document 2), and the role of orexin in controlling sleep and wakefulness has been also attracted.

From the studies using a transgenic mouse having denatured orexin neurons and a double transgenic mouse obtained by crossing this mouse with orexin overexpressing transgenic mouse, it was clarified that narcolepsy-like symptoms that appear by degeneration of orexin neurons disappear due to sustained expression of orexin. Similarly, when orexin peptide was intraventricularly administered to a transgenic mouse having denatured orexin neuron, improvement of narcolepsy-like symptoms was also observed (non-patent document 3). Studies of orexin type 2 receptor knockout mice have suggested that orexin type 2 receptor is important for maintaining arousal (non-patent document 4, non-patent document 5). Such background suggests that orexin type 2 receptor agonists become therapeutic drugs for narcolepsy or therapeutic drugs for other sleep disorders exhibiting excessive sleepiness (non-patent document 6).

In addition, it is suggested that a peptidic agonist that selectively acts on the orexin type 2 receptor improves obesity due to high fat diet load in mice (non-patent document 7).

In addition, it is suggested that intraventricular administration of orexin peptide shortens the systemic anesthetic time of rat (non-patent document 8).

In addition, it is suggested that patients with sleep apnea syndrome show low orexin A concentration levels in plasma (non-patent document 9).

In addition, it is suggested that intraventricular administration of orexin peptide improves memory retention of senescence-accelerated model mouse (SAMP8) with cognitive dysfunction (non-patent document 10).

In addition, it is suggested that Orexin type 2 receptor agonist will be a therapeutic drug for cardiac failure (patent document 1, non-patent document 11).

In addition, it is suggested that the daytime sleepiness of Parkinson's disease patients is caused by orexin nerve fallout (non-patent document 12).

In addition, it is suggested that orexin regulates bone formation and bone loss, and orexin type 2 receptor agonist will be a therapeutic drug for diseases related to bone loss such as osteoporosis, rheumatoid arthritis and the like (patent document 2).

In addition, it is suggested that orexin receptor agonist is useful for the prophylaxis or treatment of sepsis, severe sepsis and septic shock, since the mortality was significantly improved by mere continuous administration of orexin from the periphery in septic shock model mouse (patent document 3).

Therefore, a compound having an orexin type 2 receptor agonist activity is expected to be useful as a novel therapeutic drug for narcolepsy, idiopathic hypersomnia, hypersomnia, sleep apnea syndrome, disturbance of consciousness such as coma and the like, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis and the like, further, anesthetic antagonist, a prophylactic or therapeutic drug for side effects and complications due to anesthesia.

As sulfonamide derivatives, a compound represented by the formula (I)

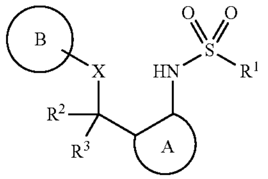

wherein each symbol is as described in the document (Patent Document 4) has been reported.

In addition, as compounds having an orexin type 2 receptor agonist activity, the following compounds have been reported.

A compound represented by the formula

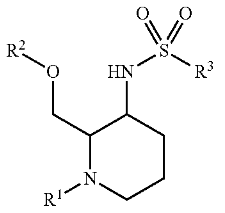

wherein each symbol is as described in the document (Patent Document 5).

A compound represented by the formula

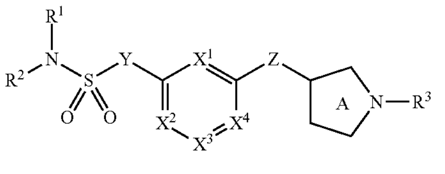

wherein each symbol is as described in the document (Patent Document 6).

A compound represented by the formula

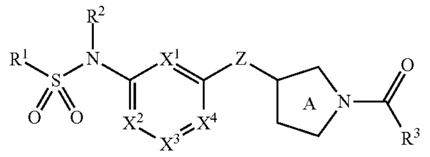

wherein each symbol is as described in the document (Patent Document 7).

A compound represented by the formula

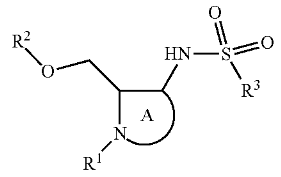

wherein each symbol is as described in the document (Patent Document 8).

A compound represented by the formula

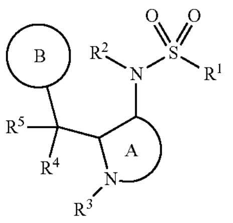

wherein each symbol is as described in the document (Patent Document 9).

A compound represented by the formula (I)

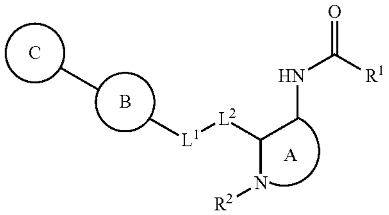

wherein each symbol is as described in the document (Patent Document 10).

A compound represented by the formula (I)

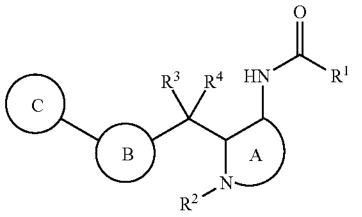

wherein each symbol is as described in the document (Patent Document 11).

A compound represented by the formula (I)

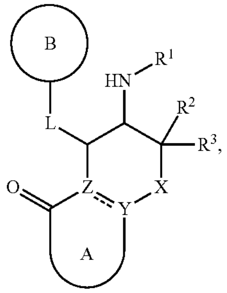

wherein each symbol is as described in the document (Patent Document 12).

A compound represented by the formula (I)

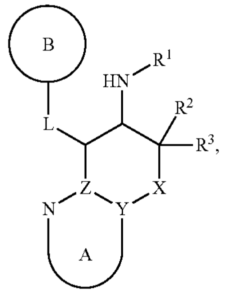

wherein each symbol is as described in the document (Patent Document 13).

A compound represented by the formula (I)

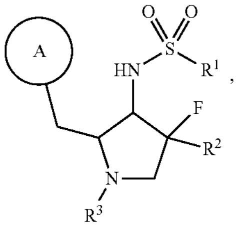

wherein each symbol is as described in the document (Patent Document 14).

A compound represented by the formula

I

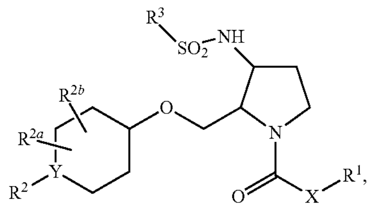

wherein each symbol is as described in the document (Patent Document 15).

A compound represented by the formula

I

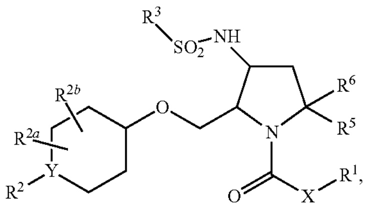

wherein each symbol is as described in the document (Patent Document 16).

A compound represented by the formula (I)

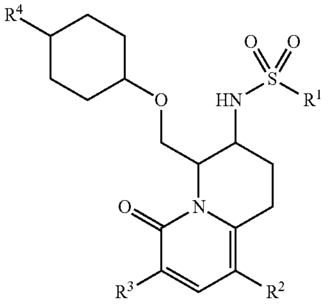

wherein each symbol is as described in the document (Patent Document 17).

A compound represented by the formula (I-A)

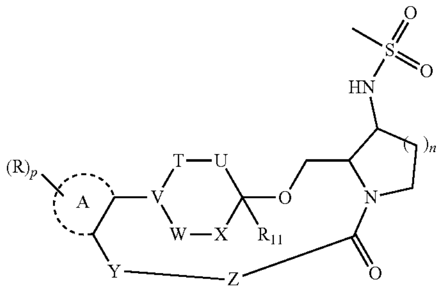

wherein each symbol is as described in the document (Patent Document 18).

A compound represented by the formula (I-A)

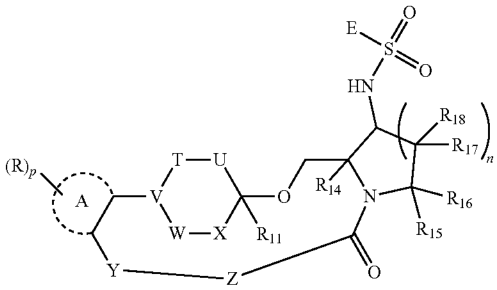

wherein each symbol is as described in the document (Patent Document 19).

A compound represented by the formula (I-A)

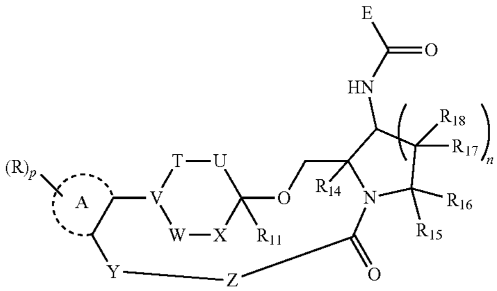

wherein each symbol is as described in the document (Patent Document 20).

A compound represented by the formula (I-A)

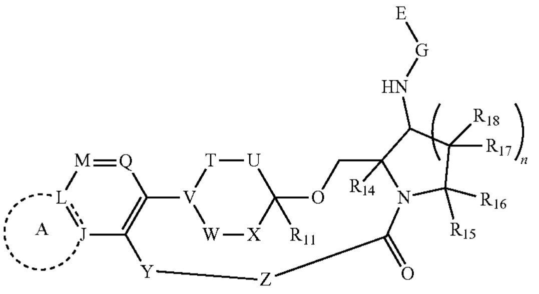

wherein each symbol is as described in the document (Patent Document 21).

A compound represented by the formula (I-A)

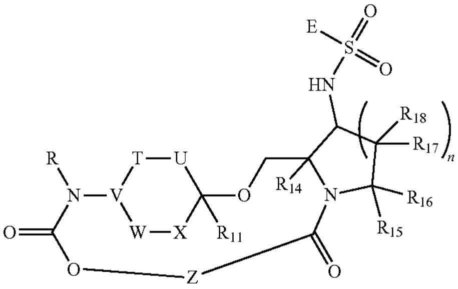

wherein each symbol is as described in the document (Patent Document 22).

A compound represented by the formula (I')

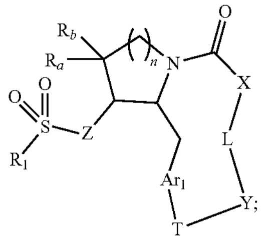

wherein each symbol is as described in the document (Patent Document 23).

A compound represented by the formula (I)

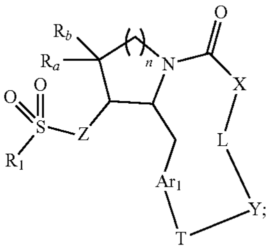

wherein each symbol is as described in the document (Patent Document 24).

A compound represented by the formula

I

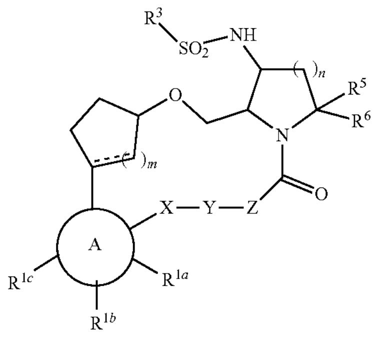

wherein each symbol is as described in the document (Patent Document 25).

Development of a novel compound having an orexin type 2 receptor agonist activity is desired.

DOCUMENT LIST

Patent Document

[Patent Document 1] WO 2015/073707 A1
[Patent Document 2] WO 2015/048091 A1
[Patent Document 3] WO 2015/147240 A1
[Patent Document 4] WO 2012/137982 A9
[Patent Document 5] WO 2017/135306 A1
[Patent Document 6] WO 2018/164191 A1
[Patent Document 7] WO 2018/164192 A1
[Patent Document 8] WO 2019/027003 A1
[Patent Document 9] WO 2019/027058 A1
[Patent Document 10] WO 2020/004536 A1
[Patent Document 11] WO 2020/004537 A1
[Patent Document 12] WO 2020/122092 A1
[Patent Document 13] WO 2020/122093 A1
[Patent Document 14] WO 2020/158958 A1
[Patent Document 15] WO 2020/167701 A1
[Patent Document 16] WO 2020/167706 A1
[Patent Document 17] WO 2021/106975 A1
[Patent Document 18] WO 2021/108628 A1
[Patent Document 19] WO 2022/140316 A1
[Patent Document 20] WO 2022/232025 A1
[Patent Document 21] WO 2022/251302 A1
[Patent Document 22] WO 2022/251304 A1
[Patent Document 23] WO 2022/051583 A1
[Patent Document 24] WO 2023/167925 A1
[Patent Document 25] WO 2022/109117 A1

Non-Patent Document

[Non-Patent Document 1] Cell, Vol. 92, 573-585, 1998
[Non-Patent Document 2] Cell, Vol. 98, 365-376, 1999
[Non-Patent Document 3] Proc. Natl. Acad. Sci. USA, Vol. 101, 4649-4654, 2004
[Non-Patent Document 4] Cell, Vol. 98, 437-451, 1999
[Non-Patent Document 5] Neuron, Vol. 38, 715-730, 2003
[Non-Patent Document 6] CNS Drugs, Vol. 27, 83-90, 2013
[Non-Patent Document 7] Cell Metabolism, Vol. 9, 64-76, 2009
[Non-Patent Document 8] Neuroscience, Vol. 121, 855-863, 2003
[Non-Patent Document 9] Respiration, Vol. 71, 575-579, 2004
[Non-Patent Document 10] Peptides, Vol. 23, 1683-1688, 2002
[Non-Patent Document 11] Journal of the American College of Cardiology. Vol. 66, 2015, Pages 2522-2533
[Non-Patent Document 12] Brain. Vol. 130, 2007, Pages 1586-1595

SUMMARY OF THE INVENTION

Problems to be Solved by the Invention

The present invention aims to provide a heterocyclic compound having an orexin type 2 receptor agonist activity.

Means of Solving the Problems

The present inventors have found that a compound represented by the following formula (I) or a salt thereof (sometimes to be referred to as compound (I) in the present specification) has an orexin type 2 receptor agonist activity. As a result of further studies, they have completed the present invention.

Accordingly, the present invention relates to the followings.

[1]

A compound represented by the formula (I):

(I)

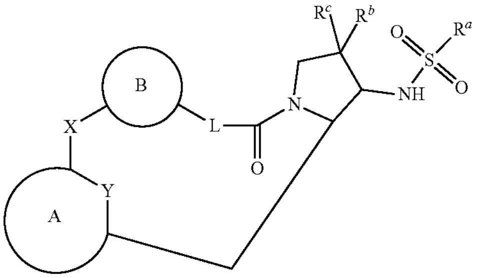

wherein

Ring A is an optionally substituted $C_{6-14}$ aryl group, or an optionally substituted 5- or 6-membered monocyclic aromatic heterocyclic group, where Y is a ring atom C or N, where the C is attached to hydrogen or an optional substituent;

X is —O—, —S—, —$NR^1$—, —$CR^2R^3$—, —O—($CR^2R^3$)—, —($CR^2R^3$)—O—, or an optionally substituted $C_{3-6}$ cycloalkyl group, wherein the left hand portion of X is attached to a ring carbon atom on Ring A that is adjacent to Y and the right hand portion of X is attached to Ring B;

$R^1$ is hydrogen, or an optionally substituted $C_{1-6}$ alkyl group;

$R^2$ and $R^3$ are independently hydrogen, halogen, or an optionally substituted $C_{1-6}$ alkyl group;

Ring B is an optionally substituted $C_{6-14}$ aryl group, or an optionally substituted 5- or 6-membered monocyclic aromatic heterocyclic group;

L is —$C(R^4R^5)$—$NR^6$—, —$C(R^4R^5)$—O—, —O—$C(R^4R^5)$—, —$NR^6$—$C(R^4R^5)$—, —$C(R^4R^5)$—$C(R^7R^8)$—, wherein the left hand portion of L is attached to Ring B and the right hand portion of L is attached to the carbonyl group;

$R^4$ and $R^5$ are independently hydrogen, halogen, or an optionally substituted $C_{1-6}$ alkyl group;

$R^6$ is hydrogen, or an optionally substituted $C_{1-6}$ alkyl group;

$R^7$ and $R^8$ are independently hydrogen, halogen, or an optionally substituted $C_{1-6}$ alkyl group;

$R^4$ and $R^6$, taken together with the atoms to which they are attached, form an optionally substituted 3- to 8-membered monocyclic non-aromatic heterocyclic ring; or $R^4$ and $R^5$, or $R^4$ and $R^7$, taken together with the atom or atoms to which they are attached form an optionally substituted 3- to 8-membered monocyclic non-aromatic heterocyclic ring, or an optionally substituted $C_{3-10}$ cycloalkyl group;

$R^a$ is a $C_{1-6}$ alkyl group, a $C_{3-4}$ cycloalkyl group, or a mono- or di-$C_{1-6}$ alkylamino group, wherein each of $C_{1-6}$ alkyl group, $C_{3-4}$ cycloalkyl group, and mono- or di-$C_{1-6}$ alkylamino group is optionally substituted;

$R^b$ is a hydrogen atom or a halogen atom; and $R^c$ is a hydrogen atom or a halogen atom;

or a salt thereof.

[2]

The compound or salt of the above-mentioned [1], wherein Ring A is

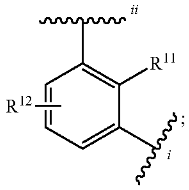

wherein i is the point of attachment to the bridge methylene and ii is the point of attachment to X; and $R^{11}$ and $R^{12}$ are independently hydrogen, halogen, or optionally halogenated $C_{1-6}$ alkyl group.

[3]

The compound or salt of the above-mentioned [1] or [2], wherein

Ring B is selected from:

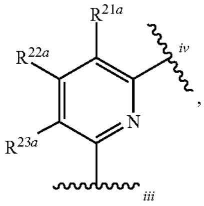
,
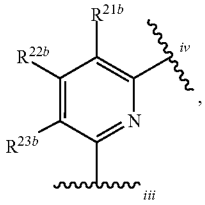
,
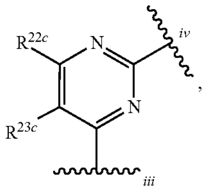
,
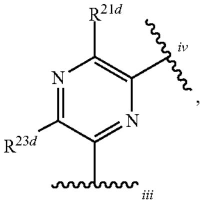
, and
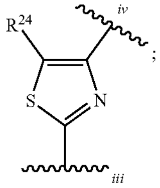

wherein iv is the point of attachment to L and iii is the point of attachment to X;

$R^{21a}$, $R^{21b}$, $R^{21d}$, $R^{22a}$, $R^{22b}$, $R^{22c}$, $R^{23a}$, $R^{23b}$, $R^{23c}$ and $R^{23d}$ are independently selected from hydrogen, halogen, an optionally halogenated $C_{1-6}$ alkyl group, $C_{1-6}$ alkoxyl group and a $C_{3-6}$ cycloalkyl group; and $R^{24}$ is selected from hydrogen, halogen, an optionally halogenated $C_{1-6}$ alkyl group, and a $C_{3-6}$ cycloalkyl group.

[4]

The compound or salt of the above-mentioned [1], [2], or [3], wherein

Ring A is

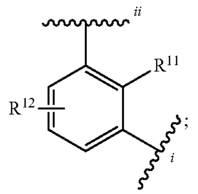

wherein i is the point of attachment to the bridge methylene and ii is the point of attachment to X; and $R^{11}$ and $R^{12}$ are independently hydrogen, halogen, or $C_{1-6}$ alkyl group;

X is —O—, —$CR^2R^3$—, —O—($CR^2R^3$)—, or —($CR^2R^3$)—O—, wherein the left hand portion of X is attached to a ring carbon atom on Ring A that is adjacent to Y and the right hand portion of X is attached to Ring B;

$R^2$ and $R^3$ are independently hydrogen, halogen, or $C_{1-6}$ alkyl group optionally substituted by 1 to 3 substituents independently selected from halogen and $C_{1-6}$ alkyl group;

Ring B is selected from:

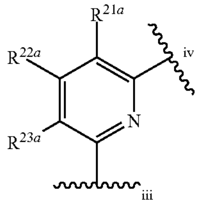

,

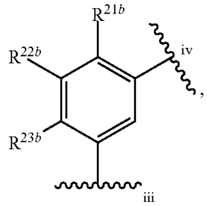

,

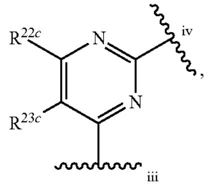

,

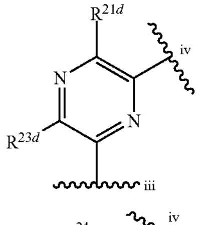

, and

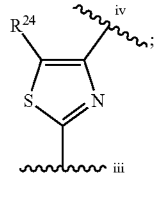

;

wherein iv is the point of attachment to L and iii is the point of attachment to X;

$R^{21a}$, $R^{21b}$, $R^{21d}$, $R^{22a}$, $R^{22b}$, $R^{22c}$, $R^{23a}$, $R^{23b}$, $R^{23c}$ and $R^{23d}$ are independently selected from hydrogen, halogen, an optionally halogenated $C_{1-6}$ alkyl group, $C_{1-6}$ alkoxyl group and a $C_{3-6}$ cycloalkyl group;

$R^{24}$ is hydrogen or a $C_{1-6}$ alkyl group;

L is —$C(R^4R^5)$—$NR^6$—, —$C(R^4R^5)$—O—, —O—C($R^4R^5$)—, —$NR^6$—$C(R^4R^5)$—, or —$C(R^4R^5)$—C($R^7R^8$)—, wherein the left hand portion of L is attached to Ring B and the right hand portion of L is attached to the carbonyl group;

$R^4$ and $R^5$ are independently hydrogen, or $C_{1-6}$ alkyl group;

$R^6$ is hydrogen, or an optionally halogenated $C_{1-6}$ alkyl group;

$R^7$ and $R^8$ are independently hydrogen; or when L is —$C(R^4R^5)$—$NR^6$— or —$NR^6$—$C(R^4R^5)$—, $R^4$ and $R^6$ together with the atoms to which they are attached form a 3- to 8-membered monocyclic non-aromatic heterocyclic ring optionally substituted by 1 to 3 substituents independently selected from halogen and $C_{1-6}$ alkoxyl group, and $R^5$ is hydrogen; or when L is —$C(R^4R^5)$—$C(R^7R^8)$—, $R^4$ and $R^7$ together with the carbon atoms to which they are attached form a $C_{3-10}$ cycloalkyl group, and $R^5$ and $R^8$ are both hydrogen;

$R^a$ is a $C_{1-6}$ alkyl group optionally substituted by 1 to 3 substituents independently selected from halogen atoms and $C_{1-6}$ alkoxyl group, a $C_{3-4}$ cycloalkyl group, or a mono- or di-$C_{1-6}$ alkylamino group;

$R^b$ is a hydrogen atom or a halogen atom; and $R^c$ is a hydrogen atom or a halogen atom.

[5]

The compound or salt of the above-mentioned [1], [2], [3] or [4], wherein

Ring A is a phenyl group optionally further substituted by 1 to 2 halogen atoms, where Y is a ring atom C attached to hydrogen or halogen;

X is —O—, wherein the left hand portion of X is attached to a ring carbon atom on Ring A that is adjacent to Y and the right hand portion of X is attached to Ring B;

Ring B is a pyridine ring optionally substituted by 1, 2 or 3 substituents independently selected from halogen and $C_{1-6}$ alkyl group;

L is —$CH_2$—NH—, wherein the left hand portion of L is attached to Ring B and the right hand portion of L is attached to the carbonyl group;

$R^a$ is a $C_{1-6}$ alkyl group optionally substituted by 1 to 3 halogen atoms, or a $C_{3-4}$ cycloalkyl group;

$R^b$ is a halogen atom; and $R^c$ is a halogen atom.

[6]

The compound or salt of the above-mentioned [1] to [5], wherein

Ring A is a phenyl group optionally further substituted by 1 to 2 halogen atoms, where Y is a ring atom C attached to halogen;

X is —O—, wherein the left hand portion of X is attached to a ring carbon atom on Ring A that is adjacent to Y and the right hand portion of X is attached to Ring B;

Ring B is a pyridine ring optionally substituted by 1, 2 or 3 $C_{1-6}$ alkyl groups;

L is —$CH_2$—NH—, wherein the left hand portion of L is attached to Ring B and the right hand portion of L is attached to the carbonyl group;

$R^a$ is a $C_{1-6}$ alkyl group optionally substituted by 1 to 3 halogen atoms;

$R^b$ is a halogen atom; and $R^c$ is a halogen atom.

[7]

The compound according to the above-mentioned [1], wherein the compound is selected from the group consisting of:

N-[(15aS,16R)-17,17-difluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl] methanesulfonamide;

N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide;

N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]ethanesulfonamide;

1-fluoro-N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide;

N-[(15aS,16R)-7-chloro-17,17,20-trifluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide;

N-[(15aS,16R)-5,17,17,20-tetrafluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]methanesulfonamide;

N-[(15aS,16R)-7-chloro-5,17,17,20-tetrafluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide; and N-[(15aS,16R)-17,17,20-trifluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]propane-2-sulfonamide;

or a salt thereof.

[8]

A pharmaceutical composition comprising the compound as defined in any one of the above-mentioned [1] to [7] or a salt thereof, and a pharmacologically acceptable carrier.

[9]

A medicament comprising the compound as defined in any one of the above-mentioned [1] to [7] or a salt thereof.

[10]

The medicament according to the above-mentioned [9], which is an orexin type 2 receptor agonist.

[11]

The medicament according to the above-mentioned [9], which is an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, or side effects and complications due to anesthesia.

[12]

The medicament according to the above-mentioned [9], which is an agent for the prophylaxis or treatment of narcolepsy, idiopathic hypersomnia, hypersomnia, or sleep apnea syndrome.

[13]

The medicament according to the above-mentioned [9], which is an agent for the prophylaxis or treatment of narcolepsy.

[14]

A method for the prophylaxis or treatment of a disease or disorder associated with an orexin type 2 receptor in a mammal in need thereof comprising administering to the mammal a therapeutically effective amount of the compound as defined in any one of the above-mentioned [1] to [7] or a salt thereof.

[15]

The method of above-mentioned [14], wherein the disease or disorder is selected from the group consisting of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, and side effects and complications due to anesthesia.

[16]

The method of above-mentioned or [15], wherein the disease or disorder is selected from the group consisting of narcolepsy, idiopathic hypersomnia, hypersomnia, and sleep apnea syndrome.

[17]

The method of above-mentioned [14], [15], or [16], wherein the disease or disorder is narcolepsy.

[18]

The compound as defined in any of the above-mentioned [1] to [7], or a salt thereof, for use in therapy.

[19]

The compound or salt according to the above-mentioned [18], wherein the therapy comprises treatment of a disease or disorder associated with an orexin type 2 receptor.

[20]

The compound or salt according to the above-mentioned [19], wherein the disease or disorder is selected from the group consisting of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, and side effects and complications due to anesthesia.

[21]

The compound or salt according to the above-mentioned [19], wherein the disease or disorder is selected from the group consisting of narcolepsy, idiopathic hypersomnia, hypersomnia, and sleep apnea syndrome.

[22]

The compound or salt according to the above-mentioned [19], wherein the disease or disorder is narcolepsy.

[23]

Use of the compound as defined in any of the above-mentioned [1] to [7] or a salt thereof, in the manufacture of a medicament for the treatment of a disease or disorder associated with an orexin type 2 receptor.

[24]

Use according to the above-mentioned [23], wherein the disease or disorder is selected from the group consisting of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, and side effects and complications due to anesthesia.

[25]

Use according to the above-mentioned [23], wherein the disease or disorder is selected from the group consisting of narcolepsy, idiopathic hypersomnia, hypersomnia, and sleep apnea syndrome.

[26]

Use according to the above-mentioned [23], wherein the disease or disorder is narcolepsy.

Effect of the Invention

The compound of the present invention has an orexin type 2 receptor agonist activity, and is useful as an agent for the prophylaxis or treatment of narcolepsy.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, fluoromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent (s) selected from the following Substituent group A.

[Substituent Group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),

(55) a $C_{1-6}$ alkylsulfonylamino group (e.g., methylsulfonylamino, ethylsulfonylamino),

(56) a $C_{6-14}$ arylsulfonylamino group optionally substituted by a $C_{1-6}$ alkyl group (e.g., phenylsulfonylamino, toluenesulfonylamino),

(57) an optionally halogenated $C_{1-6}$ alkyl group,

(58) a $C_{2-6}$ alkenyl group,

(59) a $C_{2-6}$ alkynyl group,

(60) a $C_{3-10}$ cycloalkyl group,

(61) a $C_{3-10}$ cycloalkenyl group, and

(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent (s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group, a 3- to 14-membered non-aromatic heterocyclic group, an amino group and a mono- or di-$C_{1-6}$ alkyl-amino group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), N—$C_{1-6}$ alkyl-N',N'-di-$C_{1-6}$ alkylhydrazine-carbonyl group, a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tri-cyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi- or tri-cyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

In the present specification, examples of the "$C_{3-6}$ cycloalkyl group" include cyclopropyl, cyclobutyl, cyclopentyl and cyclohexyl. In the present specification, examples of the "$C_{3-4}$ cycloalkyl group" include cyclopropyl and cyclobutyl.

In the present specification, examples of the "mono- or di-$C_{1-6}$ alkylamino group" include methylamino, dimethylamino, ethylamino, diethylamino, propylamino, isopropylamino, butylamino, isobutylamino, sec-butylamino, tert-butylamino, pentylamino, isopentylamino, neopentylamino, 1-ethylpropylamino, hexylamino, isohexylamino, 1,1-dimethylbutylamino, 2,2-dimethylbutylamino, 3,3-dimethylbutylamino, 2-ethylbutylamino and the like.

The definition of each symbol in the formula (I) is explained in detail in the following.

$R^a$ is a $C_{1-6}$ alkyl group, $C_{3-4}$ cycloalkyl group, or mono- or di-$C_{1-6}$ alkylamino group, wherein each of $C_{1-6}$ alkyl group, $C_{3-4}$ cycloalkyl group, and mono- or di-$C_{1-6}$ alkylamino group is optionally substituted.

Examples of the substituent of the above-mentioned "optionally substituted $C_{1-6}$ alkyl group", "optionally substituted mono- or di-$C_{1-6}$ alkylamino group" and "optionally substituted $C_{3-4}$ cycloalkyl group" include substituents selected from Substituent group A. The number of the substituents is preferably 1 to 3. When the number of the substituents is 2 or more, the respective substituents may be the same or different.

$R^a$ is preferably (1) an optionally substituted $C_{1-6}$ alkyl group (e.g., methyl, ethyl, isopropyl), (2) an optionally substituted mono- or di-$C_{1-6}$ alkylamino group (e.g., methylamino, dimethylamino), or (3) an optionally substituted $C_{3-4}$ cycloalkyl group (e.g., cyclopropyl).

$R^a$ is preferably (1) a $C_{1-6}$ alkyl group (e.g., methyl, ethyl, isopropyl) optionally substituted by 1 to 3 substituents independently selected from halogen atoms (e.g., a fluorine atom) and $C_{1-6}$ alkoxyl group (e.g., methoxy), (2) a $C_{3-4}$ cycloalkyl group (e.g., cyclopropyl), or (3) a mono- or di-$C_{1-6}$ alkylamino group (e.g., methylamino, dimethylamino).

$R^a$ is more preferably (1) a $C_{1-6}$ alkyl group (e.g., methyl, ethyl, isopropyl) optionally substituted by 1 to 3 halogen atoms (e.g., a fluorine atom), or (2) a $C_{3-4}$ cycloalkyl group (e.g., cyclopropyl).

$R^a$ is further more preferably a $C_{1-6}$ alkyl group (e.g., methyl) optionally substituted by 1 to 3 halogen atoms (e.g., a fluorine atom).

$R^b$ is a hydrogen atom, or a halogen atom (e.g., a fluorine atom); and $R^c$ is a hydrogen atom, or a halogen atom (e.g., a fluorine atom).

Preferably, $R^b$ and $R^c$ are both (1) a hydrogen atom, or (2) a halogen atom (e.g., a fluorine atom); or (3) one of $R^b$ and Re is a hydrogen atom and the other is a halogen atom (e.g., a fluorine atom).

More preferably, $R^b$ is a halogen atom (e.g., a fluorine atom); and $R^c$ is a halogen atom (e.g., a fluorine atom).

Ring A is an optionally substituted $C_{6-14}$ aryl group (e.g., phenyl), or an optionally substituted 5- or 6-membered monocyclic aromatic heterocyclic group, where Y is a ring atom C or N, where the C is attached to hydrogen or an optional substituent Ring A optionally has substituent (s) in addition to —$CH_2$-pyrrolidine ring and X in the formula (I). Examples of the substituent include the above-mentioned "substituent" selected from Substituent group A. The number of the substituents is preferably 1 to 3. When the number of the substituents is 2 or more, the respective substituents may be the same or different.

Ring A is preferably a phenyl group optionally further substituted by 1 to 2 substituents selected from (i) a halogen atom (e.g., a fluorine atom), and (ii) a $C_{1-6}$ alkyl group (e.g., methyl), where Y is a ring atom C attached to hydrogen or halogen (e.g., a fluorine atom).

Ring A is more preferably a phenyl group optionally further substituted by 1 to 2 halogen atoms (e.g., a fluorine atom), where Y is a ring atom C attached to hydrogen or halogen (e.g., a fluorine atom).

Ring A is more preferably a phenyl group optionally further substituted by 1 to 2 halogen atoms (e.g., a fluorine atom), where Y is a ring atom C attached to halogen (e.g., a fluorine atom).

Preferably, Ring A is

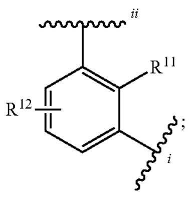

wherein i is the point of attachment to the bridge methylene and ii is the point of attachment to X; and $R^{11}$ and $R^{12}$ are independently hydrogen, halogen (e.g., a fluorine atom), or optionally halogenated $C_{1-6}$ alkyl group (e.g., methyl).

Preferably, $R^{11}$ and $R^{12}$ are independently hydrogen, halogen (e.g., a fluorine atom), or $C_{1-6}$ alkyl group (e.g., methyl).

More preferably, $R^{11}$ is hydrogen or halogen (e.g., a fluorine atom) and $R^{12}$ is hydrogen.

X is —O—, —S—, —$NR^1$—, —$CR^2R^3$—, —O—($CR^2R^3$)—, —($CR^2R^3$)—O—, or an optionally substituted $C_{3-6}$ cycloalkyl group, wherein the left hand portion of X is attached to a ring carbon atom on Ring A that is adjacent to Y and the right hand portion of X is attached to Ring B, where:

$R^1$ is hydrogen, or an optionally substituted $C_{1-6}$ alkyl group; and $R^2$ and $R^3$ are independently hydrogen, halogen, or an optionally substituted $C_{1-6}$ alkyl group.

Examples of the substituent of the above-mentioned "optionally substituted $C_{1-6}$ alkyl group", and "optionally substituted $C_{3-6}$ cycloalkyl group" include substituents selected from Substituent group A. The number of the substituents is preferably 1 to 3. When the number of the substituents is 2 or more, the respective substituents may be the same or different.

Preferably, X is —O—, —$CR^2R^3$—, —O—($CR^2R^3$)—, or —($CR^2R^3$)—O—, wherein the left hand portion of X is attached to a ring carbon atom on Ring A that is adjacent to Y and the right hand portion of X is attached to Ring B, where $R^2$ and $R^3$ are independently hydrogen, halogen (e.g., a fluorine atom), or $C_{1-6}$ alkyl group (e.g., methyl) optionally substituted by 1 to 3 substituents independently selected from halogen and $C_{1-6}$ alkyl group.

Preferably, X is —O—, —$CR^2R^3$—, —O—($CR^2R^3$)—, or —($CR^2R^3$)—O—, wherein the left hand portion of X is attached to a ring carbon atom on Ring A that is adjacent to Y and the right hand portion of X is attached to Ring B, where $R^2$ and $R^3$ are independently hydrogen, halogen (e.g., a fluorine atom), or $C_{1-6}$ alkyl group (e.g., methyl).

More preferably, X is —O—, wherein the left hand portion of X is attached to a ring carbon atom on Ring A that is adjacent to Y and the right hand portion of X is attached to Ring B.

Ring B is an optionally substituted $C_{6-14}$ aryl group, or an optionally substituted 5- or 6-membered monocyclic aromatic heterocyclic group.

Ring B optionally has substituent (s) in addition to L and X in the formula (I). Examples of the substituent include the above-mentioned "substituent" selected from Substituent group A. The number of the substituents is preferably 1 to 3. When the number of the substituents is 2 or more, the respective substituents may be the same or different.

Preferably, Ring B is (1) an optionally further substituted $C_{6-14}$ aryl group (e.g., phenyl), or (2) an optionally further substituted 5- or 6-membered monocyclic aromatic heterocycle group (e.g., thiazole, pyridine, pyrimidine, pyrazine).

More preferably, Ring B is (1) a phenyl group, optionally substituted by 1 to 3 substituents selected from a halogen atom (e.g., a chlorine atom) and a $C_{1-6}$ alkyl group (e.g., methyl), (2) a 5- or 6-membered monocyclic aromatic heterocyclic group (e.g., thiazole, pyridine, pyrimidine, pyrazine) which is optionally substituted by 1 to 3 substituents (specifically 1 to 3 substituents for the pyridine, 1 or 2 substituents for the thiazole, pyrimidine and pyrazine) selected from (a) a halogen atom (e.g., a fluorine atom, a chlorine atom, a bromine atom), (b) an optionally halogenated $C_{1-6}$ alkyl group (e.g., methyl, ethyl, difluoromethyl), (c) a $C_{3-6}$ cycloalkyl group (e.g., cyclopropyl), and (d) a $C_{1-6}$ alkoxy group (e.g., methoxy).

More preferably, Ring B is a pyridine ring optionally substituted by 1, 2 or 3 substituents independently selected from halogen (e.g., a fluorine atom, a chlorine atom) and $C_{1-6}$ alkyl group (e.g., methyl).

More preferably, Ring B is a pyridine ring optionally substituted by 1, 2 or 3 $C_{1-6}$ alkyl groups (e.g., methyl).

More preferably, Ring B is selected from:

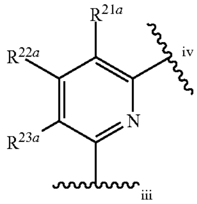
,
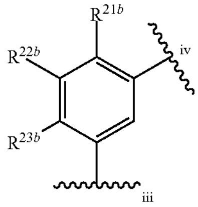
,
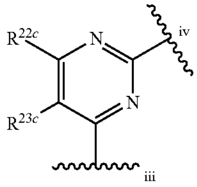
,
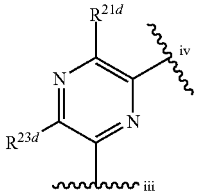
, and
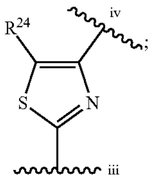
;

wherein iv is the point of attachment to L and iii is the point of attachment to X;

$R^{21a}$, $R^{21b}$, $R^{21d}$, $R^{22a}$, $R^{22b}$, $R^{22c}$, $R^{23a}$, $R^{23b}$, $R^{23c}$ and $R^{23d}$ are independently selected from hydrogen, halogen (e.g., fluorine atom, chlorine atom, bromine atom), an optionally halogenated $C_{1-6}$ alkyl group (e.g., methyl, ethyl, difluoromethyl), $C_{1-6}$ alkoxyl group (e.g., methoxy) and a $C_{3-6}$ cycloalkyl group (e.g., cyclopropyl);

$R^{24}$ is selected from hydrogen, halogen, an optionally halogenated $C_{1-6}$ alkyl group, and a $C_{3-6}$ cycloalkyl group.

More preferably, $R^{24}$ is hydrogen or a $C_{1-6}$ alkyl group.

L is —$C(R^4R^5)$—$NR^6$—, —$C(R^4R^5)$—O—, —O—$C(R^4R^5)$—, —$NR^6$—$C(R^4R^5)$—, —$C(R^4R^5)$—$C(R^7R^8)$—, wherein the left hand portion of L is attached to Ring B and the right hand portion of L is attached to the carbonyl group;

$R^4$ and $R^5$ are independently hydrogen, halogen, or an optionally substituted $C_{1-6}$ alkyl group;

$R^6$ is hydrogen, or an optionally substituted $C_{1-6}$ alkyl group;

$R^7$ and $R^8$ are independently hydrogen, halogen, or an optionally substituted $C_{1-6}$ alkyl group; or $R^4$ and $R^6$, taken together with the atoms to which they are attached, form an optionally substituted 3- to 8-membered monocyclic non-aromatic heterocyclic ring; or $R^4$ and $R^5$, or $R^4$ and $R^7$, taken together with the atom or atoms to which they are attached form an optionally substituted 3- to 8-membered monocyclic non-aromatic heterocyclic ring, or an optionally substituted $C_{3-10}$ cycloalkyl group.

Examples of the substituent of the above-mentioned "optionally substituted $C_{1-6}$ alkyl group", "optionally substituted 3- to 8-membered monocyclic non-aromatic heterocyclic ring" and "optionally substituted $C_{3-10}$ cycloalkyl group" include substituents selected from Substituent group A. The number of the substituents is preferably 1 to 3. When the number of the substituents is 2 or more, the respective substituents may be the same or different Preferably, L is L is —$C(R^4R^5)$—$NR^6$—, —$C(R^4R^5)$—O—, —O—$C(R^4R^5)$—, —$NR^6$—$C(R^4R^5)$—, or —$C(R^4R^5)$—$C(R^7R^8)$—, wherein the left hand portion of L is attached to Ring B and the right hand portion of L is attached to the carbonyl group;

$R^4$ and $R^5$ are independently hydrogen, or $C_{1-6}$ alkyl group (e.g., methyl);

$R^6$ is hydrogen, or an optionally halogenated $C_{1-6}$ alkyl group (e.g., methyl, difluoroethyl);

$R^7$ and $R^8$ are hydrogen; or when L is —$C(R^4R^5)$—$NR^6$— or —$NR^6$—$C(R^4R^5)$—, $R^4$ and $R^6$ together with the atoms to which they are attached form a 3- to 8-membered monocyclic non-aromatic heterocyclic ring (e.g., an azetidine ring, a pyrrolidine ring) optionally substituted by 1 to 3 substituents independently selected from halogen (e.g., a fluorine atom) and $C_{1-6}$ alkoxyl group (e.g., methoxy), and $R^5$ is hydrogen; or when L is —$C(R^4R^5)$—$C(R^7R^8)$—, $R^4$ and $R^7$ together with the carbon atoms to which they are attached form a $C_{3-10}$ cycloalkyl group (e.g., cyclopropyl) and $R^5$ and $R^8$ are both hydrogen.

More preferably, L is —$CH_2$—NH—, wherein the left hand portion of L is attached to Ring B and the right hand portion of L is attached to the carbonyl group.

Preferable examples of compound (I) include the following compounds.

[Compound A]

Compound (I) wherein $R^a$ is (1) an optionally substituted $C_{1-6}$ alkyl group (e.g., methyl, ethyl, isopropyl, fluoromethyl, difluoromethyl, methoxymethyl), (2) an optionally substituted mono- or di-$C_{1-6}$ alkylamino group (e.g., methylamino, dimethylamino), or (3) an optionally substituted $C_{3-4}$ cycloalkyl group (e.g., cyclopropyl);

$R^b$ is (1) a hydrogen atom, or (2) a halogen atom (e.g. a fluorine atom);

$R^c$ is (1) a hydrogen atom, or (2) a halogen atom (e.g. a fluorine atom);

Ring A is (1) an optionally substituted $C_{6-14}$ aryl group (e.g., phenyl), or (2) an optionally substituted 5- or 6-membered monocyclic aromatic heterocyclic group, where Y is a ring atom C or N, where the C is attached to hydrogen or an optional substituent;

Ring B is (1) an optionally substituted $C_{6-14}$ aryl group (e.g., phenyl), or (2) an optionally substituted 5- or 6-membered monocyclic aromatic heterocyclic group (e.g., thiazole, pyridine, pyrimidine, pyrazine);

X is (1) —O—, (2) —S—, (3) —$NR^1$—, (4) —$CR^2R^3$—, (5) —O—$(CR^2R^3)$—, (6) —$(CR^2R^3)$—O—, or (7) an optionally substituted $C_{3-6}$ cycloalkyl group, wherein the left hand portion of X is attached to a ring carbon atom on Ring A that is adjacent to Y and the right hand portion of X is attached to Ring B;

$R^1$ is hydrogen, or an optionally substituted $C_{1-6}$ alkyl group $R^2$ and $R^3$ are independently hydrogen, halogen (e.g. a fluorine atom), or an optionally substituted $C_{1-6}$ alkyl group (e.g. methyl);

L is (1) —$C(R^4R^5)$—$NR^6$—, (2) —$C(R^4R^5)$—O—, (3) —O—$C(R^4R^5)$—, (4) —$NR^6$—$C(R^4R^5)$—, (5) —$C(R^4R^5)$—$C(R^7R^8)$—, wherein the left hand portion of L is attached to Ring B and the right hand portion of L is attached to the carbonyl group; and $R^4$ and $R^5$ are independently hydrogen, halogen, or an optionally substituted $C_{1-6}$ alkyl group (e.g. methyl);

$R^6$ is hydrogen, or an optionally substituted $C_{1-6}$ alkyl group (e.g. methyl, difluoroethyl);

$R^7$ and $R^8$ are independently hydrogen, halogen, or an optionally substituted $C_{1-6}$ alkyl group; or $R^4$ and $R^6$, taken together with the atoms to which they are attached, form an optionally substituted 3- to 8-membered monocyclic non-aromatic heterocyclic ring (e.g. an azetidine ring or a pyrrolidine ring optionally substituted by 1 to 3 substituents independently selected from halogen (e.g., a fluorine atom) and $C_{1-6}$ alkoxyl group (e.g., methoxy)); or $R^4$ and $R^5$, or $R^4$ and $R^7$, taken together with the atom or atoms to which they are attached form an optionally substituted 3- to 8-membered monocyclic non-aromatic heterocyclic ring, or an optionally substituted $C_{3-10}$ cycloalkyl group (e.g. cyclopropyl).

[Compound B]

Compound (I) wherein $R^a$ is (1) a $C_{1-6}$ alkyl group (e.g., methyl, ethyl, isopropyl) optionally substituted by 1 to 3 substituents independently selected from halogen atoms (e.g., a fluorine atom) and $C_{1-6}$ alkoxyl group (e.g., methoxy), (2) a $C_{3-4}$ cycloalkyl group (e.g., cyclopropyl), or (3) a mono- or di-$C_{1-6}$ alkylamino group (e.g., methylamino, dimethylamino);

$R^b$ is (1) a hydrogen atom, or (2) a halogen atom (e.g. a fluorine atom);

$R^c$ is (1) a hydrogen atom, or (2) a halogen atom (e.g. a fluorine atom);

Ring A is a phenyl group optionally further substituted by 1 to 2 substituents selected from a halogen atom (e.g., a fluorine atom) and $C_{1-6}$ alkyl group (e.g., methyl), where Y is a ring atom C attached to hydrogen or halogen (e.g., a fluorine atom);

Ring B is (1) a phenyl group, optionally substituted by 1 to 3 substituents selected from a halogen atom (e.g., a chlorine atom), (2) a 5- or 6-membered monocyclic aromatic heterocyclic group (e.g., thiazole, pyridine, pyrimidine, pyrazine), of the pyridine which is optionally substituted by 1 to 3 substituents and the thiazole, pyrimidine and pyrazine which are selected from 1 or 2 substituents, the substituents in all cases selected from (a) a halogen atom (e.g., a fluorine atom, a chlorine atom, a bromine atom), (b) an optionally halogenated $C_{1-6}$ alkyl group (e.g., methyl, ethyl, difluoromethyl), (c) a $C_{3-6}$ cycloalkyl group (e.g., cyclopropyl), and (d) a $C_{1-6}$ alkoxy group (e.g., methoxy);

X is (1) —O—, (2) —$CR^2R^3$—, (3) —O—($CR^2R^3$)—, or (4) —($CR^2R^3$)—O—, wherein the left hand portion of X is attached to a ring carbon atom on Ring A that is adjacent to Y and the right hand portion of X is attached to Ring B;

$R^2$ and $R^3$ are independently (1) hydrogen, (2) halogen (e.g. a fluorine atom), or (3) $C_{1-6}$ alkyl group (e.g. methyl) optionally substituted by 1 to 3 substituents independently selected from halogen and $C_{1-6}$ alkyl group;

L is (1) —$C(R^4R^5)$—$NR^6$—, (2) —$C(R^4R^5)$—O—, (3) —O—$C(R^4R^5)$—, (4) —$NR^6$—$C(R^4R^5)$—, (5) —$C(R^4R^5)$—$C(R^7R^8)$—, wherein the left hand portion of L is attached to Ring B and the right hand portion of L is attached to the carbonyl group; and $R^4$ and $R^5$ are independently (1) hydrogen, or (2) $C_{1-6}$ alkyl group (e.g., methyl);

$R^6$ is (1) hydrogen, or (2) an optionally halogenated $C_{1-6}$ alkyl group (e.g. methyl, difluoroethyl);

$R^7$ and $R^8$ are each hydrogen; or when L is —$C(R^4R^5)$—$NR^6$— or —$NR^6$—$C(R^4R^5)$—, $R^4$ and $R^6$ together with the atoms to which they are attached form a 3- to 8-membered monocyclic non-aromatic heterocyclic ring (e.g. an azetidine ring or a pyrrolidine ring) optionally substituted by 1 to 3 substituents independently selected from halogen (e.g., a fluorine atom) and $C_{1-6}$ alkoxyl group (e.g., methoxy), and $R^5$ is hydrogen; or when L is —$C(R^4R^5)$—$C(R^7R^8)$—, $R^4$ and $R^7$ together with the atoms to which they are attached form a $C_{3-10}$ cycloalkyl group (e.g. cyclopropyl), and $R^5$ and $R^8$ are both hydrogen.

[Compound C]

Compound (I) wherein

Ring A is a phenyl group optionally further substituted by 1 to 2 halogen atoms (e.g., a fluorine atom), where Y is a ring atom C attached to hydrogen or halogen (e.g., a fluorine atom);

X is —O—, wherein the left hand portion of X is attached to a ring carbon atom on Ring A that is adjacent to Y and the right hand portion of X is attached to Ring B;

Ring B is a pyridine ring optionally substituted by 1, 2 or 3 substituents independently selected from halogen (e.g., a fluorine atom, a chlorine atom) and $C_{1-6}$ alkyl (e.g., methyl);

L is —$CH_2$—NH—, wherein the left hand portion of L is attached to Ring B and the right hand portion of L is attached to the carbonyl group;

$R^a$ is a $C_{1-6}$ alkyl group (e.g., methyl, ethyl, isopropyl) optionally substituted by 1 to 3 halogen atoms (e.g., a fluorine atom), or a $C_{3-4}$ cycloalkyl group (e.g., cyclopropyl);

$R^b$ is a halogen atom (e.g., a fluorine atom); and $R^c$ is a halogen atom (e.g., a fluorine atom).

[Compound D]

Compound (I) wherein

Ring A is a phenyl group optionally further substituted by 1 to 2 halogen atoms (e.g., a fluorine atom), where Y is a ring atom C attached to halogen (e.g., a fluorine atom);

X is —O—, wherein the left hand portion of X is attached to a ring carbon atom on Ring A that is adjacent to Y and the right hand portion of X is attached to Ring B;

Ring B is a pyridine ring optionally substituted by 1, 2 or 3 $C_{1-6}$ alkyl groups (e.g., methyl);

L is —$CH_2$—NH—, wherein the left hand portion of L is attached to Ring B and the right hand portion of L is attached to the carbonyl group;

$R^a$ is a $C_{1-6}$ alkyl group (e.g., methyl) optionally substituted by 1 to 3 halogen atoms (e.g., a fluorine atom);

$R^b$ is a halogen atom (e.g., a fluorine atom); and $R^c$ is a halogen atom (e.g., a fluorine atom).

[Compound E]

Compound (I) wherein

Ring A is a phenyl group optionally further substituted by 1 to 2 halogen atoms (e.g., a fluorine atom), where Y is a ring atom C attached to halogen (e.g., a fluorine atom);

X is —O—, wherein the left hand portion of X is attached to a ring carbon atom on Ring A that is adjacent to Y and the right hand portion of X is attached to Ring B;

Ring B is

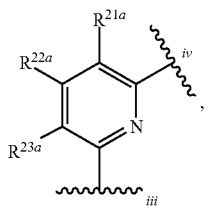

where $R^{21a}$, $R^{22a}$ and $R^{23a}$ are independently hydrogen or $C_{1-6}$ alkyl (e.g. methyl).

L is —$CH_2$—NH—, wherein the left hand portion of L is attached to Ring B and the right hand portion of L is attached to the carbonyl group;

$R^a$ is a $C_{1-6}$ alkyl group (e.g., methyl) optionally substituted by 1 to 3 halogen atoms (e.g., a fluorine atom);

$R^b$ is a halogen atom (e.g., a fluorine atom); and $R^c$ is a halogen atom (e.g., a fluorine atom).

Specific examples of compound (I) include the compounds of the below-mentioned Examples 1 to 111.

Specifically, compound (I) is preferably

N-[(15aS,16R)-17,17-difluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl] methanesulfonamide or a salt thereof (Example 2);

N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide or a salt thereof (Example 4);

N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]ethanesulfonamide or a salt thereof (Example 5);

1-fluoro-N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide or a salt thereof (Example 19);

N-[(15aS,16R)-7-chloro-17,17,20-trifluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide or a salt thereof (Example 22);

N-[(15aS,16R)-5,17,17,20-tetrafluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]methanesulfonamide or a salt thereof (Example 36);

N-[(15aS,16R)-7-chloro-5,17,17,20-tetrafluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide or a salt thereof (Example 58); or N-[(15aS,16R)-17,17,20-trifluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]propane-2-sulfonamide or a salt thereof (Example 97).

As a salt of a compound represented by the formula (I), a pharmacologically acceptable salt is preferable, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

The production method of the compound of the present invention is explained below.

The raw material compound and reagent used and the compound obtained in each step in the following production method may be each in a form of a salt, and examples of such salt include those similar to the salts of the compound represented by the formula (I), and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents–20 equivalents, preferably 0.8 equivalents–5 equivalents, relative to the substrate, unless otherwise specified. When the reagent is used as a catalyst, the reagent is used in an amount of 0.001 equivalent–1 equivalent, preferably 0.01 equivalent–0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N, N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

anhydrides: acetic anhydride and the like;

organic acids: formic acid, acetic acid, trifluoroacetic acid and the like;

inorganic acids: hydrochloric acid, sulfuric acid and the like;

esters: ethyl acetate and the like;

ketones: acetone, methyl ethyl ketone and the like;

water.

The above-mentioned solvent can be used in a mixture of two or more kinds thereof in an appropriate ratio.

When a base is used for the reaction in each step, examples thereof include those described in Examples and the following bases.

inorganic bases: sodium hydroxide, magnesium hydroxide, sodium carbonate, calcium carbonate, sodium hydrogen carbonate and the like;

organic bases: triethylamine, diethylamine, pyridine, 4-dimethylaminopyridine, N, N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropylamide, lithium hexamethyldisilazide and the like;

organic lithiums: n-butyllithium and the like.

When an acid or an acid catalyst is used for the reaction in each step, examples thereof include those described in Examples and the following acids and acid catalysts.

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like;

Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N, N-dimethylhydrazone and the like, and the like.

Examples of the protecting group for a carboxyl group include ester-type protecting groups such as methyl ester and the like; amide-type protecting groups such as N, N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as acid anhydrides, activated esters, sulfates and the like. Examples of the activating agent of the carboxylic acid include carbodiimide condensing agents such as 1-ethyl-3-(3-dimethylaminopropyl) carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; 0-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis (diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When carbonylation reaction is carried out in each step, examples of the carbonylation agent to be used include 1,1-carbonyldiimidazole (CDI), triphosgene, di(N-succinimidyl) carbonate (DSC), and the like. In addition, a base can be added to the reaction system, and examples thereof include inorganic bases and organic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis (4-methoxyphenyl)-1,3,2,4-dithiadiphosphetane-2,4-disulfide (Lawesson reagent) etc.) can also be used instead of phosphorus pentasulfide.

When sulfonylation reaction is carried out in each step, examples of the sulfonylation agent to be used include sulfonyl chloride, sulfamoyl chloride and the like. In addition, a base can be added to the reaction system, and examples thereof include inorganic bases and organic bases and the like.

When Wohl-Ziegler reaction is carried out in each step, examples of the halogenating agent to be used include N-iodosuccinimide (NIS), N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N, N'-dicyclohexylcarbodiimide, alumina, polyphosphoric acid and the like.

Examples of the "protecting group" for $PG^1$, $PG^2$, $PG^3$, and $PG^4$ include those exemplified as the above-mentioned "protecting group for an amino group and a hydroxy group.

Examples of the "leaving group" for $LG^1$, $LG^2$, $LG^3$, $LG^4$, and $LG^5$ include halogen atoms, optionally halogenated $C_{1-6}$ alkylsulfonyloxy (e.g., methanesulfonyloxy, ethanesulfonyloxy, trifluoromethanesulfonyloxy), $C_{6-14}$ arylsulfonyloxy optionally substituted by $C_{1-6}$ alkyl (e.g., benzenesulfonyloxy, toluenesulfonyloxy) and the like. Compound (I) can be produced from compound (1a)-(4a) and (1b)-(4b) according to the method shown in the following Scheme 1. In the formulas, the symbols are as defined above.

Scheme 1

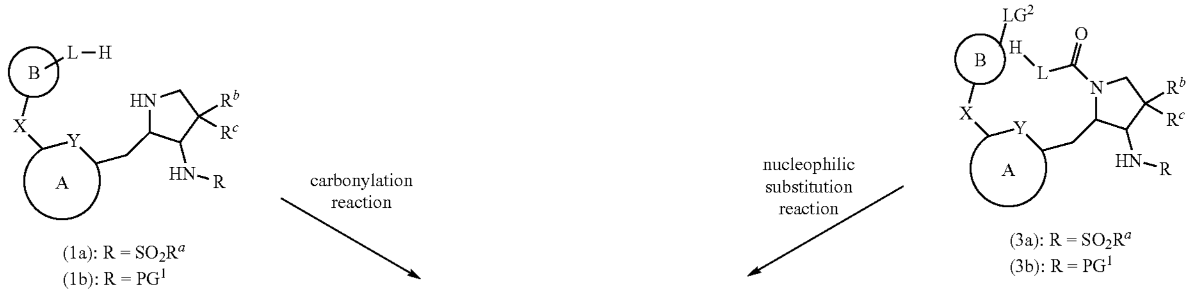

(1a): R = $SO_2R^a$
(1b): R = $PG^1$ (3a): R = $SO_2R^a$
(3b): R = $PG^1$

-continued

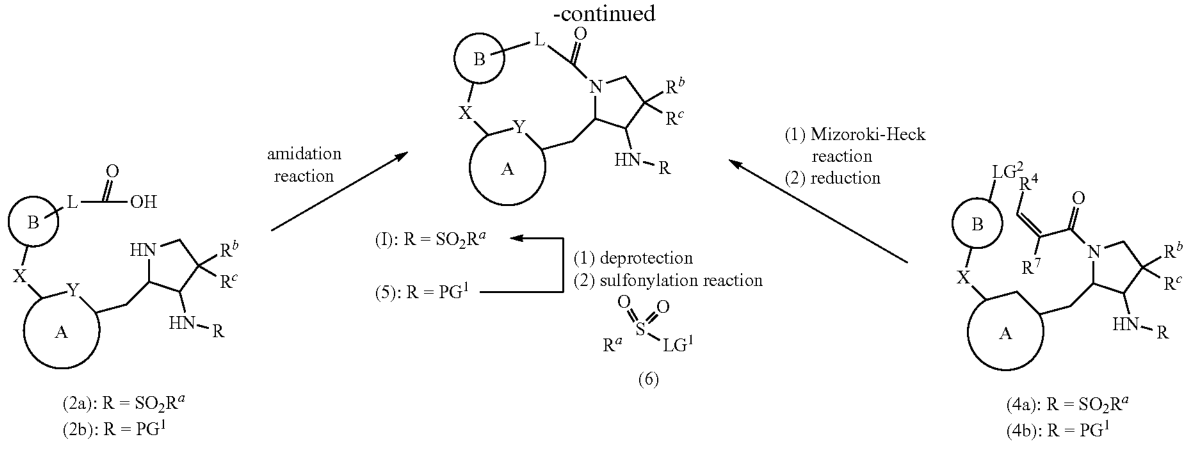

Compound (I) can be produced by subjecting compound (1a) to a carbonylation reaction.

Compound (I) can be produced by subjecting compound (2a) to a amidation reaction.

Compound (I) can be produced by subjecting compound (3a) to a nucleophilic substitution reaction.

Compound (I) can be produced by subjecting compound (4a) to a Mizoroki-Heck reaction followed by reduction. Examples of the metal catalyst to be used for Mizoroki-Heck reaction include palladium compounds such as palladium(II) acetate and the like. A phosphine ligand can be also added to the reaction system, and examples thereof include triphenylphosphine and the like. In addition, a base can be added to the reaction system, and examples thereof include inorganic bases and organic bases and the like.

Compound (5) can be produced by subjecting compound (1a) to a carbonylation reaction.

Compound (5) can be produced by subjecting compound (2a) to a amidation reaction.

Compound (5) can be produced by subjecting compound (3a) to a nucleophilic substitution reaction.

Compound (5) can be produced by subjecting compound (4a) to a Mizoroki-Heck reaction followed by reduction.

Compound (I) can be produced by subjecting compound (5) to a deprotection followed by sulfonylation reaction with compound (6). Compound (6) may be commercially easily available or can be produced according to a method known per se.

Compound (1a) and (1b) can be produced from compound (7a) and (7b) according to the method shown in the following Scheme 2, respectively. In the formulas, $R^r$ is cyano or —$COOR^s$, $R^s$ is an optionally substituted $C_{1-6}$ alkyl group, $M^1$ is a metal, and the other symbols are as defined above.

Scheme 2
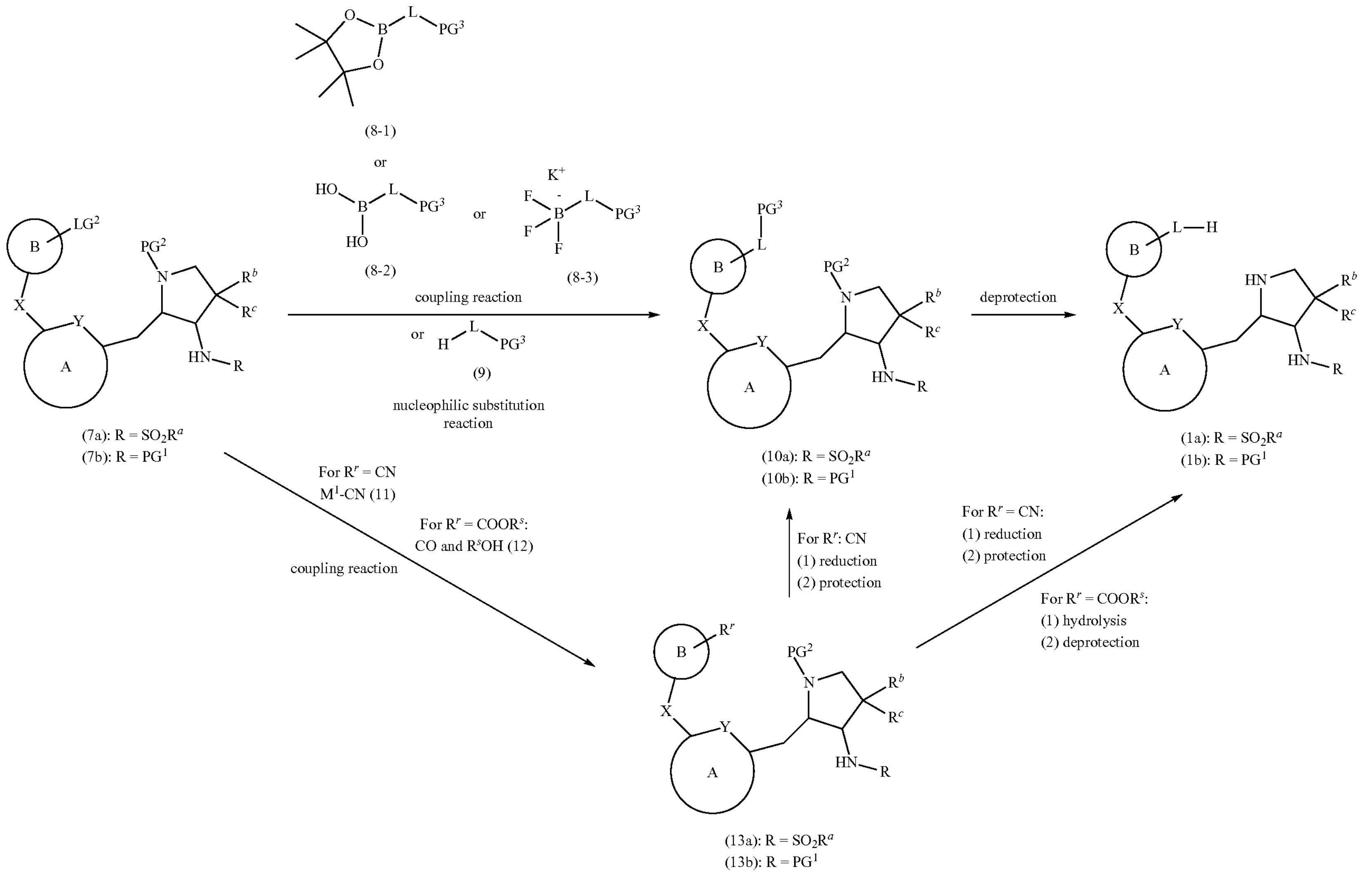

Compound (10a) and (10b) can be produced by subjecting compound (7a) and (7b) to a coupling reaction with compound (8-1), respectively. Compound (10a) and (10b) can be produced by subjecting compound (7a) and (7b) to a coupling reaction with compound (8-2), respectively. In addition, compound (10a) and (10b) can be produced by subjecting compound (7a) and (7b) to a coupling reaction with compound (8-3), respectively. Compound (10a) and (10b) can be also produced by subjecting compound (7a) and (7b) to a nucleophilic substitution reaction with compound (9), respectively.

When $R^r$ is cyano, compound (13a) and (13b) can be produced by subjecting compound (7a) and (7b) to a coupling reaction with compound (11). Examples of compound (11) to be used include zinccyanide and the like. Examples of the metal catalyst to be used include tetrakis(triphenylphosphine)palladium(0) and the like.

When $R^r$ is —$COOR^s$, compound (13a) and (13b) can also be also produced by subjecting compound (7a) and (7b) to a coupling reaction with carbon monoxide and compound (12). Examples of the metal catalyst to be used include [1,1'-bis(diphenylphosphino) ferrocene]palladium(II) dichloride and the like.

When $R^r$ is cyano, compound (10a) and (10b) can be produced by subjecting compound (13a) and (13b) to a reduction followed by protection, respectively.

Compound (1a) and (1b) can be produced by subjecting compound (10a) and (10b) to a deprotection, respectively.

When $R^r$ is cyano, compound (1a) and (1b) can be produced by subjecting compound (13a) and (13b) to a reduction followed by deprotection, respectively. When $R^r$ is —$COOR^s$, compound (1a) and (1b) can be produced by subjecting compound (13a) and (13b) to a hydrolysis followed by deprotection, respectively.

Compound (2a) and (2b) can be produced from compound (7a) and (7b) according to the method shown in the following Scheme 3, respectively. In the formulas, $R^t$ is an optionally substituted $C_{1-6}$ alkyl group, and the other symbols are as defined above.

Scheme 3

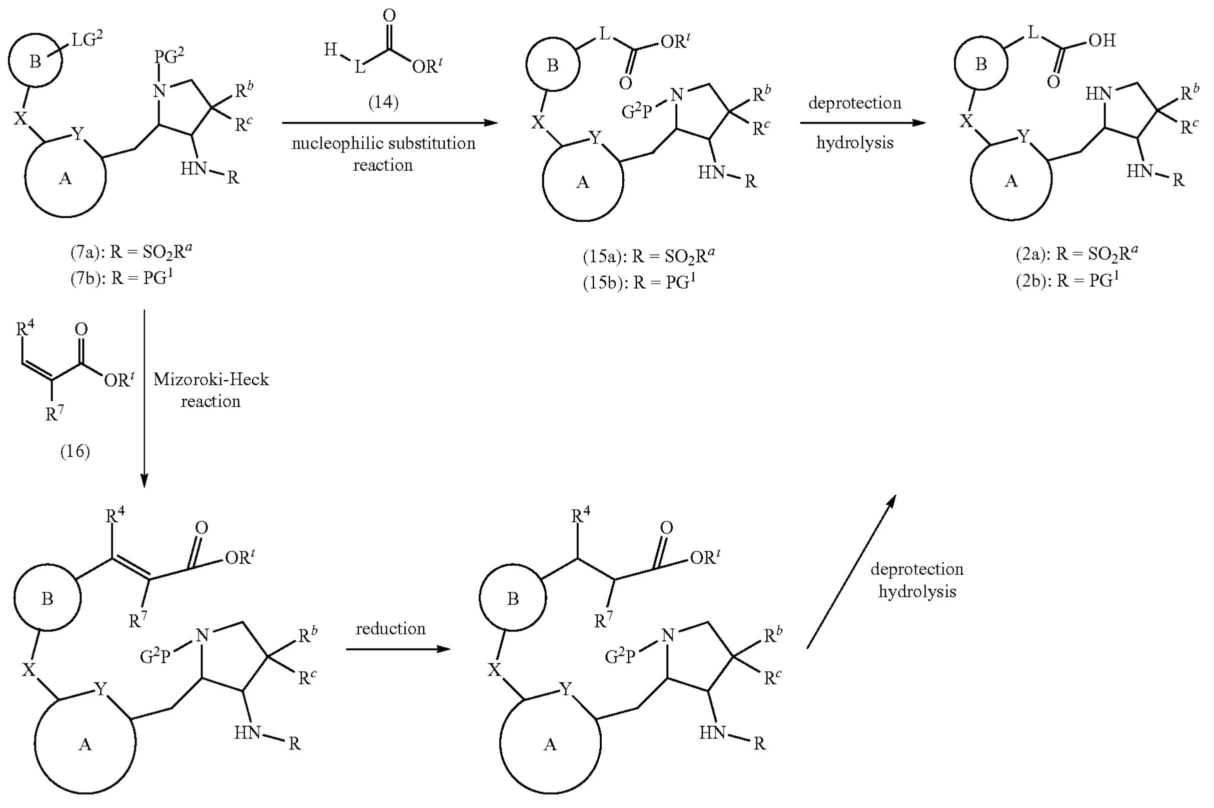

(7a): R = $SO_2R^a$
(7b): R = $PG^1$ (15a): R = $SO_2R^a$
(15b): R = $PG^1$ (2a): R = $SO_2R^a$
(2b): R = $PG^1$ (17a): R = $SO_2R^a$
(17b): R = $PG^1$ (18a): R = $SO_2R^a$
(18b): R = $PG^1$

Compound (15a) and (15b) can be produced by subjecting compound (7a) and (7b) to a nucleophilic substitution reaction with compound (14), respectively.

Compound (17a) and (17b) can be produced by subjecting compound (7a) and (7b) to a Mizoroki-Heck reaction with compound (16), respectively.

Compound (18a) and (18b) can be produced by subjecting compound (17a) and (17b) to a reduction, respectively.

Compound (2a) and (2b) can be produced by subjecting compound (15a) and (15b) to a deprotection followed by hydrolysis, respectively. Compound (2a) and (2b) can be also produced by subjecting compound (18a) and (18b) to a deprotection followed by hydrolysis, respectively.

Compound (3a) and (3b) can be produced from compound (7a) and (7b) according to the method shown in the following Scheme 4, respectively.

Scheme 4

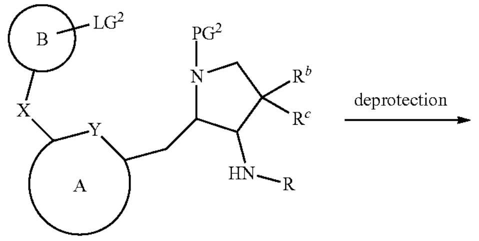

(7a): R = $SO_2R^a$
(7b): R = $PG^1$

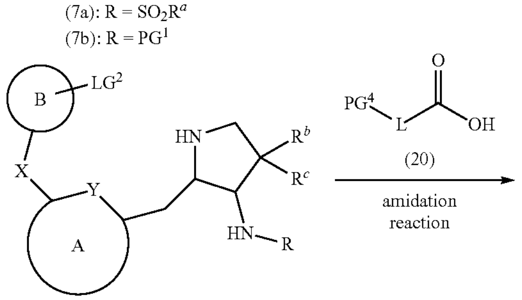

(19a): R = $SO_2R^a$
(19b): R = $PG^1$

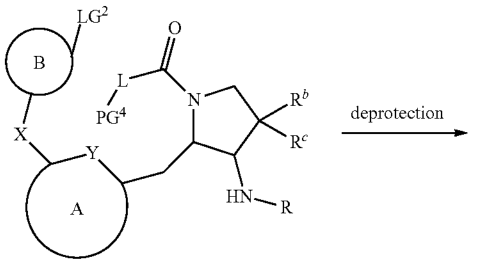

(21a): R = $SO_2R^a$
(21b): R = $PG^1$

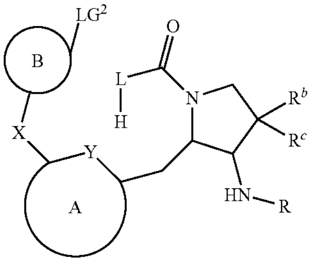

(3a): R = $SO_2R^a$
(3b): R = $PG^1$

Compound (19a) and (19b) can be produced by subjecting compound (7a) and (7b) to a deprotection, respectively.

Compound (21a) and (21b) can be produced by subjecting compound (19a) and (19b) to a amidation reaction with compound (20), respectively.

Compound (3a) and (3b) can be produced by subjecting compound (21a) and (21b) to a deprotection, respectively.

Compound (4a) and (4b) can be produced from compound (19a) and (19b) according to the method shown in the following Scheme 5, respectively.

Scheme 5

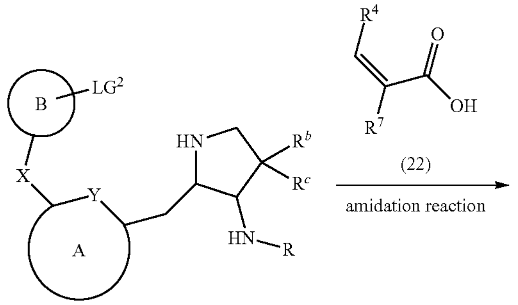

(19a): R = $SO_2R^a$
(19b): R = $PG^1$

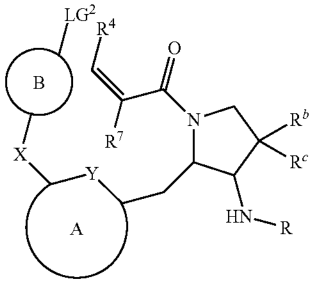

(4a): R = $SO_2R^a$
(4b): R = $PG^1$

Compound (4a) and (4b) can be produced by subjecting compound (19a) and (19b) to an amidation reaction with compound (22), respectively.

Compound (7aa), (7ba), (13aa), and (13ba) can be produced from compound (23a) and (23b) according to the method shown in the following Scheme 6. In the formulas, $X^a$ is —O—, —S—, —$NR^1$—, —($CR^2R^3$)—O—, Ru is $R^r$ and $LG^2$, and the other symbols are as defined above.

Scheme 6

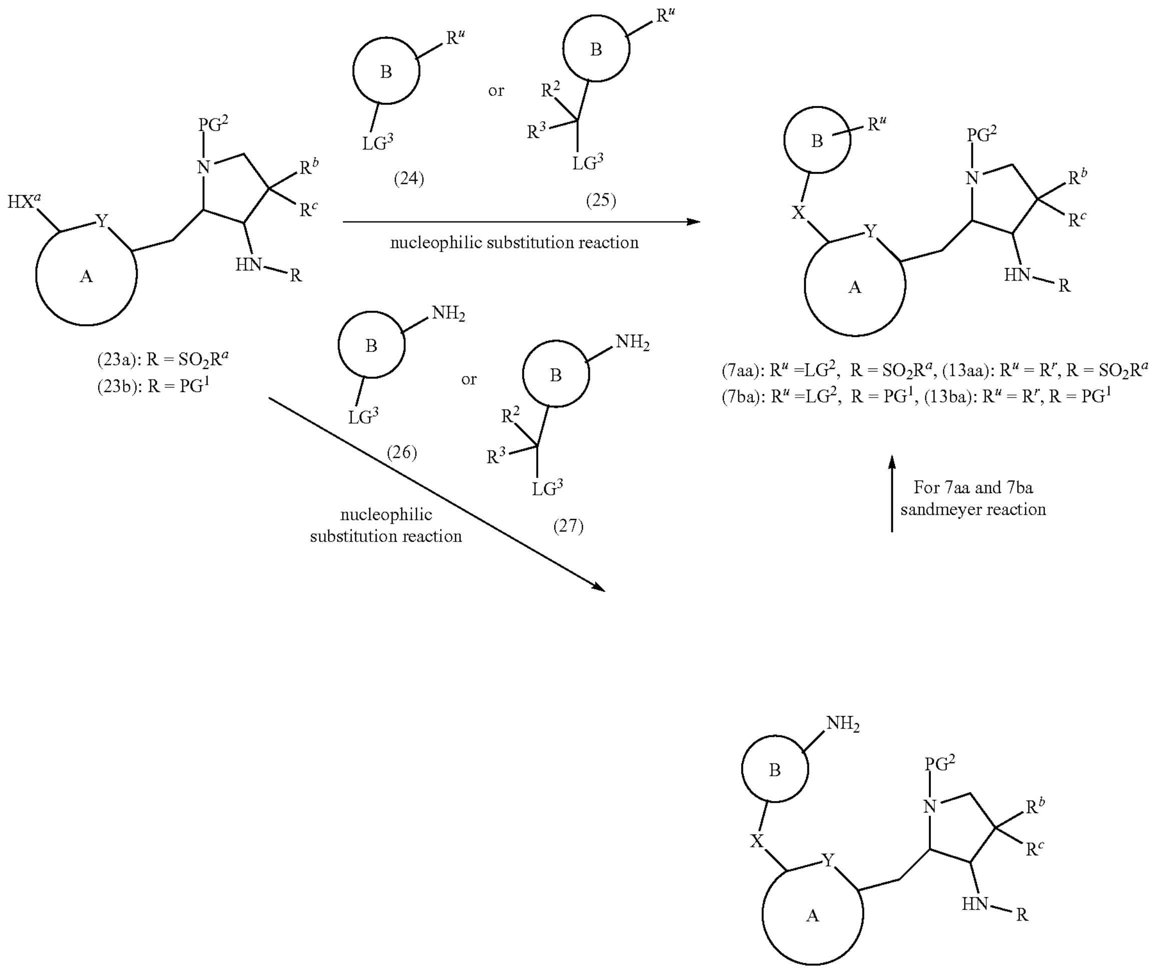

(24)

(25)

(23a): R = $SO_2R^a$
(23b): R = $PG^1$ (7aa): $R^u$ = $LG^2$, R = $SO_2R^a$, (13aa): $R^u$ = $R^r$, R = $SO_2R^a$
(7ba): $R^u$ = $LG^2$, R = $PG^1$, (13ba): $R^u$ = $R^r$, R = $PG^1$ (26)

(27)

(28a): R = $SO_2R^a$
(28b): R = $PG^1$

Compound (7aa), (7ba), (13aa), and (13ba) can be produced by subjecting compound (23a) and (23b) to a nucleophilic substitution reaction with compound (24). When $X^a$ is —O—, compound (7aa), (7ba), (13aa), and (13ba) can be also produced by subjecting compound (23a) and (23b) to a nucleophilic substitution reaction with compound (25).

Compound (28a) and (28b) can be produced by subjecting compound (23a) and (23b) to a nucleophilic substitution reaction with compound (26). When $X^a$ is —O—, compound (28a) and (28b) can be also produced by subjecting compound (23a) and (23b) to a nucleophilic substitution reaction with compound (27).

Compound (7aa) and (7ba) can be produced by subjecting compound (28a) and (28b) to a sandmeyer reaction. Sandmeyer rection is carried out according to a method known per se, for example, the method described in Organic Name Reactions, the Reaction Mechanism and Essence, Revised Edition (Hideo Togo, Kodansha); Strategic Applications of Named Reactions in Organic Synthesis (translated by Kiyoshi Tomioka, Kagakudojin) or the like, or the method described in Examples.

Compound (13ab), (13bb), (15ab), and (15bb) can be produced from compound (29a) and (29b) according to the method shown in the following Scheme 7. In the formulas, $X^b$ is —$CR^2R^3$— and optionally substituted $C_{3-4}$ cycloalkyl group, $R^v$ is $R^r$ and -L-$COOR^t$, and the other symbols are as defined above.

Scheme 7

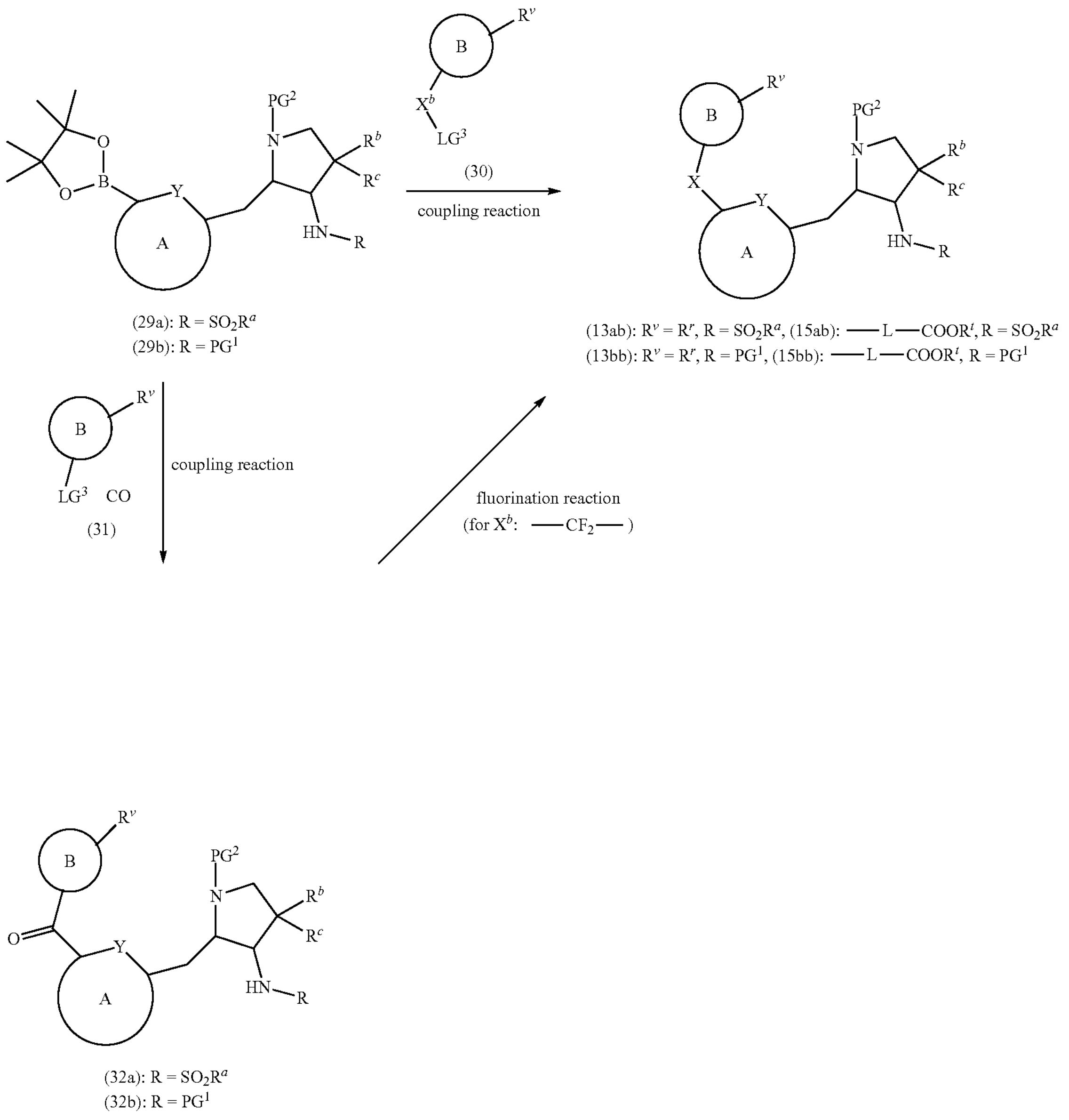

(29a): R = $SO_2R^a$
(29b): R = $PG^1$ (13ab): $R^v = R^r$, R = $SO_2R^a$, (15ab): $-L-COOR^t$, R = $SO_2R^a$
(13bb): $R^v = R^r$, R = $PG^1$, (15bb): $-L-COOR^t$, R = $PG^1$ (32a): R = $SO_2R^a$
(32b): R = $PG^1$

Compound (13ab), (13bb), (15ab), and (15bb) can be produced by subjecting compound (29a) and (29b) to a coupling reaction with compound (30).

Compound (32a) and (32b) can be produced by subjecting compound (29a) and (29b) to a coupling reaction with carbon monoxide and compound (31).

Compound (13ab), (13bb), (15ab), and (15bb) can be produced by subjecting compound (32a) and (32b) to a fluorination reaction. Examples of the fluorination reagent to be used include (diethylamino) sulfur trifluoride, bis(2-methoxyethyl)aminosulfur trifluoride and the like.

Compound (23aa), (23ba), (23ab), and (23bb) can be produced from compound (33) according to the method shown in the following Scheme 8. In the formulas, $R^w$ is an optionally substituted $C_{1-6}$ alkyl group, $M^2$ is a metal, and the other symbols are as defined above.

Scheme 8
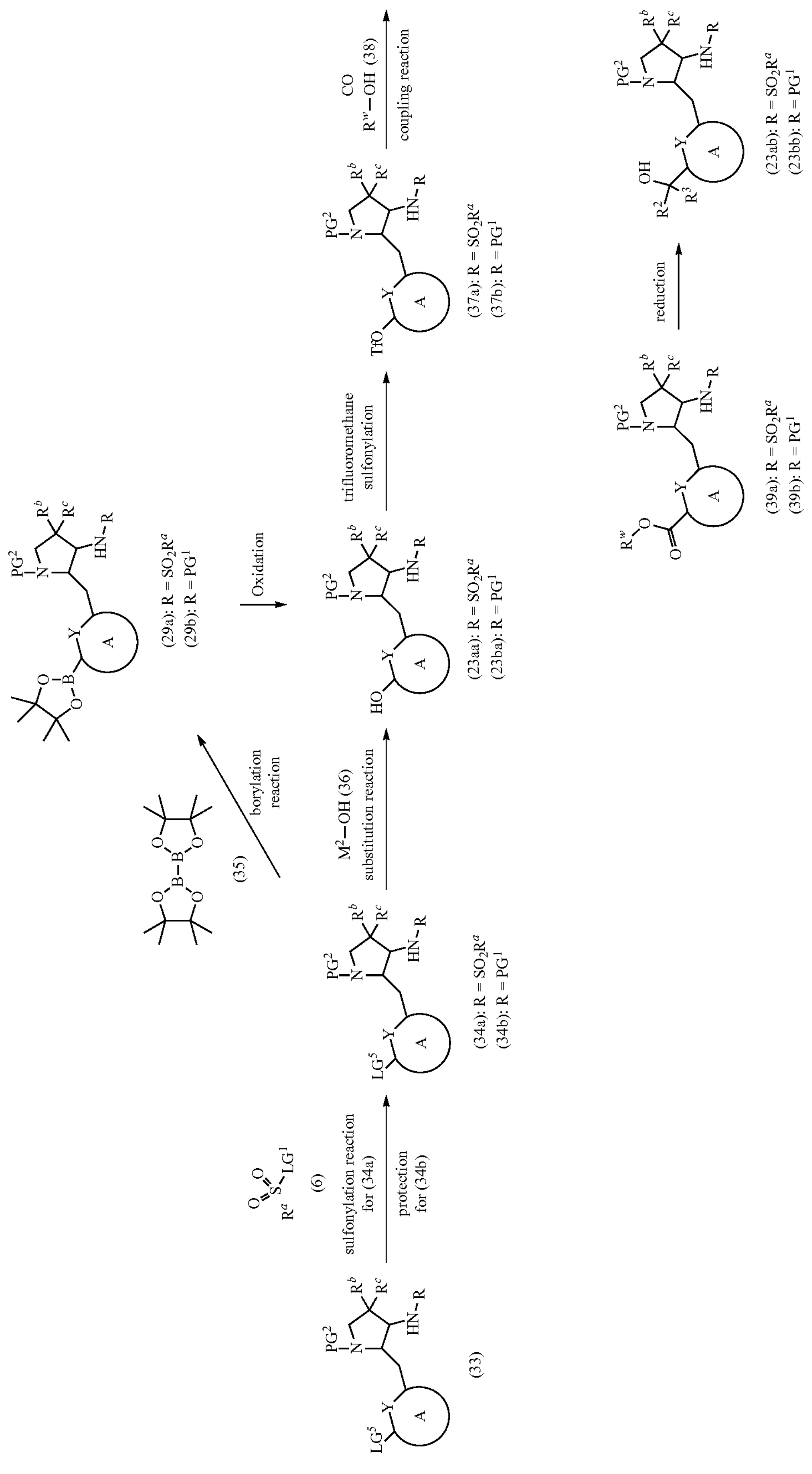
(33)
(34a): R = $SO_2R^a$
(34b): R = $PG^1$
(29a): R = $SO_2R^a$
(29b): R = $PG^1$
(23aa): R = $SO_2R^a$
(23ba): R = $PG^1$
(37a): R = $SO_2R^a$
(37b): R = $PG^1$
(39a): R = $SO_2R^a$
(39b): R = $PG^1$
(23ab): R = $SO_2R^a$
(23bb): R = $PG^1$ Compound (33) can be produced according to a method known per se, for example, the method described in "WO2020158958", "WO2019027058", or the method described in Examples.

Compound (34a) can be produced by subjecting compound (33) to a sulfonylation reaction with compound (6).

Compound (34b) can be produced by subjecting compound (33) to a protection.

Compound (29a) and (29b) can be produced by subjecting compound (34a) and (34b) to a borylation reaction with compound (35). Examples of the metal catalyst to be used include [1,1'-bis(diphenylphosphino) ferrocene]palladium (II) dichloride and the like. In addition, a base can be added to the reaction system, and examples thereof include inorganic bases and organic bases and the like.

Compound (23aa) and (23ba) can be produced by subjecting compound (34a) and (34b) to a substitution reaction with compound (36). Examples of compound (36) to be used include potassium hydroxide and the like. Examples of the metal catalyst to be used include tris(dibenzylideneacetone) dipalladium(0) and the like. Examples of the phosphine ligand to be used include 2-di-tert-butylphosphino-2',4',6'-triisopropylbiphenyl and the like.

Compound (23aa) and (23ba) can be produced by subjecting compound (29a) and (29b) to a oxidation reaction. Examples of the oxidation reagent to be used include sodium peroxoborate tetrahydrate, perboric acid sodium salt tetrahydrate and the like.

Compound (37a) and (37b) can be produced by subjecting compound (23aa) and (23ba) to a trifluoromethanesulfonylation. Examples of the trifluoromethanesulfonylation reagent to be used include trifluoromethanesulfonic anhydride and the like.

Compound (39a) and (39b) can be produced by subjecting compound (37a) and (37b) to a coupling reaction with carbon monoxide and compound (38).

Compound (23ab) and (23bb) can be produced by subjecting compound (39a) and (39b) to a reduction.

In the thus-obtained compound (I), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production method, when a starting compound has an amino group, a carboxyl group, a hydroxy group, a carbonyl group or a mercapto group as a substituent, a protecting group generally used in the peptide chemistry may be introduced into these groups, and the object compound can be obtained by removing the protecting group as necessary after the reaction.

Compound (I) obtained by the above-mentioned production method can be isolated and purified by a known means, such as solvent extraction, liquid conversion, phase transfer, crystallization, recrystallization, chromatography and the like.

When compound (I) contains optical isomer, stereoisomer, regio isomer, conformational isomer, and rotamer, these compounds are also included in compound (I), and each can be obtained as a single product by a synthesis method or a separation method known per se. For example, when an optical isomer exists in compound (I), an optical isomer resolved from the compound is also encompassed in compound (I).

Here, an optical isomer can be produced by a method known per se.

Compound (I) may be a crystal.

A crystal of compound (I) (hereinafter sometimes to be abbreviated as the crystal of the present invention) can be produced by crystallizing compound (I), by applying a crystallization method known per se.

In the present specification, the melting point means a melting point measured, for example, by micro melting point apparatus (Yanako, MP-500D or Buchi, B-545), DSC (differential scanning calorimetry analysis) apparatus (METTLER TOLEDO, DSC1) and the like.

Generally, the melting point sometimes varies depending on the measurement device, measurement condition and the like. The crystal in the present specification may be a crystal showing a melting point different from the values described in the present specification as long as the difference is within a general error range.

The crystal of the present invention is superior in the physicochemical properties (e.g., melting point, solubility, stability) and biological properties (e.g., pharmacokinetics (absorbability, distribution, metabolism, excretion), efficacy expression), and is extremely useful as a medicament.

Compound (I) may be used as a prodrug. A prodrug of the compound (I) means a compound which is converted to the compound (I) of the present invention with a reaction due to an enzyme, an gastric acid, etc. under the physiological condition in the living body, that is, a compound which is converted to the compound (I) of the present invention with oxidation, reduction, hydrolysis, etc. according to an enzyme; a compound which is converted to the compound (I) of the present invention by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.);

a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.);

a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl) methyl esterification, cyclohexyloxycarbonylethyl esterification and methylamidation, etc.)

and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, a prodrug may form a salt, and as such salt, those exemplified as a salt of the compound represented by the above-mentioned formula (I) can be mentioned.

Compound (I) may be labeled with an isotope (e.g., $^{3}H$, $^{13}C$, $^{14}C$, $^{18}F$, $^{35}S$, $^{125}I$) and the like.

Compound (I) labeled with or substituted by an isotope can be used, for example, as a tracer used for Positron Emission Tomography (PET) (PET tracer), and is useful in the field of medical diagnosis and the like.

Furthermore, compound (I) may be a hydrate or a non-hydrate, or a non-solvate (e.g., anhydride), or a solvate (e.g., hydrate).

Compound (I) also encompasses a deuterium conversion form wherein 1H is converted to 2H (D).

Furthermore, compound (I) may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization method known per se.

Compound (I) or a prodrug thereof (hereinafter sometimes to be simply abbreviated as the compound of the present invention) can be used as it is or in the form of a pharmaceutical composition (also referred to as a medicament) by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the above-mentioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the above-mentioned pharmaceutical composition include oral preparations such as tablet (including sugar-coated tablet, film-coated tablet, sublingual tablet, orally disintegrating tablet, buccal tablet), capsule (including soft capsule, microcapsule), pill, granule, powder, troche, syrup, liquid, emulsion, suspension, aerosol, films (e.g., orally disintegrable films, oral mucosa-adhesive film) and the like; and parenteral agents such as injection (e.g., subcutaneous injection, intravenous injection, intramuscular injection, intraperitoneal injection, drip infusion), external preparation (e.g., transdermal absorption type preparation, ointment, lotion, adhesive preparation), suppository (e.g., rectal suppository, vaginal suppository), pellet, nasal preparation, pulmonary preparation (inhalant), eye drop and the like. The compound and medicament of the present invention can be respectively safely administered orally or parenterally (e.g., intrarectal, intravenous, intraarterial, intramuscular, subcutaneous, intraorgan, intranasal, intradermal, instillation, intracerebral, intravaginal, intraperitoneal, intratumoral, proximal tumor administrations, and administration to the lesion).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, and the precipitated calcium carbonate, gelatin, gum arabic, pullulan, carnauba wax and the like may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D-55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, red ferric oxide and the like may also be used during coating.

Since the compound of the present invention shows low toxicity (e.g., acute toxicity, chronic toxicity, genetic toxicity, reproductive toxicity, cardiotoxicity, carcinogenicity) and less side effects, it can be used as a prophylactic or therapeutic agent, or diagnostic agent for various diseases in mammals (e.g., human, bovine, horse, dog, cat, monkey, mouse, rat).

Moreover, the compound of the present invention is expected to be superior in central migration.

The compound of the present invention has an excellent an orexin type 2 receptor agonist activity, and may treat, prevent or ameliorate the risk of various neurological and psychiatric diseases associated with an orexin type 2 receptor. The compound of the present invention is useful as an agent for the prophylaxis or treatment of various diseases such as narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Kleine Levin syndrome, major depression with hypersomnia, Lewy body dementia, Parkinson's disease, progressive supranuclear paralysis, Prader-Willi syndrome, Moebius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalitis, limbic encephalitis, Hashimoto's encephalopathy), coma, loss of consciousness, obesity (e.g., malignant mastocytosis, exogenous obesity, hyperinsulinar obesity, hyperplasmic obesity, hypop hyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), insulin resistance syndrome, Alzheimer's disease, disturbance of consciousness such as coma and the like, side effects and complications due to anesthesia, sleep disturbance, sleep problem, insomnia, Intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, sudden death, polycysticovarian disease, craniopharingioma, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity such as lowering the risk of left ventricular hypertrophy, migraine pain, headache, neuropathic pain, Parkinson's disease, psychosis, schizophrenia, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, posttraumatic stress disorder, separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's disease, amyotrophic lateral sclerosis, multiple sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury (TBI).

Particularly, the compound of the present invention is useful as an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer's disease, obesity, insulin resistance syndrome, cardiac failure, diseases related to bone loss, sepsis, disturbance of consciousness such as coma and the like, side effects and complications due to anesthesia, and the like, or anesthetic antagonist.

In some aspects, the compound of the present invention is useful as an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia, Alzheimer's disease, obesity, insulin resistance syndrome, cardiac failure, diseases related to bone loss, sepsis, disturbance of consciousness, side effects and complications due to anesthesia.

In some aspects, the compound of the present invention is useful as an agent for the prophylaxis or treatment of narcolepsy, idiopathic hypersomnia, hypersomnia, or sleep apnea syndrome.

In some aspects, the compound of the present invention is useful as an agent for the prophylaxis or treatment of narcolepsy.

Central disorders of hypersomnolence (CDH) are characterized by excessive daytime sleepiness in the absence of other sleep disorders but with the setting of adequate and regular sleep habits. Central disorders of hypersomnolence (CDH) include narcolepsy type 1, narcolepsy type 2 and idiopathic hypersomnia. Kleine-Levin syndrome as well as insufficient sleep syndrome and hypersomnia caused by a medical condition, medication or substance, or psychiatric condition are also considered central orders of hypersomnolence. Evaluation of central disorders of hypersomnolence (CDH) includes sleep testing in the sleep lab (polysomnography, PSG) followed by a multiple sleep latency test (MSLT).

Symptoms that are associated with narcolepsy involve abnormal intrusions of REM sleep features into wake: for example, sleep-related hallucinations, sleep paralysis, or vivid dreams and dream-reality confusion. These symptoms can also occur in people without a sleep disorder.

Some patients with narcolepsy also experience cataplexy (narcolepsy, type 1) which is loss of muscle tone triggered by emotion, typically laughter or anticipation. Cataplexy can be generalized or partial and isn't associated with any loss of consciousness. This muscle weakness typically improves within seconds to minutes.

Patients with idiopathic hypersomnia (IDH) often describe excessive daytime sleepiness, prolonged sleep duration (more than 10-11 hours of sleep nightly), and severe difficulty waking up in the morning (sleep inertia). In contrast to narcolepsy, patients with IDH often describe long, unrefreshing daytime naps. Another common symptom of IDH is "brain fog," a feeling of cognitive clouding during the day. Klein-Levin syndrome is a rare disorder of cyclic hypersomnia.

An aspect of the disclosure is a method for treating a subject having one or more central disorders of hypersomnolence (CDH), the method comprising administering to the subject a compound of the present invention.

Another aspect of the disclosure is the use of a compound of the present invention for the manufacture of an agent for treating one or more central disorders of hypersomnolence (CDH) in a subject.

Another aspect of the disclosure is a compound of the present invention for use in treating one or more central disorders of hypersomnolence (CDH) in a subject.

Another aspect is a method or use of the previous aspects, wherein the subject is narcoleptic. In one aspect, the subject has been diagnosed with narcolepsy type 1. In another aspect, the subject has been diagnosed with narcolepsy type 2. In still another aspect, the subject has been diagnosed with idiopathic hypersomnia.

Another aspect is a method or use of the previous aspects, wherein administering the compound of the invention reduces daytime sleepiness, reduces instances of loss of muscle control, and/or reduces instances of interrupted sleep in the subject.

Another aspect is a method or use wherein a compound of the present invention is administered in an amount effective to reduce excessive daytime sleepiness in adults with narcolepsy.

Another aspect is a method or use wherein a compound of the present invention is administered in an amount effective to increase in mean sleep latency.

Another aspect is a method or use wherein a compound of the present invention is administered in an amount effective to reduce cataplexy events.

Another aspect is a method or use wherein a compound of the present invention is administered in an amount effective to decrease disrupted nocturnal sleep in the subject.

While the dose of the compound of the present invention varies depending on the subject of administration, administration route, target disease, symptom and the like, for example, when the compound of the present invention is administered orally or parenterally to an adult patient, its dose is for example, about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other drugs (hereinafter to be abbreviated as concomitant drug).

By combining the compound of the present invention and a concomitant drug, a superior effect, for example, (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof, or the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the preparation.

Similar contents may be employed even when the compound of the present invention and a concomitant drug are separately formulated into preparations.

Examples of the concomitant drug include the followings. A therapeutic drug for narcolepsy (e.g., methylphenidate, amphetamine, pemoline, phenelzine, protriptyline, sodium oxybate, modafinil, caffeine), antiobesity drug (amphetamine, benzfetamine, bromocriptine, bupropion, diethylpropion, exenatide, fenfluramine, liothyronine, liraglutide, mazindol, methamphetamine, octreotide, octreotide, orlistat, phendimetrazine, phendimetrazine, phenmetrazine, phentermine, Qnexa (registered trade mark), phenylpropanolamine, pramlintide, propylhexedrine, recombinant leptin, sibutramine, topiramate, zimelidine, zonisamide, Lorcaserin, metformin), acetylcholine esterase inhibitor (e.g., donepezil, rivastigmine, galanthamine, zanapezil, idebenone, tacrine), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N, N-dimethylamino)ethyl]tetralin, 6-(4-biphenylyl)methoxy-2-(N, N-dimethylamino)methyltetralin, 6-(4-biphenylyl)methoxy-2-(N, N-dipropylamino)methyltetralin, 2-(N, N-dimethylamino)methyl-6-(4'-methoxybiphenyl-4-yl)methoxytetralin, 6-(4-biphenylyl)methoxy-2-[2-(N, N-diethylamino)ethyl]tetralin, 2-[2-(N, N-dimethylamino)ethyl]-6-(4'-methylbiphenyl-4-yl)methoxytetralin, 2-[2-(N, N-dimethylamino)ethyl]-6-(4'-methoxybiphenyl-4-yl)methoxytetralin, 6-(2',4'-dimethoxybiphenyl-4-yl)methoxy-2-[2-(N, N-dimethylamino)ethyl]tetralin, 6-[4-(1,3-benzodioxol-5-yl)phenyl]methoxy-2-[2-(N, N-dimethylamino)ethyl]tetralin, 6-(3',4'-dimethoxybiphenyl-4-yl)methoxy-2-[2-(N, N-dimethylamino)ethyl]tetralin, an optically active form thereof, a salt thereof and a hydrate thereof, OM99-2 (WO01/00663)), Y secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation-regenerate promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl] isoindoline, 5,6-dimethoxy-2-[3-(4-isopropylphenyl)-2,2,4,6,7-pentamethyl-2,3-dihydro-1-benzofuran-5-yl] isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anticytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil (citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-$HT_{1A}$ agonist, (buspirone hydrochloride, tandospirone citrate, osemozotan hydrochloride etc.), 5-$HT_{2A}$ antagonist, 5-$HT_{2A}$ inverse agonist, 5-$HT_3$ antagonist (cyamemazine etc.), heart non-selective β inhibitor (propranolol hydrochloride, oxprenolol hydrochloride etc.), histamine H1 antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent and the like.

Two or more kinds of the above-mentioned concomitant drug may be used in a mixture at an appropriate ratio.

When the compound of the present invention is applied to each of the above-mentioned diseases, it can also be used in combination with biologics (e.g., antibody drug, nucleic acid or nucleic acid derivative, aptamer drug, vaccine preparation), or can be used in combination with a gene therapy method and the like, or can also be used in combination with a treatment in psychiatric field without using drugs.

Examples of the antibody drug and vaccine preparation include vaccine preparation against angiotensin II, vaccine preparation against CETP, CETP antibody, antibody against TNFα antibody and other cytokines, amyloid B vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to an enzyme or protein involved in blood lipid metabolism (e.g., a gene relating to metabolism, excretion and absorption of cholesterol or triglyceride or HDL-cholesterol or blood phospholipid), a treatment method using a gene relating to an enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

EXAMPLES

The present invention is described in further detail in Examples, Test Examples, and Formulation Examples below. However, the present invention is not intended to be limited by them, and various changes or modifications may be made therein without departing from the scope of the present invention.

In Examples below, the term "room temperature" usually means approximately 10° C. to approximately 35° C. A ratio used for a mixed solvent represents a volume to volume ratio unless otherwise specified. Unless otherwise specified, "%" represents wt %.

Unless particularly specified, the elution in column chromatography in the Examples was performed under observation by TLC (thin layer chromatography). For TLC observation, 60 $F_{254}$ manufactured by Merck was used as a TLC plate, and the solvent used as an elution solvent for column chromatography was used as a developing solvent. For detection, a UV detector was employed. The term "NH" in silica gel column chromatography represents that an aminopropylsilane-functionalized silica gel was used. The term "Diol" means use of 3-(2,3-dihydroxypropoxy) propylsilane-functionalized silica gel. The term "C18" used in HPLC (high-performance liquid chromatography) represents that an octadecyl-functionalized silica gel was used. A ratio used for elution solvents represents a volume to volume ratio unless otherwise specified.

ACD/SpecManager (trade name) software or the like was used in the 1H NMR analysis. Very broad peaks for protons of hydroxy groups, amino groups, and the like are not always indicated. MS was measured by LC/MS. As an ionization method, ESI method or APCI method was used. The data indicates experimentally measured values (found). Generally, a molecular ion peak is observed, and a fragment ion peak is occasionally observed. In the case of a salt, a molecular ion peak or fragment ion peak of a free form is generally observed.

The units for sample concentration (c) in optical rotation ($[\alpha]_D$) measurements are in g/100 mL.

Elemental analysis values (Anal.) are shown as calculated values (Calcd) and experimentally measured values (Found).

The peak by powder X-ray diffraction in Examples means the peak measured using Cu Kα-ray as a source by Ultima IV (Rigaku Corporation, Japan) at room temperature. The measurement conditions are as follows.

Electric pressure/Electric current: 40 kV/50 mA
Scan speed: 6 degree/min
Scan range of 2 Theta: 2-35 degree The crystallinity by powder X-ray diffraction in Examples was calculated by Hermans method.

In Examples below, the following abbreviations are used:

mp: melting point
MS: mass spectrum
M: molar concentration, molarity
$CDCl_3$: deuterated chloroform
DMSO-$d_6$: deuterated dimethyl sulfoxide
$^1$H NMR: proton nuclear magnetic resonance
LC/MS: liquid chromatograph-mass spectrometer
ESI: electrospray ionization
APCI: atmospheric pressure chemical ionization
Et2O: diethyl ether
DIPEA: diisopropylethylamine
IPE: diisopropyl ether
CPME: cyclopentyl methyl ether
NMP: N-methyl-2-pyrrolidone
TFA: trifluoroacetic acid
THF: tetrahydrofuran
DMSO: dimethyl sulfoxide
DMA: N,N-dimethylacetamide
DME: 1,2-dimethoxyethane
DMF: N, N-dimethylformamide
Pd2 (dba)3: tris(dibenzylideneacetone)dipalladium(0)
TEA: triethylamine
MeOH: methanol
EtOH: ethanol
EtOAc: ethyl acetate
CH2Cl2: dichloromethane
PE: petroleum ether
MsCl: methansulfonyl chloride
CDI: 1,1'-carbonyldiimidazole
BOC2O: di-tert-butyl dicarbonate
PyBOP: benzotriazol-1-yloxytripyrrolidinophosphonium hexafluorophosphate
HATU: 1-[bis(dimethylamino)methylene]-1H-1, 2, 3-triazolo[4,5-b]pyridinium 3-oxide hexafluorophosphat
Pd(Ph3P) 4: tetrakis(triphenylphosphine)palladium(0)
Pd(OAc)2: palladium(II) acetate
Pd(dppf)Cl2·CH2Cl2: [1,1'-bis(diphenylphosphino) ferrocene]palladium(II) dichloride dichloromethane adduct
tBuXPhos: 2-di-tert-butylphosphino-2',4',6'-triisopropylbiphenyl
XPhos Pd G3: methanesulfonato (2-dicyclohexylphosphino-2',4',6'-tri-i-propyl-1,1'-biphenyl) (2'-amino-1,1'-biphenyl-2-yl) palladium(II)
SFC: supercritical fluid chromatography Example 1

N-[(15aS,16S)-7-Methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide A) tert-Butyl (2S,3S)-2-[(3-bromophenyl)methyl]-3-[(methanesulfonyl)amino]pyrrolidine-1-carboxylate To a solution of tert-butyl (2S,3S)-3-amino-2-[(3-bromophenyl)methyl]pyrrolidine-1-carboxylate (5.00 g) in CH2Cl2 (50 mL) was added TEA (4.27 g). The mixture was stirred at 20° C. for 30 minutes. Then MsCl (1.44 g) was added to the mixture at 0° C. slowly. The mixture was stirred at 20° C. under nitrogen atmosphere for 2 hours. The reaction was quenched with water (50 mL) and stirred for 10 min. Then it was extracted with CH2Cl2 and washed with brine. The organic layer was dried over anhydrous sodium sulfate, filtered and concentrated under reduced pressure. The residue was purified by silica gel column chromatography (CH2Cl2/MeOH) to obtain the title compound (5.05 g).

$^1$H NMR (400 MHZ, DMSO-$d_6$) δ 1.05 (9H, s), 1.20-1.35 (2H, m), 1.82-1.92 (1H, m), 2.07-2.15 (1H, m), 2.30-2.40 (1H, m), 2.84-2.91 (2H, m), 2.94 (3H, s), 3.80-3.90 (1H, m), 7.14-7.18 (1H, m), 7.20-7.25 (1H, m), 7.35-7.40 (2H, m), 7.50-7.56 (1H, m).

B) tert-Butyl (2S,3S)-3-[(methanesulfonyl)amino]-2-{[3-(4,4,5,5-tetramethyl-1,3,2-dioxaborolan-2-yl)phenyl]methyl}pyrrolidine-1-carboxylate To a mixture of tert-butyl (2S,3S)-2-[(3-bromophenyl)methyl]-3-[(methanesulfonyl)amino]pyrrolidine-1-carboxylate (5.05 g) and bis(pinacolato)diboron (4.44 g) in toluene (50 mL) were added XPhos Pd G3 (493 mg) and potassium acetate (2.29 g). It was stirred at 100° C. for 2 hours under nitrogen atmosphere. The reaction mixture was poured into water and extracted with EtOAc. The organic layer was washed with brine, dried over anhydrous sodium sulfate and concentrated under reduced pressure to obtain the title compound (8.75 g).

MS: $[M-Boc+H]^+$ 381.0

C) tert-Butyl (2S,3S)-2-[(3-hydroxyphenyl)methyl]-3-[(methanesulfonyl)amino]pyrrolidine-1-carboxylate To a mixture of tert-butyl (2S,3S)-3-[(methanesulfonyl) amino]-2-{[3-(4,4,5,5-tetramethyl-1,3,2-dioxaborolan-2-yl) phenyl]methyl}pyrrolidine-1-carboxylate (5.60 g) in THF (50 mL) and water (50 mL) was added sodium peroxoborate tetrahydrate (4.48 g). It was stirred at 25° C. for 2 hours. The reaction mixture was poured into water and extracted with EtOAc. The organic layer was washed with brine, dried over anhydrous sodium sulfate and concentrated under reduced pressure. The residue was purified by silica gel column chromatography (CH2Cl2/MeOH) to obtain the title compound (3.50 g).

MS: $[M-Boc+H]^+$ 271.1

D) tert-Butyl (2S,3S)-2-({3-[(6-cyano-3-methylpyridin-2-yl)oxy]phenyl}methyl)-3-[(methanesulfonyl) amino]pyrrolidine-1-carboxylate To a solution of tert-butyl (2S,3S)-2-[(3-hydroxyphenyl) methyl]-3-[(methanesulfonyl)amino]pyrrolidine-1-carboxylate (2.00 g) in DMA (15 mL) was added 6-chloro-5-methylpicolinonitrile (906 mg) and cesium carbonate (2.64 g). The mixture was stirred at 80° C. under nitrogen atmosphere for 12 hours. The reaction mixture was diluted with water and extracted with EtOAc. The organic layer was washed with brine and dried by anhydrous sodium sulfate, filtered and concentrated. The residue was purified by silica gel column chromatography (EtOAc/PE) to obtain the title compound (759 mg).

$^1H$ NMR (400 MHZ, DMSO-$d_6$) δ 1.08-1.33 (9H, m), 1.80-1.91 (1H, m), 2.00-2.13 (1H, m), 2.37 (3H, s), 2.87 (3H, s), 3.12-3.30 (4H, m), 3.80-3.92 (1H, m), 4.02-4.11 (1H, m), 6.92-7.21 (3H, m), 7.33 (1H, t, J=8.0 Hz), 7.41-7.55 (1H, m), 7.68 (1H, d, J=7.2 Hz), 7.90-7.97 (1H, m).

E) tert-Butyl (2S,3S)-2-[(3-{[6-(aminomethyl)-3-methylpyridin-2-yl]oxy}phenyl)methyl]-3-[(methanesulfonyl)amino]pyrrolidine-1-carboxylate To a solution of tert-butyl (2S,3S)-2-({3-[(6-cyano-3-methylpyridin-2-yl)oxy]phenyl}methyl)-3-[(methanesulfonyl)amino]pyrrolidine-1-carboxylate (759 mg) in MeOH (10 mL) was added nickel (II) chloride hexahydrate (371 mg). Then sodium borohydride (177 mg) was added to the mixture at 0° C. The mixture was stirred at 0° C. for 2 hours. The reaction was quenched by saturated ammonium chloride aqueous solution at 0° C. slowly, then extracted with EtOAc. The organic layer was washed with brine, dried over anhydrous sodium sulfate, filtered and concentrated. The residue was purified by silica gel column chromatography (CH2Cl2/MeOH containing 0.3% ammonium hydroxide) to obtain the title compound (371 mg).

MS: $[M+H]^+$ 491.2

F) N-{(2S,3S)-2-[(3-{[6-(Aminomethyl)-3-methylpyridin-2-yl]oxy}phenyl)methyl]pyrrolidin-3-yl}methanesulfonamide dihydrochloride tert-Butyl (2S,3S)-2-[(3-{[6-(aminomethyl)-3-methylpyridin-2-yl]oxy}phenyl)methyl]-3-[(methanesulfonyl) amino]pyrrolidine-1-carboxylate (371 mg) in 4 M hydrogen chloride in dioxane (5 mL) was stirred at 25° C. for 2 hours. The mixture was concentrated under vacuum to obtain the title compound (446 mg).

MS: $[M+H]^+$ 391.1

G) N-[(15aS,16S)-7-Methyl-1-oxo-2,3,15a,16,17,18-hexahydro-1H,15H-4,8-(azeno)-10,14 (metheno) pyrrolo[1,2-j][1,8,10]oxadiazacycloheptadecin-16-yl]methanesulfonamide To a solution of N-{(2S,3S)-2-[(3-{[6-(aminomethyl)-3-methylpyridin-2-yl]oxy}phenyl)methyl]pyrrolidin-3-yl}methanesulfonamide dihydrochloride (410 mg) in DMF (410 mL) were added CDI (158 mg) and DIPEA (686 mg). The reaction mixture was stirred at 25° C. under nitrogen atmosphere for 12 hours to the mixture A. In a similar manner to the synthesis of mixture A, the mixture B was obtained using N-{(2,3S)-2-[(3-{[6-(aminomethyl)-3-methylpyridin-2-yl]oxy}phenyl)methyl]pyrrolidin-3-yl}methanesulfonamide dihydrochloride (446 mg) in DMF (450 mL) were added CDI (172 mg) and DIPEA (746 mg). The mixture A and B were combined and concentrated under vacuum. The residue was purified by preparative HPLC (column: Boston Prime C18, mobile phase: 0.05% ammonium hydroxide aqueous solution/acetonitrile) to obtain the title compound (230 mg).

$^1H$ NMR (400 MHZ, DMSO-$d_6$) δ 1.71-1.85 (1H, m), 2.02-2.12 (1H, m), 2.26 (3H, s), 2.76-2.87 (3H, m), 3.01 (3H, s), 3.06-3.15 (1H, m), 3.75-3.86 (2H, m), 4.19-4.27 (1H, m), 4.43-4.53 (1H, m), 6.00 (1H, dd, J=9.6, 3.6 Hz), 6.86-6.92 (2H, m), 7.10-7.14 (1H, m), 7.17-7.25 (2H, m), 7.55-7.67 (2H, m).

Example 2

N-[(15aS,16R)-17,17-Difluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide A) tert-Butyl (2S,3R)-2-[(3-chlorophenyl)methyl]-4,4-difluoro-3-[(methanesulfonyl)amino]pyrrolidine-1-carboxylate To a solution of tert-butyl (2S,3R)-3-amino-2-[(3-chlorophenyl)methyl]-4,4-difluoropyrrolidine-1-carboxylate (1.00 g) in CH2Cl2 (15 mL) was added TEA (875 mg). The mixture was stirred at 20° C. for 30 minutes. Then MsCl (400 mg) was added to the mixture at 0° C. slowly. The mixture was stirred at 20° C. under nitrogen atmosphere for 2 hours. The reaction was quenched with water and stirred for 10 minutes. Then it was extracted with CH2Cl2 and washed with brine. The organic layer was dried by anhydrous sodium sulfate, filtered and concentrated under reduced pressure. The residue was purified by silica gel column chromatography (MeOH/CH2Cl2) to obtain the title compound (1.07 g).

$^1H$ NMR (400 MHZ, DMSO-$d_6$) δ 1.06 (9H, s), 2.90 (2H, dd, J=13.6, 4.4 Hz), 2.99 (3H, s), 3.75-3.85 (2H, m), 4.27-4.32 (1H, m), 4.47-4.56 (1H, m), 7.19 (1H, s), 7.20-7.40 (3H, m), 8.17 (1H, d, J=9.6 Hz).

B) tert-Butyl (2S,3R)-4,4-difluoro-3-[(methanesulfonyl)amino]-2-{[3-(4,4,5,5-tetramethyl-1,3,2-dioxaborolan-2-yl)phenyl]methyl}pyrrolidine-1-carboxylate To a solution of tert-butyl (2S,3R)-2-[(3-chlorophenyl) methyl]-4,4-difluoro-3-[(methanesulfonyl)amino]pyrrolidine-1-carboxylate (970 mg) in toluene (20 mL) was added bis(pinacolato)diboron (869 mg), XPhos Pd G3 (97 mg) and potassium acetate (448 mg). The reaction mixture was stirred at 100° C. under nitrogen atmosphere for 12 hours. The reaction mixture was diluted with water and extracted with EtOAc. The organic layer was washed with brine and dried by anhydrous sodium sulfate, filtered and concentrated to obtain the title compound (1.87 g).

MS: $[M+Na]^+$ 539.1

C) tert-Butyl (2S,3R)-4,4-difluoro-2-[(3-hydroxyphenyl)methyl]-3-[(methanesulfonyl)amino]pyrrolidine-1-carboxylate To a solution of tert-butyl (2S,3R)-4,4-difluoro-3-[(methanesulfonyl)amino]-2-{[3-(4,4,5,5-tetramethyl-1,3,2-dioxaborolan-2-yl)phenyl]methyl}pyrrolidine-1-carboxylate (1.87 g) in THF (10 mL) and water (10 mL) was added sodium perborate tetyahydrate (1.39 g) at 0° C. The mixture was stirred at 20° C. for 2 hours. The reaction was quenched with water and extracted with EtOAc. The organic layer was washed with brine, dried over anhydrous sodium sulfate, filtered and concentrated under reduced pressure. The residue was purified by silica gel column chromatography (MeOH/CH2Cl2) to give the title compound (774 mg).

MS: $[M+Na]^+$ 429.1

D) tert-Butyl (2S,3R)-2-({3-[(6-cyano-3-methylpyridin-2-yl)oxy]phenyl}methyl)-4,4-difluoro-3-[(methanesulfonyl)amino]pyrrolidine-1-carboxylate To a solution of tert-butyl (2S,3R)-4,4-difluoro-2-[(3-hydroxyphenyl)methyl]-3-[(methanesulfonyl)amino]pyrrolidine-1-carboxylate (770 mg) in DMA (10 mL) was added 6-chloro-5-methyl-pyridine-2-carbonitrile (318 mg) and cesium carbonate (926 mg). The mixture was stirred at 80° C. under nitrogen atmosphere for 12 hours. The reaction mixture was diluted with water and extracted with EtOAc. The organic layer was washed with brine and dried by anhydrous sodium sulfate, filtered and concentrated under reduced pressure. The residue was purified by silica gel column chromatography (EtOAc/PE) to give the title compound (713 mg).

$^1H$ NMR (400 MHZ, DMSO-$d_6$) δ 1.05-1.14 (9H, m), 2.37 (3H, s), 2.56-2.64 (1H, m), 2.70-2.81 (1H, m), 2.87-2.97 (3H, m), 3.70-3.91 (2H, m), 4.29-4.38 (1H, m), 4.41-4.59 (1H, m), 6.95-7.20 (3H, m), 7.23-7.42 (1H, m), 7.69 (1H, d, J=7.6 Hz), 7.94 (1H, dd, J=7.2, 0.8 Hz), 8.05-8.20 (1H, m).

E) tert-Butyl (2S,3R)-2-[(3-{[6-(aminomethyl)-3-methylpyridin-2-yl]oxy}phenyl)methyl]-4,4-difluoro-3-[(methanesulfonyl)amino]pyrrolidine-1-carboxylate To a solution of tert-butyl (2S,3R)-2-({3-[(6-cyano-3-methylpyridin-2-yl)oxy]phenyl}methyl)-4,4-difluoro-3-[(methanesulfonyl)amino]pyrrolidine-1-carboxylate (790 mg) in MeOH (10 mL) was added sodium borohydride (171 mg). Then nickel (II) chloride hexahydrate (359 mg) was added to the mixture at 0° C. The mixture was stirred at 0° C. for 2 hours. The reaction was quenched by ammonium chloride aqueous solution at 0° C. slowly then extracted with EtOAc and washed with brine. The organic layer was dried by anhydrous sodium sulfate, filtered and concentrated to give the title compound (676 mg).

MS: $[M+H]^+$ 527.3

F) N-{(2S,3R)-2-[(3-{[6-(Aminomethyl)-3-methylpyridin-2-yl]oxy}phenyl)methyl]-4,4-difluoropyrrolidin-3-yl}methanesulfonamide dihydrochloride A mixture of tert-butyl (2S,3R)-2-[(3-{[6-(aminomethyl)-3-methylpyridin-2-yl]oxy}phenyl)methyl]-4,4-difluoro-3-[(methanesulfonyl)amino]pyrrolidine-1-carboxylate (200 mg) and 4 M hydrogen chloride in dioxane (5 mL) was stirred at 20° C. for 1 hour. The mixture was concentrated to obtain the title compound (200 mg).

MS: $[M+H]^+$ 427.1

G) N-[(15aS,16R)-17,17-Difluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide To a solution of N-{(2S,3R)-2-[(3-{[6-(aminomethyl)-3-methylpyridin-2-yl]oxy}phenyl)methyl]-4,4-difluoropyrrolidin-3-yl}methanesulfonamide dihydrochloride (200 mg) in DMF (200 mL) was added CDI (71 mg) and DIPEA (310 mg). The reaction mixture was stirred at 25° C. under nitrogen atmosphere for 2 hours. The mixture was stirred at 20° C. for 12 hours. The reaction mixture was diluted with water and extracted with EtOAc. The organic layer was washed with brine and dried by anhydrous sodium sulfate, filtered and concentrated under reduced pressure. The residue was purified by preparative HPLC (column: Boston Prime C18, mobile phase: 10 mM ammonium bicarbonate aqueous solution (containing 0.05% ammonium hydroxide)/acetonitrile) to obtain the title compound (13.8 mg).

$^1H$ NMR (400 MHZ, DMSO-$d_6$) δ 2.27 (3H, s), 2.54-2.63 (1H, m), 2.84 (1H, dd, J=13.6, 4.4 Hz), 3.08 (3H, s), 3.60-3.72 (1H, m), 3.75-3.90 (2H, m), 4.27-4.44 (2H, m), 4.55-4.62 (1H, m), 6.32 (1H, dd, J=9.2, 2.8 Hz), 6.85-6.92 (2H, m), 7.03 (1H, d, J=7.2 Hz), 7.18 (1H, s), 7.23 (1H, t, J=8.0 Hz), 7.56 (1H, d, J=7.6 Hz), 7.74 (1H, brs).

Example 4

N-[(15aS,16R)-17,17,20-Trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide A) 3-Chloro-2-fluorophenylalanine hydrochloride To a mixture of 1-(bromomethyl)-3-chloro-2-fluorobenzene (55.0 g), diethyl acetamidomalonate (56.1 g) and EtOH (400 mL) was added 20% sodium ethoxide ethanol solution (88 g) at 0° C. The mixture was refluxed for 2 hr 30 min, and cooled to room temperature. The impurity was removed by filtration, the filtrate was concentrated under reduced pressure, and a mixture of the residue and 6 M hydrochloric acid (500 mL) was refluxed for 15 hr. The reaction solution was concentrated under reduced pressure, and the obtained residue was washed with isopropanol/diisopropyl ether to give the title compound (67.1 g).

MS: $[M+H]^+$ 217.8.

B) N-(tert-Butoxycarbonyl)-3-chloro-2-fluorophenylalanine

To a mixture of 3-chloro-2-fluorophenylalanine hydrochloride (67.1 g), 1 M aqueous sodium hydroxide solution (528 mL) and DME (480 mL) was added $Boc_2O$ (63.4 g) at room temperature. The mixture was stirred at room temperature for 2 hr 30 min, and poured into ice water. The mixture was basified with 1 M aqueous sodium hydroxide solution, and the aqueous layer was washed with diethyl ether. The aqueous layer was acidified with 1 M hydrochloric acid, and extracted with EtOAc. The organic layer was separated, washed with water and saturated brine, dried over anhydrous magnesium sulfate, and concentrated under reduced pressure. The obtained solid was washed with diisopropyl ether/hexane to give the title compound (63.8 g).

MS: $[M-H]^-$ 316.0.

C) tert-Butyl {3-(3-chloro-2-fluorophenyl)-1-[methoxy(methyl)amino]-1-oxopropan-2-yl}carbamate To a mixture of N-(tert-butoxycarbonyl)-3-chloro-2-fluorophenylalanine (63.8 g), N-methoxymethanamine hydrochloride (21.5 g), HOBt (29.8 g), TEA (44.7 g) and DMF (425 mL) was added N-(3-dimethylaminopropyl)-N'-ethylcarbodiimide hydrochloride (46.2 g) at 0° C. The mixture was stirred at room temperature for 15 hr, and the reaction mixture was added to aqueous sodium hydrogen carbonate solution, and extracted with EtOAc/THF. The organic layer was separated, washed with water and saturated brine, dried over anhydrous magnesium sulfate, and concentrated under reduced pressure. The obtained solid was washed with diisopropyl ether/hexane to give the title compound (70.0 g).

MS, found: 260.9.

D) tert-Butyl {3-(3-chloro-2-fluorophenyl)-1-[methoxy(methyl)amino]-1-oxopropan-2-yl}(4-methoxybenzyl) carbamate To a mixture of tert-butyl {3-(3-chloro-2-fluorophenyl)-1-[methoxy(methyl)amino]-1-oxopropan-2-yl}carbamate (70.0 g) and DMF (390 mL) was added 60% sodium hydride (10.1 g) at 0° C. The mixture was stirred at 0° C. for 5 min, and then at room temperature for 10 min, and to the reaction mixture were added 1-(chloromethyl)-4-methoxybenzene (60.7 g) and tetrabutylammonium iodide (7.16 g) at 0° C. The mixture was stirred at room temperature for 2 hr 30 min, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (90.7 g).

MS: $[M+H]^+$ 481.1.

E) tert-Butyl [1-(3-chloro-2-fluorophenyl)-3-oxopropan-2-yl][(4-methoxyphenyl)methyl]carbamate To a mixture of tert-butyl {3-(3-chloro-2-fluorophenyl)-1-[methoxy(methyl)amino]-1-oxopropan-2-yl}(4-methoxybenzyl) carbamate (90.7 g) and Et20 (500 mL) was added lithium aluminium hydride (9.30 g) by small and small at −78° C. The mixture was stirred at −15° C. for 1 hr 30 min, and to the reaction mixture were added dropwise sequentially EtOAc and 10% aqueous potassium hydrogensulfite solution at −78° C. The mixture was stirred at room temperature for 15 min, and to the mixture was added water. The insoluble substance was removed by filtration through Celite, and the filtrate was extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (74.7 g).

MS: $[M-H]^-$ 420.0.

F) Ethyl 4-{(tert-butoxycarbonyl) [(4-methoxyphenyl)methyl]amino}-5-(3-chloro-2-fluorophenyl)-2,4,5-trideoxy-2,2-difluoropentonate To a mixture of zinc (37.0 g) and THF (500 mL) was added TMSCl (3.85 g) under argon atmosphere at room temperature. The mixture was stirred at room temperature for 15 min, and ethyl bromo(difluoro)acetate (71.9 g) was added dropwise to the mixture with vigorously stirring at room temperature while keeping the internal temperature of about 50° C. The mixture was stirred at room temperature for 15 min, and to the mixture was added dropwise a mixture of tert-butyl [1-(3-chloro-2-fluorophenyl)-3-oxopropan-2-yl][(4-methoxyphenyl)methyl]carbamate (74.7 g) and THE (100 mL), while keeping the internal temperature of about 40° C. The mixture was stirred at room temperature for 2 hr, and added to 5% aqueous potassium hydrogensulfite solution under ice cooling, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (61.6 g).

MS, found: 490.0.

G) 5-[(3-Chloro-2-fluorophenyl)methyl]-3,3-difluoro-4-hydroxy-1-[(4-methoxyphenyl)methyl]pyrrolidin-2-one To a mixture of ethyl 4-{(tert-butoxycarbonyl) [(4-methoxyphenyl)methyl]amino}-5-(3-chloro-2-fluorophenyl)-2,4,5-trideoxy-2,2-difluoropentonate (61.6 g) and EtOH (160 mL) was added 4 M hydrogen chloride CPME solution (282 mL) at room temperature. The mixture was stirred at room temperature for 2 hr, and the reaction solution was concentrated. To the obtained residue were added EtOH (360 mL) and DIPEA (43.8 g). The mixture was stirred at 70° C. for 1 hr 30 min, and the reaction mixture was poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane), and the obtained solid was washed with diisopropyl ether/hexane to give the title compound (36.1 g).

MS: $[M+H]^+$ 399.9.

H) 5-[(3-Chloro-2-fluorophenyl)methyl]-3,3-difluoro-4-hydroxypyrrolidin-2-one

To a mixture of 5-[(3-chloro-2-fluorophenyl)methyl]-3,3-difluoro-4-hydroxy-1-[(4-methoxyphenyl)methyl]pyrrolidin-2-one (36.1 g), $CH_3CN$ (315 mL) and water (105 mL) was added ammonium hexanitratocerate (IV) (99 g) at room temperature. The mixture was stirred at room temperature for 4 hr, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane), and then NH silica gel column chromatography (MeOH/EtOAc) to give the title compound (22.7 g).

MS: $[M-H]^-$ 278.0.

I) tert-Butyl 2-[(3-chloro-2-fluorophenyl)methyl]-4,4-difluoro-3-hydroxypyrrolidine-1-carboxylate To a mixture of 5-[(3-chloro-2-fluorophenyl)methyl]-3,3-difluoro-4-hydroxypyrrolidin-2-one (22.7 g) and THF (350 mL) was added dropwise 1 M borane-THF complex THE solution (284 mL) at room temperature. The mixture was slowly warmed to 60° C., and stirred for 4 hr. Water was added dropwise to the mixture at 0° C., and the mixture was stirred at room temperature for 10 min, and concentrated under reduced pressure. To the residue was added 1 M hydrochloric acid (500 mL), and the mixture was vigorously stirred at 60° C. for 1 hr 30 min. The mixture was slowly added to 1 M aqueous sodium hydroxide solution under ice cooling, basified with potassium carbonate, saturated with salt, and extracted with EtOAc/THF. The organic layer was separated, washed with water and saturated brine, dried over anhydrous magnesium sulfate, and concentrated under reduced pressure. To a mixture of the obtained residue, sodium hydrogen carbonate (6.83 g) and THF (190 mL)/water (210 mL) was added a solution of $Boc_2O$ (19.5 g) in THF (20 mL) at room temperature. The mixture was vigorously stirred at room temperature for 15 hr, poured into water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (22.2 g).

MS, found: 265.9.

J) rac-tert-Butyl (2S,3S)-2-[(3-chloro-2-fluorophenyl)methyl]-4,4-difluoro-3-[(trifluoromethanesulfonyl)oxy]pyrrolidine-1-carboxylate To a mixture of tert-butyl 2-[(3-chloro-2-fluorophenyl)methyl]-4,4-difluoro-3-hydroxypyrrolidine-1-carboxylate (22.1 g), pyridine (96 g) and Et20 (355 mL) was added dropwise trifluoromethanesulfonic anhydride (51.2 g) under argon atmosphere at 0° C. The mixture was stirred at room temperature for 2 hr 30 min, poured into ice water, and extracted with EtOAc/hexane. The organic layer was separated, washed with 10% aqueous citric acid solution, aqueous sodium hydrogen carbonate solution, water and saturated brine, dried over anhydrous magnesium sulfate, and concentrated under reduced pressure. The residue was purified by silica gel column chromatography (EtOAc/hexane) to give the title compound (22.4 g).

MS, found: 397.9.

K) rac-tert-Butyl (2S,3R)-3-azido-2-[(3-chloro-2-fluorophenyl)methyl]-4,4-difluoropyrrolidine-1-carboxylate To a mixture of rac-tert-butyl (2S,3S)-2-[(3-chloro-2-fluorophenyl)methyl]-4,4-difluoro-3-[(trifluoromethanesulfonyl)oxy]pyrrolidine-1-carboxylate (22.4 g) and $CH_3CN$ (265 mL) was added tetra-n-butylammonium azide (38.3 g) at room temperature. The mixture was slowly warmed to 80° C., stirred for 1 hr, poured into ice water, and extracted with EtOAc. The organic layer was separated, washed with water and saturated brine, dried over anhydrous magnesium sulfate, and concentrated under reduced pressure. The residue was purified by silica gel column chromatography (EtOAc/hexane) to give the title compound (16.2 g).

MS, found: 290.9.

L) rac-tert-Butyl (2S,3R)-3-amino-2-[(3-chloro-2-fluorophenyl)methyl]-4,4-difluoropyrrolidine-1-carboxylate To a mixture of rac-tert-butyl (2S,3R)-3-azido-2-[(3-chloro-2-fluorophenyl)methyl]-4,4-difluoropyrrolidine-1-carboxylate (16.2 g) and THF (200 mL)/water (5 mL) was added $PPh_3$ (13.1 g) under argon atmosphere at room temperature. The mixture was stirred at 55° C. for 18 hr, added to aqueous sodium hydrogen carbonate solution under ice cooling, and extracted with EtOAc/THF. The organic layer was separated, washed with water and saturated brine, dried over anhydrous magnesium sulfate, and concentrated under reduced pressure. The residue was purified by NH silica gel column chromatography (EtOAc/hexane) to give the title compound and by-product, respectively. To a mixture of the obtained by-product and THE (100 mL)/water (10 mL) was added 40% aqueous methanamine solution (3.22 g) at room temperature. The mixture was stirred at 70° C. for 15 hr, poured into water, and extracted with EtOAc. The organic layer was separated, washed with water and saturated brine, dried over anhydrous magnesium sulfate, and concentrated under reduced pressure. The residue was purified by NH silica gel column chromatography (EtOAc/hexane) to give the title compound (14.6 g), combined with the title compound obtained above.

MS, found: 308.9.

M) tert-Butyl (2S,3R)-3-amino-2-[(3-chloro-2-fluorophenyl)methyl]-4,4-difluoropyrrolidine-1-carboxylate rac-tert-Butyl (2S,3R)-3-amino-2-[(3-chloro-2-fluorophenyl)methyl]-4,4-difluoropyrrolidine-1-carboxylate (14.6 g) was resolved by HPLC (column: CHIRALPAK IA, 50 mmID×500 mmL, 20 μm, mobile phase: hexane/ethanol/diethylamine=800/200/1) to give the title compound (6.84 g) with shorter retention time (column: CHIRALPAK IA, 4.6 mmID×250 mmL, 5 μm, mobile phase: hexane/ethanol/diethylamine=800/200/1).

MS, found: 309.1.

N) tert-Butyl (2S,3R)-2-[(3-chloro-2-fluorophenyl)methyl]-4,4-difluoro-3-[(methanesulfonyl)amino]pyrrolidine-1-carboxylate To a mixture of tert-butyl (2S,3R)-3-amino-2-[(3-chloro-2-fluorophenyl)methyl]-4,4-difluoropyrrolidine-1-carboxylate (20 g), TEA (22.9 ml) in EtOAc (274 ml) was added MsCl (4.67 ml) at 0° C. The mixture was stirred at room temperature for 1 hour. To the mixture was added ammonium chloride aqueous solution. The organic layer was separated, washed with sodium hydrogen carbonate aqueous solution and brine, passed through NH silica gel pad and concentrated under reduced pressure. The residue was solidified and triturated with Et20 to give the title compound (22.5 g).

MS: $[M-H]^-$ 441.0

O) tert-Butyl (2S,3R)-4,4-difluoro-2-[(2-fluoro-3-hydroxyphenyl)methyl]-3-[(methanesulfonyl)amino]pyrrolidine-1-carboxylate To a mixture of tert-butyl (2S,3R)-2-[(3-chloro-2-fluorophenyl)methyl]-4,4-difluoro-3-[(methanesulfonyl)amino]

pyrrolidine-1-carboxylate (15 g×2 batches), Pd2 (dba) 3 (1.55 g×2 batches), and tBuXPhos (2.88 g×2 batches) in DME (135 mL×2 batches) was added 8 M potassium hydroxide aqueous solution (12.7 mL×2 batches). The mixture was stirred at 120° C. for 2 hours in a middle pressure reactor. The mixture was quenched with 1 M hydrochloric acid and extracted with EtOAc. The organic layer was separated and concentrated under reduced pressure. The residue was purified by silica gel column chromatography (EtOAc/hexane) and crystallized with IPE-hexane to give the title compound (17.0 g).

MS: $[M-H]^-$ 422.9

P) tert-Butyl (2S,3R)-2-({3-[(6-cyano-3-methylpyridin-2-yl)oxy]-2-fluorophenyl}methyl)-4,4-difluoro-3-[(methanesulfonyl)amino]pyrrolidine-1-carboxylate A mixture of tert-butyl (2S,3R)-4,4-difluoro-2-[(2-fluoro-3-hydroxyphenyl)methyl]-3-[(methanesulfonyl)amino]pyrrolidine-1-carboxylate (5.9 g), 6-chloro-5-methylpicolinonitrile (2.33 g), Cs2CO3 (9.06 g), and DMF (60 mL) was stirred at 120° C. for 5 hours. The mixture was quenched with water and extracted with EtOAc. The organic layer was separated, washed with water and brine, dried over anhydrous magnesium sulfate and concentrated under reduced pressure. The residue was purified by silica gel column chromatography (EtOAc/hexane) to give the title compound (5.62 g).

MS: $[M-H]^-$ 539.0

Q) tert-Butyl (2S,3R)-2-({3-[(6-{[(tert-butoxycarbonyl)amino]methyl}-3-methylpyridin-2-yl)oxy]-2-fluorophenyl}methyl)-4,4-difluoro-3-[(methanesulfonyl)amino]pyrrolidine-1-carboxylate Sodium borohydride (1.967 g) was added to a solution of tert-butyl (2S,3R)-2-({3-[(6-cyano-3-methylpyridin-2-yl)oxy]-2-fluorophenyl}methyl)-4,4-difluoro-3-[(methanesulfonyl)amino]pyrrolidine-1-carboxylate (5.62 g) and cobalt (II) chloride (2.70 g) in MeOH (120 mL) at 0° C. The mixture was stirred at room temperature for 1 hour. Then, Boc2O (3.62 mL) was added to the reaction mixture at room temperature and it was stirred at room temperature for 1 hour. The solvent was removed by concentration, and EtOAc and sodium hydrogen carbonate aqueous solution were added to the residue. Insoluble solid was removed by celite, and the mixture was extracted with EtOAc. The organic layer was dried over anhydrous magnesium sulfate, and concentrated under reduced pressure. The residue was purified by silica gel column chromatography (EtOAc/hexane) to give the title compound (4.82 g).

MS: $[M+H]^+$ 645.2

R) N-{(2S,3R)-2-[(3-{[6-(Aminomethyl)-3-methylpyridin-2-yl]oxy}-2-fluorophenyl)methyl]-4,4-difluoropyrrolidin-3-yl}methanesulfonamide dihydrochloride To a solution of tert-butyl (2S,3R)-2-({3-[(6-{[(tert-butoxycarbonyl)amino]methyl}-3-methylpyridin-2-yl)oxy]-2-fluorophenyl}methyl)-4,4-difluoro-3-[(methanesulfonyl)amino]pyrrolidine-1-carboxylate (4.82 g) in EtOAc (50 mL) was added 4 M hydrogen chloride in EtOAc (50 mL) at room temperature. The mixture was stirred at room temperature overnight. The resulting precipitate was collected by filtration, and washed with EtOAc to give the title compound (3.85 g).

MS: $[M+H]^+$ 445.1

S) N-[(15aS,16R)-17,17,20-Trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide To a suspension of di(N-succinimidyl) carbonate (6.67 g) and DIPEA (33.8 g) in THF (dry) (4200 ml) was added dropwise a solution of N-{(2S,3R)-2-[(3-{[6-(aminomethyl)-3-methylpyridin-2-yl]oxy}-2-fluorophenyl)methyl]-4,4-difluoropyrrolidin-3-yl}methanesulfonamide dihydrochloride (16.9 g) in DMF (dry) (200 ml) at 0° C. over 60 minutes. The mixture was stirred at room temperature for 16 hours and concentrated to a small volume. EtOAc and water were added to the residue and partitioned. The aqueous layer was extracted with EtOAc. The combined organic layers were washed with water, brine, dried over anhydrous sodium sulfate, and concentrated under reduced pressure. The residue was purified by NH silica gel column chromatography (EtOAc/hexane). To a solution of the residue thus obtained in EtOAc (600 ml) was added activated carbon Ecosorb C-941 (1 g) at 55° C., and the mixture was stirred at 55° C. for 1 hour. Insoluble materials were filtered off and the filtrate was concentrated under reduced pressure. The residue was crystallized from EtOH-heptane to give the title compound (6.16 g) 1H NMR (400 MHZ, DMSO-$d_6$) δ 2.30 (3H, s), 2.65 (1H, br d, J=12.7 Hz), 2.76-2.87 (1H, m), 3.11 (3H, s), 3.60 (1H, br d, J=14.7 Hz), 3.68-3.88 (2H, m), 4.27-4.48 (2H, m), 4.52-4.62 (1H, m), 6.14 (1H, br d, J=8.6 Hz), 6.85 (1H, d, J=7.1 Hz), 6.96-7.03 (1H, m), 7.07 (1H, t, J=7.7 Hz), 7.11-7.18 (1H, m), 7.48-7.61 (1H, m), 8.17 (1H, d, J=9.5 Hz)

Example 5

N-[(15aS,16R)-17,17,20-Trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]ethanesulfonamide A) tert-Butyl (2S,3R)-2-[(3-chloro-2-fluorophenyl)methyl]-3-[(ethanesulfonyl)amino]-4,4-difluoropyrrolidine-1-carboxylate To a solution of tert-butyl (2S,3R)-3-amino-2-[(3-chloro-2-fluorophenyl)methyl]-4,4-difluoropyrrolidine-1-carboxylate (80.0 g×2 batches) in CH2Cl2 (560 mL×2 batches) was added TEA (67.0 g×2 batches) and ethanesulfonyl chloride (42.0 g×2 batches) at 0° C. The reaction mixture was stirred at 25° C. under nitrogen atmosphere for 13 hours. The reaction mixture was poured into water and extracted with CH2Cl2. The organic layer was washed with brine, dried over anhydrous sodium sulfate and filtered, concentrated under reduced pressure. The residue was purified by silica gel column chromatography (EtOAc/PE) to obtain the title compound (184 g).

MS: $[M-Boc+H]^+$ 357.1

B) tert-Butyl (2S,3R)-3-[(ethanesulfonyl)amino]-4,4-difluoro-2-[(2-fluoro-3-hydroxyphenyl)methyl]pyrrolidine-1-carboxylate To a mixture of tert-butyl (2S,3R)-2-[(3-chloro-2-fluorophenyl)methyl]-3-[(ethanesulfonyl)amino]-4,4-difluoropyrrolidine-1-carboxylate (27.0 g×5 batches), Pd2 (dba) 3 (16.0 g×5 batches), and tBuXPhos (8.00 g×5 batches) in dioxane (243 mL×5 batches) was added 2 M potassium hydroxide aqueous solution (89.0 mL×5 batches). The mixture was degassed and purged with nitrogen for 3 times. The mixture was stirred at reflux for 2 hours under nitrogen atmosphere. The reaction mixture was poured into water and extracted with EtOAc. The organic layer was washed with brine, dried over anhydrous sodium sulfate and filtered, concentrated under reduced pressure. The residue was purified by silica gel column chromatography (EtOAc/PE) to obtain the title compound (85.0 g).

$^1$H NMR (400 MHZ, DMSO-$d_6$) δ 1.01 (9H, s), 1.27 (3H, t, J=7.2 Hz), 2.93 (1H, d, J=13.6 Hz), 3.07-3.18 (3H, m), 3.63-3.76 (1H, m), 3.83-3.96 (1H, m), 4.31 (1H, d, J=8.4 Hz), 4.42-4.57 (1H, m), 6.56-6.63 (1H, m), 6.83 (2H, t, J=6.8 Hz), 8.18 (1H, d, J=9.2 Hz), 9.65 (1H, s)

C) tert-Butyl (2S,3R)-2-({3-[(6-cyano-3-methylpyridin-2-yl)oxy]-2-fluorophenyl}methyl)-3-[(ethanesulfonyl)amino]-4,4-difluoropyrrolidine-1-carboxylate A mixture of tert-butyl (2S,3R)-3-[(ethanesulfonyl)amino]-4,4-difluoro-2-[(2-fluoro-3-hydroxyphenyl)methyl]pyrrolidine-1-carboxylate (80.0 g), 6-chloro-5-methylpicolinonitrile (42.0 g), cesium carbonate (119 g) in DMA (560 mL) was stirred at 120° C. for 12 hours under nitrogen atmosphere. The reaction mixture was poured into water and extracted with EtOAc. The organic layer was washed with brine, dried over anhydrous sodium sulfate and filtered, concentrated under reduced pressure. The residue was purified by silica gel column chromatography (EtOAc/PE) to obtain the title compound (80.0 g).

MS: $[M+Na]^+$ 577.1

D) tert-Butyl (2S,3R)-2-[(3-{[6-(aminomethyl)-3-methylpyridin-2-yl]oxy}-2-fluorophenyl)methyl]-3-[(ethanesulfonyl)amino]-4,4-difluoropyrrolidine-1-carboxylate To a solution of tert-butyl (2S,3R)-2-({3-[(6-cyano-3-methylpyridin-2-yl)oxy]-2-fluorophenyl}methyl)-3-[(ethanesulfonyl)amino]-4,4-difluoropyrrolidine-1-carboxylate (36.1 g×2 batches) in MeOH (252 mL×2 batches) was added nickel (II) chloride hexahydrate (16.0 g×2 batches) and sodium borohydride (7.00 g×2 batches) at 0° C. The mixture was stirred at 0° C. for 2 hours. The reaction was quenched by ammonium chloride aqueous solution at 0° C. Then the mixture was extracted with EtOAc. The organic layer was washed with brine, dried over anhydrous sodium sulfate, filtered and concentrated to obtain the title compound (70.0 g).

MS: $[M+H]^+$ 559.3

E) N-{(2S,3R)-2-[(3-{[6-(Aminomethyl)-3-methylpyridin-2-yl]oxy}-2-fluorophenyl)methyl]-4,4-difluoropyrrolidin-3-yl}ethanesulfonamide dihydrochloride A mixture of tert-butyl (2S,3R)-2-[(3-{[6-(aminomethyl)-3-methylpyridin-2-yl]oxy}-2-fluorophenyl)methyl]-3-[(ethanesulfonyl)amino]-4,4-difluoropyrrolidine-1-carboxylat (70.0 g) in 4 M hydrogen chloride in EtOAc (783 mL) was stirred at 25° C. for 30 minutes under nitrogen atmosphere. The reaction mixture was concentrated under reduced pressure to give the residue (67.0 g). Then, the 52.0 g of the residue was purified by reversed-phase HPLC (column: Agela C18, mobile phase: 0.4% hydrochloric acid/MeOH) to obtain the title compound (26 g).

MS: $[M+H]^+$ 459.0

F) N-[(15aS,16R)-17,17,20-Trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]ethanesulfonamide To a mixture of di(N-succinimidyl) carbonate (2.00 g×6 batches) and 4-methylmorpholine (4.00 g×6 batches) in THF (4.11 L×6 batches) was dropped a solution of N-{(2S,3R)-2-[(3-{[6-(aminomethyl)-3-methylpyridin-2-yl]oxy}-2-fluorophenyl)methyl]-4,4-difluoropyrrolidin-3-yl}ethanesulfonamide dihydrochloride (4.00 g×6 batches) in DMF (58.0 mL×6 batches) at 25° C. for 30 minutes. Then DIPEA (8.00 g×6 batches) was added in one portion. Finally, the mixture was stirred at 25° C. for 12 hours. The reaction mixture was concentrated under reduced pressure to remove THF. The crude product was purified by preparative HPLC (column: Phenomenex Titank C18, mobile phase: 10 mM ammonium bicarbonate aqueous solution/acetonitrile) to obtain the title compound (4.60 g). 1H NMR (400 MHZ, DMSO-$d_6$) δ 1.29 (3H, t, J=7.2 Hz), 2.30 (3H, s), 2.61-2.69 (1H, m), 2.78-2.89 (1H, m), 3.16-3.21 (2H, m), 3.60 (1H, d, J=14.4 Hz), 3.70-3.86 (2H, m), 4.24-4.45 (2H, m), 4.52 (1H, t, J=9.6 Hz), 6.14 (1H, d, J=8.8 Hz), 6.85 (1H, d, J=7.2 Hz), 6.96-7.16 (3H, m), 7.55 (1H, d, J=7.2 Hz), 8.16 (1H, s).

Example 7

N-[(1S,19aS)-11-Methyl-5-oxo-2,3,6,7,19,19a-hexahydro-1H, 5H-8,12-(azeno)-14,18-(metheno) pyrrolo[2,1-h][1,9]oxazacycloheptadecin-1-yl]methanesulfonamide A) tert-Butyl (2S,3S)-2-{[3-({6-[(3-tert-butoxy-3-oxoprop-1-en-1-yl]-3-methylpyridin-2-yl}oxy)phenyl]methyl}-3-[(methanesulfonyl)amino]pyrrolidine-1-carboxylate To a mixture of tert-butyl (2S,3S)-2-({3-[(6-chloro-3-methylpyridin-2-yl)oxy]phenyl}methyl)-3-[(methanesulfonyl)amino]pyrrolidine-1-carboxylate (495 mg), Pd(OAc) 2 (10 mg) and ditert-butyl-(2-phenylphenyl)phosphane (26 mg) in DMF (5 mL) was added tert-butyl prop-2-enoate (640 mg) and TEA (177 mg) at 25° C., and the mixture was stirred at 120° C. for 13 hours under nitrogen atmosphere. The reaction mixture was poured into water and extracted with EtOAc. The organic layer was washed with brine, dried over anhydrous sodium sulfate and concentrated under reduced pressure. The residue was purified by silica gel column chromatography (PE/EtOAc) to obtain the title compound (457 mg).

MS: $[M+H]^+$ 588.2

B) tert-Butyl (2S,3S)-2-[(3-{[6-(3-tert-butoxy-3-oxopropyl)-3-methylpyridin-2-yl]oxy}phenyl)methyl]-3-[(methanesulfonyl)amino]pyrrolidine-1-carboxylate To a mixture of tert-butyl (2S,3S)-2-{[3-({6-[3-tert-butoxy-3-oxoprop-1-en-1-yl]-3-methylpyridin-2-yl}oxy)phenyl]methyl}-3-[(methanesulfonyl)amino]pyrrolidine-1-carboxylate (457 mg) in MeOH (5 mL) was added 10% palladium on carbon (wetted with 55% water, 60 mg) at 25°

C., the mixture was stirred at 25° C. for 3 hours under hydrogen atmosphere. The mixture was filtered and the filtrate was concentrated under reduced pressure to give the title compound (411 mg).

MS: $[M+H]^+$ 590.2

C) 3-{6-[3-({(2S,3S)-3-[(Methanesulfonyl)amino] pyrrolidin-2-yl}methyl) phenoxy]-5-methylpyridin-2-yl}propanoic acid A mixture of tert-butyl (2S,3S)-2-[(3-{[6-(3-tert-butoxy-3-oxopropyl)-3-methylpyridin-2-yl]oxy}phenyl)methyl]-3-[(methanesulfonyl)amino]pyrrolidine-1-carboxylate (67 mg) in 4 M hydrogen chloride in dioxane (1 mL) was stirred at 25° C. for 2 hours. The reaction mixture was concentrated under reduced pressure to give the title compound (48 mg).

MS: $[M+H]^+$ 434.2

D) N-[(1S,19aS)-11-Methyl-5-oxo-2,3,6,7,19,19a-hexahydro-1H, 5H-8,12-(azeno)-14,18-(metheno) pyrrolo[2,1-h][1,9]oxazacycloheptadecin-1-yl]methanesulfonamide To a solution of 3-{6-[3-{(2S,3S)-3-[(methanesulfonyl) amino]pyrrolidin-2-yl}methyl) phenoxy]-5-methylpyridin-2-yl}propanoic acid (75 mg) in THF (750 mL) was added PyBOP (125 mg) and TEA (81 mg) at 25° C., the mixture was stirred at 25° C. for 4 hours. The reaction mixture was concentrated under reduced pressure. The residue was purified by preparative HPLC (column: Boston Prime C18, mobile phase: 0.05% ammonia hydroxide aqueous solution/acetonitrile) followed by lyophilization. The residue thus obtained was further purified by SFC (column: DAICEL CHIRALPAK IG, mobile phase: $CO_2$/EtOH (containing 0.1% ammonium hydroxide) to obtain the title compound (14.4 mg).

$^1H$ NMR (400 MHZ, DMSO-$d_6$) δ 1.69-1.83 (1H, m), 2.01-2.09 (1H, m), 2.20-2.34 (4H, m), 2.66-2.76 (1H, m), 2.81-2.91 (3H, m), 3.01 (3H, s), 3.16-3.29 (2H, m), 3.39-3.45 (1H, m), 3.74-3.86 (1H, m), 4.30-4.39 (1H, m), 6.85-6.96 (3H, m), 7.10-7.16 (1H, m), 7.19-7.28 (1H, m), 7.55 (1H, d, J=8.0 Hz), 7.71 (1H, d, J=4.0 Hz).

Example 10

N-[(15aS,16R,17S)-17,20-Difluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]methanesulfonamide A) Benzyl (2S,3R,4S)-4-fluoro-2-{[2-fluoro-3-(4,4,5,5-tetramethyl-1,3,2-dioxaborolan-2-yl)phenyl] methyl}-3-[(methanesulfonyl)amino]pyrrolidine-1-carboxylate To a mixture of benzyl (2S,3R,4S)-2-[(3-chloro-2-fluorophenyl)methyl]-4-fluoro-3-[(methanesulfonyl)amino]pyrrolidine-1-carboxylate (1 g) in toluene (15 mL) were added bis(pinacolato)diboron (0.830 g), potassium acetate (0.428 g) and XPhos Pd G3 (0.092 g) at room temperature. The mixture was stirred at 100° C. under nitrogen atmosphere for 2 hours. The mixture was purified by silica gel column chromatography (EtOAc/hexane) to give the title compound (0.961 g).

MS: $[M+H]^+$ 551.2

B) Benzyl (2S,3R,4S)-4-fluoro-2-[(2-fluoro-3-hydroxyphenyl)methyl]-3-[(methanesulfonyl)amino] pyrrolidine-1-carboxylate To a mixture of benzyl (2S,3R,4S)-4-fluoro-2-{[2-fluoro-3-(4,4,5,5-tetramethyl-1,3,2-dioxaborolan-2-yl)phenyl] methyl}-3-[(methanesulfonyl)amino]pyrrolidine-1-carboxylate (962.5 mg) in THE (5.0 mL) and water (5.0 mL) was added sodium peroxoborate tetrahydrate (538 mg) at 0° C. The mixture was stirred at 0° C. to room temperature for 1.5 hours. The mixture was quenched with 1 M hydrochloric acid and extracted with EtOAc. The organic layer was separated, washed with sodium thiosulfate aqueous solution, water, and brine, dried over anhydrous sodium sulfate and concentrated under reduced pressure. The residue was purified by silica gel column chromatography (EtOAc/hexane). The residue was washed with EtOAc-IPE to give the title compound (460 mg).

MS: $[M+H]^+$ 441.0

C) Benzyl (2S,3R,4S)-2-({3-[(6-cyano-3-methylpyridin-2-yl)oxy]-2-fluorophenyl}methyl)-4-fluoro-3-[(methanesulfonyl)amino]pyrrolidine-1-carboxylate A mixture of benzyl (2S,3R,4S)-4-fluoro-2-[(2-fluoro-3-hydroxyphenyl)methyl]-3-[(methanesulfonyl)amino]pyrrolidine-1-carboxylate (500 mg), 6-chloro-5-methylpicolinonitrile (217 mg) and cesium carbonate (462 mg) in DMA (3 mL) was stirred at 100° C. under nitrogen atmosphere overnight. The mixture was quenched with ammonium chloride aqueous solution at room temperature and extracted with EtOAc. The organic layer was separated, washed with water and brine, dried over anhydrous sodium sulfate and concentrated under reduced pressure. The residue was purified by NH silica gel column chromatography (EtOAc/hexane) to give the title compound (431 mg).

MS: $[M+H]^+$ 557.1

D) Benzyl (2S,3R,4S)-2-(3-((6-(aminomethyl)-3-methylpyridin-2-yl)oxy)-2-fluorobenzyl)-4-fluoro-3-(methylsulfonamido) pyrrolidine-1-carboxylate To a solution of benzyl (2S,3R,4S)-2-({3-[(6-cyano-3-methylpyridin-2-yl)oxy]-2-fluorophenyl}methyl)-4-fluoro-3-[(methanesulfonyl)amino]pyrrolidine-1-carboxylate (430.5 mg) and nickel chloride hexahydrate (184 mg) in MeOH (15 mL) was added sodium borohydride (88 mg) at 0° C. The mixture was stirred at the same temperature for 30 minutes. After concentration of the resulting mixture, the residue was purified by NH silica gel column chromatography (MeOH/EtOAc) to give the title compound (312 mg).

MS: $[M+H]^+$ 561.2

E) N-{(2S,3R,4S)-2-[(3-{[6-(Aminomethyl)-3-methylpyridin-2-yl]oxy}-2-fluorophenyl)methyl]-4-fluoropyrrolidin-3-yl}methanesulfonamide dihydrobromide To benzyl (2S,3R,4S)-2-(3-((6-(aminomethyl)-3-methylpyridin-2-yl)oxy)-2-fluorobenzyl)-4-fluoro-3-(methylsulfonamido) pyrrolidine-1-carboxylate (311.5 mg) was added 30% hydrogen bromide in acetic acid (10 mL) at room temperature. The mixture was stirred at room temperature for 15 minutes then the solvent was coevaporated twice with toluene. The residue was washed with EtOAc and IPE to give the title compound (378 mg).

MS: $[M+H]^+$ 427.1

F) N-[(15aS,16R,17S)-17,20-Difluoro-7-methyl-1-oxo-2,3,15a,16,17,18-hexahydro-1H,15H-4,8-(azeno)-14,10-(metheno) pyrrolo[1,2-j][1,8,10]oxa-diazacycloheptadecin-16-yl]methanesulfonamide To a solution of CDI (99 mg) and DIPEA (0.582 mL) in THF (dry) (250 mL) was added N-{(2S,3R,4S)-2-[(3-{[6-(aminomethyl)-3-methylpyridin-2-yl]oxy}-2-fluorophenyl) methyl]-4-fluoropyrrolidin-3-yl}methanesulfonamide dihydrobromide (327.0 mg) in DMF (dry) (12.50 mL) dropwise over 30 minutes at room temperature. The mixture was stirred at room temperature under argon atmosphere for 2 hours. After THE was removed under reduced pressure, to the residue was added THF (dry) (250 mL) and DMF (dry) (12.5 mL). The mixture was stirred at room temperature overnight. After THE was removed under reduced pressure, the mixture was quenched with sodium hydrogen carbonate aqueous solution and extracted with EtOAc. The organic layer was separated, washed with brine twice, dried over anhydrous sodium sulfate and concentrated under reduced pressure. The crude material was purified by preparative HPLC (column: YMC-Actus Triant C18, mobile phase: 10 mM ammonium bicarbonate aqueous solution/acetonitrile) to give the title compound (42.0 mg).

$^1$H NMR (400 MHZ, DMSO-$d_6$) δ 2.26-2.34 (3H, m), 2.68 (1H, br d, J=12.6 Hz), 2.97 (1H, br t, J=12.8 Hz), 3.09 (3H, s), 3.49-3.75 (3H, m), 3.86-4.03 (1H, m), 4.35-4.46 (2H, m), 5.28 (1H, dt, J=56.6, 4.6 Hz), 6.00 (1H, br d, J=8.8 Hz), 6.83 (1H, d, J=7.2 Hz), 6.90-7.17 (3H, m), 7.54 (1H, d, J=7.0 Hz), 7.74 (1H, d, J=8.4 Hz).

Example 19

1-Fluoro-N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10] oxadiazacycloheptadecin-16-yl]methanesulfonamide A) tert-Butyl (2S,3R)-3-{[(benzyloxy) carbonyl] amino}-2-[(3-chloro-2-fluorophenyl)methyl]-4,4-difluoropyrrolidine-1-carboxylate To a stirred mixture of tert-butyl (2S,3R)-3-amino-2-[(3-chloro-2-fluorophenyl)methyl]-4,4-difluoropyrrolidine-1-carboxylate (54.2 g) and sodium hydrogen carbonate (26.2 g) in THF (550 mL) and water (275 mL) was added benzyl chloroformate (23.3 mL) at 0° C. The mixture was stirred at room temperature overnight. The mixture was diluted with water and extracted with EtOAc. The organic layer was separated and dried over anhydrous magnesium sulfate. The organic layer was passed through the NH silica gel pad, eluted with EtOAc, and concentrated under reduced pressure to give the title compound (81.5 g). This product was subjected to the next reaction without further purification.

MS: [M−H]$^-$ 496.9

B) tert-Butyl (2S,3R)-3-{[(benzyloxy) carbonyl] amino}-4,4-difluoro-2-{[2-fluoro-3-(4,4,5,5-tetramethyl-1,3,2-dioxaborolan-2-yl)phenyl] methyl}pyrrolidine-1-carboxylate To a degassed mixture of tert-butyl (2S,3R)-3-{[(benzyloxy) carbonyl]amino}-2-[(3-chloro-2-fluorophenyl) methyl]-4,4-difluoropyrrolidine-1-carboxylate (3.76 g), bis (pinacolato)diboron (2.87 g) and potassium acetate (1.48 g) in toluene (37.7 mL) was added XPhos Pd G3 (0.319 g). The mixture was stirred at 100° C. for 5 hours under argon atmosphere. After cooling, the reaction mixture was purified by silica gel column chromatography (EtOAc/hexane) to give the title compound (3.17 g).

MS: [M−H]$^-$ 589.2

C) tert-Butyl (2S,3R)-3-{[(benzyloxy) carbonyl] amino}-4,4-difluoro-2-[(2-fluoro-3-hydroxyphenyl) methyl]pyrrolidine-1-carboxylate To a solution of tert-butyl (2S,3R)-3-{[(benzyloxy) carbonyl]amino}-4,4-difluoro-2-{[2-fluoro-3-(4,4,5,5-tetramethyl-1,3,2-dioxaborolan-2-yl)phenyl]methyl}pyrrolidine-1-carboxylate (3.17 g) in THF (26.8 mL) and water (26.8 mL) was added perboric acid sodium salt tetrahydrate (1.65 g) at 0° C. The mixture was stirred at room temperature for 3 hours. The mixture was acidified (pH=3~4) with 1 M hydrochloric acid at 0° C. and extracted with EtOAc. The organic layer was washed with water and brine, and concentrated under reduced pressure. The residue was purified by silica gel column chromatography (EtOAc/hexane) to give the title compound (2.47 g).

MS: [M−H]$^-$ 479.1

D) tert-Butyl (2S,3R)-3-amino-4,4-difluoro-2-[(2-fluoro-3-hydroxyphenyl)methyl]pyrrolidine-1-carboxylate A mixture of tert-butyl (2S,3R)-3-{[(benzyloxy) carbonyl]amino}-4,4-difluoro-2-[(2-fluoro-3-hydroxyphenyl) methyl]pyrrolidine-1-carboxylate (2.47 g) and 10% palladium on carbon (wetted with 55% water, 0.243 g) in EtOH (25.7 mL) was hydrogenated under balloon pressure at room temperature for 14 hours. Catalyst was removed by filtration and washed with EtOH and THF. The filtrate was concentrated under reduced pressure to give the title compound (1.77 g).

MS: [M−H]$^-$ 345.0

E) tert-Butyl (2S,3R)-3-{[(benzyloxy) carbonyl] amino}-2-({3-[(6-cyano-3-methylpyridin-2-yl)oxy]-2-fluorophenyl}methyl)-4,4-difluoropyrrolidine-1-carboxylate A mixture of tert-butyl (2S,3R)-3-amino-4,4-difluoro-2-[(2-fluoro-3-hydroxyphenyl)methyl]pyrrolidine-1-carboxylate (1.77 g), 6-chloro-5-methylpicolinonitrile (0.819 g) and cesium carbonate (3.33 g) in DMF (dry) (17.0 mL) was stirred at 120° C. under argon atmosphere for 1 hour. After cooling to 0° C., potassium carbonate (0.706 g) and benzyl chloroformate (1.08 ml) were added to the mixture. The reaction mixture was warmed to room temperature and stirred for 2 hours. The mixture was diluted with EtOAc and water and the solution was extracted with EtOAc. The extract was washed with brine. The solution was passed through NH silica gel and the filtrate was concentrated under reduced pressure. The residue was purified by silica gel column chromatography (EtOAc/hexane) to give the title compound (2.88 g).

MS: [M−H]$^-$ 595.1

F) tert-Butyl (2S,3R)-3-{[(benzyloxy) carbonyl] amino}-2-({3-[(6-{[(tert-butoxycarbonyl)amino] methyl}-3-methylpyridin-2-yl)oxy]-2-fluorophenyl}methyl)-4,4-difluoropyrrolidine-1-carboxylate Sodium borohydride (1.63 g) was slowly added to a solution of tert-butyl (2S,3R)-3-{[(benzyloxy) carbonyl]

amino}-2-({3-[(6-cyano-3-methylpyridin-2-yl)oxy]-2-fluorophenyl}methyl)-4,4-difluoropyrrolidine-1-carboxylate (5.13 g) and cobalt (II) chloride (2.23 g) in MeOH (50 mL) at 0° C. The mixture was stirred at 0° C. for 1 hour. Di-t-butyl dicarbonate (2.99 mL) was added to the reaction mixture at 0° C. and it was stirred at room temperature for 1 hour. Sodium hydrogen carbonate aqueous solution was added to the reaction mixture at room temperature and the solid was removed by filtration. The filtrate was extracted with EtOAc. The organic layer was washed with water and brine, dried over anhydrous sodium sulfate, and concentrated under reduced pressure. The residue was purified by silica gel column chromatography (EtOAc/hexane) to give the title compound (3.46 g).

MS: $[M-H]^-$ 699.1

G) Benzyl {(2S,3R)-2-[(3-{[6-(aminomethyl)-3-methylpyridin-2-yl]oxy}-2-fluorophenyl)methyl]-4,4-difluoropyrrolidin-3-yl}carbamate TFA (9.0 mL) was added to tert-butyl (2S,3R)-3-{[(benzyloxy) carbonyl]amino}-2-({3-[(6-{[(tert-butoxycarbonyl) amino]methyl}-3-methylpyridin-2-yl)oxy]-2-fluorophenyl}methyl)-4,4-difluoropyrrolidine-1-carboxylate (4.51 g) at room temperature. The mixture was stirred at room temperature for 30 minutes. It was concentrated under reduced pressure. The residue was purified by NH silica gel column chromatography (MeOH/EtOAc) to give the title compound (3.00 g).

MS: $[M+H]^+$ 501.1

H) Benzyl [(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]carbamate A solution of benzyl {(2S,3R)-2-[(3-{[6-(aminomethyl)-3-methylpyridin-2-yl]oxy}-2-fluorophenyl)methyl]-4,4-difluoropyrrolidin-3-yl}carbamate (2.51 g) in DMF (dry) (81 mL) was added to a solution of di(N-succinimidyl) carbonate (1.41 g) and N-methylmorpholine (1.10 mL) in THF (dry) (2430 mL) at room temperature over 40 minutes. After being stirred for 1 hour at room temperature, DIPEA (8.57 mL) was added to the reaction mixture. It was stirred at room temperature for 1.5 hours then at 70° C. for 2 hours. The solvent was removed under reduced pressure. Water was added to the residue and the mixture was extracted with EtOAc. The organic layer was washed with water and brine, and concentrated under reduced pressure. The residue was purified by silica gel column chromatography (EtOAc/hexane) to give the title compound (2.08 g).

MS: $[M+H]^+$ 527.2

I) (15aS,16R)-16-Amino-17,17,20-trifluoro-7-methyl-2,3,15a,16,17,18-hexahydro-1H,15H-4,8-(azeno)-10,14-(metheno) pyrrolo[1,2-j][1,8,10]oxadiazacycloheptadecin-1-one A mixture of benzyl [(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]carbamate (8.22 g) and 20% palladium hydroxide on activated carbon (400 mg) in MeOH (80 mL) was hydrogenated under balloon pressure at room temperature for 12 hours. The catalyst was removed by filtration and the filtrate was concentrated under reduced pressure to give the title compound (5.38 g).

MS: $[M+H]^+$ 393.1

J) 1-Fluoro-N-[(15aS,16R)-17,17,20-trifluoro-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide A solution of fluoromethanesulfonyl chloride (0.790 g) in THF (dry) (10 mL) was added to a solution of (15aS,16R)-16-amino-17,17,20-trifluoro-7-methyl-2,3,15a,16,17,18-hexahydro-1H,15H-4,8-(azeno)-10,14-(metheno) pyrrolo[1,2-j][1,8,10]oxadiazacycloheptadecin-1-one (2.00 g) in pyridine (10 mL) at 5° C. The mixture was stirred at room temperature under nitrogen atmosphere for 1.5 hours. The mixture was purified by NH silica gel column chromatography (EtOAc/hexane and MeOH/EtOAc) and silica gel column chromatography (EtOAc/hexane) followed by recrystallization from EtOAc-heptane to give the title compound (1.76 g).

$^1H$ NMR (400 MHZ, DMSO-$d_6$) δ 2.30 (3H, s), 2.62-2.69 (1H, m), 2.79-2.88 (1H, m), 3.56-3.64 (1H, m), 3.71-3.88 (2H, m), 4.29-4.46 (2H, m), 4.50-4.58 (1H, m), 5.41-5.66 (2H, m), 6.14-6.19 (1H, m), 6.85 (1H, d, J=7.2 Hz), 6.97-7.12 (3H, m), 7.53-7.56 (1H, m), 8.79-8.94 (1H, m).

Example 22

N-[(15aS,16R)-7-Chloro-17,17,20-trifluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide A) tert-Butyl (2S,3R)-2-[(3-chloro-2-fluorophenyl) methyl]-3-[(cyclopropanesulfonyl)amino]-4,4-difluoropyrrolidine-1-carboxylate To a stirred solution of tert-butyl (2S,3R)-3-amino-2-[(3-chloro-2-fluorophenyl)methyl]-4,4-difluoropyrrolidine-1-carboxylate (6.2 g) in pyridine (50 mL) was added dropwise cyclopropanesulfonyl chloride (3.64 mL) while cooling with an ice bath. The mixture was stirred at 50° C. for 3 hours. The mixture was quenched with water at room temperature and extracted with EtOAc. The organic layer was separated, dried over anhydrous sodium sulfate and concentrated under reduced pressure. The residue was purified by silica gel column chromatography (EtOAc/hexane) to give the title compound (7.00 g).

MS: $[M-H]^-$ 467.9

B) tert-Butyl (2S,3R)-3-[(cyclopropanesulfonyl) amino]-4,4-difluoro-2-[(2-fluoro-3-hydroxyphenyl) methyl]pyrrolidine-1-carboxylate The mixture of tert-butyl (2S,3R)-2-[(3-chloro-2-fluorophenyl)methyl]-3-[(cyclopropanesulfonyl)amino]-4,4-difluoropyrrolidine-1-carboxylate (5000 mg), potassium hydroxide (1795 mg), Pd2dba3 (488 mg), tBuXPhos (906 mg), DME (6 mL) and water (2 mL) was heated at 120° C. for 1 hour under microwave irradiation. The mixture was acidified with ammonium chloride aqueous solution and extracted with EtOAc. The organic layer was separated, washed with water and brine, dried over anhydrous magnesium sulfate and concentrated under reduced pressure. The residue was purified by silica gel column chromatography (EtOAc/hexane) to give the title compound (3600 mg).

MS: $[M-H]^-$ 449.0

C) tert-Butyl (2S,3R)-2-({3-[(3-chloro-6-cyanopyridin-2-yl)oxy]phenyl}methyl)-3-[(cyclopropanesulfonyl)amino]-4,4-difluoropyrrolidine-1-carboxylate To a solution of tert-butyl (2S,3R)-3-[(cyclopropanesulfonyl)amino]-4,4-difluoro-2-[(2-fluoro-3-hydroxyphenyl)

methyl]pyrrolidine-1-carboxylate (3000 mg) and cesium carbonate (4520 mg) in DMF (dry) (50 mL) was added 5-chloro-6-fluoropicolinonitrile (1194 mg) at room temperature. The mixture was stirred at 90° C. for 1 hour. The mixture was diluted with EtOAc. The organic layer was separated, washed with brine, dried over anhydrous sodium sulfate and concentrated under reduced pressure. The residue was purified by silica gel column chromatography (EtOAc/hexane) to give the title compound (3860 mg).

MS: $[M+CH_3CN]^+$ 609.0

D) tert-Butyl (2S,3R)-2-({3-[(6-{[(tert-butoxycarbonyl)amino]methyl}-3-chloropyridin-2-yl)oxy]-2-fluorophenyl}methyl)-3-[(cyclopropanesulfonyl)amino]-4,4-difluoropyrrolidine-1-carboxylate Sodium borohydride (382 mg) was added to a solution of tert-butyl (2S,3R)-2-({3-[(3-chloro-6-cyanopyridin-2-yl)oxy]phenyl}methyl)-3-[(cyclopropanesulfonyl)amino]-4,4-difluoropyrrolidine-1-carboxylate (2960 mg) and cobalt (II) chloride (1309 mg) in MeOH (60 mL) at 0° C. The mixture was stirred at room temperature for 2 hours. Then, di-t-butyl dicarbonate (1.756 mL) was added to the reaction mixture at room temperature and it was stirred at room temperature for 1 hour. The solvent was removed by concentration, and EtOAc and sodium hydrogen carbonate aqueous solution were added to the residue. Insoluble solid was removed by celite, and the mixture was extracted with EtOAc. The organic layer was dried over anhydrous magnesium sulfate, and concentrated under reduced pressure. The residue was purified by silica gel column chromatography (EtOAc/hexane) to give the title compound (2700 mg).

MS: $[M+Na]^+$ 713.1

E) N-{(2S,3R)-2-[(3-{[6-(Aminomethyl)-3-chloropyridin-2-yl]oxy}-2-fluorophenyl)methyl]-4,4-difluoropyrrolidin-3-yl}cyclopropanesulfonamide dihydrochloride To a solution of tert-butyl (2S,3R)-2-({3-[(6-{[(tert-butoxycarbonyl)amino]methyl}-3-chloropyridin-2-yl)oxy]-2-fluorophenyl}methyl)-3-[(cyclopropanesulfonyl)amino]-4,4-difluoropyrrolidine-1-carboxylate (2730 mg) in MeOH (30 mL) was added 4 M hydrogen chloride in EtOAc (19.75 mL) at 0° C. After 30 minutes stirring at 0° C., the mixture was allowed to warm to room temperature and stirred overnight. After rough concentration under reduced pressure, EtOAc was added and the precipitate was collected to give the title compound (2120 mg).

MS: $[M+H]^+$ 491.0

F) N-[(15aS,16R)-7-Chloro-17,17,20-trifluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide To a solution of di(N-succinimidyl) carbonate (963 mg) and DIPEA (3.94 mL) in THF (dry) (2000 mL) was added N-{(2S,3R)-2-[(3-{[6-(aminomethyl)-3-chloropyridin-2-yl]oxy}-2-fluorophenyl)methyl]-4,4-difluoropyrrolidin-3-yl}cyclopropanesulfonamide dihydrochloride (2120 mg) in DMF (dry) (30 mL) dropwise over 5 minutes at room temperature. After concentration under reduced pressure, the mixture was quenched with sodium hydrogen carbonate aqueous solution and extracted with EtOAc. The organic layer was separated, washed with brine twice, dried over anhydrous magnesium sulfate and concentrated under reduced pressure. The residue was purified by NH silica gel column chromatography (EtOAc/hexane and MeOH/EtOAc) followed by recrystallization from EtOAc-heptane to give the title compound (960 mg).

$^1H$ NMR (300 MHZ, DMSO-$d_6$) δ 0.98-1.10 (4H, m), 2.65-2.95 (3H, m), 3.60-3.92 (3H, m), 4.23-4.49 (2H, m), 4.49-4.62 (1H, m), 6.26 (1H, br d, J=9.0 Hz), 6.99-7.13 (3H, m), 7.15-7.25 (1H, m), 7.90 (1H, d, J=7.9 Hz), 8.22 (1H, br d, J=9.0 Hz).

Example 33

N-[(15aS,16S)-7-Methyl-1-oxo-1,2,15a,16,17,18-hexahydro-15H-4,8-(azeno)-10,14-(metheno) pyrrolo[1,2-d][1,12,4]dioxazacycloheptadecin-16-yl]methanesulfonamide A) tert-Butyl (2S,3S)-2-({3-[(6-chloro-3-methylpyridin-2-yl)oxy]phenyl}methyl)-3-[(methanesulfonyl){[2-(trimethylsilyl)ethoxy]methyl}amino]pyrrolidine-1-carboxylate To a solution tert-butyl (2S,3S)-2-({3-[(6-chloro-3-methylpyridin-2-yl)oxy]phenyl}methyl)-3-[(methanesulfonyl)amino]pyrrolidine-1-carboxylate (1.00 g) in THF (10 mL) was added 60% sodium hydride (97 mg) at 0° C. The mixture was stirred at 0° C. for 0.1 hours, 2-(chloromethoxy)ethyl](trimethyl)silane (403 mg) was added dropwise to the mixture. The mixture was stirred at 20° C. for 2 hours. The mixture was diluted with water, and it was extracted with EtOAc. The organic layer was washed with brine, dried over anhydrous sodium sulfate, filtered and concentrated under reduced pressure. The residue was purified by silica gel column chromatography (EtOAc/PE) to give the title compound (0.98 g).

$^1H$ NMR (400 MHZ, DMSO-$d_6$) δ −0.02 (9H, s), 0.80-0.88 (2H, m), 1.02-1.15 (9H, m), 1.20-1.25 (2H, m), 2.05-2.34 (5H, m), 2.75-2.94 (1H, m), 3.06 (3H, s), 3.36-3.58 (3H, m), 4.02-4.26 (2H, m), 4.40-4.82 (2H, m), 6.78-7.20 (4H, m), 7.24-7.36 (1H, m), 7.68-7.90 (1H, m).

B) tert-Butyl (2S,3S)-2-[(3-{[6-(2-tert-butoxy-2-oxoethoxy)-3-methylpyridin-2-yl]oxy}phenyl)methyl]-3-[(methanesulfonyl){[2-(trimethylsilyl)ethoxy]methyl}amino]pyrrolidine-1-carboxylate A mixture of tert-butyl (2,3S)-2-({3-[(6-chloro-3-methylpyridin-2-yl)oxy]phenyl}methyl)-3-[(methanesulfonyl){[2-(trimethylsilyl)ethoxy]methyl}amino]pyrrolidine-1-carboxylate (500 mg), tert-butyl hydroxyacetate (211 mg), 2-(di-t-butylphosphino)-3,6-dimethoxy-2'-4'-6'-tri-i-propyl-1,1'-biphenyl (19 mg), cesium carbonate (520 mg) and ditert-butyl-[3,6-dimethoxy-2-(2,4,6-triisopropylphenyl)phenyl]phosphane; methanesulfonic acid; palladium; 2-phenylaniline (34 mg) in DME (5 mL) was heated under nitrogen atmosphere and microwave irradiation at 100° C. for 1 hour. The reaction mixture was filtered and concentrated under reduced pressure. The residue was purified by silica gel column chromatography (EtOAc/PE) to give the title compound (260 mg).

MS: $[M+H]^+$ 722.3

C) N-[(15aS,16S)-7-Methyl-1-oxo-1,2,15a,16,17,18-hexahydro-15H-4,8-(azeno)-10,14-(metheno) pyrrolo[1,2-d][1,12,4]dioxazacycloheptadecin-16-yl]methanesulfonamide A solution of compound tert-butyl (2S,3S)-2-[(3-{[6-(2-tert-butoxy-2-oxoethoxy)-3-methylpyridin-2-yl]

oxy}phenyl)methyl]-3-[(methanesulfonyl){[2-(trimethylsilyl)ethoxy]methyl}amino]pyrrolidine-1-carboxylate (210 mg) in 4 M hydrogen chloride in dioxane (4.20 mL) was stirred at 25° C. for 2 hours. The mixture was concentrated under reduced pressure. A mixture of the residue thus obtained (130 mg), PyBOP (215 mg), TEA (139 mg) in THF (300 mL) was degassed and purged with nitrogen for 3 times, and then the mixture was stirred at 25° C. for 12 hours under nitrogen atmosphere. The mixture was concentrated under reduced pressure. The residue was purified by preparative HPLC (column: Welch Xtimate C18, mobile phase: 10 mM ammonium bicarbonate aqueous solution (containing 0.05% ammonium hydroxide)/acetonitrile) followed by purification by SFC (column: DAICEL CHIRALPAK AD, mobile phase: $CO_2$/EtOH (containing 0.1% ammonium hydroxide) to give the title compound (3.9 mg).

$^1$H NMR (400 MHZ, DMSO-$d_6$) δ 1.65-1.81 (1H, m), 1.99-2.06 (1H, m), 2.19 (3H, s), 2.81-2.87 (1H, m), 3.01 (3H, s), 3.06-3.12 (1H, m), 3.16-3.18 (2H, m), 3.79-3.87 (1H, m), 4.24-4.46 (2H, m), 4.05-4.68 (1H, m), 6.55 (1H, d, J=8.0 Hz), 6.87 (1H, s), 6.94-6.97 (1H, m), 7.18-7.30 (2H, m), 7.63 (1H, d, J=8.0 Hz), 7.84 (1H, d, J=5.6 Hz).

Example 36

N-[(15aS,16R)-5,17,17,20-Tetrafluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]methanesulfonamide

A) tert-Butyl (2S,3R)-2-({3-[(6-amino-3-bromo-5-fluoropyridin-2-yl)oxy]-2-fluorophenyl}methyl)-4,4-difluoro-3-[(methanesulfonyl)amino]pyrrolidine-1-carboxylate Cesium carbonate (1535 mg) was added to a solution of tert-butyl (2S,3R)-4,4-difluoro-2-[(2-fluoro-3-hydroxyphenyl)methyl]-3-[(methanesulfonyl)amino]pyrrolidine-1-carboxylate (1000 mg) and 5-bromo-3,6-difluoropyridin-2-amine (739 mg) in NMP (7854 μl) at room temperature. The mixture was stirred at 150° C. for 5.5 hours under microwave irradiation. The mixture was poured into water at room temperature and extracted with EtOAc. The organic layer was separated, washed with brine, dried over anhydrous magnesium sulfate and concentrated under reduced pressure. The residue was purified by silica gel column chromatography (EtOAc/hexane) to give the title compound (792 mg).

MS: $[M+Na]^+$ 635.0

B) tert-Butyl (2S,3R)-2-({3-[(6-amino-5-fluoro-3-methylpyridin-2-yl)oxy]-2-fluorophenyl}methyl)-4,4-difluoro-3-[(methanesulfonyl)amino]pyrrolidine-1-carboxylate To a solution of tert-butyl (2S,3R)-2-({3-[(6-amino-3-bromo-5-fluoropyridin-2-yl)oxy]-2-fluorophenyl}methyl)-4,4-difluoro-3-[(methanesulfonyl)amino]pyrrolidine-1-carboxylate (791 mg) and trimethylboroxine (0.541 ml) in DME (5 ml) was added potassium carbonate (446 mg) at room temperature. The mixture was stirred at room temperature for 10 minutes. PdCl2 (dppf) (94 mg) was added at room temperature. The mixture was heated at 90° C. overnight. The mixture was filtered. The filtrate was diluted with EtOAc and poured into water at room temperature. The organic layer was separated, washed with water and brine, dried over anhydrous sodium sulfate, and concentrated under reduced pressure. The residue was purified by silica gel column chromatography (EtOAc/hexane) to give the title compound (640 mg).

MS: $[M+H]^+$ 549.1

C) tert-Butyl (2S,3R)-2-({3-[(6-bromo-5-fluoro-3-methylpyridin-2-yl)oxy]-2-fluorophenyl}methyl)-4,4-difluoro-3-[(methanesulfonyl)amino]pyrrolidine-1-carboxylate tert-Butylnitrite (196 μl) was added to a solution of tert-butyl (2S,3R)-2-({3-[(6-amino-5-fluoro-3-methylpyridin-2-yl)oxy]-2-fluorophenyl}methyl)-4,4-difluoro-3-[(methanesulfonyl)amino]pyrrolidine-1-carboxylate (639 mg) and copper[I] bromide (234 mg) in acetonitrile (5824 μl) at room temperature. The mixture was stirred at 60° C. for 1.5 hours. To the mixture was added EtOAc and water. The precipitate was removed by celite. The organic layer of the filtrate was separated, washed with sodium thiosulfate aqueous solution and brine, dried over anhydrous sodium sulfate and concentrated under reduced pressure. The residue was purified by silica gel column chromatography (EtOAc/hexane) to give the title compound (363 mg).

MS: $[M-H]^-$ 611.0

D) tert-Butyl (2S,3R)-2-({3-[(6-{[(tert-butoxycarbonyl)amino]methyl}-5-fluoro-3-methylpyridin-2-yl)oxy]-2-fluorophenyl}methyl)-4,4-difluoro-3-[(methanesulfonyl)amino]pyrrolidine-1-carboxylate A mixture of tert-butyl (2S,3R)-2-({3-[(6-bromo-5-fluoro-3-methylpyridin-2-yl)oxy]-2-fluorophenyl}methyl)-4,4-difluoro-3-[(methanesulfonyl)amino]pyrrolidine-1-carboxylate (363 mg), potassium [[(tert-Butoxycarbonyl)amino]methyl]trifluoroborate (281 mg), Pd(OAc) 2 (13.31 mg), potassium carbonate (164 mg) and 2-dicyclohexylphosphino-2',6'-dimethoxy-1,1'-biphenyl (48.7 mg) in toluene (2470 μl) and water (494 μl) was stirred at 85° C. overnight under argon atomosphere. Water was added, and the mixture was extracted with EtOAc. The organic layer was separated, washed with brine, dried over anhydrous magnesium sulfate and concentrated under reduced pressure. The residue was purified by silica gel column chromatography (EtOAc/hexane) to give the title compound (362 mg).

MS: $[M+Na]^+$ 685.2

E) N-[(15aS,16R)-5,17,17,20-Tetrafluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]methanesulfonamide TFA (1 ml) was added to tert-butyl (2S,3R)-2-({3-[(6-{[(tert-butoxycarbonyl)amino]methyl}-5-fluoro-3-methylpyridin-2-yl)oxy]-2-fluorophenyl}methyl)-4,4-difluoro-3-[(methanesulfonyl)amino]pyrrolidine-1-carboxylate (362 mg) at room temperature. The mixture was stirred at room temperature for 30 minutes. After evaporation of the solvent with toluene, the residue was purified by NH silica gel column chromatography (MeOH/EtOAc). A solution of the residue thus obtained in DMF (dry) (5 mL) was added dropwise to a mixture of di(N-succinimidyl) carbonate (155 mg) and 4-methylmorpholine (0.363 mL) in THF (dry) (180 mL) at room temperature over 30 minutes. The mixture was stirred at room temperature for 30 minutes. Then DIPEA (0.961 mL) was added. The mixture was stirred at 60° C. under Ar for 30 minutes. The mixture was evaporated. The residue was diluted with EtOAc, poured into water at room temperature and extracted with EtOAc. The organic layer was separated, washed with water and brine, dried over anhydrous magnesium sulfate, and concentrated under reduced pressure. The residue was purified by silica gel column chromatography (EtOAc/hexane). The residue was solidified with EtOAc-hexane to give the title compound (102 mg).

$^1$H NMR (300 MHZ, DMSO-$d_6$) δ 2.32 (3H, s), 2.65 (1H, br d, J=13.2 Hz), 2.73-2.90 (1H, m), 3.11 (3H, s), 3.60-3.95 (3H, m), 4.19-4.47 (2H, m), 4.50-4.62 (1H, m), 6.20 (1H, br d, J=9.0 Hz), 6.94-7.24 (3H, m), 7.58 (1H, dd, J=9.4, 0.8 Hz), 8.18 (1H, d, J=9.4 Hz).

Example 40

N-[(15aS,16S)-2,7-Dimethyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide A) N-[(4-Methoxyphenyl)methyl]-N-[(15aS,16S)-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide To a solution of N-[(15aS,16S)-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide (460 mg) in DMF (5 mL) was added cesium carbonate (360 mg), sodium iodide (17 mg) and 4-methoxybenzyl chloride (208 mg), and it was stirred at 80° C. under nitrogen atmosphere for 15 hours. The reaction mixture was poured into water and extracted with EtOAc. The organic layer was washed with brine, dried over anhydrous sodium sulfate and concentrated under reduced pressure. The residue was purified by silica gel column chromatography (CH2Cl2/MeOH) to give the title compound (463 mg).

MS: $[M+H]^+$ 537.5

B) N-[(15aS,16S)-2,7-Dimethyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]-N-[(4-methoxyphenyl)methyl]methanesulfonamide To a mixture of N-[(4-methoxyphenyl)methyl]-N-[(15aS,16S)-7-methyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide (463 mg) in DMF (5 mL) was added 60% sodium hydride (104 mg) at 0° C., and the mixture was stirred at 0° C. under nitrogen atmosphere for 30 minutes. Then iodomethane (367 mg) was added to the mixture and it was stirred at 60° C. for 13 hours. The reaction mixture was poured into water and extracted with EtOAc. The organic layer was washed with brine, dried over anhydrous sodium sulfate and concentrated under reduced pressure. The residue was purified by silica gel column chromatography (PE/EtOAc) to give the title compound (302 mg).

MS: $[M+H]^+$ 551.1

C) N-[(15aS,16S)-2,7-Dimethyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]methanesulfonamide To a mixture of N-[(15aS,16S)-2,7-dimethyl-1-oxo-2,3,15a,16,17,18-hexahydro-1H,15H-4,8-(azeno)-10,14-(metheno) pyrrolo[1,2-j][1,8,10]oxadiazacycloheptadecin-16-yl]-N-[(4-methoxyphenyl)methyl]methanesulfonamide (272 mg) in CH2Cl2 (3 mL) was added methanesulfonic acid (285 mg) at 25° C., and then it was stirred at 25° C. for 2 hours. The reaction mixture was concentrated under reduced pressure. The residue was purified by preparative HPLC (column: Boston Prime C18, mobile phase: 0.05% ammonium hydroxide aqueous solution/acetonitrile), and most of acetonitrile was removed under reduced pressure and the remaining solvent was removed by lyophilization to give the title compound (136.2 mg).

$^1$H NMR (400 MHZ, DMSO-$d_6$) δ 1.90-2.01 (1H, m), 2.15-2.25 (1H, m), 2.78 (3H, s), 2.41 (3H, s), 2.55-2.65 (1H, m), 2.85-2.95 (1H, m), 2.99 (3H, s), 3.05-3.16 (1H, m), 3.35-3.45 (1H, m), 3.70-3.85 (1H, m), 3.90-4.00 (1H, m), 4.45-4.55 (1H, m), 4.65-4.75 (1H, m), 6.80-6.90 (2H, m), 6.97 (1H, d, J=7.6 Hz), 7.12 (1H, s), 7.24 (1H, t, J=8.0 Hz), 7.47 (1H, d, J=7.2 Hz), 7.57 (1H, d, J=7.6 Hz).

Example 51

N-[(15aS,16R)-17,17,20-Trifluoro-3,7-dimethyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]methanesulfonamide (optical isomer)

A) tert-Butyl (2S,3R)-2-[(3-{[6-(1-aminoethyl)-3-methylpyridin-2-yl]oxy}-2-fluorophenyl)methyl]-4,4-difluoro-3-[(methanesulfonyl)amino]pyrrolidine-1-carboxylate To a solution of tert-butyl (2S,3R)-2-({3-[(6-cyano-3-methylpyridin-2-yl)oxy]-2-fluorophenyl}methyl)-4,4-difluoro-3-[(methanesulfonyl)amino]pyrrolidine-1-carboxylate (328 mg) in THF (4 mL) was added 1 M methylmagnesium bromide in THF (6.07 mL) dropwise at room temperature. The mixture was stirred at room temperature for 2 hours. Then 1 M methylmagnesium bromide in THF (6.07 mL) was added, and the mixture was stirred at room temperature for 3 hours. The mixture was cooled to 0° C., and MeOH (10 mL) was added dropwise. Then sodium borohydride (68.9 mg) was added, and the mixture was stirred at room temperature overnight. The mixture was quenched with ammonium chloride aqueous solution at 0° C. and extracted with EtOAc. The organic layer was separated, washed with brine, dried over anhydrous magnesium sulfate and concentrated under reduced pressure. The residue was purified by NH silica gel column chromatography (EtOAc/hexane and MeOH/EtOAc) to give the title compound (238 mg).

MS: $[M+H]^+$ 559.2

B) N-{(2S,3R)-2-[(3-{[6-(1-Aminoethyl)-3-methylpyridin-2-yl]oxy}-2-fluorophenyl)methyl]-4,4-difluoropyrrolidin-3-yl}methanesulfonamide TFA (2 mL) was added to tert-butyl (2S,3R)-2-[(3-{[6-(1-aminoethyl)-3-methylpyridin-2-yl]oxy}-2-fluorophenyl)methyl]-4,4-difluoro-3-[(methanesulfonyl)amino]pyrrolidine-1-carboxylate (238 mg) in a flask at room temperature. The mixture was stirred at room temperature for 1 hour. After evaporation of the solvent with toluene, the residue was purified by NH silica gel column chromatography (MeOH/EtOAc) to give the title compound (175 mg).

MS: $[M+H]^+$ 459.2

C) N-[(15aS,16R)-17,17,20-Trifluoro-3,7-dimethyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]methanesulfonamide (optical isomer)

To a mixture of di(N-succinimidyl) carbonate (100 mg), DIPEA (0.400 mL) and THF (300 mL) was dropped a solution of N-{(2S,3R)-2-[(3-{[6-(1-aminoethyl)-3-methylpyridin-2-yl]oxy}-2-fluorophenyl)methyl]-4,4-difluoropyrrolidin-3-yl}methanesulfonamide (175 mg) in DMF (10 mL) at room temperature over 30 minutes. The mixture was stirred at room temperature for 1 hour and at 60° C. overnight. The mixture was evaporated. The residue was diluted with EtOAc, poured into water at room temperature and extracted with EtOAc. The organic layer was separated, washed with brine, dried over anhydrous magnesium sulfate, and concentrated under reduced pressure. The residue was purified by silica gel column chromatography (EtOAc/hexane) to give two fraction. Less polar fraction was purified by preparative HPLC (column: YMC-Actus Triant C18, mobile phase: 10 mM ammonium bicarbonate aqueous solution/acetonitrile) to give the title compound (14.3 mg) from less polar fraction.

$^1$H NMR (300 MHZ, DMSO-$d_6$) δ 1.05 (3H, br s), 2.29 (3H, s), 2.71-2.93 (2H, m), 3.16 (3H, s), 3.40-3.69 (1H, m), 3.98-4.37 (2H, m), 4.43-4.74 (2H, m), 5.57-5.78 (1H, m), 6.88 (1H, d, J=7.3 Hz), 7.07-7.26 (3H, m), 7.56 (1H, dd, J=7.4, 0.8 Hz), 8.29 (1H, br d, J=8.4 Hz).

Example 54

N-[(16aS,17R)-18,18,21-Trifluoro-7-methyl-1-oxo-2,3,16a,17,18,19-hexahydro-1H,9H, 16H-4,8-(azeno)-11,15-(metheno) pyrrolo[2,1-h][1,9,11]oxadiazacyclooctadecin-17-yl]methanesulfonamide

A) tert-Butyl (2S,3R)-2-({3-[(6-chloro-3-methylpyridin-2-yl)methoxy]-2-fluorophenyl}methyl)-4,4-difluoro-3-[(methanesulfonyl)amino]pyrrolidine-1-carboxylate To a mixture of tert-butyl (2S,3R)-4,4-difluoro-2-[(2-fluoro-3-hydroxyphenyl)methyl]-3-[(methanesulfonyl)amino]pyrrolidine-1-carboxylate (444 mg), cesium carbonate (1.1 g) and DMF (8 mL) was added a solution of 6-chloro-2-(chloromethyl)-3-methylpyridine (222 mg) in DMF (1 mL) at room temperature, and the mixture was stirred at 50° C. for 2 hours. The mixture was quenched with water and extracted with EtOAc. The organic layer was separated, dried over anhydrous magnesium sulfate and concentrated under reduced pressure. The residue was purified by silica gel column chromatography (EtOAc/hexane) to give the title compound (494 mg).

MS: $[M+H]^+$ 564.2

B) tert-Butyl (2S,3R)-2-({3-[(6-cyano-3-methylpyridin-2-yl)methoxy]-2-fluorophenyl}methyl)-4,4-difluoro-3-[(methanesulfonyl)amino]pyrrolidine-1-carboxylate To a mixture of tert-butyl (2S,3R)-2-({3-[(6-chloro-3-methylpyridin-2-yl)methoxy]-2-fluorophenyl}methyl)-4,4-difluoro-3-[(methanesulfonyl)amino]pyrrolidine-1-carboxylate (184.4 mg), zinc cyanide (122.2 mg) and DMF (3 mL) was added Pd(Ph3P)4 (38 mg) at room temperature, and the mixture was stirred at 120° C. for 2 hours. The mixture was quenched with water and extracted with EtOAc. The organic layer was separated, dried over anhydrous magnesium sulfate and concentrated under reduced pressure. The residue was purified by silica gel column chromatography (EtOAc/hexane) to give the title compound (184 mg).

MS: $[M+H-(tBu)]^+$ 449.1

C) tert-Butyl (2S,3R)-2-({3-[(6-{[(tert-butoxycarbonyl)amino]methyl}-3-methylpyridin-2-yl)methoxy]-2-fluorophenyl}methyl)-4,4-difluoro-3-[(methanesulfonyl)amino]pyrrolidine-1-carboxylate To a mixture of tert-butyl (2S,3R)-2-({3-[(6-cyano-3-methylpyridin-2-yl)methoxy]-2-fluorophenyl}methyl)-4,4-difluoro-3-[(methanesulfonyl)amino]pyrrolidine-1-carboxylate (181 mg), cobalt (II) chloride (49.8 mg) and MeOH (3 mL) was added sodium borohydride (42.8 mg) at 0° C., and the mixture was stirred at 0° C. for 1 hour. Boc2O (0.2 mL) was added, and the mixture was stirred at room temperature for 2 hours. The mixture was quenched with ammonium chloride aqueous solution and extracted with EtOAc. The organic layer was separated, dried over anhydrous magnesium sulfate and concentrated under reduced pressure. The residue was purified by NH silica gel column chromatography (EtOAc/hexane) to give the title compound (184 mg).

MS: $[M+H]^+$ 659.3

D) N-[(16aS,17R)-18,18,21-Trifluoro-7-methyl-1-oxo-2,3,16a,17,18,19-hexahydro-1H,9H, 16H-4,8-(azeno)-11,15-(metheno) pyrrolo[2,1-h][1,9,11]oxadiazacyclooctadecin-17-yl]methanesulfonamide To a solution of tert-butyl (2S,3R)-2-({3-[(6-{[(tert-butoxycarbonyl)amino]methyl}-3-methylpyridin-2-yl)methoxy]-2-fluorophenyl}methyl)-4,4-difluoro-3-[(methanesulfonyl)amino]pyrrolidine-1-carboxylate (58.5 mg) in MeOH (1 mL) was added 4 M hydrogen chloride in CPME (0.2 mL) at room temperature, and the mixture was stirred at room temperature overnight. The mixture was concentrated under reduced pressure. A solution of the residue in DMF (2 mL) was added to a mixture of di(N-succinimidyl) carbonate (27.9 mg), N-methylmorpholine (80 μL) and THE (30 mL) at room temperature, and the mixture was stirred at room temperature for 3 hours. DIPEA (157 μL) was added, and the mixture was stirred at room temperature for 3 hours, at 60° C. overnight. The mixture was quenched with sodium hydrogen carbonate aqueous solution and extracted with EtOAc. The organic layer was separated, dried over anhydrous magnesium sulfate and concentrated under reduced pressure. The crude material was purified by preparative HPLC (column: YMC-Actus Triant C18, mobile phase: 10 mM ammonium bicarbonate aqueous solution/acetonitrile). Then the desired fractions were concentrated, crystallized from hexane-EtOAc, and collected by filtration to give the title compound (6.2 mg).

1H NMR (300 MHZ, DMSO-$d_6$) δ 2.15-2.46 (6H, m), 2.75-3.03 (1H, m), 3.09 (3H, s), 3.70-4.64 (5H, m), 5.11-5.75 (2H, m), 6.37-6.85 (3H, m), 6.86-7.13 (1H, m), 7.37-7.58 (1H, m), 8.04-8.38 (1H, m).

Example 56

N-[(15aS,16R,17S)-17,20-Difluoro-7-methyl-1-oxo-2,3,15a,16,17,18-hexahydro-1H,9H,15H-8,4-(azeno)-10,14-(metheno) pyrrolo[1,2-c][1,3]diazacycloheptadecin-16-yl]ethanesulfonamide

A) Benzyl (2S,3R,4S)-3-[(ethanesulfonyl)amino]-4-fluoro-2-{[2-fluoro-3-(4,4,5,5-tetramethyl-1,3,2-dioxaborolan-2-yl)phenyl]methyl}pyrrolidine-1-carboxylate XPhos Pd G3 (0.179 g) was added to a mixture of benzyl (2S,3R,4S)-2-[(3-chloro-2-fluorophenyl)methyl]-3-[(ethanesulfonyl)amino]-4-fluoropyrrolidine-1-carboxylate (2.0 g), bis(pinacolato)diboron (3.22 g) and potassium acetate (0.830 g) in toluene (20 mL) at room temperature under argon atmosphere. The mixture was stirred at 100° C. under argon atmosphere for 2 hours. The insoluble material was removed by filtration, and the filtrate was concentrated under reduced pressure. The residue was purified by silica gel column chromatography (EtOAc/hexane) to give the title compound (2.204 g).

MS: $[M+H]^+$ 565.2

B) Benzyl (2S,3R,4S)-2-({3-[(6-cyano-3-methylpyridin-2-yl)methyl]-2-fluorophenyl}methyl)-3-[(ethanesulfonyl)amino]-4-fluoropyrrolidine-1-carboxylate Pd(dppf)Cl2·CH2Cl2 (141 mg) was added to a mixture of benzyl (2S,3R,4S)-3-[(ethanesulfonyl)amino]-4-fluoro-2-{[2-fluoro-3-(4,4,5,5-tetramethyl-1,3,2-dioxaborolan-2-yl)phenyl]methyl}pyrrolidine-1-carboxylate (972 mg), 6-(chloromethyl)-5-methylpicolinonitrile (287 mg), and 2 M sodium carbonate aqueous solution (2.58 mL) in DME (9 mL) was stirred under microwave irradiation at 120° C. for 1 hour. EtOAc and water was added to the reaction mixture at room temperature, then the insoluble material was removed by filtration. The organic layer of the filtrate was separated. The aqueous layer was extracted with EtOAc. The organic layer was washed with water and brine, dried over anhydrous magnesium sulfate and concentrated under reduced pressure. The residue was purified by silica gel column chromatography (EtOAc/hexane) to give the title compound (713 mg).

MS: $[M+H]^+$ 569.2

C) Benzyl (2S,3R,4S)-2-[(3-{[6-(aminomethyl)-3-methylpyridin-2-yl]methyl}-2-fluorophenyl)methyl]-3-[(ethanesulfonyl)amino]-4-fluoropyrrolidine-1-carboxylate Sodium borohydride (118 mg) was added to a mixture of benzyl (2S,3R,4S)-2-({3-[(6-cyano-3-methylpyridin-2-yl)methyl]-2-fluorophenyl}methyl)-3-[(ethanesulfonyl)amino]-4-fluoropyrrolidine-1-carboxylate (356 mg) and cobalt (II) chloride (163 mg) in MeOH (3 mL) at 0° C. under argon atmosphere. The mixture was stirred at 0° C. under argon atmosphere for 5 hours. EtOAc and water was added to the reaction mixture at room temperature, then the insoluble material was removed by filtration. The organic layer of the filtrate was separated. The aqueous layer was extracted with EtOAc. The organic layer was washed with water and brine, dried over anhydrous magnesium sulfate and concentrated under reduced pressure. The residue was purified by NH silica gel column chromatography (MeOH/EtOAc) to give the title compound (128 mg).

MS: $[M+H]^+$ 573.2

D) N-{(2S,3R,4S)-2-[(3-{[6-(Aminomethyl)-3-methylpyridin-2-yl]methyl}-2-fluorophenyl)methyl]-4-fluoropyrrolidin-3-yl}ethanesulfonamide A mixture of benzyl (2S,3R,4S)-2-[(3-{[6-(aminomethyl)-3-methylpyridin-2-yl]methyl}-2-fluorophenyl)methyl]-3-[(ethanesulfonyl)amino]-4-fluoropyrrolidine-1-carboxylate (128 mg) and 10% palladium on carbon (wetted with 55% water, 23.79 mg) in MeOH (2 mL) was hydrogenated under balloon pressure at room temperature for 3 hours. The catalyst was removed by filtration and the filtrate was concentrated under reduced pressure to give the title compound (90 mg).

MS: $[M+H]^+$ 439.1

E) N-[(15aS,16R,17S)-17,20-Difluoro-7-methyl-1-oxo-2,3,15a,16,17,18-hexahydro-1H,9H,15H-8,4-(azeno)-10,14-(metheno) pyrrolo[1,2-c][1,3]diazacycloheptadecin-16-yl]ethanesulfonamide A solution of N-{(2S,3R,4S)-2-[(3-{[6-(aminomethyl)-3-methylpyridin-2-yl]methyl}-2-fluorophenyl)methyl]-4-fluoropyrrolidin-3-yl}ethanesulfonamide (90 mg) in THE (8 mL) was added to a mixture of di(N-succinimidyl) carbonate (52.6 mg) and 4-methylmorpholine (0.027 mL) in THF (42 mL) at 0° C. The mixture was stirred at 0° C. for 1 hour. DIPEA (0.108 mL) was added to the reaction mixture at 0° C. The mixture was stirred at room temperature overnight. The reaction mixture was concentrated under reduced pressure. EtOAc and water was added to the residue at room temperature, then the organic layer was separated. The aqueous layer was extracted with EtOAc. The organic layer was washed with water and brine, dried over anhydrous magnesium sulfate and concentrated under reduced pressure. The residue was purified by NH silica gel column chromatography (MeOH/EtOAc). The solid was crystallized from EtOAc-hexane to give the title compound (3.70 mg).

$^1H$ NMR (400 MHZ, $CDCl_3$) § 1.41-1.52 (3H, m), 2.32-2.43 (3H, m), 2.59-2.79 (1H, m), 3.07-3.25 (2H, m), 3.36-3.77 (2H, m), 3.84-4.25 (4H, m), 4.26-4.71 (3H, m), 4.96 (1H, br d, J=9.4 Hz), 5.08-5.32 (1H, m), 6.37 (1H, br s), 6.78-6.92 (1H, m), 6.93-7.22 (3H, m), 7.29-7.44 (1H, m).

Example 58

N-[(15aS,16R)-7-Chloro-5,17,17,20-tetrafluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide A) tert-Butyl (2S,3R)-2-({3-[(6-amino-3-chloro-5-fluoropyridin-2-yl)oxy]-2-fluorophenyl}methyl)-3-[(cyclopropanesulfonyl)amino]-4,4-difluoropyrrolidine-1-carboxylate Cesium carbonate (17.07 g) was added to a solution of tert-butyl (2S,3R)-3-[(cyclopropanesulfonyl)amino]-4,4-difluoro-2-[(2-fluoro-3-hydroxyphenyl)methyl]pyrrolidine-1-carboxylate (11.80 g) and 5-chloro-3,6-difluoropyridin-2-amine (7.76 g) in NMP (131 mL) at room temperature. The mixture was stirred at 150° C. for 5 hours. The mixture was cooled to room temperature, diluted with EtOAc, and passed through a celite pad. The celite pad was washed with EtOAc. The filtrate was poured into water and brine. The mixture was filtered through a celite pad. The organic layer of the filtrate was separated, and the aqueous layer was extracted with EtOAc. The combined organic layers was washed with water and brine, dried over anhydrous sodium sulfate and concentrated under reduced pressure. The residue was purified by silica gel column chromatography (EtOAc/hexane) to give the title compound (12.67 g).

MS: $[M+H]^+$ 595.1

B) tert-Butyl (2S,3R)-2-({3-[(6-bromo-3-chloro-5-fluoropyridin-2-yl)oxy]-2-fluorophenyl}methyl)-3-[(cyclopropanesulfonyl)amino]-4,4-difluoropyrrolidine-1-carboxylate tert-Butylnitrite (3.57 mL) was added to a mixture of tert-butyl (2S,3R)-2-({3-[(6-amino-3-chloro-5-fluoropyridin-2-yl)oxy]-2-fluorophenyl}methyl)-3-[(cyclopropanesulfonyl)amino]-4,4-difluoropyrrolidine-1-carboxylate (12.67 g) and copper[I] bromide (4.28 g) in acetonitrile (130 mL) at room temperature. The mixture was stirred at 60° C. for 1 hour. The mixture was cooled to room temperature. To the mixture was added EtOAc and water. The precipitate was removed through a celite pad. The filterate was poured into EtOAc and sodium thiosulfate aqueous solution at room temperature. The organic layer was separated, washed with water and brine, dried over anhydrous sodium sulfate and concentrated under reduced pressure. The residue was purified by silica gel column chromatography (EtOAc/hexane). The residue was suspended in IPE (16 mL) and the mixture was stirred at room temperature overnight. Precipitated solid was collected by filtration, washed with IPE, and dried under reduced pressure to give the title compound (8.07 g).

MS: $[M-H]^-$ 658.0

C) tert-Butyl (2S,3R)-2-({3-[(6-{[(tert-butoxycarbonyl)amino]methyl}-3-chloro-5-fluoropyridin-2-yl)oxy]-2-fluorophenyl}methyl)-3-[(cyclopropanesulfonyl)amino]-4,4-difluoropyrrolidine-1-carboxylate A mixture of tert-butyl (2S,3R)-2-({3-[(6-bromo-3-chloro-5-fluoropyridin-2-yl)oxy]-2-fluorophenyl}methyl)-3-[(cyclopropanesulfonyl)amino]-4,4-difluoropyrrolidine-1-carboxylate (8.07 g), potassium [[(tert-butoxycarbonyl)amino]methyl]trifluoroborate (3.48 g) and potassium carbonate (3.39 g) in toluene (81 mL) and water (16 mL) was degassed with nitrogen for 10 minutes. 2-Dicyclohexylphosphino-2',6'-dimethoxy-1,1'-biphenyl (2.011 g) and Pd(OAc) 2 (0.550 g) were added at room temperature. The mixture was stirred at 85° C. under nitrogen atmosphere for 4.5 hours. Water and EtOAc were added at room temperature and the mixture was filtered with a celite pad. The organic layer of the filtrate was separated, washed with brine, dried over anhydrous sodium sulfate and concentrated under reduced pressure. The residue was purified by silica gel column chromatography (EtOAc/hexane) to give the title compound (2.92 g).

MS: $[M-H]^-$ 707.2

D) N-{(2S,3R)-2-[(3-{[6-(Aminomethyl)-3-chloro-5-fluoropyridin-2-yl]oxy}-2-fluorophenyl)methyl]-4,4-difluoropyrrolidin-3-yl}cyclopropanesulfonamide TFA (20 mL) was added tert-butyl (2S,3R)-2-({3-[(6-{[(tert-butoxycarbonyl)amino]methyl}-3-chloro-5-fluoropyridin-2-yl)oxy]-2-fluorophenyl}methyl)-3-[(cyclopropanesulfonyl)amino]-4,4-difluoropyrrolidine-1-carboxylate (3.813 g) at room temperature. The mixture was stirred at room temperature for 30 minutes. The mixture was evaporated. The residue was purified by NH silica gel column chromatography (MeOH/EtOAc) to obtain the title compound (2.351 g).

MS: $[M+H]^+$ 509.0

E) N-[(15aS,16R)-7-Chloro-5,17,17,20-tetrafluoro-1-oxo-2,3,15a,16,17,18-hexahydro-1H,15H-4,8-(azeno)-14,10-(metheno) pyrrolo[1,2-j][1,8,10]oxadiazacycloheptadecin-16-yl]cyclopropanesulfonamide To a mixture of di(N-succinimidyl) carbonate (0.637 g) and DIPEA (3.16 mL) in THF (dry) (900 mL) was dropped a solution of N-{(2S,3R)-2-[(3-{[6-(aminomethyl)-3-chloro-5-fluoropyridin-2-yl]oxy}-2-fluorophenyl)methyl]-4,4-difluoropyrrolidin-3-yl}cyclopropanesulfonamide (1.15 g) in DMF (dry) (30 mL) at room temperature over 30 minutes. The mixture was stirred at room temperature overnight. The mixture was evaporated to give the residue A.

In a similar manner to the synthesis of residue A, the residue B was obtained using di(N-succinimidyl) carbonate (0.637 g), DIPEA (3.16 mL), THE (dry) (900 mL), N-{(2S,3R)-2-[(3-{[6-(aminomethyl)-3-chloro-5-fluoropyridin-2-yl]oxy}-2-fluorophenyl)methyl]-4,4-difluoropyrrolidin-3-yl}cyclopropanesulfonamide (1.15 g), and DMF (dry) (30 mL).

The residue A and B were combined and diluted with EtOAc and poured into water at room temperature. The organic layer was separated, washed with water and brine, dried over anhydrous sodium sulfate, and concentrated under reduced pressure. The residue was purified by silica gel column chromatography (EtOAc/hexane) followed by recrystallization from EtOAc-hexane to give the title compound (1.11 g).

$^1H$ NMR (400 MHZ, $CDCl_3$) δ 1.02-1.38 (4H, m), 2.52-2.63 (1H, m), 2.75-2.86 (1H, m), 2.91-3.02 (1H, m), 3.77-3.98 (2H, m), 3.99-4.24 (2H, m), 4.26-4.44 (1H, m), 4.46-4.71 (1H, m), 4.72-4.88 (1H, m), 4.93 (1H, br d, J=10.0 Hz), 7.03-7.11 (1H, m), 7.11-7.22 (2H, m), 7.48 (1H, d, J=7.7 Hz).

Example 59

N-[(16aS,17R,21aS)-18,18,22-Trifluoro-8-methyl-21-oxo-2,3,16a,17,18,19,21,21a-octahydro-1H,16H-5,9-(azeno)-11,15-(metheno)dipyrrolo[1,2-g: 1',2'-j][1,5,7,10]oxatriazacycloheptadecin-17-yl]methanesulfonamide A) tert-Butyl (2S,3R)-2-({3-[(2-chloro-5-methylpyrimidin-4-yl)oxy]-2-fluorophenyl}methyl)-4,4-difluoro-3-[(methanesulfonyl)amino]pyrrolidine-1-carboxylate 2,4-Dichloro-5-methylpyrimidine (75 μL) was added to a solution of tert-butyl (2S,3R)-4,4-difluoro-2-[(2-fluoro-3-hydroxyphenyl)methyl]-3-[(methanesulfonyl)amino]pyrrolidine-1-carboxylate (250 mg) and potassium carbonate (200 mg) in DMF (dry) (3.0 mL) at room temperature. The mixture was stirred at room temperature under argon atmosphere overnight and then poured into iced water and extracted with EtOAc. The organic layer was separated, washed with brine, dried over anhydrous magnesium sulfate and concentrated under reduced pressure. The residue was purified by silica gel column chromatography (EtOAc/hexane) to give the title compound (246 mg).

MS: $[M+H]^+$ 551.2

B) N-[(2S,3R)-2-({3-[(2-Chloro-5-methylpyrimidin-4-yl)oxy]-2-fluorophenyl}methyl)-4,4-difluoropyrrolidin-3-yl]methanesulfonamide hydrochloride 4 M Hydrogen chloride in EtOAc (1.0 mL) was added to a solution of tert-butyl (2S,3R)-2-({3-[(2-chloro-5-methylpyrimidin-4-yl)oxy]-2-fluorophenyl}methyl)-4,4-difluoro-3-[(methanesulfonyl)amino]pyrrolidine-1-carboxylate (122 mg) in THF (1.0 mL) at room temperature. The mixture was stirred at room temperature under nitrogen atmosphere for 2.5 hours and then concentrated to give the title compound (108 mg)

MS: $[M+H]^+$ 451.1

C) tert-Butyl (25)-2-{(2S,3R)-2-({3-[(2-chloro-5-methylpyrimidin-4-yl)oxy]-2-fluorophenyl}methyl)-4,4-difluoro-3-[(methanesulfonyl)amino]pyrrolidine-1-carbonyl}pyrrolidine-1-carboxylate HATU (110 mg) was added to a solution of N-[(2S,3R)-2-({3-[(2-chloro-5-methylpyrimidin-4-yl)oxy]-2-fluorophenyl}methyl)-4,4-difluoropyrrolidin-3-yl]methanesulfonamide hydrochloride (108 mg), (tert-butoxycarbonyl)-L-proline (56 mg) and DIPEA (120 μL) in THF (dry) (1.0 mL) and DMF (dry) (1.0 mL) at room temperature. The mixture was stirred at room temperature under argon atmosphere overnight. HATU (40 mg), DIPEA (60 μL) and (tert-butoxycarbonyl)-L-proline (25 mg) were added and stirring was continued for 5 hours. The mixture was poured into water and extracted with EtOAc. The organic layer was separated, washed with sodium hydrogen carbonate aqueous solution and brine, dried over anhydrous magnesium sulfate and concentrated under reduced pressure. The residue was purified by silica gel column chromatography (EtOAc/hexane) to give the title compound (116 mg).

MS: $[M-Boc+H]^+$ 548.2

D) N-[(2S,3R)-2-({3-[(2-Chloro-5-methylpyrimidin-4-yl)oxy]-2-fluorophenyl}methyl)-4,4-difluoro-1-L-prolylpyrrolidin-3-yl]methanesulfonamide hydrochloride 4 M Hydrogen chloride in EtOAc (1.0 mL) was added to a solution of tert-butyl (2S)-2-{(2S,3R)-2-({3-[(2-chloro-5-methylpyrimidin-4-yl)oxy]-2-fluorophenyl}methyl)-4,4-difluoro-3-[(methanesulfonyl)amino]pyrrolidine-1-carbonyl}pyrrolidine-1-carboxylate (115 mg) in THF (1.0 mL) at room temperature. The mixture was stirred at room temperature under argon atmosphere for 2 hours and then concentrated to give the title compound (104 mg).

MS: $[M+H]^+$ 548.3

E) N-[(16aS,17R,21aS)-18,18,22-Trifluoro-8-methyl-21-oxo-2,3,16a,17,18,19,21,21a-octahydro-1H,16H-5,9-(azeno)-11,15-(metheno)dipyrrolo[1,2-g: 1',2'-j][1,5,7,10]oxatriazacycloheptadecin-17-yl]methanesulfonamide DIPEA (150 μL) was added to a solution of N-[(2S,3R)-2-({3-[(2-chloro-5-methylpyrimidin-4-yl)oxy]-2-fluorophenyl}methyl)-4,4-difluoro-1-L-prolylpyrrolidin-3-yl]methanesulfonamide hydrochloride (104 mg) in DMF (dry) (2 mL) and acetonitrile (30 mL) at room temperature. The mixture was stirred at 80° C. under argon atmosphere overnight and then concentrated. The residue was purified by preparative HPLC (column: YMC-Actus Triant C18, mobile phase: 10 mM ammonium bicarbonate aqueous solution/acetonitrile) to give the title compound (33.6 mg).

$^1H$ NMR (400 MHZ, DMSO-$d_6$) δ 1.71-1.96 (3H, m), 2.18 (3H, s), 2.24-2.34 (1H, m), 2.73 (1H, br d, J=11.7 Hz), 2.87-2.99 (1H, m), 3.11 (3H, s), 3.34-3.53 (2H, m), 3.97-4.18 (3H, m), 4.44-4.64 (2H, m), 6.94-7.06 (2H, m), 7.21 (1H, t, J=6.1 Hz), 8.15 (1H, s), 8.19-8.34 (1H, m).

Example 62

N-[(15aS,16R)-7-Chloro-17,17,20-trifluoro-1-oxo-1,2,15a,16,17,18-hexahydro-15H-4,8-(azeno)-14,10-(metheno) pyrrolo[1,2-d][1,12,4]dioxazacycloheptadecin-16-yl]methanesulfonamide A) tert-Butyl (2S,3R)-2-({3-[(3-chloro-6-fluoropyridin-2-yl)oxy]-2-fluorophenyl}methyl)-4,4-difluoro-3-[(methanesulfonyl)amino]pyrrolidine-1-carboxylate To a solution of tert-butyl (2S,3R)-4,4-difluoro-2-[(2-fluoro-3-hydroxyphenyl)methyl]-3-[(methanesulfonyl) amino]pyrrolidine-1-carboxylate (424 mg) in DMF (3 mL) was added 3-chloro-2,6-difluoropyridine (150 mg) and cesium carbonate (652 mg) at room temperature. The mixture was stirred at room temperature under a dry atmosphere for 1 hour. The residue was purified by silica gel column chromatography (EtOAc/hexane) to obtain the title compound (381 mg).

MS: $[M-H]^-$ 552.0

B) N-[(2S,3R)-2-({3-[(3-Chloro-6-fluoropyridin-2-yl)oxy]-2-fluorophenyl}methyl)-4,4-difluoropyrrolidin-3-yl]methanesulfonamide hydrochloride A mixture of tert-butyl (2S,3R)-2-({3-[(3-chloro-6-fluoropyridin-2-yl)oxy]-2-fluorophenyl}methyl)-4,4-difluoro-3-[(methanesulfonyl)amino]pyrrolidine-1-carboxylate (381.4 mg) in 4 M hydrogen chloride in CPME (10 mL) was stirred at room temperature under a dry atmosphere overnight. The mixture was concentrated to obtain the title compound (338 mg).

MS: $[M-H]^-$ 452.9

C) 2-{(2,3R)-2-({3-[(3-Chloro-6-fluoropyridin-2-yl) oxy]-2-fluorophenyl}methyl)-4,4-difluoro-3-[(methanesulfonyl)amino]pyrrolidin-1-yl}-2-oxoethyl acetate To a solution of N-[(2S,3R)-2-({3-[(3-chloro-6-fluoropyridin-2-yl)oxy]-2-fluorophenyl}methyl)-4,4-difluoropyrrolidin-3-yl]methanesulfonamide hydrochloride (337.6 mg) in THE (7 mL) were added TEA (0.288 mL) and acetoxyacetyl chloride (0.081 mL) at 0° C. The mixture was stirred at 0° C. under a dry atmosphere for 2 hours. The reaction mixture was diluted with EtOAc and then poured into water. The organic layer was separated, washed with water and brine, dried over anhydrous sodium sulfate, filtered and concentrated. The residue was purified by silica gel column chromatography (EtOAc/hexane) to obtain the title compound (309 mg).

MS: $[M+H]^+$ 554.1

D) N-[(15aS,16R)-7-Chloro-17,17,20-trifluoro-1-oxo-1,2,15a,16,17,18-hexahydro-15H-4,8-(azeno)-14,10-(metheno) pyrrolo[1,2-d][1,12,4]dioxazacycloheptadecin-16-yl]methanesulfonamide To a solution of 2-{(2S,3R)-2-({3-[(3-chloro-6-fluoropyridin-2-yl)oxy]-2-fluorophenyl}methyl)-4,4-difluoro-3-[(methanesulfonyl)amino]pyrrolidin-1-yl}-2-oxoethyl acetate (309 mg) in THF (20 mL) and EtOH (20 mL) was added 1 M sodium hydroxide aqueous solution (4 ml) at room temperature. The mixture was stirred at room temperature for 30 minutes. The mixture was concentrated under reduced pressure. The residue was diluted with EtOAc and then poured into ammonium chloride aqueous solution. The organic layer was separated, washed with water and brine, dried over anhydrous sodium sulfate, filtered and concentrated. The residue was purified by silica gel column chromatography (EtOAc/hexane) and NH silica gel column chromatography (EtOAc/hexane) to obtain the title compound (251 mg).

$^1H$ NMR (300 MHZ, DMSO-$d_6$) δ 2.65-2.99 (2H, m), 3.07-3.16 (3H, m), 3.57-3.76 (1H, m), 4.09-4.23 (1H, m), 4.26-4.55 (3H, m), 4.56-4.69 (1H, m), 6.61-6.73 (1H, m), 7.05-7.32 (3H, m), 7.86-8.00 (1H, m), 8.26 (1H, br s).

Example 68

N-[(16aS,17S)-7-Methyl-1-oxo-2,3,16a, 17,18,19-hexahydro-1H, 10H, 16H-4,8-(azeno)-11,15-(metheno) pyrrolo[1,2-j][1,8,10]oxadiazacyclooctadecin-17-yl]methanesulfonamide A) tert-Butyl (2S,3S)-2-[(3-bromophenyl)methyl]-3-[(methanesulfonyl){[2-(trimethylsilyl)ethoxy]methyl}amino]pyrrolidine-1-carboxylate To a solution of tert-butyl (2S,3S)-2-[(3-bromophenyl)methyl]-3-[(methanesulfonyl)amino]pyrrolidine-1-carboxylate (2000 mg) in DMF (dry) (15 ml) was added 60% sodium hydride (240 mg) and the reaction mixture was stirred for 5 minutes at room temperature. Then to the mixture was added 2-(chloromethoxy)ethyl](trimethyl)silane (0.980 ml) and the reaction mixture was stirred for 2 hours at room temperature. The mixture was quenched with ammonium chloride aqueous solution and extracted with EtOAc. The organic layer was separated, washed with brine and dried over anhydrous magnesium sulfate and concentrated under reduced pressure. The residue was purified by silica gel column chromatography (EtOAc/hexane) to obtain the title compound (2470 mg).

MS: $[M+Na]^+$ 587.0

B) tert-Butyl (2S,3S)-3-[(methanesulfonyl){[2-(trimethylsilyl)ethoxy]methyl}amino]-2-{[3-(methoxycarbonyl)phenyl]methyl}pyrrolidine-1-carboxylate To a solution of tert-butyl (2S,3S)-2-[(3-bromophenyl)methyl]-3-[(methanesulfonyl){[2-(trimethylsilyl)ethoxy]methyl}amino]pyrrolidine-1-carboxylate (2470 mg) and TEA (0.916 ml) in DMF (10 ml) and MeOH (3 ml) was added $PdCl_2$ (dppf) (321 mg) and the mixture was stirred at 80° C. under carbon monoxide atmosphere for 6 hours. The mixture was quenched with brine and extracted with EtOAc. The organic layer was separated, dried over anhydrous magnesium sulfate and concentrated under reduced pressure. The residue was purified by silica gel column chromatography (EtOAc/hexane) to obtain the title compound (630 mg).

MS: $[M+Na]^+$ 565.2

C) tert-Butyl (2S,3S)-2-{[3-(hydroxymethyl)phenyl]methyl}-3-[(methanesulfonyl){[2-(trimethylsilyl)ethoxy]methyl}amino]pyrrolidine-1-carboxylate To a solution of tert-butyl (2S,3S)-3-[(methanesulfonyl){[2-(trimethylsilyl)ethoxy]methyl}amino]-2-{[3-(methoxycarbonyl)phenyl]methyl}pyrrolidine-1-carboxylate (630 mg) in THE (dry) (5 ml) was added 1 M diisobutylaluminium hydride in hexane (2.90 ml) at 0° C. The mixture was stirred for 10 minutes at room temperature. Then sodium sulfate decahydrate was added and the mixture was stirred for 2 hours. After filtration and evaporation under reduced pressure, the residue was purified by silica gel column chromatography (EtOAc/hexane) to obtain the title compound (508 mg).

MS: $[M+Na]^+$ 537.2

D) tert-Butyl (2S,3S)-2-[(3-{[(6-bromo-3-methylpyridin-2-yl)oxy]methyl}phenyl)methyl]-3-[(methanesulfonyl){[2-(trimethylsilyl)ethoxy]methyl}amino]pyrrolidine-1-carboxylate To a solution of tert-butyl (2S,3S)-2-{[3-(hydroxymethyl)phenyl]methyl}-3-[(methanesulfonyl){[2-(trimethylsilyl)ethoxy]methyl}amino]pyrrolidine-1-carboxylate (508 mg) in DMF (dry) (5 ml) was added 60% sodium hydride (47.4 mg) at room temperature. The mixture was stirred at room temperature under argon atmosphere for 10 minutes. Then 6-bromo-2-fluoro-3-methylpyridine (281 mg) was added to the solution and the mixture was stirred at room temperature under argon atmosphere for 30 minutes. The mixture was quenched with water and extracted with EtOAc. The organic layer was separated, washed with brine, dried over anhydrous magnesium sulfate and concentrated under reduced pressure. The residue was purified by silica gel column chromatography (EtOAc/hexane) to give the title compound (437 mg).

MS: $[M+Na]^+$ 706.2

E) tert-Butyl (2S,3S)-2-[(3-{[(6-{[(tert-butoxycarbonyl)amino]methyl}-3-methylpyridin-2-yl)oxy]methyl}phenyl)methyl]-3-[(methanesulfonyl){[2-(trimethylsilyl)ethoxy]methyl}amino]pyrrolidine-1-carboxylate A mixture of tert-butyl (2S,3S)-2-[(3-{[(6-bromo-3-methylpyridin-2-yl)oxy]methyl}phenyl)methyl]-3-[(methanesulfonyl){[2-(trimethylsilyl)ethoxy]methyl}amino]pyrrolidine-1-carboxylate (437 mg), potassium [[(tert-Butoxycarbonyl) amino]methyl]trifluoroborate (303 mg), Pd(OAc) 2 (14.33 mg), potassium carbonate (176 mg) and 2-dicyclohexylphosphino-2',6'-dimethoxy-1,1'-biphenyl (52.4 mg) in toluene (2659 μl) and water (532 μl) was stirred at 85° C. for 4 hours under argon atmosphere. Water was added, and the mixture was extracted with EtOAc. The organic layer was separated, washed with brine, dried over anhydrous magnesium sulfate and concentrated under reduced pressure. The residue was purified by silica gel column chromatography (EtOAc/hexane) to obtain the title compound (281 mg).

MS: $[M+H]^+$ 736.3

F) N-[(16aS,17S)-7-Methyl-1-oxo-2,3,16a,17,18,19-hexahydro-1H,10H,16H-4,8-(azeno)-11,15-(metheno) pyrrolo[1,2-j][1,8,10]oxadiazacyclooctadecin-17-yl]methanesulfonamide A mixture of tert-butyl (2S,3S)-2-[(3-{[(6-{[(tert-butoxycarbonyl)amino]methyl}-3-methylpyridin-2-yl)oxy]methyl}phenyl)methyl]-3-[(methanesulfonyl){[2-(trimethylsilyl)ethoxy]methyl}amino]pyrrolidine-1-carboxylate (281 mg) in TFA (1 mL) was stirred at room temperature for 10 minutes. After evaporation, the residue was purified by NH silica gel column chromatography (MeOH/EtOAc). A solution of the residue thus obtained in DMF (dry) (1 ml) was added to a mixture of di(N-succinimidyl) carbonate (32.5 mg), N-methylmorpholine (0.013 ml) and THF (dry) (50 ml) at room temperature, and the mixture was stirred at room temperature overnight. DIPEA (0.201 ml) was added, and the mixture was stirred at room temperature for 1 hour. The mixture was concentrated under reduced pressure. The mixture was quenched with brine and extracted with EtOAc. The organic layer was separated, washed with brine, dried over anhydrous magnesium sulfate and concentrated under reduced pressure. The crude material was purified by preparative HPLC (column: YMC-Actus Triant C18, mobile phase: 10 mM ammonium bicarbonate aqueous solution/acetonitrile) to give the title compound (6.1 mg).

$^1H$ NMR (300 MHZ, $CDCl_3$) δ 1.75-1.90 (1H, m), 2.20 (3H, s), 2.26-2.47 (2H, m), 3.06 (3H, s), 3.16-3.32 (2H, m), 3.80-4.08 (3H, m), 4.35 (1H, ddd, J=10.3, 6.9, 3.2 Hz), 4.51 (1H, dd, J=16.0, 6.2 Hz), 4.87 (2H, br dd, J=6.0, 3.0 Hz), 5.26 (1H, d, J=12.4 Hz), 5.45 (1H, d, J=12.4 Hz), 6.53 (1H, d, J=7.5 Hz), 6.91-7.01 (1H, m), 7.09-7.17 (2H, m), 7.21-7.25 (1H, m), 7.48 (1H, s).

Example 97

N-[(15aS,16R)-17,17,20-Trifluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]propane-2-sulfonamide

A) tert-Butyl (2S,3R)-2-[(3-chloro-2-fluorophenyl)methyl]-4,4-difluoro-3-[(propane-2-sulfonyl)amino]pyrrolidine-1-carboxylate To a solution of tert-butyl (2S,3R)-3-amino-2-[(3-chloro-2-fluorophenyl)methyl]-4,4-difluoropyrrolidine-1-carboxylate (4.0 g) in CH2Cl2 (22 mL), in a water bath at ambient temperature, was added 2,3,4,6,7,8,9,10-octahydropyrimido[1,2-a]azepine (4.1 mL) followed by isopropylsulfonyl chloride (1.9 mL). The mixture was stirred at room temperature for 24 hours. A saturated ammonium chloride aqueous solution was added to the mixture. The organic layer was separated, washed sequentially with sodium bicarbonate aqueous solution and brine, filtered, and concentrated under reduced pressure. The residue was purified by silica gel column chromatography (EtOAc/heptane) to give the title compound (3.1 g).

MS: [M+2H (−tBu)]$^+$ 415.2

B) tert-Butyl (2S,3R)-4,4-difluoro-2-{[2-fluoro-3-(4,4,5,5-tetramethyl-1,3,2-dioxaborolan-2-yl)phenyl]methyl}-3-[(propane-2-sulfonyl)amino]pyrrolidine-1-carboxylate To a nitrogen-sparged mixture of tert-butyl (2S,3R)-2-[(3-chloro-2-fluorophenyl)methyl]-4,4-difluoro-3-[(propane-2-sulfonyl)amino]pyrrolidine-1-carboxylate (987 mg), potassium acetate (411 mg) and bis(pinacolato)diboron (798 mg) in toluene (8.4 mL) was added (SP-4-3)-[dicyclohexyl[2',4',6'-tris(1-methylethyl) [1,1'-biphenyl]-2-yl]phosphine](methanesulfonato) [2'-(methylamino) [1,1'-biphenyl]-2-yl]palladium (180 mg). The mixture was sparged with nitrogen, then stirred at 80° C. for 16 hours. The mixture was diluted with MeOH, filtered through a pad of celite, and the filtrate was concentrated under reduced pressure. The residue was purified by silica gel column chromatography (MeOH/CH2Cl2) to give the title compound (882 mg).

MS: [M+2H (−tBu)]$^+$ 507.2.

C) tert-Butyl (2S,3R)-4,4-difluoro-2-[(2-fluoro-3-hydroxyphenyl)methyl]-3-[(propane-2-sulfonyl)amino]pyrrolidine-1-carboxylate To a solution of tert-butyl (2S,3R)-4,4-difluoro-2-{[2-fluoro-3-(4,4,5,5-tetramethyl-1,3,2-dioxaborolan-2-yl)phenyl]methyl}-3-[(propane-2-sulfonyl)amino]pyrrolidine-1-carboxylate (882 mg) in 1:1 THF-water (6.2 mL) was added sodium perborate tetrahydrate (579 mg) at room temperature. The mixture was stirred at ambient temperature open to air for 16 hours. The mixture was diluted with water, filtered through a fine frit, and the filtrate was extracted with EtOAc. The organic layer was separated and concentrated under reduced pressure. The residue was purified by silica gel column chromatography (EtOAc/heptane) to give the title compound (370 mg).

MS: [M+2H (−tBu)]$^+$ 397.2.

D) tert-Butyl (2S,3R)-2-({3-[(6-cyano-3-methylpyridin-2-yl)oxy]-2-fluorophenyl}methyl)-4,4-difluoro-3-[(propane-2-sulfonyl)amino]pyrrolidine-1-carboxylate To a mixture of tert-butyl (2S,3R)-4,4-difluoro-2-[(2-fluoro-3-hydroxyphenyl)methyl]-3-[(propane-2-sulfonyl)amino]pyrrolidine-1-carboxylate (370 mg) and cesium carbonate (534 mg) in DMA (3 ml) was added 6-chloro-5-methylpicolinonitrile (249 mg). The mixture was stirred at 80° C. for 16 hours. The mixture was quenched with water and extracted with EtOAc. The organic layer was separated, washed with brine, dried over anhydrous sodium sulfate, and concentrated under reduced pressure. The residue was purified by silica gel column chromatography (EtOAc/heptane) to give the title compound (226 mg).

MS: [M+2H (−tBu)]$^+$ 513.2.

E) tert-Butyl (2S,3R)-2-[(3-{[6-(aminomethyl)-3-methylpyridin-2-yl]oxy}-2-fluorophenyl)methyl]-4,4-difluoro-3-[(propane-2-sulfonyl)amino]pyrrolidine-1-carboxylate Sodium borohydride (45 mg) was added to a solution of tert-butyl (2S,3R)-2-({3-[(6-cyano-3-methylpyridin-2-yl)oxy]-2-fluorophenyl}methyl)-4,4-difluoro-3-[(propane-2-sulfonyl)amino]pyrrolidine-1-carboxylate (226 mg) and nickel (II) chloride hexahydrate (94 mg) in MeOH (2.6 mL) at 0° C. The mixture was stirred cold for 3 hours, then at room temperature for 3 hours. The reaction was quenched with a saturated ammonium chloride aqueous solution and the mixture was extracted with EtOAc. The organic layer was separated, dried over anhydrous sodium sulfate, and concentrated under reduced pressure. The crude residue, containing the title compound (230 mg), was carried forward without purification.

MS: [M+H]$^+$ 573.3.

F) N-{(2S,3R)-2-[(3-{[6-(Aminomethyl)-3-methylpyridin-2-yl]oxy}-2-fluorophenyl)methyl]-4,4-difluoropyrrolidin-3-yl}propane-2-sulfonamide dihydrochloride A solution of tert-butyl (2S,3R)-2-[(3-{[6-(aminomethyl)-3-methylpyridin-2-yl]oxy}-2-fluorophenyl)methyl]-4,4-difluoro-3-[(propane-2-sulfonyl)amino]pyrrolidine-1-carboxylate (228 mg) in 4 M hydrogen chloride in 1,4-dioxane (4.9 mL) was stirred at ambient temperature for 2 hours. The mixture was concentrated under reduced pressure. The residue was dissolved in THF (5 mL) and then concentrated under reduced pressure to give the title compound (225 mg).

MS: [M+H]$^+$ 473.2.

G) N-[(15aS,16R)-17,17,20-Trifluoro-7-methyl-1-oxo-2,3,15a,16,17,18-hexahydro-1H,15H-4,8-(azeno)-14,10-(metheno) pyrrolo[1,2-j][1,8,10]oxadiazacycloheptadecin-16-yl]propane-2-sulfonamide N, N'-Disuccinimidyl carbonate (76 mg) was added in three portions to a mixture of N-{(2S,3R)-2-[(3-{[6-(aminomethyl)-3-methylpyridin-2-yl]oxy}-2-fluorophenyl)methyl]-4,4-difluoropyrrolidin-3-yl}propane-2-sulfonamide dihydrochloride (217 mg) and N-methylmorpholine (0.26 mL) in THF (dry) (380 mL) and DMF (dry) (15 mL) at room temperature over 5 minutes. The mixture was stirred at room temperature for 4 days and then concentrated under reduced pressure. The residue was purified by reverse phase column chromatography (column: Gemini® NX-C18, mobile phase: mM 10 ammonium bicarbonate aqueous solution/acetonitrile) to give the title compound (83 mg).

$^1$H NMR (400 MHZ, DMSO-$d_6$) δ ppm 1.33 (6H, app dd, J=6.8, 4.5 Hz), 2.31 (3H, s), 2.65 (1H, app br d, J=13.6 Hz), 2.86 (1H, app t, J=12.6 Hz), 3.26-3.30 (1H, m), 3.60 (1H, br d, J=14.18 Hz), 3.69-3.91 (2H, m), 4.24-4.46 (2H, m), 4.46-4.55 (1H, m), 6.14 (1H, br d, J=8.7 Hz), 6.86 (1H, d, J=7.28 Hz), 6.97-7.04 (1H, m), 7.05-7.13 (2H, m), 7.55 (1H, d, J=7.3 Hz), 8.11 (1H, d, J=9.8 Hz).

Example 99

N-[(15aS,16R)-17,17,20-Trifluoro-7-methyl-1-oxo-2,3,15a,16,17,18-hexahydro-1H,15H-4,8-(azeno)-14,10-(metheno) pyrrolo[1,2-j][1,7,10]oxadiazacycloheptadecin-16-yl]ethanesulfonamide A) tert-Butyl N-(6-bromo-5-methylpyridin-2-yl)glycinate To a mixture of tert-butyl 2-bromoacetate (12.6 g) and potassium carbonate (16.3 g) in NMP (220 mL) was added 6-bromo-5-methyl-pyridin-2-amine (11.0 g). The mixture was stirred at 140° C. for 18 hours under nitrogen atmosphere. The reaction mixture was diluted with water and extracted with EtOAc three times. The combined organic layers were washed with brine, dried over anhydrous sodium sulfate, filtered, and concentrated under reduced pressure. The residue was purified by silica gel column chromatography (EtOAc/PE) to give the title compound (8.33 g). 1H NMR (400 MHZ, $CDCl_3$) δ ppm 1.48 (9H, s), 2.22 (3H, s), 3.98 (2H, s), 4.96 (1H, br s), 6.32 (1H, d, J=8.2 Hz), 7.23 (1H, d, J=8.07 Hz).

B) tert-Butyl (2S,3R)-2-{[3-({6-[(2-tert-butoxy-2-oxoethyl)amino]-3-methylpyridin-2-yl}oxy)-2-fluorophenyl]methyl}-3-[(ethanesulfonyl)amino]-4,4-difluoropyrrolidine-1-carboxylate A mixture of tert-butyl N-(6-bromo-5-methylpyridin-2-yl)glycinate (206 mg), tert-butyl (2S,3R)-3-[(ethanesulfonyl)amino]-4,4-difluoro-2-[(2-fluoro-3-hydroxyphenyl) methyl]pyrrolidine-1-carboxylate (200 mg), copper iodide (17.4 mg), pyridine-2-carboxylic acid (22.5 mg) and tripotassium phosphate (242 mg) in DMSO (4 mL) was degassed and purged with nitrogen three times and stirred at 100° C. for 12 hours under nitrogen atmosphere. The reaction was cooled to room temperature and diluted with water. The mixture was extracted with EtOAc twice. The combined organic layers were washed with brine, dried over anhydrous sodium sulfate, filtered, and concentrated under reduced pressure. The residue was purified by silica gel column chromatography (EtOAc/PE) to give the title compound (97.4 mg).

MS: $[M+H]^+$ 659.2.

C) N-{6-[3-({(2S,3R)-3-[(Ethanesulfonyl)amino]-4,4-difluoropyrrolidin-2-yl}methyl)-2-fluorophenoxy]-5-methylpyridin-2-yl}glycine dihydrochloride A solution of tert-butyl (2S,3R)-2-{[3-({6-[(2-tert-butoxy-2-oxoethyl)amino]-3-methylpyridin-2-yl}oxy)-2-fluorophenyl]methyl}-3-[(ethanesulfonyl)amino]-4,4-difluoropyrrolidine-1-carboxylate (150 mg) in 4 M hydrogen chloride in 1,4-dioxane (12 mL) was stirred at 20° C. for 12 hours. The reaction mixture was concentrated under reduced pressure to give the title compound (141 mg).

MS: $[M+H]^+$ 503.0.

D) N-[(15aS,16R)-17,17,20-Trifluoro-7-methyl-1-oxo-2,3,15a,16,17,18-hexahydro-1H,15H-4,8-(azeno)-14,10-(metheno) pyrrolo[1,2-j][1,7,10]oxadiazacycloheptadecin-16-yl]ethanesulfonamide HATU (131 mg) and DIPEA (239 μL) were added to a solution of N-{6-[3-{(2,3R)-3-[(ethanesulfonyl)amino]-4,4-difluoropyrrolidin-2-yl}methyl)-2-fluorophenoxy]-5-methylpyridin-2-yl}glycine dihydrochloride (140 mg) in DMF (140 mL) at room temperature and stirred for 12 hours. The reaction mixture was concentrated to dryness. The residue was purified by preparative TLC ($SiO_2$, EtOAc/PE) to afford a mixture of the title compound and its isomer. The isomeric mixture was purified by preparative SFC (column: DAICEL CHIRALCEL OJ, mobile phase: $CO_2$/EtOH (containing 0.1% ammonium hydroxide)) to give the title compound (15.7 mg, shorter retention time). 1H NMR (400 MHZ, $CDCl_3$) δ ppm 1.42-1.53 (3H, m), 2.18-2.29 (3H, m), 2.72-3.28 (5H, m), 3.61-3.96 (2H, m), 4.00-4.38 (3H, m), 4.44-4.64 (1H, m), 4.96-5.22 (1H, m), 6.06-6.29 (1H, m), 6.95-7.18 (3H, m), 7.26 (1H, br s).

Example 100

N-[(15aS,16R)-9,9,17,17,20-Pentafluoro-7-methyl-1-oxo-2,3,15a,16,17,18-hexahydro-1H,9H,15H-4,8-(azeno)-14,10-(metheno) pyrrolo[1,2-c][1,3]diazacycloheptadecin-16-yl]ethanesulfonamide A) tert-Butyl (2S,3R)-2-{[3-(6-cyano-3-methylpyridine-2-carbonyl)-2-fluorophenyl]methyl}-3-[(ethanesulfonyl)amino]-4,4-difluoropyrrolidine-1-carboxylate A mixture of tert-butyl (2S,3R)-3-[(ethanesulfonyl) amino]-4,4-difluoro-2-{[2-fluoro-3-(4,4,5,5-tetramethyl-1,3,2-dioxaborolan-2-yl)phenyl]methyl}pyrrolidine-1-carboxylate (1.0 g), 6-bromo-5-methyl-pyridine-2-carbonitrile (424 mg), Pd(OAc) 2 (21 mg), 1,3-bis(2,4,6-trimethylphenyl) imidazol-1-ium chloride (63 mg) and cesium carbonate (1.19 g) in 1,4-dioxane (30 mL) was stirred at 80° C. under an atmosphere of carbon monoxide (50 psi) for 24 hours. The reaction mixture was concentrated under reduced pressure and the residue was purified by silica gel column chromatography (EtOAc/PE) to give the title compound (337 mg).

MS: $[M+H]^+$ 567.1.

B) tert-Butyl (2S,3R)-2-({3-[(6-cyano-3-methylpyridin-2-yl) (difluoro)methyl]-2-fluorophenyl}methyl)-3-[(ethanesulfonyl)amino]-4,4-difluoropyrrolidine-1-carboxylate tert-Butyl (2S,3R)-2-{[3-(6-cyano-3-methylpyridine-2-carbonyl)-2-fluorophenyl]methyl}-3-[(ethanesulfonyl) amino]-4,4-difluoropyrrolidine-1-carboxylate (234 mg) and bis(2-methoxyethyl)aminosulfur trifluoride (4.55 g) were combined in a reaction vessel and stirred at 65° C. for 24 hours. The reaction mixture was quenched with saturated sodium bicarbonate aqueous solution and extracted with EtOAc three times. The combined organic phases were washed with brine, dried over anhydrous sodium sulfate, filtered, and concentrated under reduced pressure. The crude isolate was purified by preparative HPLC (column: Boston Green ODS, mobile phase: 0.2% formic acid aqueous solution/acetonitrile) to give the title compound (128 mg).

MS: $[M+H]^+$ 589.0.

C) tert-Butyl (2S,3R)-2-[(3-{[6-(aminomethyl)-3-methylpyridin-2-yl](difluoro)methyl}-2-fluorophenyl)methyl]-3-[(ethanesulfonyl)amino]-4,4-difluoropyrrolidine-1-carboxylate Sodium borohydride (82.6 mg) was added to a solution of tert-butyl (2S,3R)-2-({3-[(6-cyano-3-methylpyridin-2-yl)(difluoro)methyl]-2-fluorophenyl}methyl)-3-[(ethanesulfonyl)amino]-4,4-difluoropyrrolidine-1-carboxylate (128 mg) and nickel (II) chloride hexahydrate (52.3 mg) in MeOH (5.0 mL) at 0° C. The reaction mixture was warmed to 20° C. and stirred for 2 hours. The reaction mixture was quenched with water and extracted with EtOAc three times. The combined organic phases were washed with brine, dried over anhydrous sodium sulfate, filtered, and concentrated under reduced pressure to give the title compound (98 mg).

MS: $[M+H]^+$ 593.1.

D) N-{(2S,3R)-2-[(3-{[6-(Aminomethyl)-3-methylpyridin-2-yl](difluoro)methyl}-2-fluorophenyl)methyl]-4,4-difluoropyrrolidin-3-yl}ethanesulfonamide trihydrochloride A solution of tert-butyl (2S,3R)-2-[(3-{[6-(aminomethyl)-3-methylpyridin-2-yl](difluoro)methyl}-2-fluorophenyl)methyl]-3-[(ethanesulfonyl)amino]-4,4-difluoropyrrolidine-1-carboxylate (98 mg) in 4 M hydrogen chloride in 1,4-dioxane (5.4 mL) was stirred at ambient temperature for 3 hours. The mixture was concentrated under reduced pressure to give the title compound (99.5 mg).

MS: $[M+H]^+$ 493.0.

E) N-[(15aS,16R)-9,9,17,17,20-Pentafluoro-7-methyl-1-oxo-2,3,15a,16,17,18-hexahydro-1H,9H,15H-4,8-(azeno)-14,10-(metheno) pyrrolo[1,2-c][1,3]diazacycloheptadecin-16-yl]ethanesulfonamide To a suspension of N-{(2S,3R)-2-[(3-{[6-(aminomethyl)-3-methylpyridin-2-yl](difluoro)methyl}-2-fluorophenyl)methyl]-4,4-difluoropyrrolidin-3-yl}ethanesulfonamide trihydrochloride (99.5 mg) in THF (15 mL) at 0° C. was added DIPEA (173 UL), followed by 1,1'-carbonyldiimidazole (40.2 mg). The reaction mixture was heated to 45° C. and stirred at temperature, under nitrogen atmosphere, for 16 hours. The mixture was concentrated under reduced pressure to afford the crude residue which was purified by preparative HPLC (column: Phenomenex C18, mobile phase: 10 mM ammonium bicarbonate aqueous solution (containing 0.05% ammonium hydroxide)/acetonitrile) to give the title compound (26.4 mg).

$^1$H NMR (400 MHZ, $CDCl_3$) δ ppm 1.44 (3H, dt, J=12.0, 7.3 Hz), 2.64 (3H, br d, J=11.4 Hz), 2.78-3.01 (1H, m), 3.08-3.28 (2H, m), 3.34-3.61 (1H, m), 3.69-4.15 (2H, m), 4.18-4.85 (4H, m), 5.13-5.83 (2H, m), 7.10-7.24 (2H, m), 7.38-7.68 (3H, m).

Example 102

N-[(15aS,16R)-17,17,20-Trifluoro-7-methyl-1-oxo-1,2,15a,16,17,18-hexahydro-9H,15H-4,8-(azeno)-10,14-(metheno) pyrrolo[1,2-d][1, 4]oxazacycloheptadecin-16-yl]ethanesulfonamide A) (3-Methylpyridin-2-yl)methyl acetate To a solution of (3-methyl-2-pyridyl) methanol (2.0 g) in THE (40 mL) was added acetic anhydride (2.30 mL), pyridine (2.49 mL) and DMAP (199 mg). The mixture was stirred at 20° C. for 12 hours. The reaction mixture was diluted with water and saturated aqueous sodium bicarbonate solution, then extracted with EtOAc. The organic layer was dried over anhydrous sodium sulfate, filtered, and concentrated under reduced pressure. The residue was purified by silica gel column chromatography (EtOAc/PE) to give the title compound (2.4 g).

$^1$H NMR (400 MHZ, $CDCl_3$) 0 ppm 2.13 (3H, s), 2.36 (3H, s), 5.23 (2H, s), 7.17 (1H, dd, J=7.6, 4.8 Hz), 7.49 (1H, d, J=7.0 Hz), 8.44 (1H, d, J=4.1 Hz).

B) (3-Methyl-1-oxido-pyridin-1-ium-2-yl)methyl acetate

To a solution of (3-methylpyridin-2-yl)methyl acetate (2.4 g) in CH2Cl2 (50 mL) was added m-chloroperoxybenzoic acid (4.42 g, 85% purity). The mixture was stirred at 20° C. for 2 hours. The reaction mixture was diluted with water, quenched with sodium sulfite (5 g), basified with saturated aqueous sodium bicarbonate solution until pH=8, and extracted with EtOAc. The organic layer was dried over sodium and anhydrous sulfate, filtered, concentrated under reduced pressure. The residue was purified by silica gel column chromatography (EtOAc/PE) to give the title compound (4 g).

$^1$H NMR (400 MHz, MeOH-$d_4$) δ ppm 2.09 (3H, s), 2.50 (3H, s), 5.47 (2H, s), 7.43-7.51 (2H, m), 8.27 (1H, d, J=6.2 Hz).

C) (6-Chloro-3-methylpyridin-2-yl)methyl acetate

A mixture of (3-methyl-1-oxido-pyridin-1-ium-2-yl) methyl acetate (2 g) and phosphoryl chloride (10 mL) was stirred under nitrogen atmosphere at 90° C. for 1 hour. The reaction mixture was concentrated under reduced pressure. The residue was diluted with water, basified with saturated aqueous sodium bicarbonate solution until pH=8, and extracted with EtOAc. The organic layer was dried over anhydrous sodium sulfate, filtered, and concentrated under reduced pressure. The residue was purified by silica gel column chromatography (EtOAc/PE) to give the title compound (600 mg).

$^1$H NMR (400 MHZ, $CDCl_3$) 0 ppm 2.13 (3H, s), 2.34 (3H, s), 5.18 (2H, s), 7.22 (1H, d, J=8.0 Hz), 7.37-7.48 (1H, m).

D) tert-Butyl {[6-(hydroxymethyl)-5-methylpyridin-2-yl]oxy}acetate

To a solution of (6-chloro-3-methylpyridin-2-yl)methyl acetate (400 mg), tert-butyl 2-hydroxyacetate (297 mg), cesium carbonate (1.10 g) and dicyclohexyl(2',4',6'-triisopropyl-[1,1'-biphenyl]-2-yl)phosphine (268 mg) in 1,4-dioxane (5 mL) was added Pd2 (dba) 3 (103 mg) under nitrogen atmosphere. The mixture was stirred at 100° C. for 2 hours under nitrogen atmosphere. The mixture was diluted with water and extracted with EtOAc. The organic layer was washed with brine, dried over anhydrous sodium sulfate, filtered, and concentrated under reduced pressure. The residue was purified by silica gel column chromatography (EtOAc/PE) to give the title compound (140 mg).

MS: $[M+H]^+$ 254.2.

E) tert-Butyl {[6-(chloromethyl)-5-methylpyridin-2-yl]oxy}acetate

To a solution of tert-butyl {[6-(hydroxymethyl)-5-methylpyridin-2-yl]oxy}acetate (110 mg) in CH2Cl2 (4 mL) was added thionyl chloride (207 μL). The mixture was stirred at 25° C. for 1 hour. The mixture was quenched with saturated aqueous sodium bicarbonate solution and extracted with EtOAc. The organic layer was washed with brine, dried over anhydrous sodium sulfate, filtered, and concentrated under reduced pressure to give the title compound (80 mg).

MS: $[M+H]^+$ 272.2.

F) tert-Butyl (2S,3R)-2-[(3-{[6-(2-tert-butoxy-2-oxoethoxy)-3-methylpyridin-2-yl]methyl}-2-fluorophenyl)methyl]-3-[(ethanesulfonyl)amino]-4,4-difluoropyrrolidine-1-carboxylate To a solution of tert-butyl {[6-(chloromethyl)-5-methylpyridin-2-yl]oxy}acetate (80 mg) and tert-butyl (2S,3R)-3-[(ethanesulfonyl)amino]-4,4-difluoro-2-{[2-fluoro-3-(4,4,5,5-tetramethyl-1,3,2-dioxaborolan-2-yl)phenyl]methyl}pyrrolidine-1-carboxylate (110 mg) in 1,4-dioxane (2 mL) and water (0.5 mL) was added potassium carbonate (80.7 mg) and Pd(dppf)$Cl_2$·$CH_2Cl_2$ (15.9 mg) under nitrogen atmosphere. The mixture was stirred at 100° C. for 3 hours under nitrogen atmosphere. The mixture was diluted with water and extracted with EtOAc. The organic layer was washed with brine, dried over anhydrous sodium sulfate, filtered, and concentrated under reduced pressure. The residue was purified by silica gel column chromatography (EtOAc/PE) to afford the title compound (120 mg).

MS: $[M+H]^+$ 658.3.

G) [(6-{[3-({(2S,3R)-3-[(Ethanesulfonyl)amino]-4,4-difluoropyrrolidin-2-yl}methyl)-2-fluorophenyl]methyl}-5-methylpyridin-2-yl)oxy]acetic acid dihydrochloride A solution of tert-butyl (2S,3R)-2-[(3-{[6-(2-tert-butoxy-2-oxoethoxy)-3-methylpyridin-2-yl]methyl}-2-fluorophenyl)methyl]-3-[(ethanesulfonyl)amino]-4,4-difluoropyrrolidine-1-carboxylate (120 mg) in 4 M hydrogen chloride in 1,4-dioxane (5 mL) was stirred at 25° C. for 12 hours. The mixture was concentrated under reduced pressure to give the title compound (95 mg).

MS: $[M+H]^+$ 502.3.

H) N-[(15aS,16R)-17,17,20-Trifluoro-7-methyl-1-oxo-1,2,15a,16,17,18-hexahydro-9H,15H-4,8-(azeno)-10,14-(metheno) pyrrolo[1,2-d][1, 4]oxazacycloheptadecin-16-yl]ethanesulfonamide To a solution of [(6-{[3-{(2,3R)-3-[(ethanesulfonyl)amino]-4,4-difluoropyrrolidin-2-yl}methyl)-2-fluorophenyl]methyl}-5-methylpyridin-2-yl)oxy]acetic acid mL) was added dihydrochloride (45 mg) in EtOAc (260 dibutyldiphosphonic acid (37.8 mg, 50% purity) and pyridine (130 mL). The mixture was stirred at 25° C. for 3 hours. The reaction mixture was quenched by addition water and extracted with EtOAc three times. The combined organic layers were washed with brine, dried over anhydrous sodium sulfate, filtered, and concentrated under reduced pressure. The residue was purified by preparative HPLC (column: YMC-Actus Triart C18, mobile phase: 0.1% TFA aqueous solution/acetonitrile) to give the title compound (20.5 mg).

$^1$H NMR (400 MHZ, DMSO-$d_6$) δ ppm 1.30 (3H, t, J=7.3 Hz), 2.37 (3H, s), 2.62 (1H, br d, J=14.2 Hz), 2.94 (1H, br t, J=12.9 Hz), 3.14-3.23 (2H, m), 3.93 (1H, s), 4.08-4.44 (4H, m), 4.47-4.55 (2H, m), 4.59-4.67 (1H, m), 6.47-6.56 (1H, m), 6.83-6.91 (1H, m), 6.92-6.99 (1H, m), 7.05-7.10 (1H, m), 7.44 (1H, d, J=8.3 Hz), 8.23-8.30 (1H, m).

Examples 105 and 106

N-[(9R,15aS,16R)-17,17,20-Trifluoro-7,9-dimethyl-1-oxo-2,3,15a,16,17,18-hexahydro-1H,9H,15H-4,8-(azeno)-10,14-(metheno) pyrrolo[1,2-c][1,3]diazacycloheptadecin-16-yl]ethanesulfonamide and N-[(9S,15aS,16R)-17,17,20-trifluoro-7,9-dimethyl-1-oxo-2,3,15a,16,17,18-hexahydro-1H,9H,15H-4,8-(azeno)-10,14-(metheno) pyrrolo[1,2-c][1,3]diazacycloheptadecin-16-yl]ethanesulfonamide A) 1-(3-Methylpyridin-2-yl)ethenyl trifluoromethanesulfonate To a solution of 1-(3-methyl-2-pyridyl) ethanone (2.0 g) in toluene (50 mL) at 0° C. was added trifluoromethanesulfonic anhydride (8.35 g) and DIPEA (5.2 mL). The mixture was heated to 45° C. and stirred at temperature for 1 hour. The mixture was concentrated under reduced pressure. The residue was purified by silica gel column chromatography (EtOAc/heptane) to give the title compound (1.01 g).

MS: $[M+H]^+$ 268.0.

B) tert-Butyl (2S,3R)-3-[(ethanesulfonyl)amino]-4,4-difluoro-2-({2-fluoro-3-[1-(3-methylpyridin-2-yl)ethenyl]phenyl}methyl)pyrrolidine-1-carboxylate A mixture of 1-(3-methylpyridin-2-yl)ethenyl trifluoromethanesulfonate (509 mg), tert-butyl (2S,3R)-3-[(ethanesulfonyl)amino]-4,4-difluoro-2-{[2-fluoro-3-(4,4,5,5-tetramethyl-1,3,2-dioxaborolan-2-yl)phenyl]methyl}pyrrolidine-1-carboxylate (500 mg), Pd($PPh_3$) 4 (211 mg), sodium carbonate (193 mg) in 1,4-dioxane (10 mL) and water (3 mL) was degassed and purged with nitrogen three times. The mixture was then stirred at 100° C. for 2 hours under nitrogen atmosphere and then concentrated under reduced pressure. The residue was purified by silica gel column chromatography (EtOAc/heptane) to give the title compound (650 mg).

MS: $[M+H]^+$ 540.3.

C) tert-Butyl (2S,3R)-3-[(ethanesulfonyl)amino]-4,4-difluoro-2-({2-fluoro-3-[1-(3-methylpyridin-2-yl)ethyl]phenyl}methyl)pyrrolidine-1-carboxylate To a solution of tert-butyl (2S,3R)-3-[(ethanesulfonyl)amino]-4,4-difluoro-2-({2-fluoro-3-[1-(3-methylpyridin-2-yl)ethenyl]phenyl}methyl)pyrrolidine-1-carboxylate (620 mg) in EtOH (10 mL) was added 10% palladium on carbon (418 mg) under nitrogen atmosphere. The suspension was degassed and purged with hydrogen three times, then stirred under hydrogen atmosphere (20 psi) at 25° C. for 16 hours. The mixture was filtered, and the filtrate was concentrated under reduced pressure to give the title compound (630 mg).

MS: $[M+H]^+$ 542.3.

D) tert-Butyl (2S,3R)-3-[(ethanesulfonyl)amino]-4,4-difluoro-2-({2-fluoro-3-[1-(3-methyl-1-oxido-pyridin-1-ium-2-yl)ethyl]phenyl}methyl)pyrrolidine-1-carboxylate m-Chloroperoxybenzoic acid (118 mg, 85% purity) was added to a solution of tert-butyl (2S,3R)-3-[(ethanesulfonyl)amino]-4,4-difluoro-2-({2-fluoro-3-[1-(3-methylpyridin-2-yl)ethyl]phenyl}methyl)pyrrolidine-1-carboxylate (280 mg) in CH2Cl2 (20 mL) at room temperature. The mixture was stirred at room temperature for 16 hours. The mixture was diluted with CH2Cl2 (20 mL) and then washed with a saturated aqueous sodium carbonate solution (10 mL). The phases were separated, and the organic layer was washed with a saturated aqueous sodium thiosulfate solution (10 mL), then again with saturated aqueous sodium carbonate solution (10 mL). The organic phase was dried over anhydrous sodium sulfate, filtered, and concentrated under reduced pressure to give the title compound (260 mg).

MS: $[M+H]^+$ 558.3.

E) tert-Butyl (2S,3R)-2-({3-[1-(6-cyano-3-methylpyridin-2-yl)ethyl]-2-fluorophenyl}methyl)-3-[(ethanesulfonyl)amino]-4,4-difluoropyrrolidine-1-carboxylate To a solution of tert-butyl (2S,3R)-3-[(ethanesulfonyl)amino]-4,4-difluoro-2-({2-fluoro-3-[1-(3-methyl-1-oxido-pyridin-1-ium-2-yl)ethyl]phenyl}methyl)pyrrolidine-1-carboxylate (260 mg) in 1,2-dichloroethane (5 mL) was added trimethylsilyl cyanide (91 μL) and N, N-dimethylcarbamoyl chloride (77.9 mg). The mixture was stirred at 80° C. for 5 hours and then concentrated under reduced pressure. The crude isolate was purified by silica gel column chromatography (EtOAc/PE) to give the title compound (155 mg).

MS: $[M+H]^+$ 567.1.

F) tert-Butyl (2S,3R)-2-[(3-{1-[6-(aminomethyl)-3-methylpyridin-2-yl]ethyl}-2-fluorophenyl)methyl]-3-[(ethanesulfonyl)amino]-4,4-difluoropyrrolidine-1-carboxylate Sodium borohydride (120 mg) was slowly added to a solution of tert-butyl (2S,3R)-2-({3-[1-(6-cyano-3-methylpyridin-2-yl)ethyl]-2-fluorophenyl}methyl)-3-[(ethanesulfonyl)amino]-4,4-difluoropyrrolidine-1-carboxylate (135 mg) and nickel (II) chloride hexahydrate (45.3 mg) in MeOH (12 mL) at 0° C. The mixture was stirred at 0° C. for 2 hours. The mixture was diluted with CH2Cl2 and the reaction quenched with water, resulting in precipitation of solids. The solids were removed by filtration and the phases of the filtrate were separated. Organic phase was held in reserve. The aqueous layer was extracted with CH2Cl2 three times. The combined organic layer was washed with brine, dried over anhydrous sodium sulfate, filtered, and concentrated under reduced pressure to give the title compound (136 mg).

MS: $[M+H]^+$ 571.2.

G) N-{(2S,3R)-2-[(3-{1-[6-(Aminomethyl)-3-methylpyridin-2-yl]ethyl}-2-fluorophenyl)methyl]-4,4-difluoropyrrolidin-3-yl}ethanesulfonamide trihydrochloride A solution of tert-butyl (2S,3R)-2-[(3-{1-[6-(aminomethyl)-3-methylpyridin-2-yl]ethyl}-2-fluorophenyl)methyl]-3-[(ethanesulfonyl)amino]-4,4-difluoropyrrolidine-1-carboxylate (140 mg) in 4 M hydrogen chloride in 1,4-dioxane (8 mL) was stirred at ambient temperature for 2 hours. The mixture was concentrated under reduced pressure to give the title compound (122 mg).

MS: $[M+H]^+$ 471.2.

H) N-[(9R,15aS,16R)-17,17,20-Trifluoro-7,9-dimethyl-1-oxo-2,3,15a,16,17,18-hexahydro-1H,9H,15H-4,8-(azeno)-10,14-(metheno) pyrrolo[1,2-c][1,3]diazacycloheptadecin-16-yl]ethanesulfonamide and N-[(9S,15aS,16R)-17,17,20-trifluoro-7,9-dimethyl-1-oxo-2,3,15a,16,17,18-hexahydro-1H,9H,15H-4,8-(azeno)-10,14-(metheno) pyrrolo[1,2-c] [1,3]diazacycloheptadecin-16-yl]ethanesulfonamide To a mixture of N-{(2S,3R)-2-[(3-{1-[6-(aminomethyl)-3-methylpyridin-2-yl]ethyl}-2-fluorophenyl)methyl]-4,4-difluoropyrrolidin-3-yl}ethanesulfonamide trihydrochloride (122 mg) in DMF (4.5 mL) and THE (105 mL) was added N, N'-disuccinimidyl carbonate (48.5 mg) and N-methylmorpholine (138 μL) at room temperature. The mixture was stirred at room temperature for 16 hours and then concentrated under reduced pressure. The residue was partitioned between CH2Cl2 and water. The organic layer was separated and washed with brine, dried over anhydrous sodium sulfate, filtered, and concentrated under reduced pressure. The crude isolate was purified by silica gel column chromatography (MeOH/CH2Cl2). The residue was purified by preparative HPLC (column: Boston Prime C18, mobile phase: 10 mM ammonium bicarbonate aqueous solution (containing 0.05% ammonium hydroxide)/acetonitrile) followed by purification by SFC column: DAICEL CHIRALCEL OD-H; mobile phase: $CO_2$/EtOH (containing 0.1% ammonium hydroxide)) to give diastereomer A (20 mg, shorter retention time) and diastereomer B (27 mg, longer retention time).

Diastereomer A (20 mg) was further purified by SFC (column: DAICEL CHIRALCEL OD-H; mobile phase: $CO_2$/EtOH (containing 0.1% ammonium hydroxide)) to give one of the title compound (9.5 mg, 96% purity).

$^1H$ NMR (400 MHZ, $CDCl_3$) δ ppm 1.29-1.43 (3H, m), 1.64 (3H, br d, J=5.2 Hz), 2.27-2.48 (3H, m), 2.66 (1H, br d, J=12.8 Hz), 2.95 (1H, br t, J=12.0 Hz), 3.02-3.21 (2H, m), 3.73-4.43 (5H, m), 4.44-4.59 (1H, m), 4.59-4.76 (1H, m), 4.80-4.96 (1H, m), 6.73 (1H, br d, J=7.6 Hz), 6.79-7.01 (2H, m), 7.05-7.14 (1H, m), 7.23-7.39 (1H, m).

Diastereomer B (27 mg) was further purified by SFC (column: DAICEL CHIRALPAK AD (250×30 mm×10 μm); mobile phase: ethanol (containing 0.1% ammonium hydroxide) —$CO_2$; isocratic B, 30%) to give another one of the title compound (8.5 mg). 1H NMR (400 MHZ, $CDCl_3$) 0 ppm 1.39 (3H, t, J=7.2 Hz), 1.65-1.82 (3H, m), 2.32-2.48 (4H, m), 3.03-3.19 (2H, m), 3.3-3.52 (2H, m), 3.99 (1H, br d, J=16.8 Hz), 4.12-4.34 (2H, m), 4.42 (1H, br dd, J=16.8, 4.0 Hz), 4.57-4.74 (1H, m), 4.81-5.00 (2H, m), 6.53 (1H, br s), 6.77-6.95 (3H, m), 7.32 (1H, d, J=7.8 Hz).

Example 111

N-[(2S,15aS,16R)-17,17,20-Trifluoro-2,7-dimethyl-1-oxo-1,2,15a,16,17,18-hexahydro-9H,15H-4,8-(azeno)-10,14-(metheno) pyrrolo[1,2-d][1, 4]oxazacycloheptadecin-16-yl]ethanesulfonamide A) tert-Butyl (2S,3R)-3-[(ethanesulfonyl)amino]-4,4-difluoro-2-({2-fluoro-3-[(6-fluoro-3-methylpyridin-2-yl)methyl]phenyl}methyl)pyrrolidine-1-carboxylate To a 10 mL microwave vial, equipped with stir bar and rubber septum, was added tert-butyl (2S,3R)-3-[(ethanesulfonyl)amino]-4,4-difluoro-2-{[2-fluoro-3-(4,4,5,5-tetramethyl-1,3,2-dioxaborolan-2-yl)phenyl]methyl}pyrrolidine-1-carboxylate (250 mg), Pd(dppf) $C_{12}$. CH2Cl2 (37 mg), 2-(chloromethyl)-6-fluoro-3-methyl-pyridine hydrochloride (119 mg), aqueous 2 M sodium carbonate solution (1.0 mL) and 1,2-dimethoxyethane (3.30 ml). The reaction mixture was purged with nitrogen and the rubber septum was replaced with a crimp cap. Reaction mixture was heated in a microwave reactor at 100° C. for 1 hour. The reaction mixture was diluted with water and then extracted with CH2Cl2 twice. The combined organic layers were washed with brine, dried over anhydrous sodium sulfate, decanted, and concentrated under reduced pressure. The crude isolate was purified by silica gel column chromatography (EtOAc/heptane) to give the title compound (219 mg).

MS: $[M+H]^+$ 546.5.

B) ((2S)-2-[(6-{[3-({(2S,3R)-1-(tert-Butoxycarbonyl)-3-[(ethanesulfonyl)amino]-4,4-difluoropyrrolidin-2-yl}methyl)-2-fluorophenyl]methyl}-5-methylpyridin-2-yl)oxy]propanoic acid 60% Sodium hydride (29 mg) was added portion-wise to a stirred solution of tert-butyl (2S,3R)-3-[(ethanesulfonyl)amino]-4,4-difluoro-2-({2-fluoro-3-[(6-fluoro-3-methylpyridin-2-yl)methyl]phenyl}methyl)pyrrolidine-1-carboxylate (134 and mg) the tert-butyl (S)-2-hydroxypropanoate (72 mg) in THE (dry) (1.0 mL) at room temperature. The reaction mixture was then heated at 50° C. for 3 hours. Added tert-butyl (S)-2-hydroxypropanoate (72 mg) and 60% sodium hydride (29 mg) to the mixture and stirred at 50° C. for 2 hours. Added tert-butyl (S)-2-hydroxypropanoate (72 mg) and 60% sodium hydride (29 mg) to the mixture and stirred at 50° C. for an additional 2 hours. The reaction mixture was cooled to room temperature. The reaction was quenched by addition of water and aqueous 1 M hydrochloric acid was added until pH=3. The mixture was extracted with CH2Cl2 twice and the combined organic phases were dried over anhydrous sodium sulfate, filter and concentrated under reduced pressure. The residue was purified by reverse-phase preparative HPLC (column: Gemini® NX-$C_{18}$, mobile phase: 0.05% TFA aqueous solution/acetonitrile) to give the title compound (65 mg).

MS: $[M+H]^+$ 616.5.

C) (2S)-2-[(6-{[3-{(2,3R)-3-[(Ethanesulfonyl)amino]-4,4-difluoropyrrolidin-2-yl}methyl)-2-fluorophenyl]methyl}-5-methylpyridin-2-yl)oxy]propanoic acid dihydrochloride A solution of ((2S)-2-[(6-{[3-({(2S,3R)-1-(tert-butoxycarbonyl)-3-[(ethanesulfonyl)amino]-4,4-difluoropyrrolidin-2-yl}methyl)-2-fluorophenyl]methyl}-5-methylpyridin-2-yl)oxy]propanoic acid (65 mg) in 4 M hydrogen chloride in 1,4-dioxane (0.50 mL) was stirred at room temperature for 1 hour. The solvents were removed under reduced pressure to afford the title compound (50 mg).

MS: $[M+H]^+$ 516.3.

D) N-[(2S,15aS,16R)-17,17,20-Trifluoro-2,7-dimethyl-1-oxo-1,2,15a,16,17,18-hexahydro-9H,15H-4,8-(azeno)-10,14-(metheno) pyrrolo[1,2-d][1,4]oxazacycloheptadecin-16-yl]ethanesulfonamide A solution of (25)-2-[(6-{[3-{(2,3R)-3-[(ethanesulfonyl)amino]-4,4-difluoropyrrolidin-2-yl}methyl)-2-fluorophenyl]methyl}-5-methylpyridin-2-yl)oxy]propanoic acid dihydrochloride (50 mg) in DMF (5.0 mL) was added dropwise to a solution of HATU (39 mg) and DIPEA (89 uL) in DMF (25 mL) over a period of 15 minutes. The reaction mixture was stirred at room temperature overnight. The mixture was concentrated to dryness and the residue was purified by reverse-phase preparative HPLC (Gemini® NX-C18, mobile phase: % 0.05 TFA aqueous solution/acetonitrile). The isolated product (TFA salt) was dissolved in MeOH and passed through an Agilent Technologies StratoSphere SPE PL-HCO3 MP Resin cartridge to remove TFA. The filtrate was concentrated under reduced pressure to afford the title compound (5 mg).

$^1$H NMR (400 MHZ, MeOH-$d_4$) δ ppm 1.41 (3H, t, J=7.3 Hz), 1.47 (3H, d, J=6.8 Hz), 2.38 (3H, s), 2.69-2.86 (1H, m), 3.09-3.24 (3H, m), 3.90 (1H, dd, J=14.0, 1.6 Hz), 4.07 (1H, d, J=14.1 Hz), 4.25-4.39 (3H, m), 4.70-4.81 (2H, m), 6.44 (1H, d, J=8.3 Hz), 6.82-6.92 (2H, m), 7.06-7.13 (1H, m), 7.37 (1H, d, J=8.3 Hz).

The compounds of the Examples are shown in the following tables. In these tables, MS represents an observed molecular ion (found). The compounds described in Examples 3, 6, 8, 9, 11-18, 20, 21, 23-32, 34, 35, 37-39, 41-50, 52, 53, 55, 57, 60, 61, 63-67, 69-96, 98, 101, 103, 104, and 107-110 were synthesized in the same manner as in the reaction and purification described in the above-mentioned Examples.

TABLE 1-1

| Ex. No. | IUPAC Name | Structure | MS |
|---|---|---|---|
| 1 | N-[(15aS,16S)-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide | 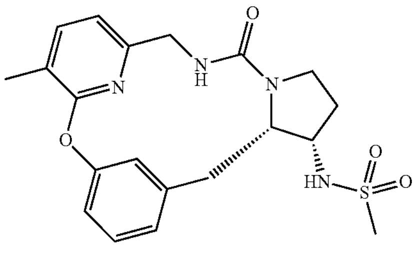 [SMILES: Cc1ccc2nc1Oc1cccc(c1)C[C@H]1[C@@H](NS(C)(=O)=O)CCN1C(=O)NC2] | 417.3 |

TABLE 1-1-continued

| Ex. No. | IUPAC Name | Structure | MS |
|---|---|---|---|
| 2 | N-[(15aS,16R)-17,17-difluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide | 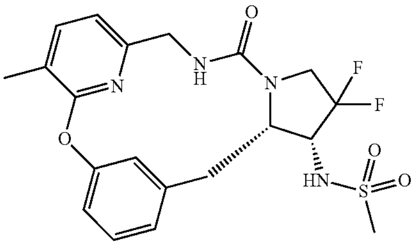 [SMILES: Cc1ccc2nc1Oc1cccc(c1)C[C@H]1[C@@H](NS(C)(=O)=O)C(F)(F)CN1C(=O)NC2] | 453.3 |
| 3 | N-[(15aS,16S)-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 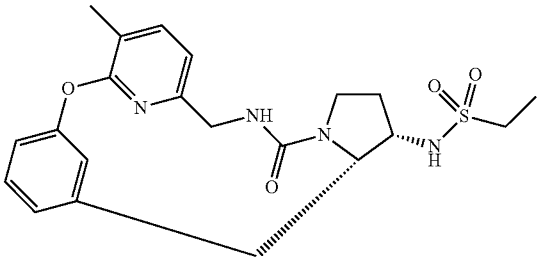 [SMILES: CCS(=O)(=O)N[C@H]1CCN2C(=O)NCc3ccc(C)c(n3)Oc3cccc(c3)C[C@@H]12] | 431.3 |
| 4 | N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide | 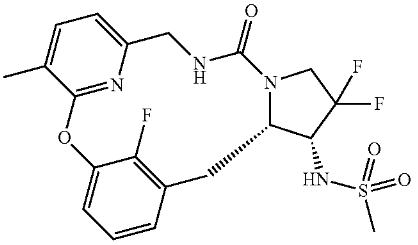 [SMILES: Cc1ccc2nc1Oc1cccc(c1F)C[C@H]1[C@@H](NS(C)(=O)=O)C(F)(F)CN1C(=O)NC2] | 471.3 |
| 5 | N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 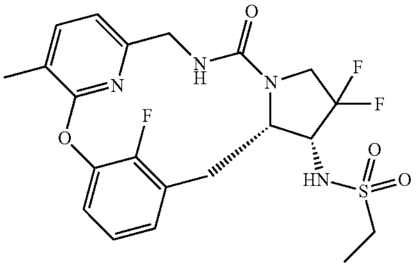 [SMILES: CCS(=O)(=O)N[C@@H]1[C@@H]2Cc3cccc(c3F)Oc3nc(ccc3C)CNC(=O)N2CC1(F)F] | 485.2 |

TABLE 1-2

| Ex. No. | IUPAC Name | Structure | MS |
|---|---|---|---|
| 6 | N-[(15aS,16R)-17,17-difluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 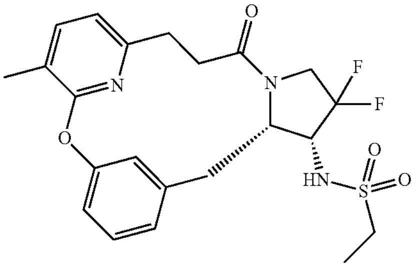 [SMILES: CCS(=O)(=O)N[C@@H]1[C@@H]2Cc3cccc(c3)Oc3nc(ccc3C)CCC(=O)N2CC1(F)F] | 467.3 |

TABLE 1-2-continued

| Ex. No. | IUPAC Name | Structure | MS |
|---|---|---|---|
| 7 | N-[(1S,19aS)-11-methyl-5-oxo-2,3,6,7,19,19a-hexahydro-1H, 5H-8,12-(azeno)-14,18-(metheno)pyrrolo[2,1-h][1,9]oxazacycloheptadecin-1-yl]methanesulfonamide | 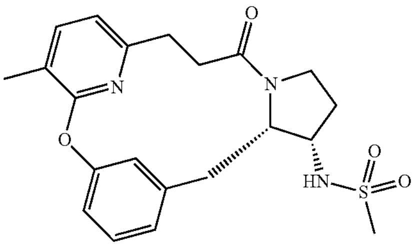 [SMILES: Cc1ccc2nc1Oc1cccc(c1)C[C@H]1[C@@H](NS(C)(=O)=O)CCN1C(=O)CC2] | 416.2 |
| 8 | N-[(15aS,16S)-7-(difluoromethyl)-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 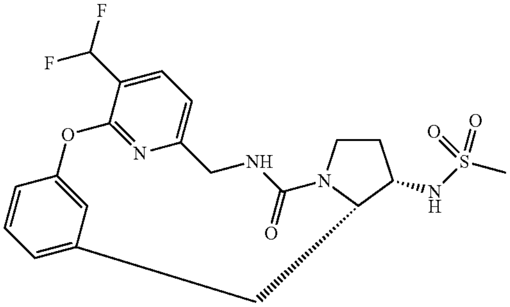 [SMILES: CS(=O)(=O)N[C@H]1CCN2C(=O)NCc3ccc(C(F)F)c(n3)Oc3cccc(c3)C[C@@H]12] | 453.3 |
| 9 | N-[rel-(15aR,16R)-11-fluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide (optical isomer) | 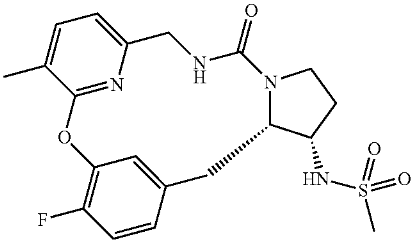 [SMILES: Cc1ccc2nc1Oc1cc(ccc1F)C[C@H]1[C@@H](NS(C)(=O)=O)CCN1C(=O)NC2] | 435.3 |
| 10 | N-[(15aS,16R,17S)-17,20-difluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 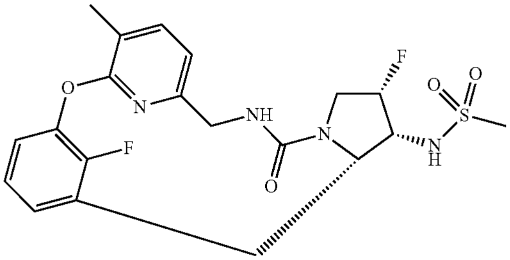 [SMILES: Cc1ccc2nc1Oc1cccc(c1F)C[C@H]1[C@@H](NS(C)(=O)=O)[C@@H](F)CN1C(=O)NC2] | 453.3 |

TABLE 1-3

| Ex. No. | IUPAC Name | Structure | MS |
|---|---|---|---|
| 11 | N,N-dimethyl-N'-[(15aS,16R)-17,17,20-trifluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]sulfuric diamide | 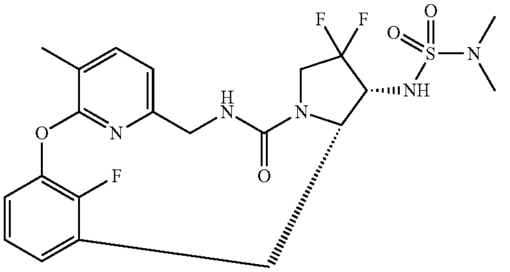 [SMILES: Cc1ccc2nc1Oc1cccc(c1F)C[C@H]1[C@@H](NS(=O)(=O)N(C)C)C(F)(F)CN1C(=O)NC2] | 500.2 |

TABLE 1-3-continued

| Ex. No. | IUPAC Name | Structure | MS |
|---|---|---|---|
| 12 | N-[(15aS,16R,17S)-7-chloro-17,20-difluoro-1-oxo-2,3,15a,16,17,18-hexahydro-1H,15H-4,8:14,10-di(metheno)pyrrolo[1,2-j][1,8,10]oxadiazacyclo-heptadecin-16-yl]methanesulfonamide | 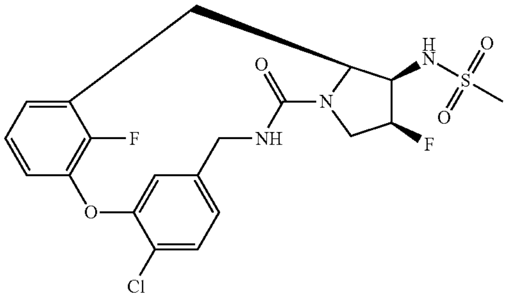 [SMILES: CS(=O)(=O)N[C@H]1[C@@H](F)CN2C(=O)NCc3ccc(Cl)c(c3)Oc3cccc(c3F)C[C@@H]12] | 472.2 |
| 13 | N'-[(15aS,16R)-7-chloro-17,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]-N,N-dimethylsulfuric diamide | 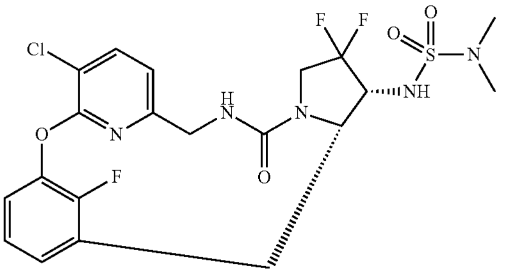 [SMILES: CN(C)S(=O)(=O)N[C@@H]1[C@@H]2Cc3cccc(c3F)Oc3nc(ccc3Cl)CNC(=O)N2CC1(F)F] | 520.2 |
| 14 | N-[(15aS,16R)-7-chloro-17,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 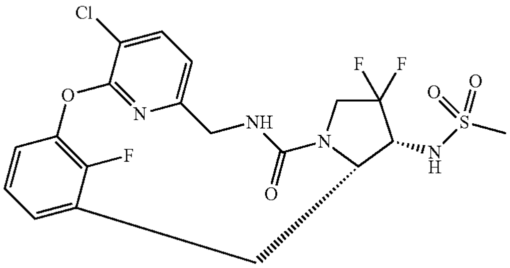 [SMILES: CS(=O)(=O)N[C@@H]1[C@@H]2Cc3cccc(c3F)Oc3nc(ccc3Cl)CNC(=O)N2CC1(F)F] | 491.2 |
| 15 | N-[(15aS,16R,17S)-7-chloro-17,20-difluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 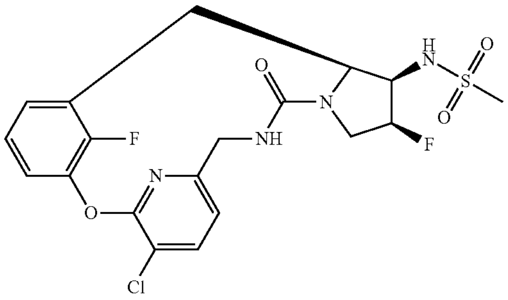 [SMILES: CS(=O)(=O)N[C@H]1[C@@H](F)CN2C(=O)NCc3ccc(Cl)c(n3)Oc3cccc(c3F)C[C@@H]12] | 473.2 |

TABLE 1-4

| Ex. No. | IUPAC Name | Structure | MS |
|---|---|---|---|
| 16 | N-[(15aS,16S)-7-chloro-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide | 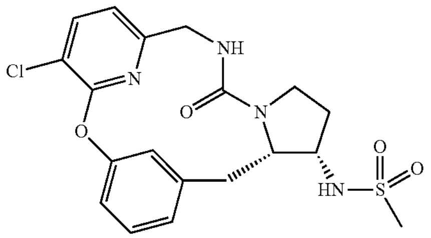 [SMILES: CS(=O)(=O)N[C@H]1CCN2C(=O)NCc3ccc(Cl)c(n3)Oc3cccc(c3)C[C@@H]12] | 437.2 |
| 17 | N-[(15aS,16R)-7-chloro-17,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 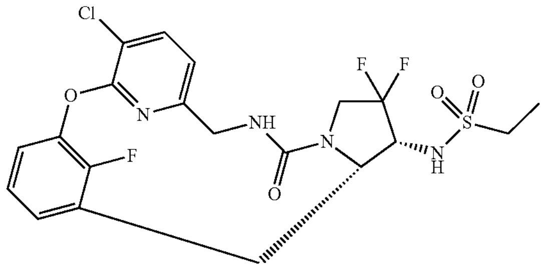 [SMILES: CCS(=O)(=O)N[C@@H]1[C@@H]2Cc3cccc(c3F)Oc3nc(ccc3Cl)CNC(=O)N2CC1(F)F] | 505.1 |
| 18 | N-[(15aS,16R,17S)-7-(difluoromethyl)-17,20-difluoro-1-oxo-2,3,15a,16,17,18-hexahydro-1H,15H-8,4-(azeno)-10,14-(metheno)pyrrolo[1,2-j][1,8,10]oxadiazacyclo-heptadecin-16-yl]methanesulfonamide | 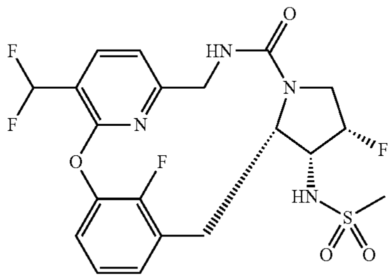 [SMILES: CS(=O)(=O)N[C@H]1[C@@H](F)CN2C(=O)NCc3ccc(C(F)F)c(n3)Oc3cccc(c3F)C[C@@H]12] | 489.2 |
| 19 | 1-fluoro-N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide | 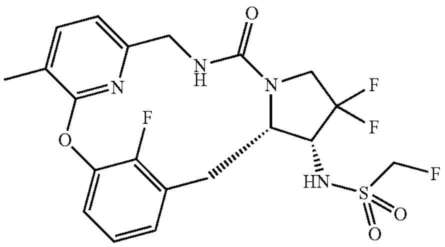 [SMILES: Cc1ccc2nc1Oc1cccc(c1F)C[C@H]1[C@@H](NS(=O)(=O)CF)C(F)(F)CN1C(=O)NC2] | 489.3 |

TABLE 1-5

| Ex. No. | IUPAC Name | Structure | MS |
|---|---|---|---|
| 20 | N-[(15aS,16S)-5,7-difluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 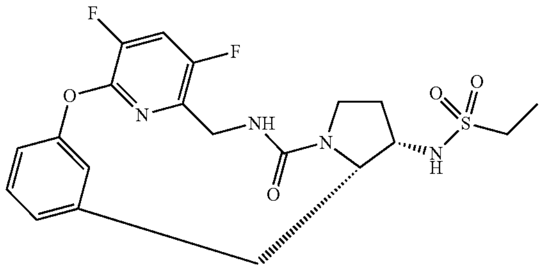 [SMILES: CCS(=O)(=O)N[C@H]1CCN2C(=O)NCc3nc(c(F)cc3F)Oc3cccc(c3)C[C@@H]12] | 453.3 |

TABLE 1-5-continued

| Ex. No. | IUPAC Name | Structure | MS |
| --- | --- | --- | --- |
| 21 | N-[(15aS,16R)-5,7,17,17,20-pentafluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 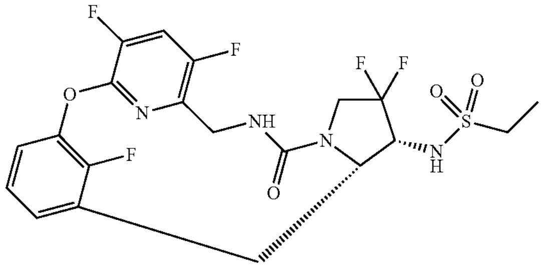 [SMILES: CCS(=O)(=O)N[C@@H]1[C@@H]2Cc3cccc(c3F)Oc3nc(c(F)cc3F)CNC(=O)N2CC1(F)F] | 507.2 |
| 22 | N-[(15aS,16R)-7-chloro-17,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]cyclopropanesulfonamide | 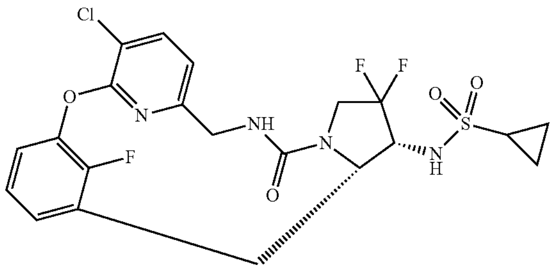 [SMILES: O=C1NCc2ccc(Cl)c(n2)Oc2cccc(c2F)C[C@H]2[C@@H](NS(=O)(=O)C3CC3)C(F)(F)CN12] | 517.2 |
| 23 | N-[(15aS,16R)-17,17,20-trifluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]cyclopropanesulfonamide | 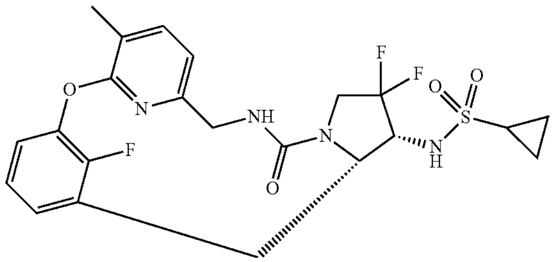 [SMILES: Cc1ccc2nc1Oc1cccc(c1F)C[C@H]1[C@@H](NS(=O)(=O)C3CC3)C(F)(F)CN1C(=O)NC2] | 497.2 |
| 24 | N-[(15aS,16R,17S)-7-chloro-17,20-difluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 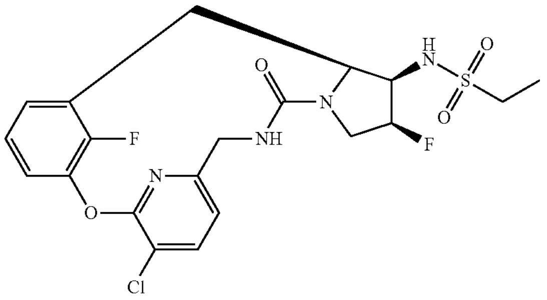 [SMILES: CCS(=O)(=O)N[C@H]1[C@@H](F)CN2C(=O)NCc3ccc(Cl)c(n3)Oc3cccc(c3F)C[C@@H]12] | 487.2 |

TABLE 1-6

| Ex. No. | IUPAC Name | Structure | MS |
| --- | --- | --- | --- |
| 25 | N-[(15aS,16R,17S)-17,20-difluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 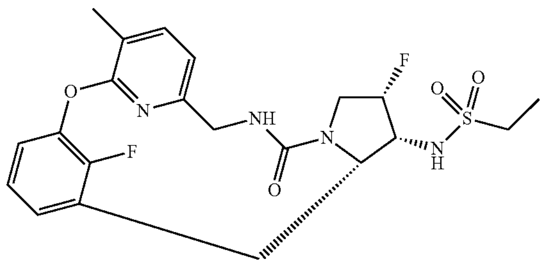 [SMILES: CCS(=O)(=O)N[C@H]1[C@@H](F)CN2C(=O)NCc3ccc(C)c(n3)Oc3cccc(c3F)C[C@@H]12] | 467.3 |

TABLE 1-6-continued

| Ex. No. | IUPAC Name | Structure | MS |
|---|---|---|---|
| 26 | N-[(15aS,16R)-17,17,20-trifluoro-7-methoxy-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 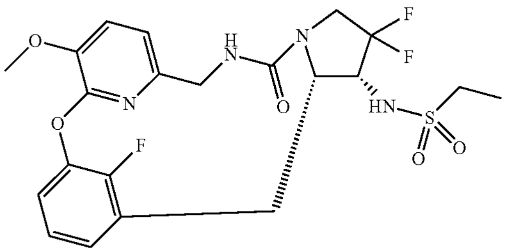 [SMILES: CCS(=O)(=O)N[C@@H]1[C@@H]2Cc3cccc(c3F)Oc3nc(ccc3OC)CNC(=O)N2CC1(F)F] | 501.2 |
| 27 | N-[(15aS,16R,17S)-7-(difluoromethyl)-17,20-difluoro-1-oxo-2,3,15a,16,17,18-hexahydro-1H,15H-8,4-(azeno)-10,14-(metheno)pyrrolo[1,2-j][1,8,10]oxadiazacyclo-heptadecin-16-yl]ethanesulfonamide | 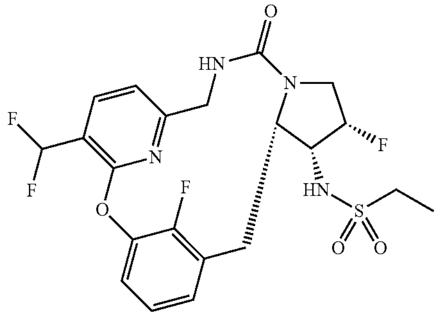 [SMILES: CCS(=O)(=O)N[C@H]1[C@@H](F)CN2C(=O)NCc3ccc(C(F)F)c(n3)Oc3cccc(c3F)C[C@@H]12] | 503.3 |
| 28 | N-[(15aS,16R,17S)-7-(difluoromethyl)-17,20-difluoro-1-oxo-2,3,15a,16,17,18-hexahydro-1H,15H-8,4-(azeno)-10,14-(metheno)pyrrolo[1,2-j][1,8,10]oxadiazacyclo-heptadecin-16-yl]cyclopropanesulfonamide | 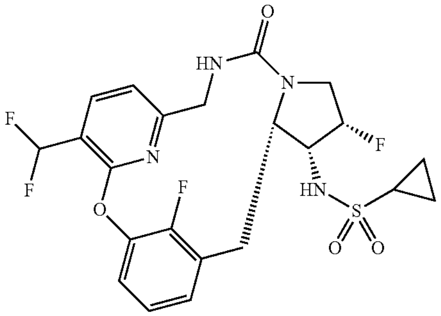 [SMILES: O=C1NCc2ccc(C(F)F)c(n2)Oc2cccc(c2F)C[C@H]2[C@@H](NS(=O)(=O)C3CC3)[C@@H](F)CN12] | 515.2 |

TABLE 1-7

| Ex. No. | IUPAC Name | Structure | MS |
|---|---|---|---|
| 29 | N-[(15aS,16R)-7-(difluoromethyl)-17,17,20-trifluoro-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 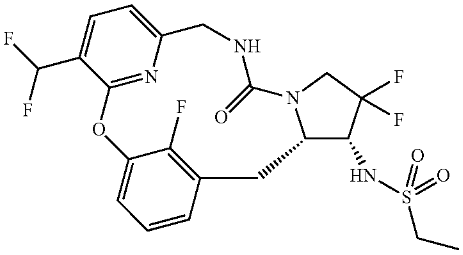 [SMILES: CCS(=O)(=O)N[C@@H]1[C@@H]2Cc3cccc(c3F)Oc3nc(ccc3C(F)F)CNC(=O)N2CC1(F)F] | 521.2 |

TABLE 1-7-continued

| Ex. No. | IUPAC Name | Structure | MS |
|---|---|---|---|
| 30 | N-[(15aS,16R)-7-chloro-5,17,17,20-tetrafluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 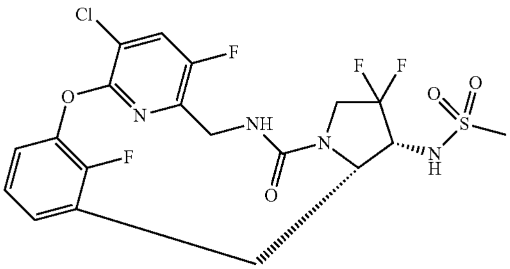 [SMILES: CS(=O)(=O)N[C@@H]1[C@@H]2Cc3cccc(c3F)Oc3nc(c(F)cc3Cl)CNC(=O)N2CC1(F)F] | 509.2 |
| 31 | N-[(15aS,16R,17S)-7,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 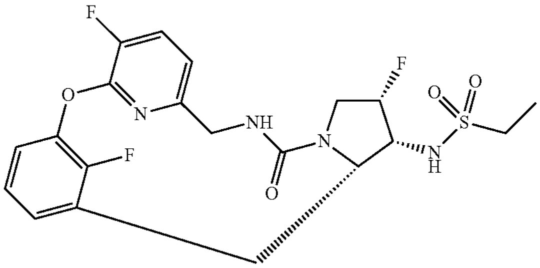 [SMILES: CCS(=O)(=O)N[C@H]1[C@@H](F)CN2C(=O)NCc3ccc(F)c(n3)Oc3cccc(c3F)C[C@@H]12] | 471.3 |
| 32 | N-[(15aS,16R)-5,17,17,20-tetrafluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 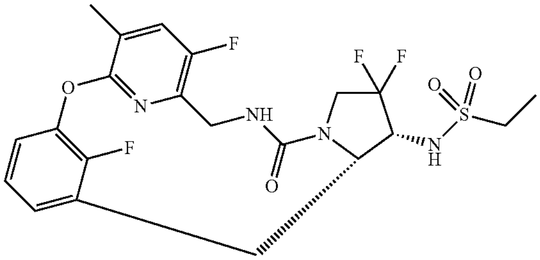 [SMILES: CCS(=O)(=O)N[C@@H]1[C@@H]2Cc3cccc(c3F)Oc3nc(c(F)cc3C)CNC(=O)N2CC1(F)F] | 503.2 |
| 33 | N-[(15aS,16S)-7-methyl-1-oxo-1,2,15a,16,17,18-hexahydro-15H-4,8-(azeno)-10,14-(metheno)pyrrolo[1,2-d][1,12,4]dioxazacyclo-heptadecin-16-yl]methanesulfonamide | 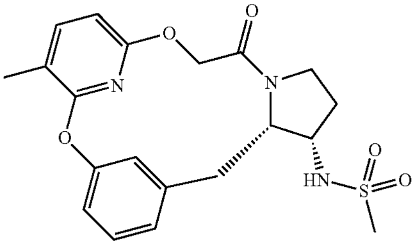 [SMILES: Cc1ccc2nc1Oc1cccc(c1)C[C@H]1[C@@H](NS(C)(=O)=O)CCN1C(=O)CO2] | 418.2 |

TABLE 1-8

| Ex. No. | IUPAC Name | Structure | MS |
|---|---|---|---|
| 34 | N'-[(15aS,16R,17S)-7-chloro-17,20-difluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]-N,N-dimethylsulfuric diamide | 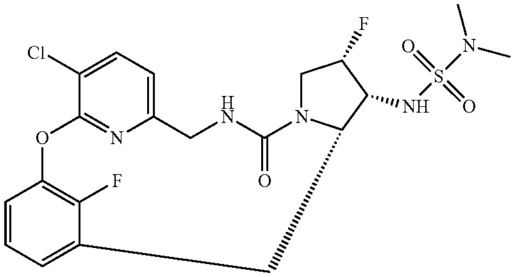 [SMILES: CN(C)S(=O)(=O)N[C@H]1[C@@H](F)CN2C(=O)NCc3ccc(Cl)c(n3)Oc3cccc(c3F)C[C@@H]12] | 502.2 |

TABLE 1-8-continued

| Ex. No. | IUPAC Name | Structure | MS |
|---|---|---|---|
| 35 | N-[(15aS,16R)-7-chloro-5,17,17,20-tetrafluoro-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 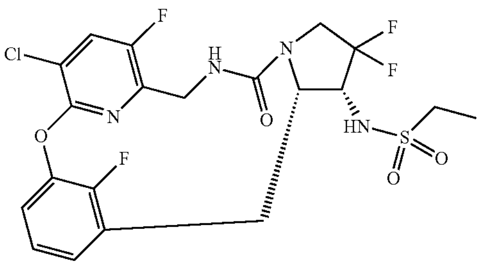 [SMILES: CCS(=O)(=O)N[C@@H]1[C@@H]2Cc3cccc(c3F)Oc3nc(c(F)cc3Cl)CNC(=O)N2CC1(F)F] | 523.1 |
| 36 | N-[(15aS,16R)-5,17,17,20-tetrafluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 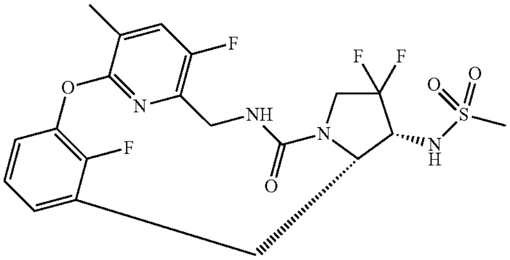 [SMILES: Cc1cc(F)c2nc1Oc1cccc(c1F)C[C@H]1[C@@H](NS(C)(=O)=O)C(F)(F)CN1C(=O)NC2] | 489.2 |
| 37 | N'-[(15aS,16R,17S)-7-(difluoromethyl)-17,20-difluoro-1-oxo-2,3,15a,16,17,18-hexahydro-1H,15H-8,4-(azeno)-10,14-(metheno)pyrrolo[1,2-j][1,8,10]oxadiazacyclo-heptadecin-16-yl]-N,N-dimethylsulfuric diamide | 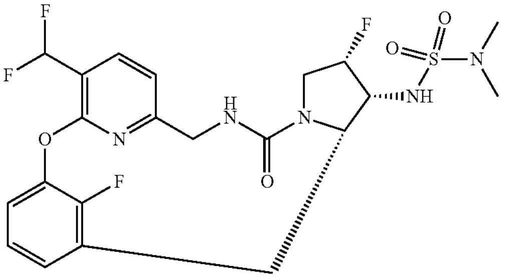 [SMILES: CN(C)S(=O)(=O)N[C@H]1[C@@H](F)CN2C(=O)NCc3ccc(C(F)F)c(n3)Oc3cccc(c3F)C[C@@H]12] | 518.2 |

TABLE 1-9

| Ex. No. | IUPAC Name | Structure | MS |
|---|---|---|---|
| 38 | N-[(15aS,16R,17S)-7-(difluoromethyl)-17,20-difluoro-1-oxo-15a,16,17,18-tetrahydro-1H,3H,15H-8,4-(azeno)-10,14-(metheno)pyrrolo[1,2-c][1,11,3]dioxazacyclo-heptadecin-16-yl]methanesulfonamide | 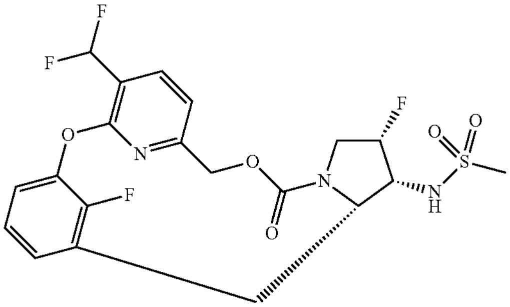 [SMILES: CS(=O)(=O)N[C@H]1[C@@H](F)CN2C(=O)OCc3ccc(C(F)F)c(n3)Oc3cccc(c3F)C[C@@H]12] | 490.2 |

TABLE 1-9-continued

| Ex. No. | IUPAC Name | Structure | MS |
|---|---|---|---|
| 39 | N-[(15aS,16R,17S)-7-chloro-17,20-difluoro-1-oxo-2,3,15a,16,17,18-hexahydro-1H,15H-4,8:14,10-di(metheno)pyrrolo[1,2-j][1,8,10]oxadiazacyclo-heptadecin-16-yl]ethanesulfonamide | 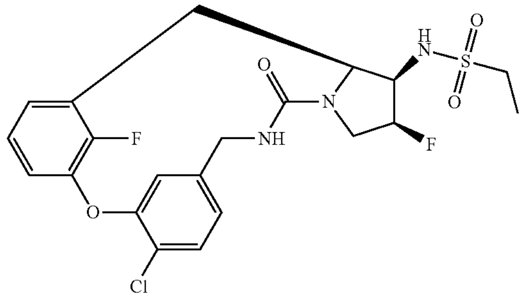 [SMILES: CCS(=O)(=O)N[C@H]1[C@@H](F)CN2C(=O)NCc3ccc(Cl)c(c3)Oc3cccc(c3F)C[C@@H]12] | 486.3 |
| 40 | N-[(15aS,16S)-2,7-dimethyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide | 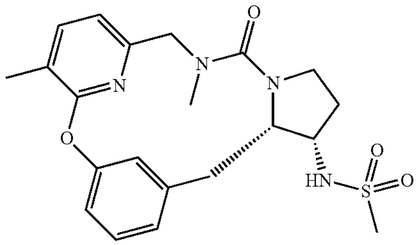 [SMILES: Cc1ccc2nc1Oc1cccc(c1)C[C@H]1[C@@H](NS(C)(=O)=O)CCN1C(=O)N(C)C2] | 431.3 |
| 41 | N-[(15aS,16R)-7-(difluoromethyl)-17,17,20-trifluoro-1-oxo-2,3,15a,16,17,18-hexahydro-1H,15H-8,4-(azeno)-10,14-(metheno)pyrrolo[1,2-j][1,8,10]oxadiazacyclo-heptadecin-16-yl]methanesulfonamide | 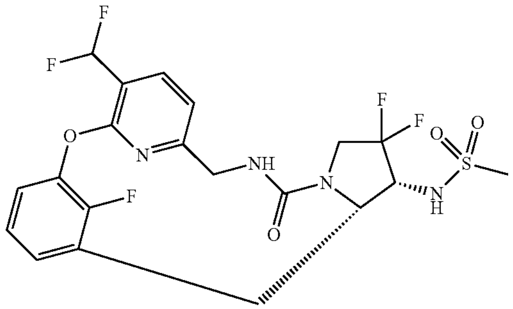 [SMILES: CS(=O)(=O)N[C@@H]1[C@@H]2Cc3cccc(c3F)Oc3nc(ccc3C(F)F)CNC(=O)N2CC1(F)F] | 507.2 |
| 42 | N-[(15aS,16R,17S)-17-fluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 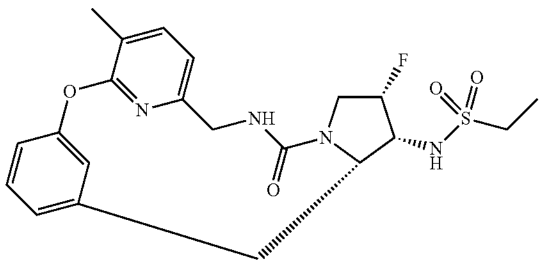 [SMILES: CCS(=O)(=O)N[C@H]1[C@@H](F)CN2C(=O)NCc3ccc(C)c(n3)Oc3cccc(c3)C[C@@H]12] | 449.2 |

TABLE 1-10

| Ex. No. | IUPAC Name | Structure | MS |
| --- | --- | --- | --- |
| 43 | 1,1-difluoro-N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]methanesulfonamide | 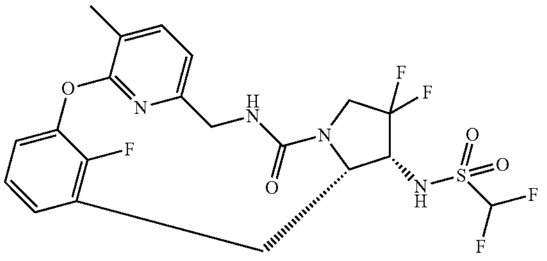 [SMILES: Cc1ccc2nc1Oc1cccc(c1F)C[C@H]1[C@@H](NS(=O)(=O)C(F)F)C(F)(F)CN1C(=O)NC2] | 507.2 |
| 44 | N-[(15aS,16R,17S)-7-chloro-17,20-difluoro-1-oxo-2,3,15a,16,17,18-hexahydro-1H,15H-4,8:14,10-di(metheno)pyrrolo[1,2-j][1,5,8,10]oxatriazacyclo-heptadecin-16-yl]methanesulfonamide | 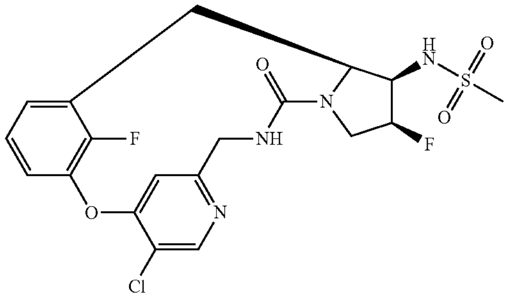 | 473.1 |
| 45 | N-[(15aS,16R)-17,17,20-trifluoro-7-methyl-1-oxo-1,2,15a,16,17,18-hexahydro-15H-4,8-(azeno)-14,10-(metheno)pyrrolo[1,2-d][1,12,4]dioxazacyclo-heptadecin-16-yl]ethanesulfonamide | 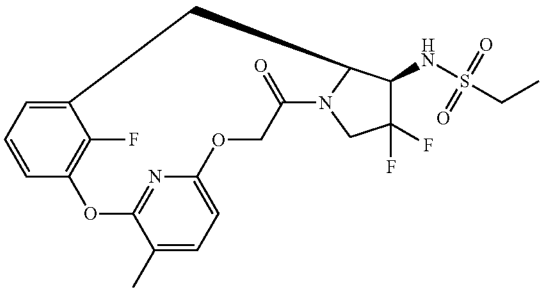 [SMILES: CCS(=O)(=O)N[C@@H]1[C@@H]2Cc3cccc(c3F)Oc3nc(ccc3C)OCC(=O)N2CC1(F)F] | 486.2 |
| 46 | 1-methoxy-N-[(15aS,16R)-17,17,20-trifluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 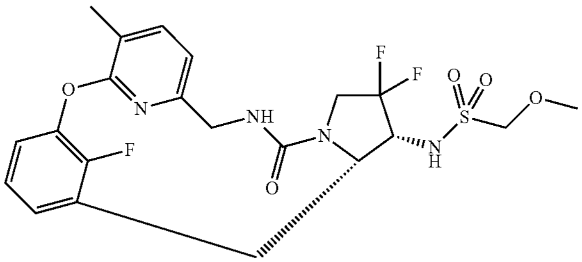 [SMILES: COCS(=O)(=O)N[C@@H]1[C@@H]2Cc3cccc(c3F)Oc3nc(ccc3C)CNC(=O)N2CC1(F)F] | 501.3 |
| 47 | N-[(15aS,16R,17S)-7-chloro-17-fluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 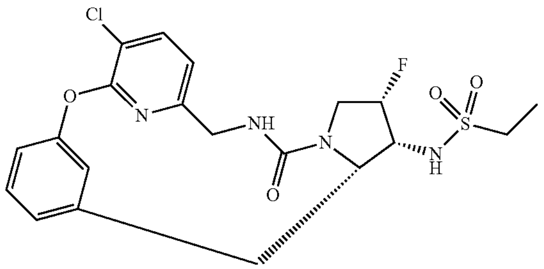 [SMILES: CCS(=O)(=O)N[C@H]1[C@@H](F)CN2C(=O)NCc3ccc(Cl)c(n3)Oc3cccc(c3)C[C@@H]12] | 469.3 |

TABLE 1-11

| Ex. No. | IUPAC Name | Structure | MS |
| --- | --- | --- | --- |
| 48 | N-[(15aS,16R)-17,17,20-trifluoro-3,7-dimethyl-1-oxo-2,3,15a,16,17,18-hexahydro-1H,15H-4,8-(azeno)-14,10-(metheno)pyrrolo[1,2-j][1,7,10]oxadiazacyclo-heptadecin-16-yl]ethanesulfonamide | 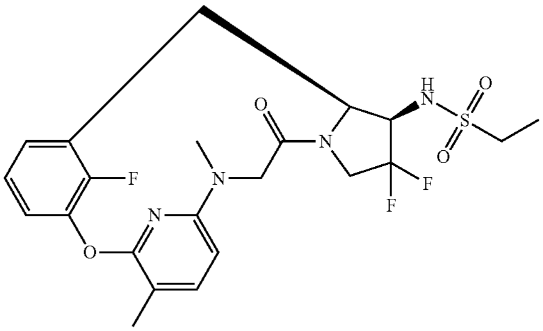 [SMILES: CCS(=O)(=O)N[C@@H]1[C@@H]2Cc3cccc(c3F)Oc3nc(ccc3C)N(C)CC(=O)N2CC1(F)F] | 499.2 |
| 49 | N-[(15aS,16R)-17,17,20-trifluoro-3,7-dimethyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide (optical isomer) | 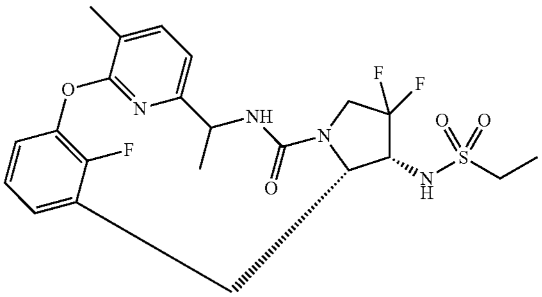 [SMILES: CCS(=O)(=O)N[C@@H]1[C@@H]2Cc3cccc(c3F)Oc3nc(ccc3C)C(C)NC(=O)N2CC1(F)F] | 499.2 |
| 50 | N-[(15aS,16R)-5,17,17,20-tetrafluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 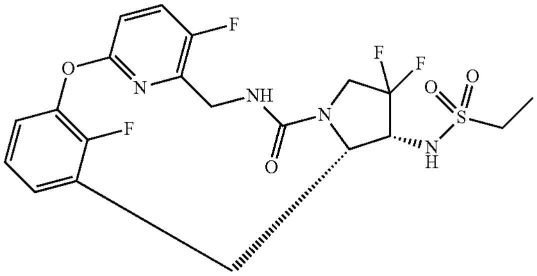 [SMILES: CCS(=O)(=O)N[C@@H]1[C@@H]2Cc3cccc(c3F)Oc3ccc(F)c(n3)CNC(=O)N2CC1(F)F] | 489.2 |
| 51 | N-[(15aS,16R)-17,17,20-trifluoro-3,7-dimethyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide (optical isomer) | 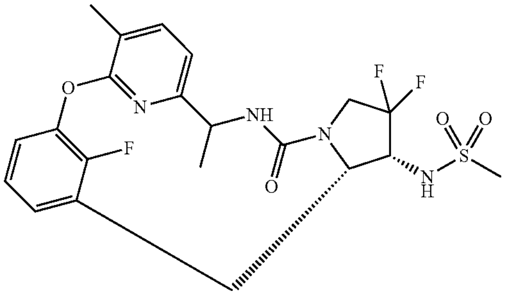 [SMILES: Cc1ccc2nc1Oc1cccc(c1F)C[C@H]1[C@@H](NS(C)(=O)=O)C(F)(F)CN1C(=O)NC2C] | 485.3 |

TABLE 1-12

| Ex. No. | IUPAC Name | Structure | MS |
|---|---|---|---|
| 52 | N-[(15aS,16R)-17,17,21-trifluoro-7-methyl-20-oxo-1,2,15a,16,17,18,20,20a-octahydro-15H-4,8-(azeno)-10,14-(metheno)azeto[1,2-g]pyrrolo[1,2-j][1,5,7,10]oxatriazacyclo-heptadecin-16-yl]methanesulfonamide (optical isomer) | 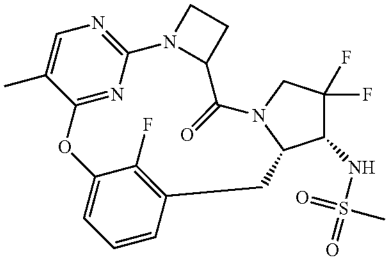 | 498.3 |
| 53 | N-[rel-(15aR,16S)-7-chloro-17,17-difluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide (optical isomer) | 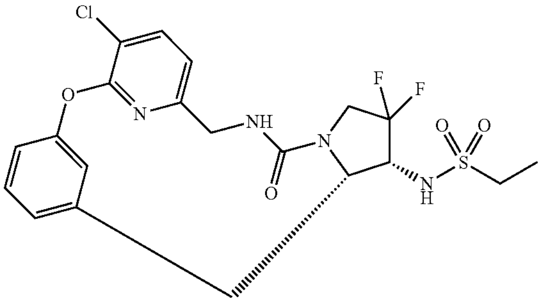 [SMILES: CCS(=O)(=O)N[C@@H]1[C@@H]2Cc3cccc(c3)Oc3nc(ccc3Cl)CNC(=O)N2CC1(F)F] | 487.0 |
| 54 | N-[(16aS,17R)-18,18,21-trifluoro-7-methyl-1-oxo-2,3,16a,17,18,19-hexahydro-1H,9H,16H-4,8-(azeno)-11,15-(metheno)pyrrolo[2,1-h][1,9,11]oxadiazacyclo-octadecin-17-yl]methanesulfonamide | 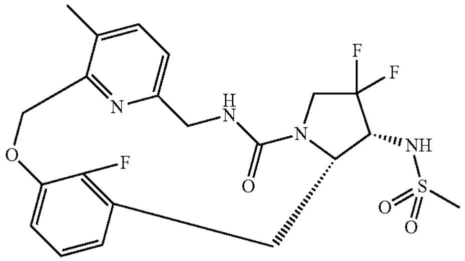 [SMILES: Cc1ccc2nc1COc1cccc(c1F)C[C@H]1[C@@H](NS(C)(=O)=O)C(F)(F)CN1C(=O)NC2] | 485.3 |
| 55 | N-[(15aS,16R,17S)-17,20-difluoro-7-methyl-1-oxo-2,3,15a,16,17,18-hexahydro-1H,15H-4,8-(azeno)-10,14-(metheno)pyrrolo[1,2-j][1,5,8,10]oxatriazacyclo-heptadecin-16-yl]ethanesulfonamide | 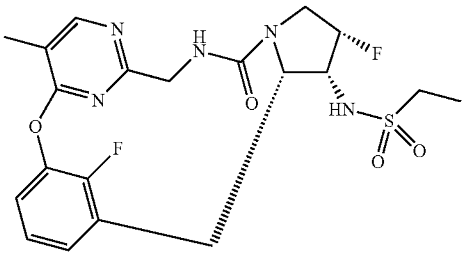 [SMILES: CCS(=O)(=O)N[C@H]1[C@@H](F)CN2C(=O)NCc3ncc(C)c(n3)Oc3cccc(c3F)C[C@@H]12] | 468.1 |
| 56 | N-[(15aS,16R,17S)-17,20-difluoro-7-methyl-1-oxo-2,3,15a,16,17,18-hexahydro-1H,9H,15H-8,4-(azeno)-10,14-(metheno)pyrrolo[1,2-c][1,3]diazacycloheptadecin-16-yl]ethanesulfonamide | 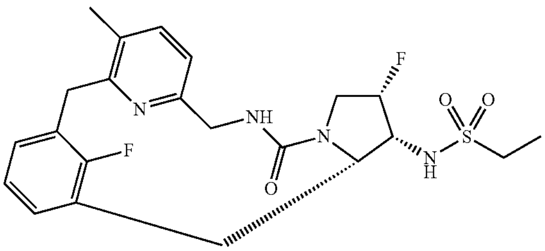 [SMILES: CCS(=O)(=O)N[C@H]1[C@@H](F)CN2C(=O)NCc3ccc(C)c(n3)Cc3cccc(c3F)C[C@@H]12] | 465.1 |

TABLE 1-13

| Ex. No. | IUPAC Name | Structure | MS |
|---|---|---|---|
| 57 | N-[(15aS,16R)-7-chloro-17,17,20-trifluoro-2-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 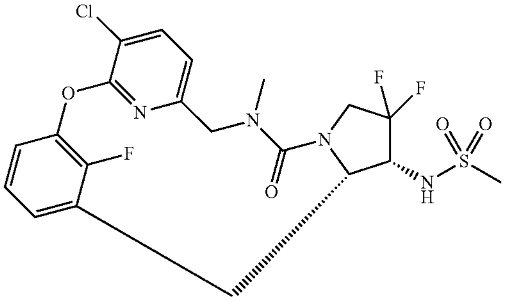 [SMILES: CN1Cc2ccc(Cl)c(n2)Oc2cccc(c2F)C[C@H]2[C@@H](NS(C)(=O)=O)C(F)(F)CN2C1=O] | 505.1 |
| 58 | N-[(15aS,16R)-7-chloro-5,17,17,20-tetrafluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]cyclopropanesulfonamide | 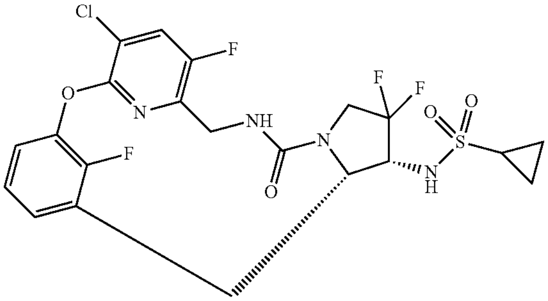 [SMILES: O=C1NCc2nc(c(Cl)cc2F)Oc2cccc(c2F)C[C@H]2[C@@H](NS(=O)(=O)C3CC3)C(F)(F)CN12] | 534.9 |
| 59 | N-[(16aS,17R,21aS)-18,18,22-trifluoro-8-methyl-21-oxo-2,3,16a,17,18,19,21,21a-octahydro-1H,16H-5,9-(azeno)-11,15-(metheno)dipyrrolo[1,2-g:1',2'-j][1,5,7,10]oxatriazacyclo-heptadecin-17-yl]methanesulfonamide | 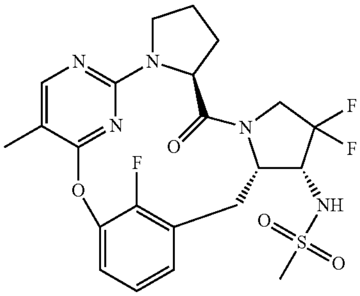 [SMILES: Cc1cnc2nc1Oc1cccc(c1F)C[C@H]1[C@@H](NS(C)(=O)=O)C(F)(F)CN1C(=O)[C@@H]1CCCN21] | 512.1 |
| 60 | N-[(15aS,16R)-7-chloro-2-(2,2-difluoroethyl)-17,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 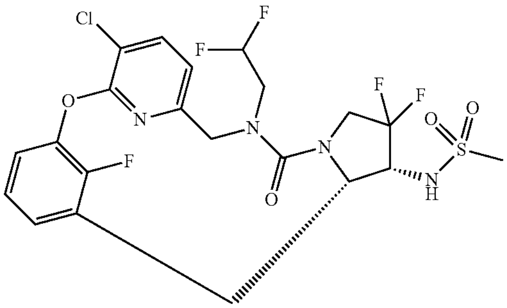 [SMILES: CS(=O)(=O)N[C@@H]1[C@@H]2Cc3cccc(c3F)Oc3nc(ccc3Cl)CN(CC(F)F)C(=O)N2CC1(F)F] | 554.9 |

TABLE 1-14

| Ex. No. | IUPAC Name | Structure | MS |
|---|---|---|---|
| 61 | N-[(1R,19aS)-2,2,20-trifluoro-11-methyl-5-oxo-2,3,6,7,19,19a-hexahydro-1H,5H-8,12-(azeno)-18,14-(metheno)pyrrolo[1,2-j][1,4,10]oxadiazacyclo-heptadecin-1-yl]ethanesulfonamide | 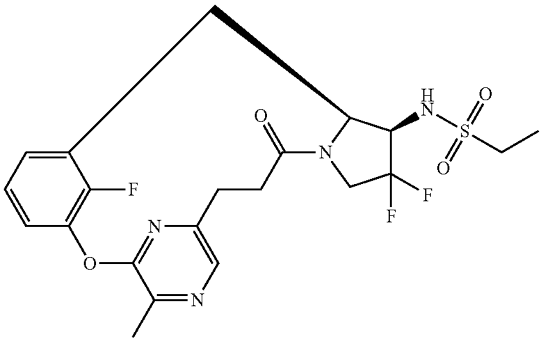 [SMILES: CCS(=O)(=O)N[C@@H]1[C@@H]2Cc3cccc(c3F)Oc3nc(cnc3C)CCC(=O)N2CC1(F)F] | 485.0 |
| 62 | N-[(15aS,16R)-7-chloro-17,17,20-trifluoro-1-oxo-1,2,15a,16,17,18-hexahydro-15H-4,8-(azeno)-14,10-(metheno)pyrrolo[1,2-d][1,12,4]dioxazacyclo-heptadecin-16-yl]methanesulfonamide | 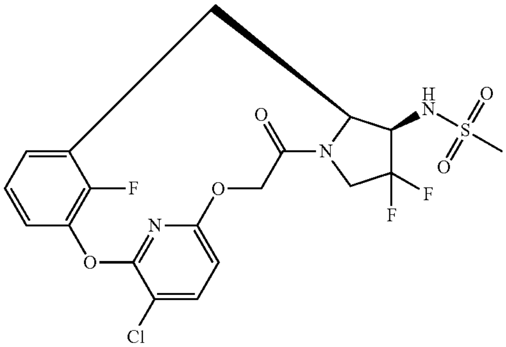 [SMILES: CS(=O)(=O)N[C@@H]1[C@@H]2Cc3cccc(c3F)Oc3nc(ccc3Cl)OCC(=O)N2CC1(F)F] | 491.9 |
| 63 | N-[(15aS,16R)-7-chloro-17,17,20-trifluoro-1-oxo-1,2,15a,16,17,18-hexahydro-15H-4,8-(azeno)-10,14-(metheno)pyrrolo[1,2-d][1,12,4]dioxazacyclo-heptadecin-16-yl]-N'-methylsulfuric diamide | 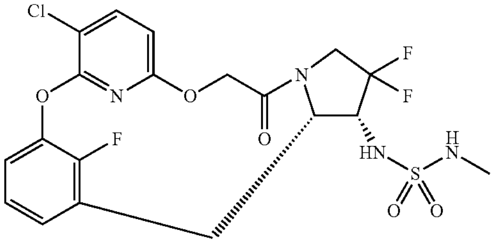 [SMILES: CNS(=O)(=O)N[C@@H]1[C@@H]2Cc3cccc(c3F)Oc3nc(ccc3Cl)OCC(=O)N2CC1(F)F] | 507.0 |
| 64 | N-[(15aS,16R)-7-chloro-17,17,20-trifluoro-1-oxo-1,2,15a,16,17,18-hexahydro-15H-4,8-(azeno)-10,14-(metheno)pyrrolo[2,1-n][1,7,3,15]dioxadiazacyclo-heptadecin-16-yl]methanesulfonamide | 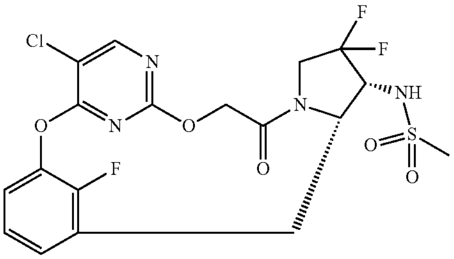 [SMILES: CS(=O)(=O)N[C@@H]1[C@@H]2Cc3cccc(c3F)Oc3nc(ncc3Cl)OCC(=O)N2CC1(F)F] | 493.0 |
| 65 | N-[(15aS,16R)-17,17,20-trifluoro-7-methyl-1-oxo-1,2,15a,16,17,18-hexahydro-15H-4,8-(azeno)-10,14-(metheno)pyrrolo[1,2-j][1,7,4,10]dioxadiazacyclo-heptadecin-16-yl]methanesulfonamide | 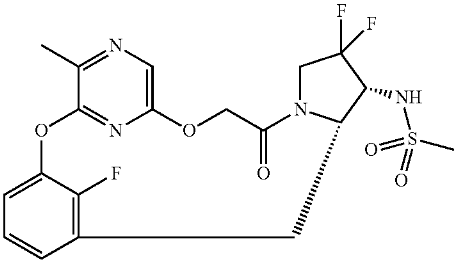 [SMILES: Cc1ncc2nc1Oc1cccc(c1F)C[C@H]1[C@@H](NS(C)(=O)=O)C(F)(F)CN1C(=O)CO2] | 473.2 |

TABLE 1-15

| Ex. No. | IUPAC Name | Structure | MS |
|---|---|---|---|
| 66 | N-[(16aS,17R)-18,18,21-trifluoro-7-methyl-1-oxo-1,2,16a,17,18,19-hexahydro-9H,16H-4,8-(azeno)-11,15-(metheno)pyrrolo[1,2-d][1,12,4]dioxazacyclo-octadecin-17-yl]methanesulfonamide | 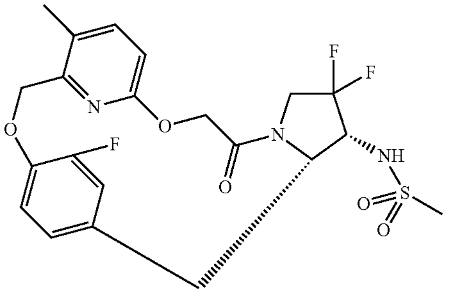 [SMILES: Cc1ccc2nc1COc1ccc(cc1F)C[C@H]1[C@@H](NS(C)(=O)=O)C(F)(F)CN1C(=O)CO2] | 486.3 |
| 67 | N-[(15aS,16R,17S)-7-chloro-17,20-difluoro-1-oxo-1,2,15a,16,17,18-hexahydro-9H,15H-4,8-(azeno)-14,10-(metheno)pyrrolo[1,2-d][1,4]oxazacycloheptadecin-16-yl]methanesulfonamide | 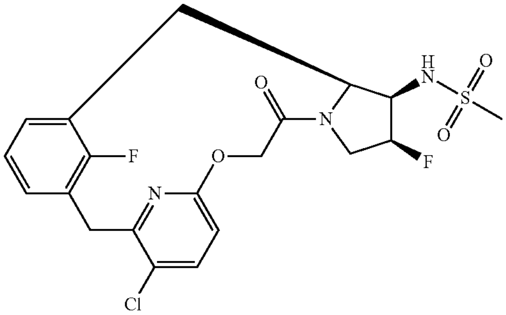 [SMILES: CS(=O)(=O)N[C@H]1[C@@H](F)CN2C(=O)COc3ccc(Cl)c(n3)Cc3cccc(c3F)C[C@@H]12] | 472.0 |
| 68 | N-[(16aS,17S)-7-methyl-1-oxo-2,3,16a,17,18,19-hexahydro-1H,10H,16H-4,8-(azeno)-11,15-(metheno)pyrrolo[1,2-j][1,8,10]oxadiazacyclo-octadecin-17-yl]methanesulfonamide | 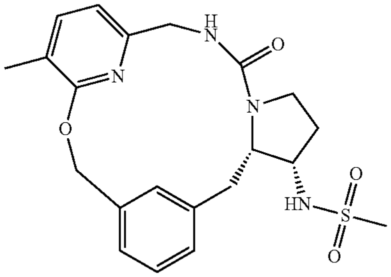 | 431.3 |
| 69 | N-[(15aS,16R,17S)-7-chloro-17-fluoro-1-oxo-1,2,15a,16,17,18-hexahydro-15H-4,8-(azeno)-14,10-(metheno)pyrrolo[1,2-d][1,12,4]dioxazacyclo-heptadecin-16-yl]ethanesulfonamide | 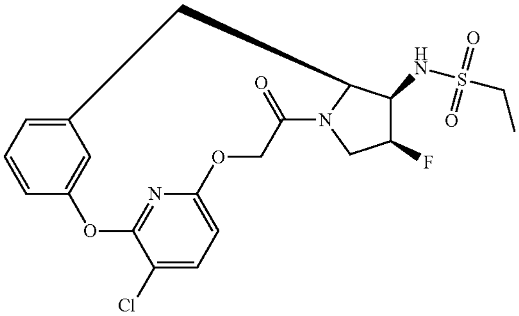 [SMILES: CCS(=O)(=O)N[C@H]1[C@@H](F)CN2C(=O)COc3ccc(Cl)c(n3)Oc3cccc(c3)C[C@@H]12] | 470.2 |
| 70 | N-[(15aS,16R,17S)-7-chloro-17-fluoro-2-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 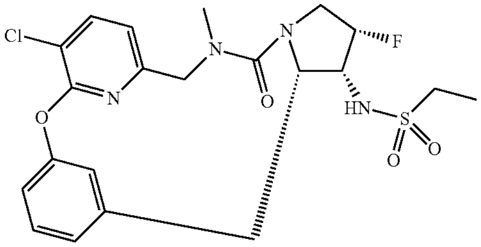 [SMILES: CCS(=O)(=O)N[C@H]1[C@@H](F)CN2C(=O)N(C)Cc3ccc(Cl)c(n3)Oc3cccc(c3)C[C@@H]12] | 483.2 |

TABLE 1-16

| Ex. No. | IUPAC Name | Structure | MS |
|---|---|---|---|
| 71 | N-[(15aS,16R,17S)-17-fluoro-7-methyl-1-oxo-1,2,15a,16,17,18-hexahydro-15H-4,8-(azeno)-10,14-(metheno)pyrrolo[2,1-n][1,7,3,15]dioxadiazacyclo-heptadecin-16-yl]ethanesulfonamide | 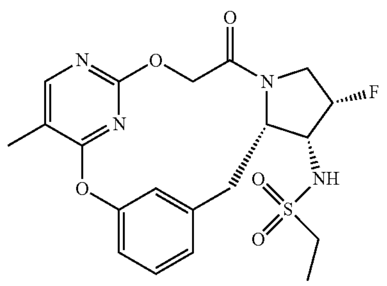 [SMILES: CCS(=O)(=O)N[C@H]1[C@@H](F)CN2C(=O)COc3ncc(C)c(n3)Oc3cccc(c3)C[C@@H]12] | 451.3 |
| 72 | N-[(15aS,16R,17S)-7-chloro-17,20-difluoro-1-oxo-1,2,15a,16,17,18-hexahydro-9H,15H-4,8-(azeno)-14,10-(metheno)pyrrolo[1,2-d][1,4]oxazacycloheptadecin-16-yl]ethanesulfonamide | 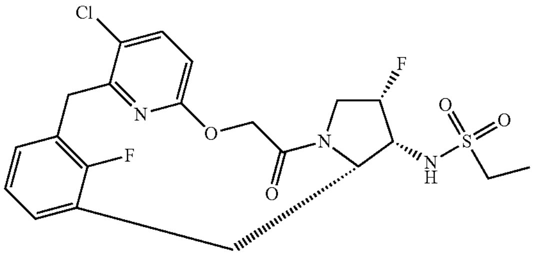 [SMILES: CCS(=O)(=O)N[C@H]1[C@@H](F)CN2C(=O)COc3ccc(Cl)c(n3)Cc3cccc(c3F)C[C@@H]12] | 486.2 |
| 73 | N-[(15aS,16R,17S)-7-chloro-17,20-difluoro-2-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]ethanesulfonamide | 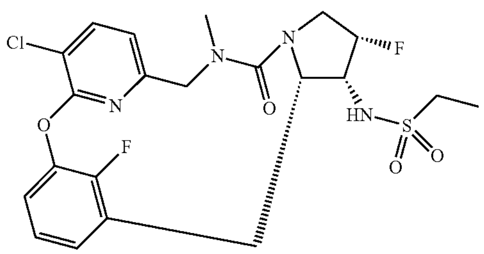 [SMILES: CCS(=O)(=O)N[C@H]1[C@@H](F)CN2C(=O)N(C)Cc3ccc(Cl)c(n3)Oc3cccc(c3F)C[C@@H]12] | 501.2 |
| 74 | N-[(2R,16aS,17R,21aS)-2,18,18,22-tetrafluoro-8-methyl-21-oxo-2,3,16a,17,18,19,21,21a-octahydro-1H,16H-5,9-(azeno)-11,15-(metheno)dipyrrolo[1,2-g:1',2'-j][1,5,7,10]oxatriazacyclo-heptadecin-17-yl]methanesulfonamide | 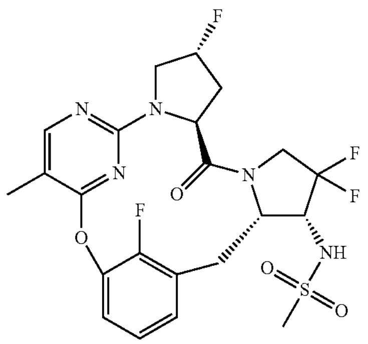 [SMILES: Cc1cnc2nc1Oc1cccc(c1F)C[C@H]1[C@@H](NS(C)(=O)=O)C(F)(F)CN1C(=O)[C@@H]1C[C@@H](F)CN21] | 530.2 |

TABLE 1-17

| Ex. No. | IUPAC Name | Structure | MS |
|---|---|---|---|
| 75 | N-[(15aS,16R)-17,17,20-trifluoro-3,7-dimethyl-1-oxo-2,3,15a,16,17,18-hexahydro-1H,15H-4,8-(azeno)-10,14-(metheno)pyrrolo[1,2-j][1,5,7,10]oxatriazacyclo-heptadecin-16-yl]methanesulfonamide | 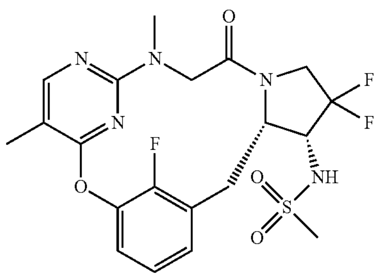 [SMILES: Cc1cnc2nc1Oc1cccc(c1F)C[C@H]1[C@@H](NS(C)(=O)=O)C(F)(F)CN1C(=O)CN2C] | 486.2 |
| 76 | N-[(15aS,16R,17S)-7-bromo-17-fluoro-1-oxo-1,2,15a,16,17,18-hexahydro-15H-4,8-(azeno)-14,10-(metheno)pyrrolo[1,2-d][1,12,4]dioxazacyclo-heptadecin-16-yl]ethanesulfonamide | 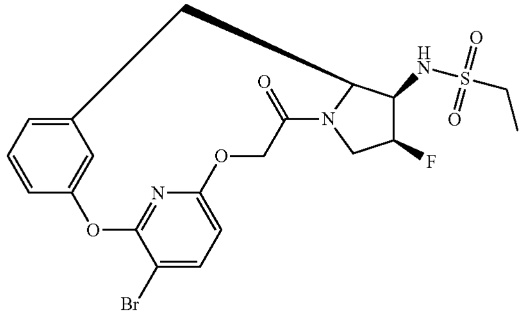 [SMILES: CCS(=O)(=O)N[C@H]1[C@@H](F)CN2C(=O)COc3ccc(Br)c(n3)Oc3cccc(c3)C[C@@H]12] | 514.1 |
| 77 | N-[(15aS,16R)-17,17,20-trifluoro-7-methyl-1-oxo-1,2,15a,16,17,18-hexahydro-15H-4,8-(azeno)-10,14-(metheno)pyrrolo[2,1-n][1,7,3,15]dioxadiazacyclo-heptadecin-16-yl]methanesulfonamide | 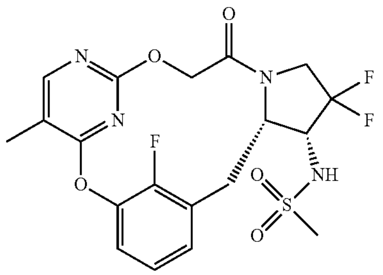 [SMILES: Cc1cnc2nc1Oc1cccc(c1F)C[C@H]1[C@@H](NS(C)(=O)=O)C(F)(F)CN1C(=O)CO2] | 473.2 |
| 78 | N-[(15aS,16R,17S)-17-fluoro-7-methyl-1-oxo-1,2,15a,16,17,18-hexahydro-15H-4,8-(azeno)-14,10-(metheno)pyrrolo[1,2-d][1,12,4]dioxazacyclo-heptadecin-16-yl]ethanesulfonamide | 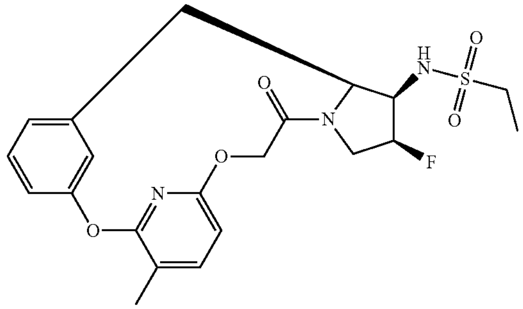 [SMILES: CCS(=O)(=O)N[C@H]1[C@@H](F)CN2C(=O)COc3ccc(C)c(n3)Oc3cccc(c3)C[C@@H]12] | 450.3 |
| 79 | N-[(15aS,16R)-7-ethyl-17,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 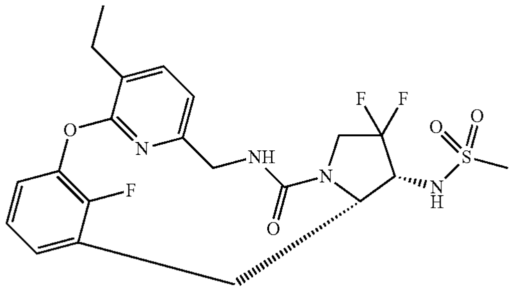 [SMILES: CCc1ccc2nc1Oc1cccc(c1F)C[C@H]1[C@@H](NS(C)(=O)=O)C(F)(F)CN1C(=O)NC2] | 485.2 |

TABLE 1-18

| Ex. No. | IUPAC Name | Structure | MS |
|---|---|---|---|
| 80 | N-[(15aS,16R,17S)-7-chloro-17,20-difluoro-1-oxo-1,2,15a,16,17,18-hexahydro-15H-4,8-(azeno)-14,10-(metheno)pyrrolo[1,2-d][1,12,4]dioxazacyclo-heptadecin-16-yl]ethanesulfonamide | 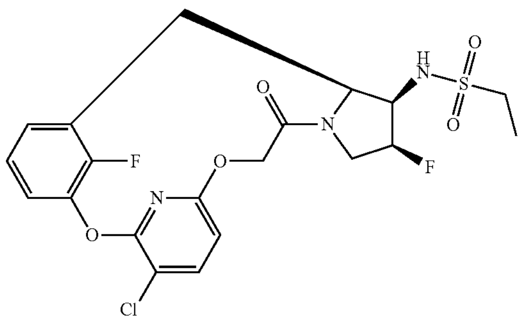 [SMILES: CCS(=O)(=O)N[C@H]1[C@@H](F)CN2C(=O)COc3ccc(Cl)c(n3)Oc3cccc(c3F)C[C@@H]12] | 488.1 |
| 81 | N-[(15aS,16R)-17,17,20-trifluoro-7-methyl-1-oxo-1,2,15a,16,17,18-hexahydro-15H-4,8-(azeno)-10,14-(metheno)pyrrolo[1,2-j][1,7,4,10]dioxadiazacyclo-heptadecin-16-yl]ethanesulfonamide | 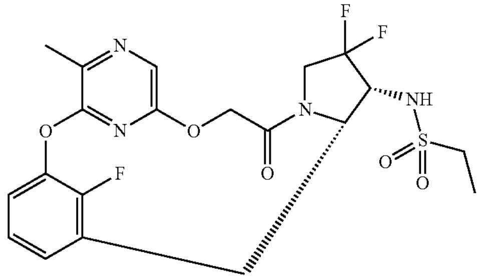 [SMILES: CCS(=O)(=O)N[C@@H]1[C@@H]2Cc3cccc(c3F)Oc3nc(cnc3C)OCC(=O)N2CC1(F)F] | 487.2 |
| 82 | N-[(1R,2S,19aS)-11-chloro-2,20-difluoro-5-oxo-2,3,6,7,19,19a-hexahydro-1H,5H-12,8-(azeno)-14,18-(metheno)pyrrolo[2,1-h][1,9]oxazacycloheptadecin-1-yl]ethanesulfonamide | 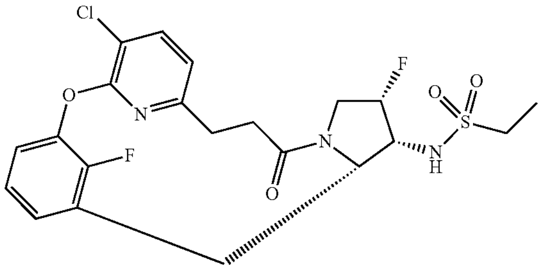 [SMILES: CCS(=O)(=O)N[C@H]1[C@@H](F)CN2C(=O)CCc3ccc(Cl)c(n3)Oc3cccc(c3F)C[C@@H]12] | 486.0 |
| 83 | N-[(2R,16aS,17R,21aS)-18,18,22-trifluoro-2-methoxy-8-methyl-21-oxo-2,3,16a,17,18,19,21,21a-octahydro-1H,16H-5,9-(azeno)-11,15-(metheno)dipyrrolo[1,2-g:1',2'-j][1,5,7,10]oxatriazacyclo-heptadecin-17-yl]methanesulfonamide | 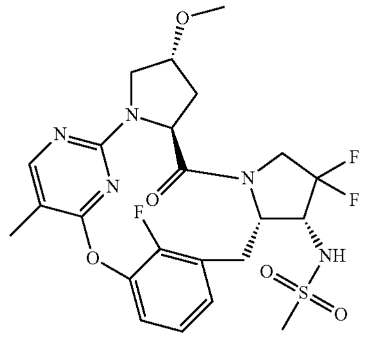 [SMILES: CO[C@@H]1C[C@H]2C(=O)N3CC(F)(F)[C@H](NS(C)(=O)=O)[C@@H]3Cc3cccc(c3F)Oc3nc(ncc3C)N2C1] | 542.0 |
| 84 | N-[(16aS,17R)-18,18,21-trifluoro-7-methyl-1-oxo-2,3,16a,17,18,19-hexahydro-1H,10H,16H-4,8-(azeno)-15,11-(metheno)pyrrolo[1,2-j][1,8,10]oxadiazacyclo-octadecin-17-yl]methanesulfonamide | 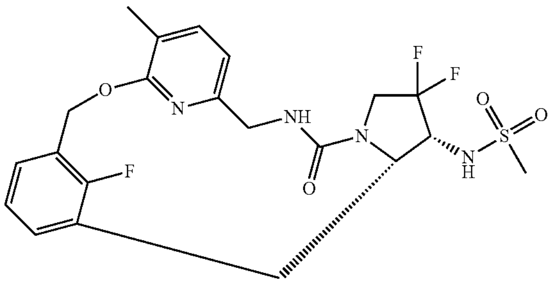 [SMILES: Cc1ccc2nc1OCc1cccc(c1F)C[C@H]1[C@@H](NS(C)(=O)=O)C(F)(F)CN1C(=O)NC2] | 485.0 |

TABLE 1-19

| Ex. No. | IUPAC Name | Structure | MS |
|---|---|---|---|
| 85 | N-[(14aS,15R)-16,16,19-trifluoro-1-oxo-2,3,14a,15,16,17-hexahydro-1H,14H-4,7-(azeno)-9,13-(metheno)pyrrolo[1,2-i][1,3,7,9]oxathiadiazacyclo-hexadecin-15-yl]methanesulfonamide | 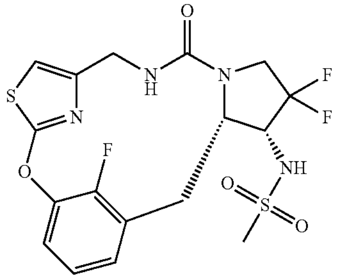 [SMILES: CS(=O)(=O)N[C@@H]1[C@@H]2Cc3cccc(c3F)Oc3nc(cs3)CNC(=O)N2CC1(F)F] | 462.9 |
| 86 | N-[rel-(15aS,16R)-11,17,17-trifluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide (optical isomer) | 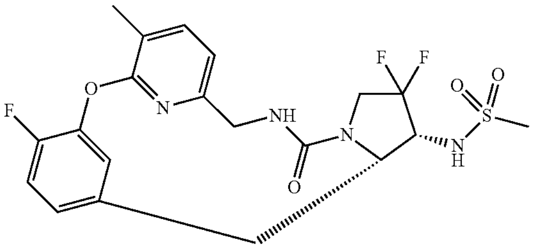 [SMILES: Cc1ccc2nc1Oc1cc(ccc1F)C[C@H]1[C@@H](NS(C)(=O)=O)C(F)(F)CN1C(=O)NC2] | 471.1 |
| 87 | N-[(15aS,16R,17S)-7-(difluoromethyl)-17-fluoro-1-oxo-1,2,15a,16,17,18-hexahydro-15H-4,8-(azeno)-14,10-(metheno)pyrrolo[1,2-d][1,12,4]dioxazacyclo-heptadecin-16-yl]ethanesulfonamide | 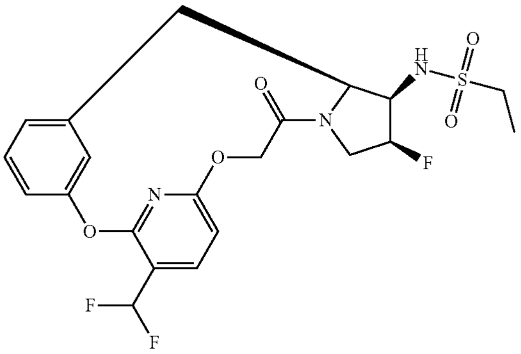 [SMILES: CCS(=O)(=O)N[C@H]1[C@@H](F)CN2C(=O)COc3ccc(C(F)F)c(n3)Oc3cccc(c3)C[C@@H]12] | 486.0 |
| 88 | N-[(15aS,16R)-7-cyclopropyl-17,17,20-trifluoro-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]methanesulfonamide | 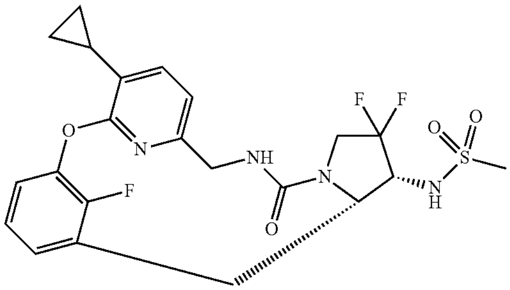 [SMILES: CS(=O)(=O)N[C@@H]1[C@@H]2Cc3cccc(c3F)Oc3nc(ccc3C3CC3)CNC(=O)N2CC1(F)F] | 497.2 |
| 89 | N-[rel-(15aS,16R)-12,17,17-trifluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide (optical isomer) | 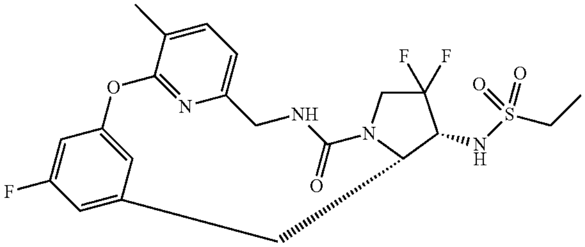 [SMILES: CCS(=O)(=O)N[C@@H]1[C@@H]2Cc3cc(F)cc(c3)Oc3nc(ccc3C)CNC(=O)N2CC1(F)F] | 485.1 |

TABLE 1-20

| Ex. No. | IUPAC Name | Structure | MS |
|---|---|---|---|
| 90 | N-[rel-(15aS,16R)-13,17,17-trifluoro-7-methyl-1-oxo-2,3,15a,16,17,18-hexahydro-1H,15H-4,8-(azeno)-14,10-(metheno)pyrrolo[1,2-j][1,8,10]oxadiazacyclohepta-decin-16-yl]ethanesulfonamide (optical isomer) | 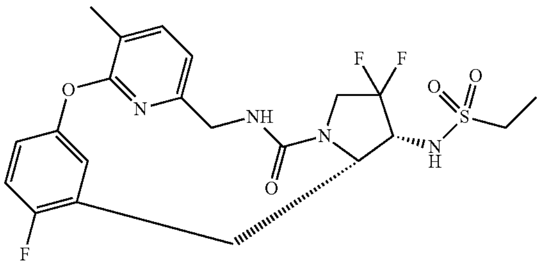 [SMILES: CCS(=O)(=O)N[C@@H]1[C@@H]2Cc3cc(ccc3F)Oc3nc(ccc3C)CNC(=O)N2CC1(F)F] | 485.0 |
| 91 | N-[rel-(15aR,16S,17R)-7-chloro-11,17-difluoro-1-oxo-1,2,15a,16,17,18-hexahydro-15H-4,8-(azeno)-14,10-(metheno)pyrrolo[1,2-d][1,12,4]dioxazacyclohepta-decin-16-yl]ethanesulfonamide (optical isomer) | 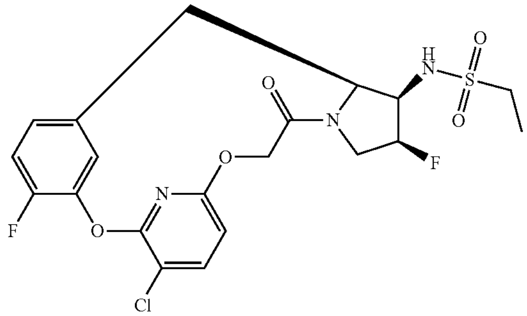 [SMILES: CCS(=O)(=O)N[C@H]1[C@@H](F)CN2C(=O)COc3ccc(Cl)c(n3)Oc3cc(ccc3F)C[C@@H]12] | 488.0 |
| 92 | N-[(15aS,16R)-7-chloro-17,17-difluoro-1-oxo-2,3,15a,16,17,18-hexahydro-1H,15H-4,8-(azeno)-14,10-(metheno)pyrrolo[1,2-j][1,8,10]oxadiazacyclohepta-decin-16-yl]methanesulfonamide | 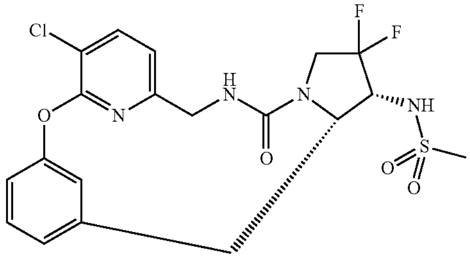 [SMILES: CS(=O)(=O)N[C@@H]1[C@@H]2Cc3cccc(c3)Oc3nc(ccc3Cl)CNC(=O)N2CC1(F)F] | 472.9 |
| 93 | N-[(15aS,16R)-7-(difluoromethyl)-17,17-difluoro-1-oxo-2,3,15a,16,17,18-hexahydro-1H,15H-4,8-(azeno)-14,10-(metheno)pyrrolo[1,2-j][1,8,10]oxadiazacyclohepta-decin-16-yl]methanesulfonamide | 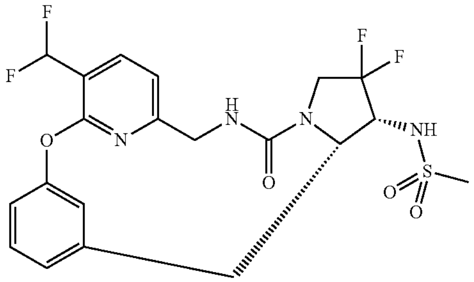 [SMILES: CS(=O)(=O)N[C@@H]1[C@@H]2Cc3cccc(c3)Oc3nc(ccc3C(F)F)CNC(=O)N2CC1(F)F] | 489.0 |
| 94 | N-[(16aS,17R)-7-chloro-18,18,21-trifluoro-1-oxo-2,3,16a,17,18,19-hexahydro-1H,10H,16H-4,8-(azeno)-15,11-(metheno)pyrrolo[1,2-j][1,8,10]oxadiazacycloocta-decin-17-yl]methanesulfonamide | 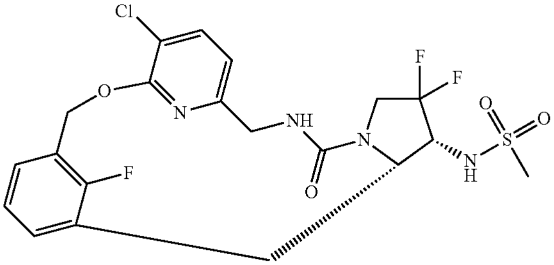 [SMILES: CS(=O)(=O)N[C@@H]1[C@@H]2Cc3cccc(c3F)COc3nc(ccc3Cl)CNC(=O)N2CC1(F)F] | 505.1 |

TABLE 1-21

| Ex. No. | IUPAC Name | Structure | MS |
|---|---|---|---|
| 95 | N-[rel-(15aS,16R)-7-chloro-11,17,17-trifluoro-1-oxo-1,2,15a,16,17,18-hexahydro-15H-4,8-(azeno)-14,10-(metheno)pyrrolo[1,2-d][1,12,4]dioxazacyclo-heptadecin-16-yl]methanesulfonamide (optical isomer) | 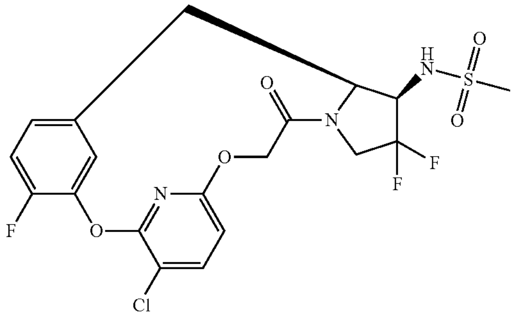 [SMILES: CS(=O)(=O)N[C@@H]1[C@@H]2Cc3ccc(F)c(c3)Oc3nc(ccc3Cl)OCC(=O)N2CC1(F)F] | 492.1 |
| 96 | N-[(15aS,16R)-7-chloro-17,17-difluoro-1-oxo-1,2,15a,16,17,18-hexahydro-15H-4,8-(azeno)-14,10-(metheno)pyrrolo[1,2-d][1,12,4]dioxazacyclo-heptadecin-16-yl]methanesulfonamide | 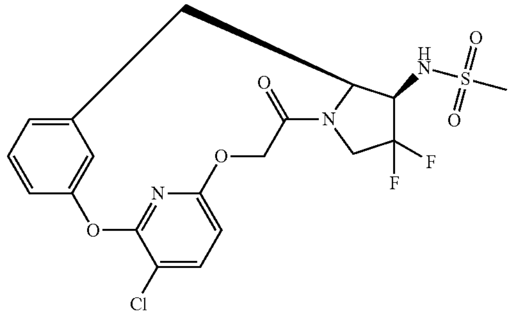 [SMILES: CS(=O)(=O)N[C@@H]1[C@@H]2Cc3cccc(c3)Oc3nc(ccc3Cl)OCC(=O)N2CC1(F)F] | 474.2 |
| 97 | N-[(15aS,16R)-17,17,20-trifluoro-7-methyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]propane-2-sulfonamide | 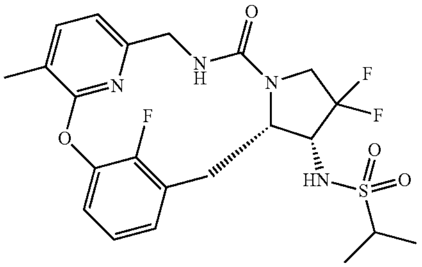 [SMILES: Cc1ccc2nc1Oc1cccc(c1F)C[C@H]1[C@@H](NS(=O)(=O)C(C)C)C(F)(F)CN1C(=O)NC2] | 499.1 |
| 98 | N-[(15aS,16R)-17,17,20-trifluoro-7,13-dimethyl-1-oxo-2,3,15a,16,17,18-hexahydro-1H,15H-4,8-(azeno)-14,10-(metheno)pyrrolo[1,2-j][1,8,10]oxadiazacyclo-heptadecin-16-yl]ethanesulfonamide | 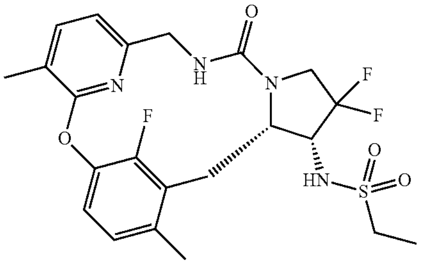 [SMILES: CCS(=O)(=O)N[C@@H]1[C@@H]2Cc3c(C)ccc(c3F)Oc3nc(ccc3C)CNC(=O)N2CC1(F)F] | 499.3 |
| 99 | N-[(15aS,16R)-17,17,20-trifluoro-7-methyl-1-oxo-2,3,15a,16,17,18-hexahydro-1H,15H-4,8-(azeno)-14,10-(metheno)pyrrolo[1,2-j][1,7,10]oxadiazacyclo-heptadecin-16-yl]ethanesulfonamide | 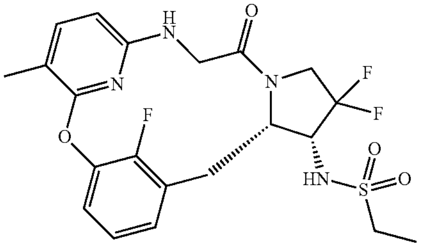 [SMILES: CCS(=O)(=O)N[C@@H]1[C@@H]2Cc3cccc(c3F)Oc3nc(ccc3C)NCC(=O)N2CC1(F)F] | 485 |

TABLE 1-22

| Ex. No. | IUPAC Name | Structure | MS |
|---|---|---|---|
| 100 | N-[(15aS,16R)-9,9,17,17,20-pentafluoro-7-methyl-1-oxo-2,3,15a,16,17,18-hexahydro-1H,9H,15H-4,8-(azeno)-14,10-(metheno)pyrrolo[1,2-c][1,3]diazacycloheptadecin-16-yl]ethanesulfonamide | 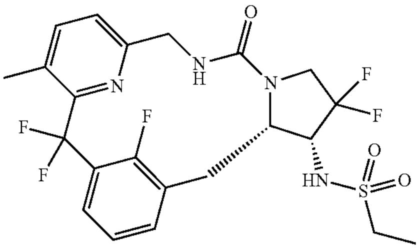 [SMILES: CCS(=O)(=O)N[C@@H]1[C@@H]2Cc3cccc(c3F)C(F)(F)c3nc(ccc3C)CNC(=O)N2CC1(F)F] | 519.2 |
| 101 | N-[(15aS,16R)-17,17,20-trifluoro-7,11-dimethyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]ethanesulfonamide | 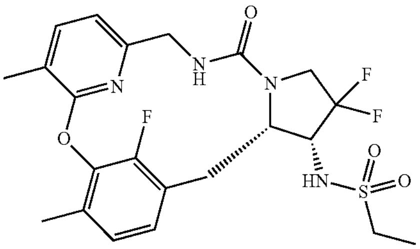 [SMILES: CCS(=O)(=O)N[C@@H]1[C@@H]2Cc3ccc(C)c(c3F)Oc3nc(ccc3C)CNC(=O)N2CC1(F)F] | 499.1 |
| 102 | N-[(15aS,16R)-17,17,20-trifluoro-7-methyl-1-oxo-1,2,15a,16,17,18-hexahydro-9H,15H-4,8-(azeno)-10,14-(metheno)pyrrolo[1,2-d][1,4]oxazacycloheptadecin-16-yl]ethanesulfonamide | 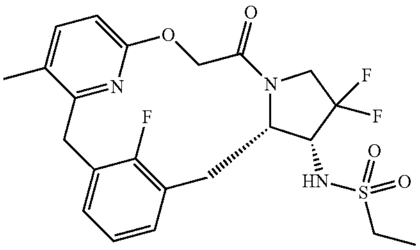 [SMILES: CCS(=O)(=O)N[C@@H]1[C@@H]2Cc3cccc(c3F)Cc3nc(ccc3C)OCC(=O)N2CC1(F)F] | 484.2 |
| 103 | N-[(15aS,16R)-17,17,20-trifluoro-7-methyl-1-oxo-2,3,15a,16,17,18-hexahydro-1H,9H,15H-4,8:10,14-di(metheno)pyrrolo[1,2-c][1,3]diazacycloheptadecin-16-yl]ethanesulfonamide | 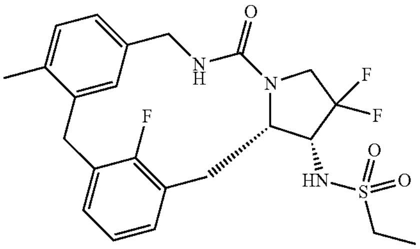 [SMILES: CCS(=O)(=O)N[C@@H]1[C@@H]2Cc3cccc(c3F)Cc3cc(ccc3C)CNC(=O)N2CC1(F)F] | 482.1 |
| 104 | N-[(15aS,16R)-17,17,20-trifluoro-7-methyl-1-oxo-2,3,15a,16,17,18-hexahydro-1H,9H,15H-4,8-(azeno)-10,14-(metheno)pyrrolo[1,2-c][1,3]diazacycloheptadecin-16-yl]ethanesulfonamide hydrochloride | 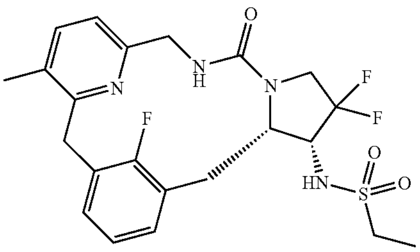 [SMILES: CCS(=O)(=O)N[C@@H]1[C@@H]2Cc3cccc(c3F)Cc3nc(ccc3C)CNC(=O)N2CC1(F)F] | 483.3 |

TABLE 1-23

| Ex. No. | IUPAC Name | Structure | MS |
|---|---|---|---|
| 105 | N-[(9R,15aS,16R)-17,17,20-trifluoro-7,9-dimethyl-1-oxo-2,3,15a,16,17,18-hexahydro-1H,9H,15H-4,8-(azeno)-10,14-(metheno)pyrrolo[1,2-c][1,3]diazacycloheptadecin-16-yl]ethanesulfonamide or N-[(9S,15aS,16R)-17,17,20-trifluoro-7,9-dimethyl-1-oxo-2,3,15a,16,17,18-hexahydro-1H,9H,15H-4,8-(azeno)-10,14-(metheno)pyrrolo[1,2-c][1,3]diazacycloheptadecin-16-yl]ethanesulfonamide | 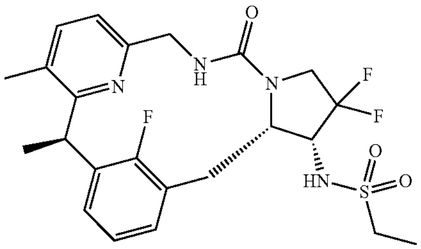 [SMILES: CCS(=O)(=O)N[C@@H]1[C@@H]2Cc3cccc(c3F)[C@@H](C)c3nc(ccc3C)CNC(=O)N2CC1(F)F] | 497.2 |
| 106 | N-[(9R,15aS,16R)-17,17,20-trifluoro-7,9-dimethyl-1-oxo-2,3,15a,16,17,18-hexahydro-1H,9H,15H-4,8-(azeno)-10,14-(metheno)pyrrolo[1,2-c][1,3]diazacycloheptadecin-16-yl]ethanesulfonamideor N-[(9S,15aS,16R)-17,17,20-trifluoro-7,9-dimethyl-1-oxo-2,3,15a,16,17,18-hexahydro-1H,9H,15H-4,8-(azeno)-10,14-(metheno)pyrrolo[1,2-c][1,3]diazacycloheptadecin-16-yl]ethanesulfonamide | 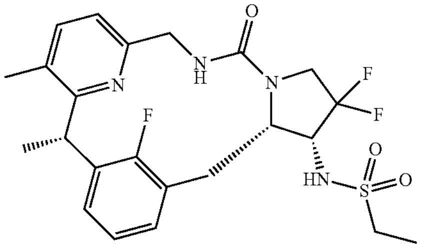 [SMILES: CCS(=O)(=O)N[C@@H]1[C@@H]2Cc3cccc(c3F)[C@H](C)c3nc(ccc3C)CNC(=O)N2CC1(F)F] | 497.2 |

TABLE 1-24

| Ex. No. | IUPAC Name | Structure | MS |
|---|---|---|---|
| 107 | N-[(1aS,6R,6aS,18aR)-15-(difluoromethyl)-5,5-difluoro-2-oxo-1,1a,2,5,6,6a,7,18a-octahydro-4H-18,14-(azeno)-12,8-(metheno)cyclopropa[k]pyrrolo[2,1-h][1,9]oxazacycloheptadecin-6-yl]methanesulfonamide or N-[(1aR,6R,6aS,18aS)-15-(difluoromethyl)-5,5-difluoro-2-oxo-1,1a,2,5,6,6a,7,18a-octahydro-4H-18,14-(azeno)-12,8-(metheno)cyclopropa[k]pyrrolo[2,1-h][1,9]oxazacycloheptadecin-6-yl]methanesulfonamide (opticalisomer) | 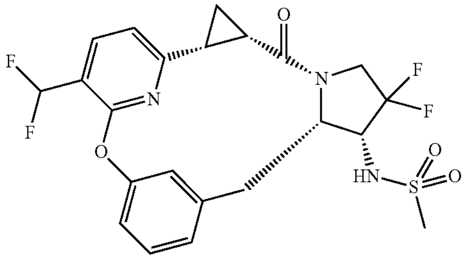 | 500.2 |
| 108 | N-[(15aS,16R)-7-chloro-17,17,20-trifluoro-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]propane-2-sulfonamide | 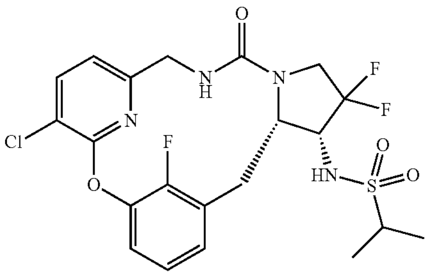 [SMILES: CC(C)S(=O)(=O)N[C@@H]1[C@@H]2Cc3cccc(c3F)Oc3nc(ccc3Cl)CNC(=O)N2CC1(F)F] | 519.3 |

TABLE 1-24-continued

| Ex. No. | IUPAC Name | Structure | MS |
|---|---|---|---|
| 109 | N-[(15aS,16R)-5,17,17,20-tetrafluoro-7-methyl-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]propane-2-sulfonamide | 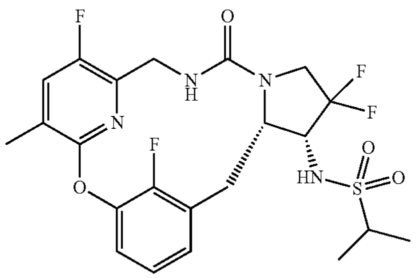 [SMILES: Cc1cc(F)c2nc1Oc1cccc(c1F)C[C@H]1[C@@H](NS(=O)(=O)C(C)C)C(F)(F)CN1C(=O)NC2] | 517.0 |

TABLE 1-25

| Ex. No. | IUPAC Name | Structure | MS |
|---|---|---|---|
| 110 | N-[(15aS,16R)-7-(difluoromethyl)-17,17,20-trifluoro-1-oxo-2,3,15a,16,17,18-hexahydro-1H,15H-4,8-(azeno)-10,14-(metheno)pyrrolo[1,2-j][1,8,10]oxadiazacyclo-heptadecin-16-yl]propane-2-sulfonamide | 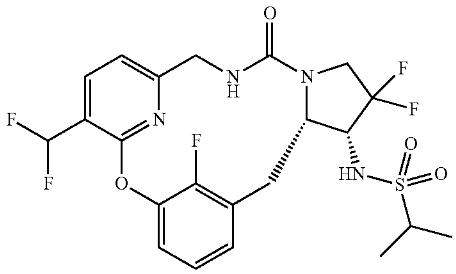 [SMILES: CC(C)S(=O)(=O)N[C@@H]1[C@@H]2Cc3cccc(c3F)Oc3nc(ccc3C(F)F)CNC(=O)N2CC1(F)F] | 535.1 |
| 111 | N-[(2S,15aS,16R)-17,17,20-trifluoro-2,7-dimethyl-1-oxo-1,2,15a,16,17,18-hexahydro-9H,15H-4,8-(azeno)-10,14-(metheno)pyrrolo[1,2-d][1,4]oxazacycloheptadecin-16-yl]ethanesulfonamide | 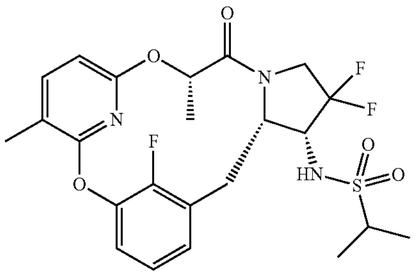 [SMILES: Cc1ccc2nc1Oc1cccc(c1F)C[C@H]1[C@@H](NS(=O)(=O)C(C)C)C(F)(F)CN1C(=O)[C@H](C)O2] | 498.4 |

Experimental Example 1: Acquisition of Cells Stably Expressing Human Orexin Type 2 Receptor (hOX2R)

In order to obtain cell clones that stably express human orexin type 2 receptor, human orexin type 2 (residues 1-444, NCBI Reference Sequence: AK314279) was constructed in a pcDNA3.1 (+) vector (Invitrogen) to express in mammalian cells. This plasmid DNA was transfected into CHO-K1 cells by electroporation, and stable clones were obtained by limiting dilution using resistance to G418 as a selection marker.

Experimental Example 2: Measurement of Orexin Type 2 Receptor Agonist Activity CHO cells in which human OX2 receptor was forcibly expressed were seeded at 10,000 cells/well into a 384-well black transparent bottom plate (BD falcon), and were incubated at 37° C., 5% $CO_2$ for 1 day after incubation at room temperature for 30 minutes. After removing the cell plate medium, assay buffer containing calcium indicator A (HBSS (Thermo Fisher Scientific), 20 mM HEPES (Thermo Fisher Scientific), 0.1% BSA (Sigma-Aldrich), 2.5 μg/mL Fluo-4 AM (Dojin Kagaku), 0.08% Pluronic F127 (Dojin Kagaku), 1.25 mM probenecid (Dojin Kagaku)) was added at 30 μL/well. After incubation in a 5% CO2 incubator at 37° C. for 30 minutes, it was incubated at room temperature for another 30 minutes. Add 10 μL/well of the test compound diluted with assay buffer B (HBSS, 20 mM HEPES, 0.1% BSA), and use FDSS μCELL (Hamamatsu Photonics) to measure the fluorescence value every 1 second for 1 minute, and then every 2 seconds for 1 minute. It was measured for 1 minute and 40 seconds. The amount of fluorescence value when DMSO is added instead of the test compound is defined as 0%, and the amount of fluorescence value when orexin A (human) (Peptide Institute) with a final concentration of 10 nM is added is defined as 100%. The activity (%) of the test compound was calculated. Table 2-1, 2-2, 2-3, and 2-4 show the activity of each compound at a concentration of 3 μM. As is clear from this result, the compound of the present invention was shown to have orexin type 2 receptor activating activity.

TABLE 2-1

| Test compound | OX2R agonist activity (3 μM, %) |
|---|---|
| 1 | 107 |
| 2 | 96 |
| 3 | 101 |
| 4 | 105 |
| 5 | 102 |
| 6 | 99 |
| 7 | 103 |
| 8 | 100 |
| 9 | 93 |
| 10 | 96 |
| 11 | 98 |
| 12 | 99 |
| 13 | 99 |
| 14 | 99 |
| 15 | 104 |
| 16 | 99 |
| 17 | 100 |
| 18 | 104 |
| 19 | 109 |
| 20 | 105 |
| 21 | 100 |
| 22 | 100 |
| 23 | 96 |
| 24 | 104 |
| 25 | 105 |
| 26 | 102 |
| 27 | 102 |
| 28 | 94 |
| 29 | 100 |
| 30 | 102 |

TABLE 2-2

| Test compound | OX2R agonist activity (3 μM, %) |
|---|---|
| 31 | 102 |
| 32 | 101 |
| 33 | 102 |
| 34 | 93 |
| 35 | 93 |
| 36 | 104 |
| 37 | 101 |
| 38 | 80 |
| 39 | 105 |
| 40 | 103 |
| 41 | 107 |
| 42 | 101 |
| 43 | 101 |
| 44 | 84 |
| 45 | 105 |
| 46 | 99 |
| 47 | 92 |
| 48 | 67 |
| 49 | 97 |
| 50 | 88 |
| 51 | 103 |
| 52 | 93 |
| 53 | 100 |
| 54 | 87 |
| 55 | 107 |
| 56 | 100 |
| 57 | 108 |
| 58 | 106 |
| 59 | 106 |
| 60 | 104 |

TABLE 2-3

| Test compound | OX2R agonist activity (3 μM, %) |
|---|---|
| 61 | 106 |
| 62 | 102 |
| 63 | 106 |

TABLE 2-3-continued

| Test compound | OX2R agonist activity (3 μM, %) |
|---|---|
| 64 | 105 |
| 65 | 102 |
| 66 | 97 |
| 67 | 103 |
| 68 | 100 |
| 69 | 101 |
| 70 | 103 |
| 71 | 99 |
| 72 | 104 |
| 73 | 101 |
| 74 | 96 |
| 75 | 95 |
| 76 | 96 |
| 77 | 104 |
| 78 | 97 |
| 79 | 102 |
| 80 | 100 |
| 81 | 102 |
| 82 | 101 |
| 83 | 96 |
| 84 | 104 |
| 85 | 95 |
| 86 | 102 |
| 87 | 105 |
| 88 | 109 |
| 89 | 114 |
| 90 | 108 |

TABLE 2-4

| Test compound | OX2R agonist activity (3 μM, %) |
|---|---|
| 91 | 106 |
| 92 | 106 |
| 93 | 109 |
| 94 | 109 |
| 95 | 103 |
| 96 | 107 |
| 97 | 108 |
| 107 | 108 |

Experimental Example 3: Measurement of Orexin Type 2 Receptor Agonist Activity CHO cells in which human OX2 receptor was forcibly expressed were seeded at 5,000 cells/well into a 384-well black transparent bottom plate (Costar) in 25 ul complete media, and were then incubated at 37° C., 5% $CO_2$ for 1 day. The next day, 25 ul of 2× calcium 5 dye (Molecular Devices) in assay buffer (HBSS (Thermo Fisher Scientific), 20 mM HEPES (Thermo Fisher Scientific), 2.5 mM probenecid). After incubation in a 5% $CO_2$ incubator at 37° C. for 40 minutes, it was incubated at room temperature for another 20 minutes. Add 5 μL/well of the test compound diluted with assay buffer B (HBSS, 20 mM HEPES), using FLIPR Tetra (Molecular Devices) to measure the fluorescence value every 1 second for 1 minute, and then every 2 seconds for 1 minute. It was measured for 1 minute and 40 seconds. The amount of fluorescence value when DMSO is added instead of the test compound is defined as 0%, and the amount of fluorescence value when orexin A (human) (Peptide Institute) with a final concentration of 10 nM is added is defined as 100%. The activity (%) of the test compound was calculated. Table 3 shows the activity of each compound at a concentration of 1 μM. As is clear from this result, the compound of the present invention was shown to have orexin type 2 receptor activating activity.

TABLE 3

| Test compound | OX2R agonist activity (1 μM, %) |
|---|---|
| 98 | 65 |
| 99 | 97 |
| 100 | 84 |
| 101 | 108 |
| 102 | 94 |
| 103 | 104 |
| 104 | 109 |
| 105 | 106 |
| 106 | 90 |
| 108 | 101 |
| 109 | 108 |
| 110 | 108 |
| 111 | 103 |

Experimental Example 4: Evaluation of Wake-Promoting Effects in Cynomolgus Monkeys The wake-promoting effects of four example compounds were evaluated by measuring the electroencephalogram (EEG) and electromyogram (EMG) in cynomolgus monkeys. Under isoflurane anesthesia (0.5-5%, Pfizer Japan Inc., Tokyo, Japan), male cynomolgus monkeys (2-3 years old, Hamri Co., Ltd., Ibaraki, Japan) were surgically implanted with radio-telemetry transmitters (L03-F3, Data Sciences International Inc., MN, USA). EEG electrodes were screwed into the skull at the parietal area. EMG electrodes were implanted on the cervical muscles. After the surgery, each monkey was given penicillin (100,000 units/head, i.m., Meiji Seika Pharma Co., Ltd., Tokyo, Japan), buprenorphine (0.02 mg/kg, i.m., Otsuka Pharmaceutical Co., Ltd., Tokyo, Japan) and prednisolone (1 mg/kg, s.c., Kyoritsu Seiyaku Co., Ltd., Tokyo, Japan) daily for one week. After at least a 1-month recovery period in home cages, the monkeys were habituated to the recording chamber placed in a soundproof room. EEG and EMG signals were recorded using the telemetry system (Ponemah software, Data Sciences International Inc., MN, USA) and the signals were analyzed using SleepSign software (Kissei Comtec Co., Ltd., Nagano, Japan). After confirming long sleep in dark phase in the experimental room, we used animals to examine the wake-promoting effect of compounds. Test compounds (3 mg/kg) suspended in 0.5% methylcellulose aqueous solution, or vehicle (i.e., 0.5% methylcellulose aqueous solution) was administered orally (p.o.) to monkeys at zeitgeber time 12 in a volume of 5 mL/kg body weight in pre-post design (n=2-4). EEG and EMG recordings were performed for 4 hours after the compound administration. The time spent in wakefulness for 4 hours after administration (% of vehicle treatment) was calculated by using SleepSign.

The example compounds tested in accordance with this example increased the wakefulness time to 500-850% (at a dose of 3 mg/kg, p.o.) when compared to the vehicle treatment group in cynomolgus monkeys.

Formulation Example 1 (Production of Capsule)

| | | |
|---|---|---|
| 1) | compound of Example 1 | 30 mg |
| 2) | crystalline cellulose | 10 mg |
| 3) | lactose | 19 mg |
| 4) | magnesium stearate | 1 mg |
| | total | 60 mg |

1), 2), 3) and 4) are mixed and filled in a gelatin capsule.

Formulation Example 2 (Production of Tablet)

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has an orexin type 2 receptor agonist activity, and is useful as an agent for the prophylaxis or treatment of narcolepsy.

The invention claimed is:

1. A compound of formula (I)

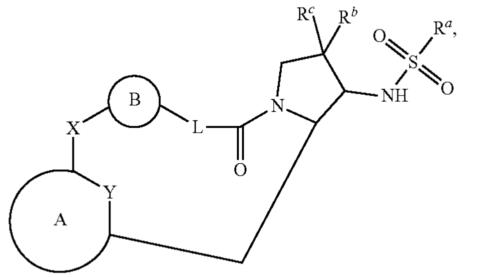

(I)

wherein

Ring A is an optionally substituted $C_{6-14}$ aryl group, or an optionally substituted 5- or 6-membered monocyclic aromatic heterocyclic group, where Y is a ring atom C or N, where the C is attached to hydrogen or an optional substituent;

X is —O—, —S—, —$NR^1$—, —$CR^2R^3$—, —O—($CR^2R^3$)—, —($CR^2R^3$)—O—, or an optionally substituted $C_{3-6}$ cycloalkyl group, wherein the left hand portion of X is attached to a ring carbon atom on Ring A that is adjacent to Y and the right hand portion of X is attached to Ring B;

$R^1$ is hydrogen, or an optionally substituted $C_{1-6}$ alkyl group;

$R^2$ and $R^3$ are independently hydrogen, halogen, or an optionally substituted $C_{1-6}$ alkyl group;

Ring B is an optionally substituted $C_{6-14}$ aryl group, or an optionally substituted 5- or 6-membered monocyclic aromatic heterocyclic group;

L is —$C(R^4R^5)$—$NR^6$—, —$C(R^4R^5)$—O—, —O—C($R^4R^5$)—, —$NR^6$—C($R^4R^5$)—, —C($R^4R^5$)—C($R^7R^8$)—, wherein the left hand portion of L is attached to Ring B and the right hand portion of L is attached to the carbonyl group;

$R^4$ and $R^5$ are independently hydrogen, halogen, or an optionally substituted $C_{1-6}$ alkyl group;

$R^6$ is hydrogen, or an optionally substituted $C_{1-6}$ alkyl group;

$R^7$ and $R^8$ are independently hydrogen, halogen, or an optionally substituted $C_{1-6}$ alkyl group; or $R^4$ and $R^6$, taken together with the atoms to which they are attached, form an optionally substituted 3- to 8-membered monocyclic non-aromatic heterocyclic ring; or $R^4$ and $R^5$, or $R^4$ and $R^7$, taken together with the atom or atoms to which they are attached form an optionally substituted 3- to 8-membered monocyclic non-aromatic heterocyclic ring, or an optionally substituted $C_{3-10}$ cycloalkyl group;

$R^a$ is a $C_{1-6}$ alkyl group, a $C_{3-4}$ cycloalkyl group, or a mono- or di-$C_{1-6}$ alkylamino group, wherein each of $C_{1-6}$ alkyl group, $C_{3-6}$ cycloalkyl group, and mono- or di-$C_{1-6}$ alkylamino group is optionally substituted;

$R^b$ is a hydrogen atom or a halogen atom; and $R^c$ is a hydrogen atom or a halogen atom;

or a salt thereof.

2. The compound according to claim 1, wherein

Ring A is

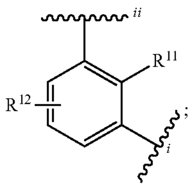

;

wherein i is the point of attachment to the bridge methylene and ii is the point of attachment to X; and $R^{11}$ and $R^{12}$ are independently hydrogen, halogen, or optionally halogenated $C_{1-6}$ alkyl group;

or a salt thereof.

3. The compound according to claim 1, wherein

Ring B is selected from:

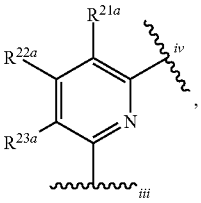

,

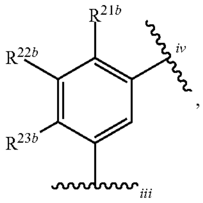

,

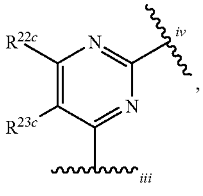

,

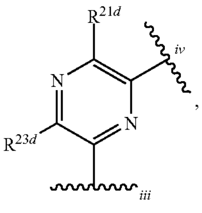

, and

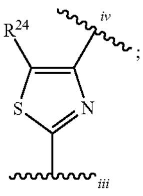

;

wherein iv is the point of attachment to L and iii is the point of attachment to X;

$R^{21a}$, $R^{21b}$, $R^{21d}$, $R^{22a}$, $R^{22b}$, $R^{22c}$, $R^{23a}$, $R^{23b}$, $R^{23c}$ and $R^{23d}$ are independently selected from hydrogen, halogen, an optionally halogenated $C_{1-6}$ alkyl group, $C_{1-6}$ alkoxyl group and a $C_{3-6}$ cycloalkyl group; and $R^{24}$ is selected from hydrogen, halogen, an optionally halogenated $C_{1-6}$ alkyl group, and a $C_{3-6}$ cycloalkyl group;

or a salt thereof.

4. The compound according to claim 1, wherein

Ring A is

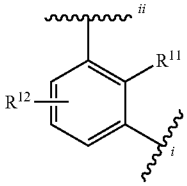

;

wherein i is the point of attachment to the bridge methylene and ii is the point of attachment to X; and $R^{11}$ and $R^{12}$ are independently hydrogen, halogen, or $C_{1-6}$ alkyl group;

X is —O—, —$CR^2R^3$—, —O—($CR^2R^3$)—, or —($CR^2R^3$)—O—, wherein the left hand portion of X is attached to a ring carbon atom on Ring A that is adjacent to Y and the right hand portion of X is attached to Ring B;

$R^2$ and $R^3$ are independently hydrogen, halogen, or $C_{1-6}$ alkyl group optionally substituted by 1 to 3 substituents independently selected from halogen and $C_{1-6}$ alkyl group;

Ring B is selected from:

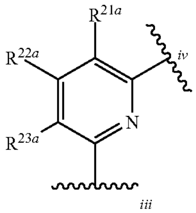

,

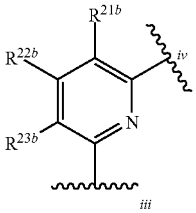

,

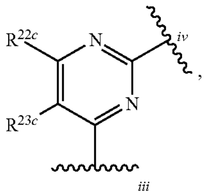

,

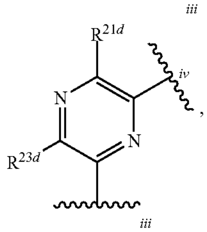

, and

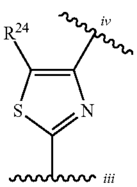

;

wherein iv is the point of attachment to L and iii is the point of attachment to X;

$R^{21a}$, $R^{21b}$, $R^{21d}$, $R^{22a}$, $R^{22b}$, $R^{22c}$, $R^{23a}$, $R^{23b}$, $R^{23c}$ and $R^{23d}$ are independently selected from hydrogen, halogen, an optionally halogenated $C_{1-6}$ alkyl group, $C_{1-6}$ alkoxyl group and a $C_{3-6}$ cycloalkyl group;

$R^{24}$ is hydrogen or a C1-6 alkyl group;

L is —C($R^4R^5$)—$NR^6$—, —C($R^4R^5$)—O—, —O—C($R^4R^5$)—, —$NR^6$—C($R^4R^5$)—, or —C($R^4R^5$)—C($R^7R^8$)—, wherein the left hand portion of L is attached to Ring B and the right hand portion of L is attached to the carbonyl group;

$R^4$ and $R^5$ are independently hydrogen, or $C_{1-6}$ alkyl group;

$R^6$ is hydrogen, or an optionally halogenated $C_{1-6}$ alkyl group;

$R^7$ and $R^8$ are independently hydrogen; or when L is —C($R^4R^5$)—$NR^6$— or —$NR^6$—C($R^4R^5$)—, $R^4$ and $R^6$ together with the atoms to which they are attached form a 3- to 8-membered monocyclic non-aromatic heterocyclic ring optionally substituted by $_1$ to 3 substituents independently selected from halogen and C1-6 alkoxyl group, and $R^5$ is hydrogen; or when L is —C($R^4R^5$)—C($R^7R^8$)—, $R^4$ and $R^7$ together with the carbon atoms to which they are attached form a $C_{3-10}$ cycloalkyl group, and $R^5$ and $R^8$ are both hydrogen;

$R^a$ is a $C_{1-6}$ alkyl group optionally substituted by 1 to 3 substituents independently selected from halogen atoms and $C_{1-6}$ alkoxyl group, a $C_{3-4}$ cycloalkyl group, or a mono- or di-$C_{1-6}$ alkylamino group;

$R^b$ is a hydrogen atom or a halogen atom; and $R^c$ is a hydrogen atom or a halogen atom;

or a pharmacologically acceptable salt thereof.

5. The compound according to claim 1, wherein

Ring A is a phenyl group optionally further substituted by 1 to 2 halogen atoms, where Y is a ring atom C attached to hydrogen or halogen;

X is —O—, wherein the left hand portion of X is attached to a ring carbon atom on Ring A that is adjacent to Y and the right hand portion of X is attached to Ring B;

Ring B is a pyridine ring optionally substituted by 1, 2 or 3 substituents independently selected from halogen and $C_{1-6}$ alkyl group;

L is —$CH_2$—NH—, wherein the left hand portion of L is attached to Ring B and the right hand portion of L is attached to the carbonyl group;

$R^a$ is a $C_{1-6}$ alkyl group optionally substituted by 1 to 3 halogen atoms, or a $C_{3-4}$ cycloalkyl group;

$R^b$ is a halogen atom; and $R^c$ is a halogen atom;

or a pharmacologically acceptable salt thereof.

6. The compound according to claim 1, wherein

Ring A is a phenyl group optionally further substituted by 1 to 2 halogen atoms, where Y is a ring atom C attached to halogen;

X is —O—, wherein the left hand portion of X is attached to a ring carbon atom on Ring A that is adjacent to Y and the right hand portion of X is attached to Ring B;

Ring B is a pyridine ring optionally substituted by 1, 2 or 3 $C_{1-6}$ alkyl groups;

L is —$CH_2$—NH—, wherein the left hand portion of L is attached to Ring B and the right hand portion of L is attached to the carbonyl group;

$R^a$ is a $C_{1-6}$ alkyl group optionally substituted by 1 to 3 halogen atoms;

$R^b$ is a halogen atom; and $R^c$ is a halogen atom;

or a pharmacologically acceptable salt thereof.

7. The compound according to claim 1, wherein the compound is selected from the group consisting of:

N-[(15aS,16R)-17,17-difluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide;

N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide;

N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]ethanesulfonamide;

1-fluoro-N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide;

N-[(15aS,16R)-7-chloro-17,17,20-trifluoro-1-oxo-2,3,15a,16,17,18-hexahydro-1H,15H-4,8-(azeno)-14,10-(metheno)pyrrolo[1,2-j][1,8,10]oxadiazacycloheptadecin-16-yl]cyclopropanesulfonamide;

N-[(15aS,16R)-5,17,17,20-tetrafluoro-7-methyl-1-oxo-2,3,15a,16,17,18-hexahydro-1H,15H-4,8-(azeno)-14,10-(metheno)pyrrolo[1,2-j][1,8,10]oxadiazacycloheptadecin-16-yl]methanesulfonamide;

N-[(15aS,16R)-7-chloro-5,17,17,20-tetrafluoro-1-oxo-2,3,15a,16,17,18-hexahydro-1H,15H-4,8-(azeno)-14,10-(metheno)pyrrolo[1,2-j][1,8,10]oxadiazacycloheptadecin-16-yl]cyclopropanesulfonamide; and N-[(15aS,16R)-17,17,20-trifluoro-7-methyl-1-oxo-2,3,15a,16,17,18-hexahydro-1H,15H-4,8-(azeno)-14,10-(metheno)pyrrolo[1,2-j][1,8,10]oxadiazacycloheptadecin-16-yl]propane-2-sulfonamide;

or a pharmacologically acceptable salt thereof.

8. The compound according to claim 1, wherein the compound is N-[(15aS,16R)-17,17-difluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide, or a pharmacologically acceptable salt thereof.

9. The compound according to claim 1, wherein the compound is N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide, or a pharmacologically acceptable salt thereof.

10. The compound according to claim 1, wherein the compound is N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]ethanesulfonamide, or a pharmacologically acceptable salt thereof.

11. The compound according to claim 1, wherein the compound is 1-fluoro-N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide, or a pharmacologically acceptable salt thereof.

12. The compound according to claim 1, wherein the compound is N-[(15aS,16R)-7-chloro-17,17,20-trifluoro-1-oxo-2,3,15a,16,17,18-hexahydro-1H,15H-4,8-(azeno)-14,10-(metheno)pyrrolo[1,2-j][1,8,10]oxadiazacycloheptadecin-16-yl]cyclopropanesulfonamide, or a pharmacologically acceptable salt thereof.

13. The compound according to claim 1, wherein the compound is N-[(15aS,16R)-5,17,17,20-tetrafluoro-7-methyl-1-oxo-2,3,15a,16,17,18-hexahydro-1H,15H-4,8-(azeno)-14,10-(metheno)pyrrolo[1,2-j][1,8,10]oxadiazacycloheptadecin-16-yl]methanesulfonamide, or a pharmacologically acceptable salt thereof.

14. The compound according to claim 1, wherein the compound is N-[(15aS,16R)-7-chloro-5,17,17,20-tetrafluoro-1-oxo-2,3,15a,16,17,18-hexahydro-1H,15H-4,8-(azeno)-14,10-(metheno)pyrrolo[1,2-j][1,8,10]oxadiazacycloheptadecin-16-yl]cyclopropanesulfonamide, or a pharmacologically acceptable salt thereof.

15. The compound according to claim 1, wherein the compound is N-[(15aS,16R)-17,17,20-trifluoro-7-methyl-1-oxo-2,3,15a,16,17,18-hexahydro-1H,15H-4,8-(azeno)-14,10-(metheno)pyrrolo[1,2-j][1,8,10]oxadiazacycloheptadecin-16-yl]propane-2-sulfonamide, or a pharmacologically acceptable salt thereof.

16. The compound according to claim 1, wherein the compound is N-[(15aS,16R)-17,17-difluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide.

17. The compound according to claim 1, wherein the compound is N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]methanesulfonamide.

18. The compound according to claim 1, wherein the compound is N-[(15aS,16R)-17,17,20-trifluoro-7-methyl-1-oxo-2,3,15a,16,17,18-hexahydro-1H,15H-4,8-(azeno)-10,14-(metheno)pyrrolo[1,2-j][1,8,10]oxadiazacycloheptadecin-16-yl]ethanesulfonamide.

19. The compound according to claim 1, wherein the compound is 1-fluoro-N-[(15aS,16R)-17,17,20-trifluoro-7-methyl-1-oxo-2,3,15a,16,17,18-hexahydro-1H,15H-4,8-

(azeno)-10,14-(metheno)pyrrolo[1,2-j][1,8,10]oxadiazacycloheptadecin-16-yl]methanesulfonamide.

20. The compound according to claim 1, wherein the compound is N-[(15 aS,16R)-7-chloro-17,17,20-trifluoro-1-oxo-2,3,15 a,16,17,18-hexahydro-1H,15H-4, 8-(azeno)-14,10-(metheno)pyrrolo[1,2-j][1,8,10]oxadiazacycloheptadecin-16-yl]cyclopropanesulfonamide.

21. The compound according to claim 1, wherein the compound is N-[(15aS,16R)-5,17,17,20-tetrafluoro-7-methyl-1-oxo-2,3,15a,16,17,18-hexahydro-1H,15H-4,8-(azeno)-14,10-(metheno)pyrrolo[1,2-j][1,8,10]oxadiazacycloheptadecin-16-yl]methanesulfonamide.

22. The compound according to claim 1, wherein the compound is N-[(15aS,16R)-7-chloro-5,17,17,20-tetrafluoro-1-oxo-2,3,15a,16,17,18-hexahydro-1H,15H-4,8-(azeno)-14,10-(metheno)pyrrolo[1,2-j][1,8,10]oxadiazacycloheptadecin-16-yl]cyclopropanesulfonamide.

23. The compound according to claim 1, wherein the compound is N-[(15 aS,16R)-17,17,20-trifluoro-7-methyl-1-oxo-2,3,15 a,16,17,18-hexahydro-1H,15H-4, 8-(azeno)-14,10-(metheno)pyrrolo[1,2-j][1,8,10]oxadiazacycloheptadecin-16-yl]propane-2-sulfonamide.

24. A pharmaceutical composition comprising the compound as defined in claim 1 or a salt thereof, and a pharmacologically acceptable carrier.

25. A pharmaceutical composition comprising the compound as defined in claim 4 or a salt thereof, and a pharmacologically acceptable carrier.

26. A pharmaceutical composition comprising the compound as defined in claim 7 or a salt thereof, and a pharmacologically acceptable carrier.

* * * * *